US012624365B2

(12) United States Patent
Ben Khaled et al.

(10) Patent No.: US 12,624,365 B2
(45) Date of Patent: May 12, 2026

(54) METHOD FOR MODULATING THE ALKALOID CONTENT OF A TOBACCO PLANT

(71) Applicant: BRITISH AMERICAN TOBACCO (INVESTMENTS) LIMITED, London (GB)

(72) Inventors: Sara Ben Khaled, London (GB); Francisco Anastacio De Abreu E Lima, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 268 days.

(21) Appl. No.: 17/597,251

(22) PCT Filed: Jul. 3, 2020

(86) PCT No.: PCT/GB2020/051602
§ 371 (c)(1),
(2) Date: Dec. 30, 2021

(87) PCT Pub. No.: WO2021/001658
PCT Pub. Date: Jan. 7, 2021

(65) Prior Publication Data
US 2022/0340922 A1     Oct. 27, 2022

(30) Foreign Application Priority Data
Jul. 3, 2019    (GB) .................................... 1909562

(51) Int. Cl.
*C12N 15/82*        (2006.01)
*A24B 15/10*        (2006.01)
*C07K 14/415*       (2006.01)

(52) U.S. Cl.
CPC .......... *C12N 15/8243* (2013.01); *A24B 15/10* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 7,798,153 B2 * | 9/2010 | Lawrence, Jr. ........ | A24B 15/10 131/352 |
| 9,277,762 B2 | 3/2016 | Davies et al. | |
| 10,006,040 B2 | 6/2018 | Vinocur et al. | |
| 2008/0090998 A1 | 4/2008 | Abad et al. | |
| 2009/0083876 A1 | 3/2009 | Coruzzi et al. | |
| 2009/0144849 A1 | 6/2009 | Lutfiyya | |
| 2009/0217406 A1 | 8/2009 | Puzio et al. | |
| 2013/0333061 A1 | 12/2013 | Wu et al. | |
| 2014/0026257 A1 | 1/2014 | Hatzfeld et al. | |
| 2016/0032299 A1 | 2/2016 | Hashimoto et al. | |
| 2016/0244777 A1 | 8/2016 | Coffin | |
| 2018/0371487 A1 | 12/2018 | Yang et al. | |
| 2019/0062776 A1 | 2/2019 | Song et al. | |

FOREIGN PATENT DOCUMENTS

| | | | |
|---|---|---|---|
| GB | 2515502 A | 12/2014 | |
| WO | 2013034459 A1 | 3/2013 | |
| WO | 2018067985 A1 | 4/2018 | |
| WO | 2018237107 A1 | 12/2018 | |
| WO | WO-2019046756 A1 * | 3/2019 | ............... A01H 5/12 |

OTHER PUBLICATIONS

Cheng, Youfa, et al. "NPY1, a BTB-NPH3-like protein, plays a critical role in auxin-regulated organogenesis in *Arabidopsis*." Proceedings of the National Academy of Sciences 104.47 (2007): 18825-18829. (Year: 2007).*

Moldoveanu, Serban C., Wayne A. Scott, and Darlene M. Lawson. "Nicotine analysis in several non-tobacco plant materials." Contributions to Tobacco & Nicotine Research 27.2 (2016): 54-59. (Year: 2016).*

Sakai, T. (2005). NPH3 and RPT2: Signal Transducers in Phototropin Signaling Pathways. In: Wada, M., Shimazaki, Ki., Iino, M. (eds) Light Sensing in Plants. Springer, Tokyo. https://doi.org/10.1007/4-431-27092-2_20 (Year: 2005).*

Liu, Ye, et al. "Computational approaches for predicting variant impact: An overview from resources, principles to applications." Frontiers in genetics 13 (2022): 981005. (Year: 2022).*

Doerks, Tobias, Amos Bairoch, and Peer Bork. "Protein annotation: detective work for function prediction." Trends in Genetics 14.6 (1998): 248-250 (Year: 1998).*

Smith, Temple F., and Xiaolin Zhang. "The challenges of genome sequence annotation or "the devil is in the details"." Nature biotechnology 15.12 (1997): 1222-1223 (Year: 1997).*

Bork, Peer, and Amos Bairoch. "Go hunting in sequence databases but watch out for the traps." Trends in Genetics 12.10 (1996): 425-427 (Year: 1996).*

Melnick, Ari, et al. "In-depth mutational analysis of the promyelocytic leukemia zinc finger BTB/POZ domain reveals motifs and residues required for biological and transcriptional functions." Molecular and Cellular Biology 20.17 (2000): 6550-6567. (Year: 2000).*

Christie, John M., et al. "Shining light on the function of NPH3/RPT2-like proteins in phototropin signaling." Plant Physiology 176.2 (2018): 1015-1024. (Year: 2018).*

Keskin, Ozlem, et al. "A new, structurally nonredundant, diverse data set of protein-protein interfaces and its implications." Protein Science 13.4 (2004): 1043-1055 (Year: 2004).*

Thornton, Janet M., et al. "From structure to function: approaches and limitations." nature structural biology 7.11 (2000): 991-994. (Year: 2000).*

(Continued)

*Primary Examiner* — Amjad Abraham
*Assistant Examiner* — Kelsey L Mcwilliams
(74) *Attorney, Agent, or Firm* — McKee, Voorhees & Sease, PLC

(57)        ABSTRACT

Disclosed are methods of modulating the alkaloid content of a plant or a part thereof by modulating the activity or expression of at least one gene encoding a BTB/POZ NPH3 domain-containing protein. Methods of reducing the content of at least one tobacco specific nitrosamine (TSNA) precursor in tobacco are also provided.

20 Claims, 35 Drawing Sheets

Specification includes a Sequence Listing.

(56) References Cited

OTHER PUBLICATIONS

Guo, Haiwei H., Juno Choe, and Lawrence A. Loeb. "Protein tolerance to random amino acid change." Proceedings of the National Academy of Sciences 101.25 (2004): 9205-9210. (Year: 2004).*

Christie et al., "Shining Light on the Function of NPH3/RPT2-Like Proteins in Phototropin Signaling1[CC-BY]", Plant Physiology, vol. 176, pp. 1015-1024, Feb. 2018.

Rhodes et al., "Signals and Signalling Pathways in PlantWound Responses", Communication in Plants, pp. 391-401, 2006.

Rushton et al., "Tobacco Transcription Factors: Novel Insights into Transcriptional Regulation in the Solanaceae1[C][W][OA]", Plant Physiology, vol. 147, pp. 280-295, May 2008.

Siminszky et al., "Conversion of nicotine to nornicotine in Nicotiana tabacum is mediated by CYP82E4, a cytochrome P450 monooxygenase", Proc Natl Acad Sci USA, vol. 102, No. 41, pp. 14919-14924, Oct. 2005.

Voelckel et al., "Herbivore-induced ethylene burst reduces fitness costs of jasmonate-and oral secretion-induced 5 defenses in Nicotiana attenuata", Oecologia, vol. 127, pp. 274-280,—2001.

Yang et al., "Potato NPH3/RPT2-Like Protein StNRL1, Targeted by a Phytophthora infestans RXLR Effector, Is a 6 Susceptibility Factor1[OPEN]", Plant Physiology, vol. 171, pp. 645-657, May 2016.

Phoenix Bioinformatics Database, AT5G67385.1-NCH1, 5 pages, 2005.

International Searching Authority in connection with PCT/GB2020/051602 filed Jul. 3, 2020, "The International Search Report and the Written Opinion of the International Searching Authority, or the Declaration", 17 pages, mailed Sep. 22, 2020.

Motchoulski et al., "*Arabidopsis* NPH3: a NPH1 Photoreceptor-Interacting Protein Essential for Phototropism", Science, vol. 286, pp. 1-5, 1999.

Guo et al., "Differential Expression of miRNAs in Response to Topping in Flue-Cured Tobacco (*Nicotiana tabacum*) Roots," PLoS One, Dec. 2011, vol. 6, No. 12, pp. 1-15.

Jiang et al., "Transcriptome Analysis Insights in Bulblet on Leaf Surface in Ornitho-galum thyrsoides," Molecular Plant Breeding, 2017, vol. 15, No. 2, pp. 519-531.

Tang, Y., "The mechanism of NtRNF217 gene regulating tobacco resistance to bacterial wilt and its drug-induced effect," Southwest University, May 2018, Master's Thesis, Chongqing, China, 79 pages.

Uniprot, "A0A1S4AA67_TOBAC," LOC107795415, Last Updated Apr. 12, 2017, BTB/POZ domain-containing protein At5g67385, 6 pages.

Wang et al., "Cloning Full-Length cDNA of GbNPR1 Gene from Gossypium barbadense and Its Expression in Transgenic Tobacco," Chinese Agricultural Sciences, 2006, vol. 39, No. 5, pp. 886-894.

* cited by examiner

FIG. 3
Nitab4.5_0000868g0020.2 amino acid sequence (SEQ ID NO. 1):

```
MVDLDSEGTEQPSTVNNMSTKKKELLSTAMKRTSDWIFSQEIPSDVTVNAGGSAFSLHKFPLVSKSGY
IRKIISESNDADVSIVEIPDIPGGSDAFELAAKFCYGINFEISTENIALLRCTAEYLEMTEDYAVGNL
VGRTEAYLNEVALKSLAGAVSILHSSESLLPIAEKVKMVSRCIDTIAYIACKDNQFCTSGRAEAGTNG
LNSSTFSNPKPMVDWWAEDLAVLRIDFFQRVLIAMMGRGFKQYALGPILMLYAQKSLRGLEIFGKGRK
KIEPKQEHEKRVVLETIVSLLPREKNALSVSFLSMLLRAAIYLETTVACRLDLEKRMALQLGQAVLDD
LLIPSYSFTGDTLFDVETVQRIIMNFLDNEMDGSRLGDEEYVSPSLSDMERVGKLMENYLAEIASDRN
LSVSKFISLAEVIPEQAKITEDGMYRAIDIYLKAHPALSDMERKKVCGVMDCQKLSREACAHAAQNDR
LPVQTVVQVLYYEQQRLREVMDGSQLVATEPPALIPSKTNQFSTDIRPISDEVSSLKRENQELKFELL
KMKMRLKEIEKPSNKSATSSPLVITHPSADKPPLPRKPSNFISSVSKKLGKFIRADGLTANKGRNKPS
KDRRHSIS
```

FIG. 4
Nitab4.5_0000868g0020.2 coding sequence (SEQ ID NO. 2):

```
ATGGTGGATCTTGATTCAGAGGGGACTGAACAACCCTCTACTGTTAACAATATGTCCACTAAAAAGAA
GGAGCTTCTTTCCACTGCTATGAAGAGGACCTCTGATTGGATTTTCTCCCAAGAGATCCCAAGTGATG
TAACTGTAAATGCAGGCGGATCCGCCTTTTCACTGCACAAGTTCCCTTTAGTTTCAAAGAGTGGCTAC
ATAAGGAAGATTATCTCAGAATCCAATGATGCTGATGTTTCTATAGTCGAAATCCCTGATATACCCGG
TGGATCAGATGCATTTGAACTTGCTGCAAAATTTTGTTATGGAATAAATTTTGAGATAAGCACAGAAA
ACATTGCCTTGCTGAGATGCACAGCGGAATATCTTGAGATGACAGAAGACTATGCAGTTGGGAATTTG
GTTGGAAGAACTGAGGCCTACTTAAATGAAGTAGCTCTTAAAAGCCTAGCTGGTGCAGTTTCAATTTT
GCATTCTTCAGAAAGCCTTCTTCCCATTGCAGAGAAAGTAAAAATGGTTAGTCGATGCATCGACACAA
TTGCATATATTGCATGCAAGGATAACCAATTCTGCACATCAGGTAGAGCAGAGGCTGGTACTAACGGA
TTGAATTCGTCCACGTTTTCAAACCCGAAGCCTATGGTTGATTGGTGGGCTGAGGATTTAGCTGTCCT
TAGAATTGATTTTTTCCAAAGGGTTCTAATTGCAATGATGGGAAGAGGATTCAAGCAGTATGCACTTG
GACCAATATTAATGCTATATGCACAGAAGTCTCTTCGAGGTTTGGAAATATTTGGAAAGGGAAGGAAA
AAAATTGAGCCAAAACAAGAACATGAAAGAGGGGTTGTTTTAGAAACAATTGTTAGTCTTCTGCCAAG
GGAGAAAAATGCATTGTCAGTTAGCTTTCTGTCAATGCTGCTCCGAGCTGCAATATATCTAGAAACCA
CAGTTGCTTGCAGGCTTGACTTGGAGAAGAGGATGGCATTGCAGCTTGGACAGGCTGTGTTAGATGAT
TTATTGATTCCTTCATATTCCTTCACAGGGGACACATTGTTTGATGTTGAAACCGTGCAGCGTATCAT
CATGAATTTCCTTGACAATGAAATGGATGGAAGTCGATTGGGAGATGAGGAGTATGTGTCTCCTTCAT
TAAGTGACATGGAGCGGGTTGGGAAACTTATGGAAAATTACCTTGCTGAAATAGCCTCAGACCGTAAT
CTATCCGTTTCAAAATTCATTAGTCTAGCTGAAGTCATCCCAGAGCAAGCAAAGATCACTGAAGATGG
GATGTACAGGGCAATTGATATTTATTTGAAGGCACATCCAGCTCTAAGTGATATGGAAAGAAAAAAAG
TTTGCGGGTGTTATGGACTGTCAAAAGCTATCTAGAGAGGCTTGTGCTCATGCTGCTCAAAATGATAGG
CTCCCTGTTCAGACAGTTGTGCAAGTACTTTACTACGAGCAGCAACGCCTTCGTGAGGTCATGGACGG
GAGCCAACTTGTAGCAACTGAACCTCCAGCTCTAATTCCTTCTAAAACTAATCAGTTCTCCACTGATA
TCCGTCCTATTTCAGATGAGGTCTCTAGTCTAAAACGAGAAATCAGGAGCTGAAATTTGAGTTGCTA
AAGATGAAAATGAGGTTGAAAGAAATTGAAAAACCTTCAAACAAATCAGCTACTAGCAGCCCTTTGGT
CATCACTCATCCATCTGCTGATAAACCTCCTTTGCCAAGAAACCATCTAATTTCATAAGCTCAGTAT
CCAAAAAGCTTGGAAAATTTATTCGAGCAGATGGACTCACAGCCAACAAAGGCCGAAATAAACCAAGT
AAAGACAGGCGTCATTCTATATCCTGA
```

FIG. 5
Nitab4.5_0000868g0020.2 genomic sequence (SEQ ID NO. 3):

```
CTGAGCTAAATCCTTTTCTACTCTATTTAACCCCAATCATTCACATAATACCTTTAATACCACTCACA
TTTCTGCTGTAGGGGCTCCTCAAACATGATCTTTGTTCTGCTAACATTAAGGCCTATAATGGGAATTG
TACCAATGCCTTGATTGATAGTGAAGATGATAACAATAATTCAATTATTAGGGGCCAGATACTGTTG
ATTAAATGCTCAGACATTGAACTAACAGAAGCAAAGGAAAAGAACATGTCTTTCTGGTTTTTGCTCCA
TAAGGAAACAGCTTAAGAGAAACCTCTACCGTAGACCGAATGTGATGGACATGGTTAAGACCCTTTAA
AGTTTCAATCATGGTGGATCTTGATTCAGAGGGGACTGAACAACCCTCTACTGTTAACAATATGTCCA
```

FIG. 5 (Continued )

Nitab4.5_0000868g0020.2 genomic sequence (SEQ ID NO. 3):

```
CTAAAAAGAAGGAGCTTCTTTCCACTGCTATGAAGAGGACCTCTGATTGGTATGCTCTATATATCTTG
ACTTCTTATTGTGCTTTGTAAAAGTAGCCAGCCCCTTTTATGTACTATTATTAATCTGTTTCTCAAGA
TACTCGCTGGAAGGATAGGTACTGACAAGTAAAGTTACCTATATAATCTTAACAGGATTTTCTCCCAA
GAGATCCCAAGTGATGTAACTGTAAATGCAGGCGGATCCGCCTTTTCACTGCACAAGGTGTGGTGTTC
TCTATGCTTTTGTCATAAGAAGTTATAACTAAACTTCACTCACAATCCAAACTGTTGTTGGTTTTAGT
TATATTCCTATTTGGATTGAGTTATCAGCCCTGGTCACACCTCAATGAGAATCTGAATTTGGTGATTT
TTTCTCTTTTCTGACGATTGAATCACAAGGTTCAATAATGATTTATTGTGTACCATGCAGTTCCCTTT
AGTTTCAAAGAGTGGCTACATAAGGAAGATTATCTCAGAATCCAATGATGCTGATGTTTCTATAGTCG
AAATCCCTGATATACCCGGTGGATCAGATGCATTTGAACTTGCTGCAAAATTTTGTTATGGAATAAAT
TTTGAGATAAGCACAGAAAACATTGCCTTGCTGAGATGCACAGCGGAATATCTTGAGATGACAGAAGA
CTATGCAGTTGGGAATTTGGTTGGAAGAACTGAGGCCTACTTAAATGAAGTAGCTCTTAAAAGCCTAG
CTGGTGCAGTTTCAATTTTGCATTCTTCAGAAAGCCTTCTTCCCATTGCAGAGAAAGTAAAAATGGTT
AGTCGATGCATCGACACAATTGCATATATTGCATGCAAGGATAACCAATTCTGCACATCAGGTAGAGC
AGAGGCTGGTACTAACGGATTGAATTCGTCCACGTTTTCAAACCCGAAGCCTATGGTTGATTGGTGGG
CTGAGGATTTAGCTGTCCTTAGAATTGATTTTTTCCAAAGGGTTCTAATTGCAATGATGGGAAGAGGA
TTCAAGCAGTATGCACTTGGACCAATATTAATGCTATATGCACAGAAGTCTCTTCGAGGTTTGGTGAG
GCCTTGTCCTATAATATAATCTGGATTATTTAGTTAAAATATTTACGCAGATAGTAATTTTTTTGTTT
ATCACAGGAAATATTTGGAAAGGGAAGGAAAAAAATTGAGCCAAAACAAGAACATGAAAAGAGGGTTG
TTTTAGAAACAATTGTTAGTCTTCTGCCAAGGGAGAAAAATGCATTGTCAGTTAGCTTTCTGTCAATG
CTGCTCCGAGCTGCAATATATCTAGAAACCACAGTTGCTTGCAGGCTTGACTTGGAGAAGAGGATGGC
ATTGCAGCTTGGACAGGCTGTGTTAGATGATTTATTGATTCCTTCATATTCCTTCACAGGGGACACAT
TGTTTGATGTTGAAACCGTGCAGCGTATCATCATGAATTTCCTTGACAATGAAATGGATGGAAGTCGA
TTGGGAGATGAGGAGTATGTGTCTCCTTCATTAAGTGACATGGAGCGGGTTGGGAAACTTATGGAAAA
TTACCTTGCTGAAATAGCCTCAGACCGTAATCTATCCGTTTCAAAATTCATTAGTCTAGCTGAAGTCA
TCCCAGAGCAAGCAAAGATCACTGAAGGATGGGATGTACAGGGCAATTGATATTTATTTGAAGGTATGC
GCGATGAAATACTTGATTAGTTATAAATTTATCTATGCATATTTACACATACAGGAGCATTTTCATAG
TTTTAGATCATGTTTAGAAAAGGAGAAAAACTTTTGCTCCCGACTGCTACATGGTAATTGGCATGCTA
AACTTAGTAATCTTGATTGAAATGCCTTCTACAACAATGTACCTCTTGGTCCTAGCATAATTATGACT
GAGAGAAGACTTTGGGAATAAACAAATCAGAAAATATGTCACCAATGAAGAACCAGTCATTTTCACA
AAATCCTTGCTCCTCAATTATTTTTTTTGCAGGCATTGCTCGGTCCGCCTCATGATTTTGACCCAAGC
CCATGTCCTATACTCCTTTACCCTACAACCATTTTGTGAGACTGATGTTGTCTGGAGTTTCGAATCTC
GTTTCTTCCCCTGTCCTGAACATCTATCTCATGGTGCATTTATCCTGCACCTGGTTTGAACTTTGAAT
ATGTGTTCAATTCAACTCACCGTGTCTTACTTAGACCATATATATATATACTAGTAGTTTTAGCTAAG
GGATATGGTATGTTAGGAAGAAGAACATTCCTCATTTCAAATGGACTTAAGGGGAAGCTCCCTTAGTA
TATTACTTAGGTATTATAGTATGTTTTTGTGAGGAATAATTTGGAGTAAAGAGTAGCTGTGAAGCATG
TTAAAGCACATGACTGAGGTGGTACTTTAAATCGTTGTGTCGCTCATCATTAGGGAATGCCAGATCAG
GCTTTTTTAATTTTTATATTCTGTTTCCGAGTATATAATTTCTTCTTGATACAGACGGTATAACAGGA
CTTAATCAGGGTAATTAATTAGTATCTGCACGTGCAAGATCAATTTAAATGTAGGTTAAATATGTTAG
TACTTAGTACCTTCTCATCATTGAAGAAATTAATAGAGGACGAACATATATATATATATATATATATA
TATATATATATTTCTCTGCACGTGTATTGCATGTGTATGCCAAATTATATAATATCTAATTTTATAAC
ATAATATTAAATATTATTAAAAAAAATTCCGAACAAATAATTATACATAAAATAAGGTACAAGTATTTA
CGAATTGATCCATGTAAATCAGCATATATTGACTTTGAAAGTTCGTCCCAAACAAACACTTTTAACTT
TGCAACCATTCTTACACGAAACAACATAATATGTAAATGTAGCTTGGTGGCTAAACTAACAAACCATA
AACTCATTGCTAATGTCTTCGTAAAAAAATGTATGTCACAAAACCGCTTAAGTTGGTAATTTAATATT
TCATGAAAAGACTTTGTAAGGCTAATTAACAAAATATTTAATTTGAATTATCTTATTTAGGGAGTAGT
ATTTAATTTTAAATATTTTATTTTGATGTTATTTTTGCAGGTTCTTTTTTCTTTTGACTTAAAAGTAT
TAATTCAATTTTTCAAGATTCATCATTAAAACACAATTTAATAGGCTATTCGAGATATAGGGAACTTG
AATATGAAATAACTTTTAAATAAGAATATGAGTAGTAATTATTTATTGCGAGCGACACAATTTTATT
TTTTTGTTAATTTTCTTAAAGAAAAAAAGAAAGAGACCGCCACTTTTGTATAATAAATACTCTTAATC
TGATTTTAAATTAATTATAATAATTGAAGTTTACTACTTGTTTAGTTTCAAAATCTGTCTGTTAAAGA
AAAATTATAACTGCTTGAATTTGGAGATGAACGATCTATGTGGAAAATAGTTTTTTTATTTGAATTTA
AAATAAATGACTTATATTGCAACATGCAAACATTGCGTCGTCTTGTCTAAAGCAGCCAGTAGGAAAGC
ATTGTCTAAATAAAAAGCCAGTAGAAAAGCCGAAACAGTAGATAAATACAACAATCATTTTCTTTCT
CCACTTCTTAAAATAATGATCACCCAATAGAAAAAAAAATATAGATTTTTTTCGTAAGTTAAATACTT
TAGATTATCTCAATATATGTGCAGAATTTTAGCACCGTTTGTGAATTAAAAATTTGAAGACTCGACTAA
ACTTTAAATAAAAAGGTCAAAAGAAAGGTATGAGTGCAATTTAATAACAAAAAAAAGGCACACAGCAA
```

FIG. 5 (Continued )

Nitab4.5_0000868g0020.2 genomic sequence (SEQ ID NO. 3):

```
AAGAAGAATACCTTTCAATGATGAATTTTATAGAATTGCTGATGAGACTAAGTAATCGGGGTGCGTTT
TTAAGTCACTCTCTGCTTAACTGTAAATAAATACATACTTATTTATTATCAAGAAGTTAGAACACTCT
TCGTCTTCTATTCCTTTAGAATATATCTGTGTGAGTTTATGGAACAAAGGCTTTTTTTTATTTGAATA
GTAAGCCAATTGTTTCTCTATCTATTCTAAAAGATGCCAAACGGTTGAAAGACAAAATCAAATGGGAA
CCGGTAGAAACTATTTTAAGCATTATTGACTAATATGAAAGATCACATCCCTTCAAATAAATTTGGTA
TTTACTTAAAATTTTTGGTATAAATAAAATTAAATTATTTAGAAAGGCATTTAGGTAATTCAACTTTT
TGGTTAAGAGCTTCCTACATATATATATATATATATATGTGCGTGGTGTGTGCAAAATATTATAGATAT
TAAGTTTTGAACCCATAATCTAAAAAATCTCATAACCTTGAACCCATTAAATTTAAATCTTGGATCCG
CCTCCTTTTGCATTGCATAGATCATTGCTACAATGTGGTGGCTCTTGTTTTCTCTTGCCTATGTTGCA
GGGCTTGCTGTGCATAGGTCTTCATACTTGAGGTCTTTTTCTATAATTTGACACCTTAATGTTAACCA
GGGTGAAATAAGGATCTGGTATCTGCTCGTTGACCCTTCGCTTTCTCCTTTCAACTGTAGGTCAAATT
TGTCATAACATCCTAAAGAATCTTGTGTGCCAATACATACTTCGTATATGGTATCTCATCCAAAAGAA
GAAGCTCGTTTATATGCTCATATATATGCAAACTGCCACCCCCCCCCCCCGGTTACTCTTTCTAATT
TAAAAGGTAAGAATAGACTCAATAGGTTTTTGCTACAGAAGCTCTGAATCTTATTGCTATTCAGTCAC
GTCACATAATAACAAGATCTAAACCATGTATACCATTTGATCTNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNTTTTTTTTTTTTTTTTTTTTTTTTGCTTTTGGTGC
CAAAGGGTATTAAGTAGCATCCATTCATTGCGTAGTGTTTCTTGAGTACATAATAGTAATCTGTTTGC
CTCTAACATCTCTAAGACAATCATAGGAAGAAATCCAAAATGTATTATCCTAGTAGACTCCTTCATCC
TACCACCAAATTTGGCTAATTGATTTGCTACTTTTGTTCTGCTCCTTGTAATTATGCTCAATCAGAGG
GTCTCCGAGCTGGCTGAGAAATGATATTAGAATAATGTGAAATCCCATTTGATGATCTTCACATATGT
TGTTAGTACATCAAATATATCTTGAACAATGAGTTGAACTTCATCAGAAAGTTTAAGCTTTTTAAAA
TGCAGAACAAAAGTGTGGAACCCTTAAACCATGCTAATGAGCATTATCTTCATACCGGTTAAAACTAC
TTTCATCTTTCTAATGTTTTTGCTGTTGCATAATTTGAAGGCACATCCAGCTCTAAGTGATATGGAAA
GAAAAAAAGTTTGCGGTGTTATGGACTGTCAAAAGCTATCTAGAGAGGCTTGTGCTCATGCTGCTCAA
AATGATAGGCTCCCTGTTCAGACAGTTGTGCAAGTACTTTACTACGAGCAGCAACGCCTTCGTGAGGT
CATGGACGGGAGCCAACTTGTAGCAACTGAACCTCCAGCTCTAATTCCTTCTAAAACTAATCAGTTCT
CCACTGATATCCGTCCTATTTCAGATGAGGTCTCTAGTCTAAAACGAGAAAATCAGGAGCTGAAATTT
GAGTTGCTAAAGATGAAAATGAGGTTGAAAGAAATTGAAAAACCTTCAAACAAATCAGCTACTAGCAG
CCCTTTGGTCATCACTCATCCATCTGCTGATAAACCTCCTTTGCCAAGAAAACCATCTAATTTCATAA
GCTCAGTATCCAAAAAGCTTGGAAAATTTATTCGAGCAGATGGACTCACAGCCAACAAAGGCCGAAAT
AAACCAAGTAAAGACAGGCGTCATTCTATATCCTGATTTGAGCTAGCTATATTTGTCGTTGGGTTGAA
GAATTATTACTGCATTGTCTGAACATATATGATACTGGATTCAAATTTTAGTTTTTATTTTAGTCGTG
CGAGTTGTATGGTAAAGTATAAATTTGGTCAGACTTTAATCCAAAAATTGTATTTAGATGGACGTGGA
CGACTTCCTGTACATTATCTATGAAAGATTTTTAATCTTGGTTTCTCTTATATGTATCTTGAAGAAAG
ATTTGCAATCTTGAGATGTACAAG
```

FIG. 6

Nitab4.5_0000651g0020.2 amino acid sequence (SEQ ID NO. 4):

```
MADLDSDGIEQPSGVNNMSTTKKELLSTAMKRTSDWIFSQEIPSDVTVNAGGSAFSLHKFPLVSKSGY
IRKIISESNDADASTVEIPDIPGGSDAFELAAKFCYGINFEISTENIALLRCTAEYLEMTEDYAVGNL
VGRTEAYLNEVALKSLAGAVSILHSSESLLPIAEKVKLVSRCIDTIAYIACKDNQFCTSGRAEPGTNG
LNSSTFSNPKPMVDWWAEDLTVLRIDFFQRVLIAMMGRGFKQYALGPILMLYAQKSLRGLEIFGKGRK
KIEPKQEHEKRVVLETIVSFLPREKNALSVSFLSMLLRAAIYLETTVACRLDLEKRMSLQLGQAVLDD
LLIPSYSFTGDTLFDVETVQRIIMNFLDNEMDGSRLGDEEYVSPSLSDMERVGKLMENYLAEIASDRN
LSVSKFISLAEVIPEQAKITEDGMYRAIDIYLKAHPALSDMERKKVCGVMDCQKLSREACAHAAQNDR
LPVQTVVQVLYYEQQRLREVMDGSQLVATEPPTLIPSKTNHFSIDIPPVSDEVSSLKRENQELKFELL
KMKMRLKEIEKPSNKSAASSPLVITHPSADKPPLPRKPSNFISSVSKKLGKFIRADGLTANKGRNKPS
KDRRHSIS
```

FIG. 7

Nitab4.5_0000651g0020.2 coding sequence (SEQ ID NO. 5):

```
ATGGCGGATCTTGATTCAGATGGGATTGAACAACCCTCTGGTGTTAACAATATGTCCACTACAAAGAA
GGAGCTTCTTTCCACTGCTATGAAGAGGACCTCTGATTGGATTTTCTCCCAAGAGATCCCAAGTGATG
TAACTGTAAATGCAGGCGGATCCGCCTTTTCACTGCACAAGTTCCCTTTAGTCTCAAAGAGTGGATAC
ATAAGGAAGATTATCTCAGAATCCAACGATGCTGATGCTTCTACAGTCGAAATCCCTGATATACCCGG
TGGATCAGACGCATTTGAACTGGCCGCAAAATTTTGTTATGGAATAAATTTTGAGATAAGCACAGAAA
ACATTGCCTTGCTGAGATGCACAGCGGAATATCTTGAGATGACAGAAGACTATGCAGTTGGGAATTTG
GTTGGAAGAACTGAGGCCTACTTAAATGAAGTAGCTCTTAAAAGCCTAGCTGGCGCAGTTTCAATTTT
GCATTCTTCCGAAAGCCTTCTTCCCATTGCAGAGAAAGTAAAACTAGTTAGTCGATGCATCGACACAA
TTGCATATATTGCATGCAAGGATAACCAATTCTGCACATCAGGTCGAGCAGAGCCTGGTACTAACGGA
TTGAATTCGTCCACGTTTTCAAACCCGAAGCCTATGGTTGATTGGTGGGCTGAGGATTTAACTGTCCT
TAGAATTGATTTTTTCCAAAGGGTTCTAATTGCAATGATGGGAAGAGGATTCAAGCAGTATGCACTTG
GACCAATATTAATGCTCTATGCACAGAAGTCTCTTCGAGGTTTGGAAATATTTGGAAAGGGAAGGAAA
AAAATTGAGCCAAAACAAGAACATGAAAAGAGGGTTGTTTTAGAAACAATTGTTAGTTTTCTGCCAAG
GGAGAAAAATGCATTGTCAGTTAGCTTTCTGTCAATGCTGCTCCGAGCTGCAATATATCTAGAAACCA
CGGTTGCTTGCAGACTTGACTTGGAGAAGAGAATGTCATTGCAGCTTGGTCAGGCTGTATTAGATGAT
CTGTTAATTCCTTCATATTCCTTCACAGGGGATACATTGTTTGATGTTGAAACCGTGCAGCGTATCAT
CATGAATTTCCTTGACAATGAAATGGATGGAAGTCGATTGGGAGATGAGGAGTATGTGTCTCCTTCAT
TAAGTGACATGGAGCGGGTTGGGAAACTTATGGAAAATTACCTTGCTGAAATAGCCTCAGACCGTAAT
CTATCCGTTTCAAAATTCATTAGTCTTGCTGAAGTCATCCCAGAGCAAGCAAAGATCACTGAAGATGG
GATGTACAGGGCTATTGATATTTATTTGAAGGCACATCCAGCTCTAAGTGACATGGAAAGAAAAAAAG
TTTGCGGTGTTATGGACTGTCAAAAGCTATCTAGAGAGGCTTGTGCTCATGCTGCTCAAAATGATAGG
CTCCCTGTTCAGACAGTTGTGCAAGTACTTTACTACGAGCAGCAACGCCTTCGTGAGGTCATGGACGG
GAGCCAACTTGTAGCAACTGAACCTCCAACTCTAATTCCTTCTAAAACGAATCACTTCTCCATTGATA
TCCCTCCTGTTTCAGATGAGGTCTCTAGTCTAAAACGAGAAAATCAGGAGCTGAAATTTGAGTTGCTA
AAGATGAAAATGAGGTTGAAAGAAATTGAAAAACCTTCAAACAAATCAGCTGCTAGCAGCCCTTTGGT
CATCACTCATCCATCTGCTGATAAACCTCCTTTGCCAAGAAAACCATCTAATTTCATTAGCTCAGTAT
CCAAAAAGCTTGGAAAATTTATTCGAGCAGATGGACTCACAGCCAACAAAGGCCGAAATAAACCAAGT
AAAGATAGGCGTCATTCTATATCCTGA
```

FIG. 8

Nitab4.5_0000651g0020.2 genomic sequence (SEQ ID NO. 6):

```
CCTACGTCCACACACTGAACTAAATCCTTTTCCACTCTATTTAACCCCAATCATTCACATAATACCTT
TAATACCATGTAGGGGCTCCTCACATATGATCTTTCTCCTGCTAACATTAAGGCCTATAATGGGAATT
GTACCAATGCCATGATTGATAGTGAAAGATGATAACAATAATGCAATTATTAGGGGCCAGATACTGTT
GATTAAATGCTCAGACATTGAACTAACAGAAGCAAAGGAAAGAACATATCTTTCTGTTTTTTGCTCC
ATAAGGAAACAGCTTAAGAGAATCCTCTACCATAGACCAAATGTGATGGAGATGGTTAAGACCCTTTA
AAGTTTCAATCATGGCGGATCTTGATTCAGATGGGATTGAACAACCCTCTGGTGTTAACAATATGTCC
ACTACAAAGAAGGAGCTTCTTTCCACTGCTATGAAGAGGACCTCTGATTGGTATGCTCTATATATCTT
GACTTCTTATTGTGCTTTCTAATAGTAGCCCCTTTTATGTACTATTATTGAATTATTATTAATCTGTT
TCTCAAGATACTCACTGGAAAGGTAATTGTAGGTATTGATAAATGAGTTACCTGTATAATCTTGACAG
GATTTTCTCCCAAGAGATCCCAAGTGATGTAACTGTAAATGCAGGCGGATCCGCCTTTTCACTGCACA
AGGTGCGTTGCGCTCTCTGCTTTTATCATAATTAAGTTACAACTAACTCCGGGTTCAATCAAAATTGT
TGTTGGTTTTAGTTAAGTTCCTATTTGGATTGAGTTATCAGCCCTGGTCACACCTCAATGAGAATATG
AATTTGGTGATTTTTTCTCTTTTCTGACGATTGAATCACAAGGTTCAATAATGATTTATTGTGTTCCA
TGCAGTTCCCTTTAGTCTCAAAGAGTGGATACATAAGGAAGATTATCTCAGAATCCAACGATGCTGAT
GCTTCTACAGTCGAAATCCCTGATATACCCGGTGGATCAGACGCATTTGAACTGGCCGCAAAATTTTG
TTATGGAATAAATTTTGAGATAAGCACAGAAAACATTGCCTTGCTGAGATGCACAGCGGAATATCTTG
AGATGACAGAAGACTATGCAGTTGGGAATTTGGTTGGAAGAACTGAGGCCTACTTAAATGAAGTAGCT
CTTAAAAGCCTAGCTGGCGCAGTTTCAATTTTGCATTCTTCCGAAAGCCTTCTTCCCATTGCAGAGAA
AGTAAAACTAGTTAGTCGATGCATCGACACAATTGCATATATTGCATGCAAGGATAACCAATTCTGCA
CATCAGGTCGAGCAGAGCCTGGTACTAACGGATTGAATTCGTCCACGTTTTCAAACCCGAAGCCTATG
GTTGATTGGTGGGCTGAGGATTTAACTGTCCTTAGAATTGATTTTTTCCAAAGGGTTCTAATTGCAAT
GATGGGAAGAGGATTCAAGCAGTATGCACTTGGACCAATATTAATGCTCTATGCACAGAAGTCTCTTC
```

FIG. 8 (Continued)

Nitab4.5_0000651g0020.2 genomic sequence (SEQ ID NO. 6):

```
GAGGTTTGGTGAGGCCTTGTCCTATAATATACTCTGGATTATTTGGTTAAAATGAAATATTTATGCAA
ATAGTAAACTTTTTTGTTTATCACAGGAAATATTTGGAAAGGGAAGGAAAAAAATTGAGCCAAAACAA
GAACATGAAAAGAGGGTTGTTTTAGAAACAATTGTTAGTTTTCTGCCAAGGGAGAAAAATGCATTGTC
AGTTAGCTTTCTGTCAATGCTGCTCCGAGCTGCAATATATCTAGAAACCACGGTTGCTTGCAGACTTG
ACTTGGAGAAGAGAATGTCATTGCAGCTTGGTCAGGCTGTATTAGATGATCTGTTAATTCCTTCATAT
TCCTTCACAGGGGATACATTGTTTGATGTTGAAACCGTGCAGCGTATCATCATGAATTTCCTTGACAA
TGAAATGGATGGAAGTCGATTGGGAGATGAGGAGTATGTGTCTCCTTCATTAAGTGACATGGAGCGGG
TTGGGAAACTTATGGAAAATTACCTTGCTGAAATAGCCTCAGACCGTAATCTATCCGTTTCAAAATTC
ATTAGTCTTGCTGAAGTCATCCCAGAGCAAGCAAAGATCACTGAAGATGGGATGTACAGGGCTATTGA
TATTTATTTGAAGGTATGCGCGATGATAATTTTTCTAATTATAATTTTTCTATGCATATTTACACATA
CAGGAGCATTTTCATAGATTTAGATCATGTTTAGAAAAGGAGAAAACCTTTTGGTCCTGATTGCTACA
TGGTAATTGGCATGCTAAACTTAATGATCTTGGTTGGGATACCTTCTATAGAAATGTTGTTCTTGGTG
CTAACACAATTCAGTCCGAGAGATGATTTTGGGAATAAGCAAAATCAGAAAATATGTCACCAATGAAG
AACCATTCGTCATCACAGAATCCTTGCCTTGGCAGGCATTGCTCGGCCAGCCTTGTGATTTTGACCCAA
TCCCATGTCTTATACTCCTTTACCCTACAACCATTTTATGAGGCTGATGTTGTCCGGAGTTTCAAATC
TCATATTTTCCCCTTTCCCAAACATCTATCTCATGGTGCATCTATTCTGTACCAGGGCAGACCTATAG
TTTTGAACATGGGATCAATTGAACTCACAATTTTTTTTTTAAAAAAAAATTATAAATTTTAAGGTTTG
AACCCATAATTTCAAAAAACTAAGAAACTTGGTAGAGGTTCATCACTACAGTGTGGTGGCTTTGTTTT
CTCTTGTCTATGTGCAGGCCTTGCTGTTTATAGGTATTCATACTTGAGGTCTTTTCTATCATTTGAAA
CCTTAATAAGGATCTTGAGTTTGCTTGTTGACGTGGACTTTTCTCCTTTCAGTTTTAGGTCAAACTAG
TAATAACATCCTAAAAAATTTGGCATGCCAATACATAGTTCATATATGGTATCTTATCCTAAAGAAGA
AGCTGTATATATAAGCTCATAGATATGTAAACTGCACTCCCTGTTACTCTCTAATTTAAAAAAAG
AGATAATGATGGACTCAATAGGTTCTCGCTACAGAAGCTCTGAATCTTATTGCTGCCCGGTCACGTAA
TAACAAGATCTTATTGTGAAATCCCAGTTGATGATGTTCACATGTTTGGTCAGTACATCAAATATATT
CTTGAACAAAGTTTCAGGTCGTTAAAATGCAGAATAAAAGTGTGGAACCAAGCTAACATGATATTGGT
ATCATCAATTAAAATCTTGTGTAATGTTTTTGGTGTTGCATAATTTGAAGGCACATCCAGCTCTAAGT
GACATGGAAAGAAAAAAAGTTTGCGGTGTTATGGACTGTCAAAAGCTATCTAGAGAGGCTTGTGCTCA
TGCTGCTCAAAATGATAGGCTCCCTGTTCAGACAGTTGTGCAAGTACTTTACTACGAGCAGCAACGCC
TTCGTGAGGTCATGGACGGGAGCCAACTTGTAGCAACTGAACCTCCAACTCTAATTCCTTCTAAAACG
AATCACTTCTCCATTGATATCCCTCCTGTTTCAGATGAGGTCTCTAGTCTAAAACGAGAAAATCAGGA
GCTGAAATTTGAGTTGCTAAAGATGAAAATGAGGTTGAAAGAAATTGAAAAACCTTCAAACAAATCAG
CTGCTAGCAGCCCTTTGGTCATCACTCATCCATCTGCTGATAAACCTCCTTTGCCAAGAAAACCATCT
AATTTCATTAGCTCAGTATCCAAAAAGCTTGGAAAATTTATTCGAGCAGATGGACTCACAGCCAACAA
AGGCCGAAATAAACCAAGTAAAGATAGGCGTCATTCTATATCCTGATTTGAGCTAGCTATATTTGTCG
TTGGGTTGAAGAATTTTACTGCATTATATTGTCTGAACATATATGATACTGGATTCAAATTTTAGCTT
TTATTTTAGTCGTGCGAGTTTTATGGTAAAGTATAAATTTGGTCATGCTTTAATCCAAAAATTGTATT
TAGATGGACGTGGACGACTTCCTGTACATTATCTATGAAAGATTTGTAATCTTG
```

FIG. 9

Nitab4.5_0009137g0040.2 amino acid sequence (SEQ ID NO. 7):

```
MVDLGSDETAQPSTTVNMFTKKKELLSNVMKRTSEWILSQEIPSDITVHVAGTSFALHKFPLVSKCGY
IRKLVAKSNDANLSVFEIPDIPGGAEAFEFAAKFCYGINFEISSGNVALLRCVAEYLDMTDDYAVGNL
VGLSEAYLNELALKSIAGAVSVLHSSEKLLPIAENIKLVNRSIDTIAYMVCKDSHFCKSGRIEVDANS
LTNSSTFSNPRTIVVDWWAEDLTVLRIDFFQRVLIAMMARGYKQYALGPVLMLYSQKSLQNLEISGNE
RKMTELRQVHEKRVVVETIVSLLPREKNALSVSFLSMLLRAAIYLETTVACRVDLERRIALQLGQAVL
DDLLIPSYSSFTEDTLFDVEIVQRIMTYFIEYEMVENQFGFNDEEYVPPLATEMEKVGELMEDYLAKI
ASDNNLSVSQFISIAEVIPEKSRITEDRMYKAIDTYLKAHPALSDIERKRVCSVMNCQKLTREACAHA
AQNERLPVQTVVQVLYFEQQRLRQVMDGSLDGADESSTDNNPVTDEVSSLKRENQDLKFELVKMKTRL
NEIEKCGDISATSTPVEITTPISSDKPRLRRKSFISSVSETLGKLYPISFGADHVIMPSASKGRYKPI
SRDRRYSIS
```

FIG. 10

Nitab4.5_0009137g0040.2 coding sequence (SEQ ID NO. 8):

```
ATGGTTGATCTTGGTTCAGACGAGACTGCACAACCTTCAACTACTGTTAACATGTTCACTAAGAAAAA
AGAGCTTCTTTCCAATGTTATGAAAAGGACCTCCGAATGGATTTTATCCCAGGAGATCCCAAGTGATA
TAACTGTTCATGTTGCAGGAACTTCCTTTGCTCTGCACAAGTTCCCACTAGTCTCAAAGTGCGGATAT
ATAAGGAAGTTGGTCGCAAAATCCAATGATGCTAATCTTTCTGTATTCGAAATCCCTGACATTCCTGG
TGGAGCAGAGGCATTTGAATTTGCAGCAAAATTTTGTTATGGAATAAACTTTGAGATAAGCTCAGGAA
ACGTCGCATTGCTTAGATGTGTAGCAGAATATCTTGATATGACAGATGACTATGCAGTTGGAAATTTG
GTAGGATTATCAGAAGCCTACTTAAACGAGTTAGCACTTAAGAGCATTGCAGGTGCAGTTTCCGTCTT
GCACTCTTCAGAAAAACTTCTTCCAATTGCAGAAAATATAAAATTGGTGAACAGAAGCATAGATACAA
TTGCATACATGGTTTGCAAGGATAGCCATTTTTGTAAGTCAGGTAGAATAGAGGTCGACGCTAATAGT
TTGACGAATTCCTCCACATTTTCAAATCCGAGGACCATTGTTGTTGATTGGTGGGCTGAGGATTTAAC
TGTCCTTAGAATTGATTTTTTCCAAAGGGTTCTAATTGCTATGATGGCTAGGGGATACAAACAGTATG
CACTTGGACCAGTATTGATGCTCTATTCGCAGAAATCCCTTCAAAATTTGGAAATATCAGGAAATGAG
AGGAAAATGACTGAGCTGAGACAAGTACATGAAAAGAGGGTTGTTGTTGAAACCATAGTTAGTCTTCT
GCCAAGGGAGAAAAATGCATTGTCAGTTAGTTTTCTCTCAATGCTTCTTCGCGCTGCAATATATCTTG
AAACCACAGTTGCTTGTAGGGTTGATCTGGAGAGGAGAATCGCGTTGCAACTTGGACAAGCTGTATTA
GATGATTTGCTAATTCCTTCATATTCTTCCTTCACAGAAGACACATTATTTGATGTTGAAATCGTGCA
ACGTATCATGACGTATTTCATTGAGTATGAAATGGTGGAAAATCAGTTTGGCTTCAACGATGAAGAGT
ATGTGCCGCCATTAGCAACTGAAATGGAGAAAGTTGGGGAACTCATGGAAGATTACCTTGCTAAAATA
GCCTCAGACAATAATCTCTCTGTTTCGCAGTTTATCAGTATTGCTGAAGTCATTCCAGAGAAATCAAG
GATCACAGAAGATAGGATGTACAAGGCCATTGACACTTATTTGAAGGCACATCCAGCTCTAAGTGACA
TTGAGAGAAAAAGAGTTTGCAGTGTTATGAACTGTCAAAAGCTAACTCGAGAAGCTTGTGCTCATGCT
GCTCAGAATGAGAGGCTCCCTGTTCAGACTGTTGTGCAAGTGCTTTACTTTGAACAACAACGCCTTCG
CCAAGTTATGGATGGTAGTCTAGACGGGGCAGATGAGTCATCCACCGACAATAACCCTGTTACAGATG
AAGTCTCAAGTCTAAAAAGAGAAATCAAGATCTAAAATTCGAGCTAGTGAAAATGAAAACGAGGTTG
AATGAAATTGAAAATGTGGTGATATATCAGCTACTAGTACCCTGTGGAGATCACCACTCCAATATC
TTCTGATAAACCTCGTCTGCGAAGAAAATCTTTCATAAGCTCAGTTTCCGAAACGCTTGGGAAACTGT
ATCCAATATCATTTGGAGCTGATCATGTAATCATGCCATCGGCCAGCAAAGGAAGATATAAACCAATT
AGTAGAGATAGGCGTTATTCGATATCATGA
```

FIG. 11

Nitab4.5_0009137g0040.2 genomic sequence (SEQ ID NO. 9):

```
CTATATCCTAATATATTTAACCCCAGTACCTTCACATAAACATATGTAACACTACTCGTGTCATGTGT
CTAGTAGAGGCTCACTCGTACACAATCTTTCCACTGCCAACTTTCTGGCCTATAATGGGAATTCTGCA
ATCTTATGATTGATACTGGCTGCTGACAGTAATATATAATGCAGTTTACGGACCAACACTGAAGTTGT
ACTTATTCCCTAACTGTTGATCTCTTATTCTTTTGTGGGTGAAAGAGAATTAATTAAAGAAGCAGGGG
AAAGGACATAGTACATACTAGTTTTTGCTTTATCAAGAATTATATAATAGGCCAATATGGTTGATCTT
GGTTCAGACGAGACTGCACAACCTTCAACTACTGTTAACATGTTCACTAAGAAAAAGAGCTTCTTTC
CAATGTTATGAAAAGGACCTCCGAATGGACGTAGTCTATCTTCAGTTATTTCTCTCTTTTGTTGT
TTCCAGCGTACTTTTACGCGTCTTTATGCAATTTTTCCGTGTAACATGATCAGTAGTGGAGGGTAAAA
TGTAGGCATTGATGAATGAGTGACCTTTATATTATCTGCAGGATTTTATCCCAGGAGATCCCAAGTGA
TATAACTGTTCATGTTGCAGGAACTTCCTTTGCTCTGCACAAGGTACAACCTTTTTCCTTGTTCTAAG
AAGTTCCTAATATATTTCAACTAGAACACAAATCAAGATTGTTCTTTTCAGTAACTAGTTACACTTAT
TATGGCAGTTACCTATAGTCATCTAAAATTATTTTATACTGTCAGTAAGTAGAAGTTAAACTCTTAAC
TAAAAGGTGAAGTCTTTGATAATGAGTACTTTTATGTTCCATGCAGTCCCACTAGTCTCAAAGTGACA
GATATATAAGGAAGTTGGTCGCAAAATCCAATGATGCTAATCTTTCTGTATTCGAAATCCCTGACATT
CCTGGTGGAGCAGAGGCATTTGAATTTGCAGCAAAATTTTGTTATGGAATAAACTTTGAGATAAGCTC
AGGAAACGTCGCATTGCTTAGATGTGTAGCAGAATATCTTGATATGACAGATGACTATGCAGTTGGAA
ATTTGGTAGGATTATCAGAAGCCTACTTAAACGAGTTAGCACTTAAGAGCATTGCAGGTGCAGTTTCC
GTCTTGCACTCTTCAGAAAAACTTCTTCCAATTGCAGAAAATATAAAATTGGTGAACAGAAGCATAGA
TACAATTGCATACATGGTTTGCAAGGATAGCCATTTTTGTAAGTCAGGTAGAATAGAGGTCGACGCTA
ATAGTTTGACGAATTCCTCCACATTTTCAAATCCGAGGACCATTGTTGTTGATTGGTGGGCTGAGGAT
TTAACTGTCCTTAGAATTGATTTTTTCCAAAGGGTTCTAATTGCTATGATGGCTAGGGGATACAAACA
GTATGCACTTGGACCAGTATTGATGCTCTATTCGCAGAAATCCCTTCAAAATTTGGTGAGTCCTCATC
CCATGAGTTTAGATTATTTGGTTAGAGATAATAACAACAACAATAACAACAATAACAACAGTGGAGTC
```

FIG. 11 (Continued)

Nitab4.5_0009137g0040.2 genomic sequence (SEQ ID NO. 9):

```
TGGGGAAGGTAATACGTACGCAGACCTTATCCCTACCCTCAGGGAGGATTATTTGGTTAGAGAAAGTA
ACATAAATAGTGATCTTTTATGTTAATCAAAATTGAACACCTATGGCCGCTGTTATATTTAATACACA
AAATGTGCGCAGTTTTTTTTTTTAACACGAAGGACTAAACCTGCTCAGTTGAATAGTTAAAGGATTAT
TTTAGACCAAGGCTCAAACATAAGAAAGTATTTTAGGCATGTGCTCAATTTGGATAATTGAAATATTT
ATGCATATGATTTTCTTGTTATTCCAGGAAATATCAGGAAATGAGAGGAAAATGACTGAGCTGAGACA
AGTACATGAAAAGAGGGTTGTTGTTGAAACCATAGTTAGTCTTCTGCCAAGGGAGAAAAATGCATTGT
CAGTTAGTTTTCTCTCAATGCTTCTTCGCGCTGCAATATATCTTGAAACCACAGTTGCTTGTAGGGTT
GATCTGGAGAGGAGAATCGCGTTGCAACTTGGACAAGCTGTATTAGATGATTTGCTAATTCCTTCATA
TTCTTCCTTCACAGAAGACACATTATTTGATGTTGAAATCGTGCAACGTATCATGACGTATTTCATTG
AGTATGAAATGGTGGAAAATCAGTTTGGCTTCAACGATGAAGAGTATGTGCCGCCATTAGCAACTGAA
ATGGAGAAAGTTGGGGAACTCATGGAAGATTACCTTGCTAAAATAGCCTCAGACAATAATCTCTCTGT
TTCGCAGTTTATCAGTATTGCTGAAGTCATTCCAGAGAAATCAAGGATCACAGAAGATAGGATGTACA
AGGCCATTGACACTTATTTGAAGGTATGCACGTTGAATCATTCGCCCGGTGGAGCAATTTTTCTATGT
GCACTAGTACACCTACAAGGGCATGATCGTATATTTAGGTCATACTAAATGTTTAATTTAATATGTAT
TATAAGCATTCATTAACTCCTCCAAAAACAAATCTTTGAAGCCAACTGCTAAATAGTAATGGCTTAAT
CAACTGCTTTAGTACCTTGATTGAAATATCAAATTCTTTAATGACATATTTTTGATAGGTTGCACCTA
AACAGTGGAAATATTGTGGCTTGGGATGTTAAGTGGTATTTGAATCCTTATGATCTCTTGCATAAATC
CATTAAAGGCATAATTCAGTTAAGTGAAGATGTTTTTTTCAATATACAAGTGAAACTAAGGGTTGAATT
TTACTTCTCTGCTACAGAAGCCATCTTATGTTAGAATTGCCCTGCATCTTAGGTTACGATATCACGTG
TTTCTGCCTATGCATTTACAGGATATTAAACATGTTATATGTTGATGTTCTTTCAAGTGTGTCATCTT
TAGATCAAATGTACAGTTTAACAAACAGTTACATTTGATAATAAGCAGGTTTATAGCTAAGCAGCTTG
TCATACTGTGGCAAGAAAGACTTTTGAAACTTCAGATCATGCTTAGTTGATCTTCGTCATAAATAAAG
GATTTTAGGTCATATACACTCATAGAAGGGGAGCCTTGGCGTAACTGGTAAAGTTACTGCCATGTGAC
CAAGAAGTCATGGGTTCGAGCCGTGAAAATAGCCTCTTGCAGAATGTAGGGTAAGGTTACGCACAATA
GACCCTAGTGGTCCGGCCCTTCCCCAGACCCCGCATATAGCGGGAGCTTAGTGCACCGGGCTGCCCTT
TTTATACACTCATAGCCTAAAAATCTTTCATACTCTCATCTCAATTTAATCGGAAATACCAGGTTATT
ACTCTATTTTTTAGGTTACTATATCAGGCTTGCTATGAATAGCTATCTACTGGTCTATGTCATTTTGA
CTTGATAATGTAAAAGAATTATGTACCGTTAGTGTACAGAACTTACTCTTAAATAATAATAAATTTAC
CGGAGAATAGTTGTCTAATCTTCTAGCTTTTTCAAAATTTGAAGGCACATCCAGCTCTAAGTGACATT
GAGAGAAAAAGAGTTTGCAGTGTTATGAACTGTCAAAAGCTAACTCGAGAAGCTTGTGCTCATGCTGC
TCAGAATGAGAGGCTCCCTGTTCAGACTGTTGTGCAAGTGCTTTACTTTGAACAACAACGCCTTCGCC
AAGTTATGGATGGTAGTCTAGACGGGGCAGATGAGTCATCCACCGACAATAACCCTGTTACAGATGAA
GTCTCAAGTCTAAAAAGAGAAAATCAAGATCTAAAATTCGAGCTAGTGAAAATGAAAACGAGGTTGAA
TGAAATTGAAAAATGTGGTGATATATCAGCTACTAGTACCCCTGTGGAGATCACCACTCCAATATCTT
CTGATAAACCTCGTCTGCGAAGAAAATCTTTCATAAGCTCAGTTTCCGAAACGCTTGGGAAACTGTAT
CCAATATCATTTGGAGCTGATCATGTAATCATGCCATCGGCCAGCAAAGGAAGATATAAACCAATTAG
TAGAGATAGGCGTTATTCGATATCATGATGCGGCTAAATTTGCCATAAAGCTGTTGGTTTTGGCTGAA
GTATTTGAATCTTTGGGAAAGCAGTAATGGATTTAGCTATATTTCTGTCTTTTGTTCTCCTTTGTTTT
ATGTTATATAAGTGTTTTAAC
```

FIG. 12

Nitab4.5_0001772g0090.2 amino acid sequence (SEQ ID NO. 10):

```
MFTKKKELLSNVMKRTSEWILSQEIPSDITVHVAGTSFALHKFPLVSKCGYIRKLVAKSNDANLSEIE
IPDIPGGAEAFEFAAKFCYGINFEISSGNIALLRCVAEYLDMTDDYAVGNLVGLSESYLNEVALKSIA
GAVSVLHSSEKLLPIAENIKLVNRSIDTIAYIVCKDSHFCKSGRIEVDANSLMNSSTLSNPRPIVVDC
WAEDLTVLRIDFFQRVLIAMMARGCKQYALGPVLMLYSQKSLQNLEISGKERKLTEQRQVHEKRVVVE
TIVSLLPREKNALAVSFLSMLLRAAIYLEPTVACRVDLERRIALQLGEAVLDDLLIPSYSSFTKDTLF
DVEIVQRIMTNFIEYEMVENRLGFNDEEYASPVGELMEDYLAKIASDNNLSVSQFISIAEVIPEQCED
RMYKAIDTYLKAHPALSDNERKRVCSVMNCQKLTREACAHAAQNERLPVQTVVQVLYHEQQRLRQVMD
GSLADADQSSADNNPVTDEFSSLKRENQDLKFELVKMKTRLKEIEKCGDKSAASTPLEITTPISSDKP
RLRRKSFISSVYEKLGKLYPISFGADHVVMPSASKGRYKPINRYRRYSIS
```

FIG. 13

Nitab4.5_0001772g0090.2 coding sequence (SEQ ID NO. 11):

```
ATGTTCACTAAGAAAAAAGAGCTTCTTTCGAATGTTATGAAAAGGACCTCCGAATGGATTTTATCCCA
GGAGATCCCAAGTGATATAACTGTTCATGTTGCAGGAACTTCCTTTGCTCTGCACAAGTTCCCACTAG
TCTCAAAGTGCGGATATATAAGGAAGTTGGTCGCAAAATCCAATGATGCTAATCTTTCTGAAATTGAA
ATCCCTGACATTCCTGGTGGAGCAGAGGCATTTGAATTTGCAGCAAAATTTTGTTATGGAATAAACTT
TGAGATAAGCTCAGGAAACATCGCATTGCTTAGATGTGTAGCAGAATATCTTGATATGACAGATGACT
ATGCAGTTGGAAATTTGGTAGGATTATCAGAATCCTACTTAAATGAAGTAGCACTTAAGAGCATTGCA
GGTGCAGTTTCCGTTCTGCACTCTTCAGAAAAACTTCTTCCCATTGCAGAAAATATAAAATTGGTGAA
CAGAAGCATAGATACAATTGCATACATAGTTTGCAAGGATAGCCATTTTTGTAAGTCAGGTAGAATAG
AGGTCGACGCTAATAGCTTGATGAATTCCTCTACATTATCAAATCCGAGGCCTATTGTTGTTGACTGC
TGGGCTGAGGATTTAACTGTCCTTAGAATTGATTTTTTCCAAAGGGTTCTAATTGCTATGATGGCTAG
GGGATGCAAACAGTATGCGCTTGGACCAGTATTGATGCTCTATTCACAGAAATCCCTTCAAAATTTGG
AAATATCAGGAAAGGAAAGGAAATTGACTGAGCAAAGACAAGTACATGAAAGAGGGTTGTTGTTGAA
ACCATTGTTAGTCTTTTGCCAAGGGAGAAAAATGCATTGGCAGTTAGTTTTCTCTCAATGCTTCTTCG
CGCTGCTATATATCTCGAAACCACAGTTGCTTGTAGAGTTGATCTGGAGAGGAGAATCGCGTTGCAAC
TTGGAGAGGCTGTATTAGATGATTTGTTGATTCCTTCATATTCTTCCTTCACAAAAGACACATTATTT
GATGTTGAAATCGTGCAACGTATCATGACGAATTTCATTGAGTATGAAATGGTGGAAAATCGGTTGGG
CTTCAACGATGAAGAGTATGCGTCTCCAGTAGGGGAACTCATGGAAGATTACCTTGCTAAAATAGCCT
CTGACAATAATCTCTCTGTTTCGCAGTTTATTAGTATTGCTGAAGTGATTCCAGAGCAATGTGAAGAT
AGGATGTACAAGGCCATTGACACTTATTTGAAGGCACATCCAGCTCTAAGTGATAATGAGAGAAAAAG
AGTTTGCAGTGTTATGAACTGTCAAAAGCTAACTCGAGAAGCTTGTGCTCATGCTGCTCAGAATGAGA
GGCTCCCTGTTCAGACTGTTGTGCAAGTGCTTTACCATGAACAACAACGCCTTCGCCAAGTTATGGAT
GGTAGTCTAGCCGATGCAGATCAGTCATCCGCCGACAATAACCCTGTTACAGATGAATTCTCAAGTCT
AAAAAGAGAAAATCAAGATCTAAAATTCGAGCTAGTGAAAATGAAAACGAGATTGAAAGAAATAGAAA
AATGTGGTGACAAATCAGCTGCTAGCACCCCTTTGGAGATCACCACTCCAATATCTTCTGATAAACCT
CGTTTGCGAAGAAAATCTTTCATAAGCTCAGTTTACGAAAAGCTTGGGAAACTGTATCCAATATCATT
TGGAGCTGATCATGTAGTCATGCCATCAGCCAGCAAAGGAAGATATAAACCAATTAATAGATATAGGC
GTTATTCTATATCATGA
```

FIG. 14

Nitab4.5_0001772g0090.2 genomic sequence (SEQ ID NO. 12):

```
CCTATTTAACCCCCGTATGTAACACTACTCGTGTCGTGTGTCTACTAGAGGCTCACTCGTACACAATC
TTTCCACTTCCAACTTTCTGGCCTATAGCGGGAATTCTGCCAATCTTATGATTGATCGTGGCTGCTGA
CGATAAGTTGATAATATATAATGCAGTTTACGGTCCAACACTGAGGCTGTACTTATTCCCCAACTGTT
GATCACTTATTCTTTTGTTGGTTGAAAGAGAATTAATTAAAGAAGCTAGCAACGGAACCAAAAGAAGC
AGGGGAAAGGACATAGTACATTCTAGTTTTTGCTTTATCAAGAATTATATAATAGGCCAATATGATGG
ATCTTGGTTCATAGGAGACTGCACAACCTTCAACTACTGTTAACATGTTCACTAAGAAAAAAGAGCTT
CTTTCGAATGTTATGAAAAGGACCTCCGAATGGTACGTATGTCCATCTTCAGTTATTTTTCTTTCTCTT
TTGTTGTTTCTCAGCGTCCTTTTCCACGTCTTTATGCAATGAGTGACCTTTTTAATATCTGCAGGATT
TTATCCCAGGAGATCCCAAGTGATATAACTGTTCATGTTGCAGGAACTTCCTTTGCTCTGCACAAGGT
ACAACCTTTTTCCTTGTTCTAAGAAGTTTCTAATATAATTTCAACTAGAACACCAATCAAGATTGTTC
TTTAACTAGTTACACTTATTATGGCAGTTACCTATAGTCATCTTAAATTAATTTGACACTGTCAGTGA
GTAGAAATTAAACTCTTAACTAAAAGGTGCAATCTTTGATAATGAGTACTTTATGTCCCATGCAGTTC
CCACTAGTCTCAAAGTGCGGATATATAAGGAAGTTGGTCGCAAAATCCAATGATGCTAATCTTTCTGA
AATTGAAATCCCTGACATTCCTGGTGGAGCAGAGGCATTTGAATTTGCAGCAAAATTTTGTTATGGAA
TAAACTTTGAGATAAGCTCAGGAAACATCGCATTGCTTAGATGTGTAGCAGAATATCTTGATATGACA
GATGACTATGCAGTTGGAAATTTGGTAGGATTATCAGAATCCTACTTAAATGAAGTAGCACTTAAGAG
CATTGCAGGTGCAGTTTCCGTTCTGCACTCTTCAGAAAAACTTCTTCCCATTGCAGAAAATATAAAAT
TGGTGAACAGAAGCATAGATACAATTGCATACATAGTTTGCAAGGATAGCCATTTTTGTAAGTCAGGT
AGAATAGAGGTCGACGCTAATAGCTTGATGAATTCCTCTACATTATCAAATCCGAGGCCTATTGTTGT
TGACTGCTGGGCTGAGGATTTAACTGTCCTTAGAATTGATTTTTTCCAAAGGGTTCTAATTGCTATGA
TGGCTAGGGGATGCAAACAGTATGCGCTTGGACCAGTATTGATGCTCTATTCACAGAAATCCCTTCAA
```

FIG. 14 (Continued)

Nitab4.5_0001772g0090.2 genomic sequence (SEQ ID NO. 12):

```
AATTTGGTGAGTCCTTATCCCATGAGTTTGGATTATTTGGTTAGAGAAAATAACAAAGTTATGGTCGC
TGTTATATTTAACACACAAAATGTGCGCAGTTTTTATGAACATGAAGGACTAAAACTGCTCAGCTGTA
TAGTTAAAGGATTATTTTATACAAACGCTCAAACATAAGAAACTATTTTGGTCATGTGCTCTATTTGT
CCAAATGAAATATTTATGCATATGATTTTCTTGTCATTCCAGGAAATATCAGGAAAGGAAAGGAAATT
GACTGAGCAAAGACAAGTACATGAAAAGAGGGTTGTTGTTGAAACCATTGTTAGTCTTTTGCCAAGGG
AGAAAAATGCATTGGCAGTTAGTTTTCTCTCAATGCTTCTTCGCGCTGCTATATATCTCGAAACCACA
GTTGCTTGTAGAGTTGATCTGGAGAGGAGAATCGCGTTGCAACTTGGAGAGGCTGTATTAGATGATTT
GTTGATTCCTTCATATTCTTCCTTCACAAAAGACACATTATTTGATGTTGAAATCGTGCAACGTATCA
TGACGAATTTCATTGAGTATGAAATGGTGGAAAATCGGTTGGGCTTCAACGATGAAGAGTATGCGTCT
CCAGTAGGGGAACTCATGGAAGATTACCTTGCTAAAATAGCCTCTGACAATAATCTCTCTGTTTCGCA
GTTTATTAGTATTGCTGAAGTGATTCCAGAGCAATGTGAAGATAGGATGTACAAGGCCATTGACACTT
ATTTGAAGGTATGCACGTTGAATCATTCGCCCGGTGGAGCAATTTTTCTGTACACTAGTACACCTACA
AGGGCATGATCGTATATTTAGGTCATACTATATGTTTAATTTAATAAGTATTATAAGCATTCATTAAC
TCCATAAACAAATCTTTGATGCCAACTGCGAAATAGTAATGGCTTAATCAACTGCTTTAGTACCTTGA
TTGAAATATCAACTTCTTTAATGACATAATTTGATAGGTTGCACCTGAACAGTGGAAATGTTGTGGCT
TGGGATGTTAAGTGGTATTTGAACCATTATGATCTCTTGCATAAATCCATTAAAGGCTTAATTTAGTT
AAGTGAAAATATGTTTCAATATACAAGTGAAACTAAGGGTTGAATTTTACTTTTCTGTTAGAGAAGCC
ATCTTATCTTAGAATTGCCCTGCATCTTAGGTTATGATATCACGTGTTTTTGCCTATGCATTTACAGG
ATTTTAAACATGTTCTATGTTGATGTTCTCTCAAGTGTGTCATCTTTAGATCAAATGTACAGTTTAAC
AAACAGTTACATTTGATAATAAGCAGGTTATAGCTAAGCAGCTCATCTTCAGACCATGCTTAGTTGA
TCTTCAACATAAATAAAGGATTTTAAGTCATATACACTCATAGCCTAAAAATCTTTCATACTCTCATA
TCAGCCTAAACTATTTTTTTAGGTTACTATATCAGGCTTGCTACGAATAGCTACCTACTTCTGTATGT
CATTTTGACTTGAAAATGCAAAGAATTACGTACTATCAGTGTACAGAACTTACTCTTATCAGGTTAC
TCTTAATAGCTGGAGCAACCTTTCCCCTGTAAATGATTAAATTCCATTTCAAGATTTTATTAGCTCTC
TGTCTTTGGCTTGATTGCCAACCTTAGGCTTCTGGTTAGCTCCCGGTGCTTCTGGTTAGCTCCCTGGT
CAGAACTGCATTTTTGTGTAAATGGAGCTAACCAACCTCTTTTCTAATGTTTTGCATCTTTTTGATGC
CAGTTATATAGCATCTTACTTCATCAAAAAAGAACTTACTCTTAAATAAACAACTCTACCAGAGATA
GTTGCTCTGATGGTAAGCACCCTCCACTTCCAACCAAGAGGTTGTGAGTTCGAATTACCCCAAGAGCA
AGGTGGGGAGTTTTTGGGGGAAGGATGCCGAGGGTCTATTGGAAACAGCCTCTCTACCCCAGGGTAG
GGGTAAGGTCTGCGTATACATTACCCTCCCCAGACCCCACTAGTGGGATTATACTTTTTTGTTGTTAT
TGTTGTTGTTGTTGTACCAGAGATAGTTGTCTAATCTTGTAGCTTTTGCAAAATTTGAAGGCACATCC
AGCTCTAAGTGATAATGAGAGAAAAAGAGTTTGCAGTGTTATGAACTGTCAAAAGCTAACTCGAGAAG
CTTGTGCTCATGCTGCTCAGAATGAGAGGCTCCCTGTTCAGACTGTTGTGCAAGTGCTTTACCATGAA
CAACAACGCCTTCGCCAAGTTATGGATGGTAGTCTAGCCGATGCAGATCAGTCATCCGCCGACAATAA
CCCTGTTACAGATGAATTCTCAAGTCTAAAAAGAGAAATCAAGATCTAAAATTCGAGCTAGTGAAAA
TGAAAACGAGATTGAAAGAAATAGAAAAATGTGGTGACAAATCAGCTGCTAGCACCCCTTTGGAGATC
ACCACTCCAATATCTTCTGATAAACCTCGTTTGCGAAGAAAATCTTTCATAAGCTCAGTTTACGAAAA
GCTTGGGAAACTGTATCCAATATCATTTGGAGCTGATCATGTAGTCATGCCATCAGCCAGCAAAGGAA
GATATAAACCAATTAATAGATATAGGCGTTATTCTATATCATGATGCAGTAAAATTTGCCATTAAGCT
GTTGGTTTTGGCAGAAGTAGATTGCACTATTTGAACTTTTGGGAAAGCAGTAATGAATTTAG
```

FIG. 15

Nitab4.5_0003312g0050.2 amino acid sequence (SEQ ID NO. 13):

```
MDKHHSQLPLAKCSRQRYSEWVFRDVPSDITIEVDGGTFSLHKFPLVSRSGRIRKLVAGHRDSDISRI
ELLSLPGGVESFELAAKFCYGVNFEITAANVAQLCCVSDYLEMTEDYSKNNLGSRAEEYLDIVACKNL
EMCVEVLKQCENLLPLADELKIVTRCIDAIASKACAEQIASSFSRLEYSSSGRLHMNRQAKCEGDWWI
EDLSVLRIDLYQRVITAMKCRGVRPESIAASLVNYAQKELTKKSSSWNQSSQPKVDVVSGSNGHEKVV
VETIVSLMPVEKLVVPITFLFGLLRSAVMLDCTVACRLDLERRIGSQLDIATLDDLLIPFFRNAGDTL
FDVDTVHRILVNFFQQEDSDEDMDDVSVFESGSPTSPSQTALFKVAKLVDNYLAEIAPDANLKLNKFI
AIAESLPAHARTVHDGLYRSIDVYLKAHQALSDPDRRRLCKLIDFQKLSQEAGSHAAQNERLPLQSIV
QVLYFEQLRLRNALFCSYHDDDHKPTHQSWRINSGALSAAMSFRDNYASLRRENRELKLELTRMRMRL
NDLEKDHVCMKKNMEKSNSGGFMSNFSKKIGKLNIFGHSSSRESCSPSKRSQVTDSKLTERT
```

FIG. 16

Nitab4.5_0003312g0050.2 coding sequence (SEQ ID NO. 14):

```
ATGGACAAACACCATTCGCAATTGCCTCTCGCCAAGTGTTCACGGCAGCGTTATAGTGAATGGGTGTT
TCGGGATGTTCCAAGTGATATAACGATAGAAGTAGATGGTGGCACATTTTCATTGCACAAGTTTCCTC
TAGTCTCGAGAAGTGGGCGAATCCGGAAGCTTGTAGCAGGGCACAGGGATTCTGATATATCAAGGATA
GAGCTACTTAGCCTACCAGGCGGAGTTGAATCATTTGAGCTGGCAGCAAAATTCTGCTACGGCGTTAA
CTTTGAGATTACAGCTGCAAATGTTGCTCAGCTTTGTTGTGTATCAGATTATCTTGAGATGACTGAGG
ACTATTCAAAGAACAATCTTGGTTCCCGAGCTGAAGAATATCTTGATATTGTTGCTTGCAAGAATCTT
GAAATGTGTGTTGAAGTCCTGAAACAATGCGAAAATCTACTTCCTTTGGCTGATGAGCTGAAAATAGT
TACCCGATGCATTGATGCTATAGCATCTAAGGCTTGCGCGGAGCAAATTGCCTCAAGTTTCTCGCGCT
TGGAATACAGTAGTTCTGGTAGACTTCATATGAACCGCCAAGCCAAGTGTGAAGGAGACTGGTGGATA
GAGGATTTGTCAGTTCTTCGTATTGACTTGTATCAACGAGTCATAACAGCGATGAAATGTCGTGGTGT
TAGGCCTGAAAGTATTGCAGCATCACTAGTGAACTACGCACAGAAGGAGTTGACAAAGAAGTCCAGTT
CCTGGAATCAATCGAGCCAACCCAAAGTTGACGTGGTTTCTGGTTCAAACGGCCATGAAAAGGTTGTG
GTCGAAACAATTGTTAGCCTTATGCCTGTTGAGAAATTGGTTGTTCCAATAACCTTTCTTTTTGGGTT
GCTGAGAAGTGCAGTGATGCTTGACTGCACAGTTGCTTGTAGACTTGATCTTGAGAGGCGGATAGGAT
CTCAATTAGACATAGCTACTCTCGATGATCTTCTAATTCCATTCTTTCGCAATGCTGGTGACACATTA
TTTGACGTTGACACAGTGCATAGAATCTTGGTTAATTTTTTTCAGCAGGAGGATAGTGATGAAGATAT
GGACGATGTCTCAGTGTTCGAGTCTGGTAGCCCTACTTCGCCATCCCAAACTGCATTATTCAAAGTCG
CAAAACTGGTGGACAATTACCTTGCTGAAATTGCACCTGATGCAAACCTAAAGCTGAACAAGTTCATA
GCAATTGCCGAAAGCTTACCAGCACATGCTCGTACTGTCCATGATGGACTTTATCGATCAATCGATGT
CTACCTCAAAGCTCATCAGGCGTTATCAGATCCAGATAGGAGAAGACTATGCAAGCTGATTGATTTTC
AGAAGCTCTCACAAGAAGCTGGATCACACGCTGCACAAAACGAACGCCTCCCACTCCAATCAATCGTG
CAGGTTCTATATTTCGAGCAACTGAGGCTTCGAAATGCCTTATTTTGTTCTTATCATGATGATGATCA
TAAGCCAACGCACCAATCGTGGAGGATCAATAGTGGTGCTTTAAGTGCAGCTATGTCTCCCCGGGATA
ATTATGCTTCTCTAAGACGAGAAAATAGGGAACTAAAACTTGAACTAACACGAATGAGGATGAGATTG
AATGACCTGGAGAAAGATCATGTTTGTATGAAGAAAAATATGGAAAAATCTAATTCCGGGGGATTCAT
GAGTAACTTCTCGAAAAAGATTGGCAAGTTAAACATTTTTGGACATAGTTCTTCAAGGGAGTCATGTT
CTCCTTCAAAGAGGTCACAAGTTACTGATTCTAAGCTAACTGAAAGAACATGA
```

FIG. 17

Nitab4.5_0003312g0050.2 genomic sequence (SEQ ID NO. 15):

```
CTCATCTTTAGCTGACTGTTTTCTTGACTTTCTCTGTTTCGACTGAACCAAAGTTTGCTAAACTTGTT
CCTTTTTTGGCACCCCTTTATCTGCTGCTAAACATTTATCCCACTCAAATTTTATAACTTCATTATAC
AGCAATAAGAATATATAAAATGCTACAGAAAGAGAGTTAATGGTGGGTATTTTAATTATTGGTACTAT
CAAGGACATGACCCACAAAAGTGGCCCATTGGTTTGGACAAGTGTAATCTATGATTTGAGCACAAACA
GTTTGACTCAAAAATGGCCAAAGAAGTAGACCAACACCAATATTTTCCACTGTGTCTTTGTCCCCCCT
TATTACTTGGCTTCTTTAACAACCTTCACGTTCTCCTGTTCTGCTTCTCAGAATTTGCAGTTTTTTCC
TCTGGATTTTCTTCACTACAGCCATGGACAAACACCATTCGCAATTGCCTCTCGCCAAGTGTTCACGG
CAGCGTTATAGTGAATGGTTTGTATTTAATAGTTCTATTTTTTTTTGGTCTATCTGGTCGCTCTGGT
TCATTTGTAGTTTTGTATTTGGTTTAACTGTACTTTAGTGATTTTTTGTCTCTAGGAACTGGAAGTG
TAAAACAGGGTTCATTTGTTGTTATGTATTTGGTTTATCTGTAATTCTTTATGAATTCTTTTTCTGTG
GGAATTGCGAAGTGCAGTCGGTTCAGATACCACAATAGAAGTGGGACGAGATAGCCATAGACTTTGTC
TTTGGATTGCTGAAGATGGCAAAGCAAGATGATGGCCGTTCGGGGTGATTATTGATTGGCTGGCCATT
AGCTCACTTCCTGCCGATGAGTATGACTTACTTTACGGACAAGTTAATCCCATATATATATATATATG
GGTTGGCTTTTGAGGGGAGGAGGTGGGGGACTTCCATTCTTTTCCTCTATTATGGTTTGTTCATAAAA
AGATAGTTTGGTGCACAAAACTCTCGCTCAGGATCAGGGAAGGATTGGACCCATATTGGGTCTA
TTGTATGCAGCGTACCTGCAATGGCTTATTTCCACAACTGAACTAGGGACTTCCTGGTCGCACGATG
ACTACTCTTACCATTGCGTTAAGGCTCCCTTCTCATAGCTACCATAGGCAAGGTGAAAATGTTTCAAC
TTTTAAAGGATTGTTGAAGTGGTAGGGGAAGACATGTAGTTAAAAAACACTTGAAGCTGTAGGGACAT
CTGAATGCATCATTTTTGCTTCAGATTTTAACAGTAGTAGAAATCTTATTGGCAATAATCGTTTGGGT
GTTTTTATGTGCTCCTTTTTTCATGTTTCTTCTGCAGTTTTCTTTCCCCACTCCTCTTTCGTGCTCTG
```

FIG. 17 (Continued)

Nitab4.5_0003312g0050.2 genomic sequence (SEQ ID NO. 15):

```
AATTATAGCCATTAGTATACTTACCAAACATAATGATTTTCTAGTTGTGAGCAATGTTTAAACGTGGC
ATAAATGCTTAGATATCTGCTTTTATAACTTGTTGCTGTCTTATATTTAATCAACTATTTTGATCTGG
TATAGGGTGTTTCGGGATGTTCCAAGTGATATAACGATAGAAGTAGATGGTGGCACATTTTCATTGCA
CAAGGTAAATCTGTCAATTCTCTTATTTGCCCACTGCGAACTGGTGATAGATTTTGCGGAGTAATTCG
CATTGTAGAGGTAATGAAACATAACGAAAAAAGACTTCTTTTGGAGAGGGGATTCGTGTTAGTCCCT
TTCATACTGTTATAGCTAAGCCTTCAGAAAATGTTAATTTCATGCCTATGAGCAAGTTCAGAGACTAT
AATGTAGCAGAGCTCCTAACATAGAGACGTGATGTGATGCAGTTTCCTCTAGTCTCGAGAAGTGGGCG
AATCCGGAAGCTTGTAGCAGGGCACAGGGATTCTGATATATCAAGGATAGAGCTACTTAGCCTACCAG
GCGGAGTTGAATCATTTGAGCTGGCAGCAAAATTCTGCTACGGCGTTAACTTTGAGATTACAGCTGCA
AATGTTGCTCAGCTTTGTTGTGTATCAGATTATCTTGAGATGACTGAGGACTATTCAAAGAACAATCT
TGGTTCCCGAGCTGAAGAATATCTTGATATTGTTGCTTGCAAGAATCTTGAAATGTGTGTTGAAGTCC
TGAAACAATGCGAAAATCTACTTCCTTTGGCTGATGAGCTGAAAATAGTTACCCGATGCATTGATGCT
ATAGCATCTAAGGCTTGCGCGGAGCAAATTGCCTCAAGTTTCTCGCGCTTGGAATACAGTAGTTCTGG
TAGACTTCATATGAACCGCCAAGCCAAGTGTGAAGGAGACTGGTGGATAGAGGATTTGTCAGTTCTTC
GTATTGACTTGTATCAACGAGTCATAACAGCGATGAAATGTCGTGGTGTTAGGCCTGAAAGTATTGCA
GCATCACTAGTGAACTACGCACAGAAGGAGTTGACAAAGAAGTCCAGTTCCTGGAATCAATCGAGCCA
ACCCAAAGTTGACGTGGTTTCTGGTTCAAACGGCCATGAAAAGGTTGTGGTCGAAACAATTGTTAGCC
TTATGCCTGTTGAGAAATTGGTTGTTCCAATAACCTTTCTTTTTGGGTTGCTGAGAAGTGCAGTGATG
CTTGACTGCACAGTTGCTTGTAGACTTGATCTTGAGAGGCGGATAGGATCTCAATTAGACATAGCTAC
TCTCGATGATCTTCTAATTCCATTCTTTCGCAATGCTGGTGACACATTATTGACGTTGACACAGTGC
ATAGAATCTTGGTTAATTTTTTTCAGCAGGAGGATAGTGATGAAGATATGGACGATGTCTCAGTGTTC
GAGTCTGGTAGCCCTACTTCGCCATCCCAAACTGCATTATTCAAAGTCGCAAAACTGGTGGACAATTA
CCTTGCTGAAATTGCACCTGATGCAAACCTAAAGCTGAACAAGTTCATAGCAATTGCCGAAAGCTTAC
CAGCACATGCTCGTACTGTCCATGATGGACTTTATCGATCAATCGATGTCTACCTCAAAGTATGTACT
ACAAATTTCTTGAAAGATGTTTTAGAAAAGCATTAATGGTTTGAGTTAAAGTTTTAAACTTAAATGT
CAGGAGAAAACTCATGGTACTTGTCTTTTCGAAAAATAACCTGTTTGCTAATGGCTTAAATGAATATG
GTACCCTTATATGAGGAGGATTAAGTACTTTACATTGAGTTTGATTTGCCTTTAATAGAATCTTCTA
ACCTAAATCCATATTTCTAAGGAAGTAAATAAAGCTTCCTTAGGCATTTCCTTAAGTTAATACTTTTGA
CTAATCATCGACGTTCATTCATGGAAATTCCAGGCTCATCAGGCGTTATCAGATCCAGATAGGAGAAG
ACTATGCAAGCTGATTGATTTTCAGAAGCTCTCACAAGAAGCTGGATCACACGCTGCACAAAACGAAC
GCCTCCCACTCCAATCAATCGTGCAGGTTCTATATTTCGAGCAACTGAGGCTTCGAAATGCCTTATTT
TGTTCTTATCATGATGATGATCATAAGCCAACGCACCAATCGTGGAGGATCAATAGTGGTGCTTTAAG
TGCAGCTATGTCTCCCCGGGATAATTATGCTTCTCTAAGACGAGAAAATAGGGAACTAAAACTTGAAC
TAACACGAATGAGGATGAGATTGAATGACCTGGAGAAAGATCATGTTTGTATGAAGAAAAATATGGAA
AAATCTAATTCCGGGGGATTCATGAGTAACTTCTCGAAAAGATTGGCAAGTTAAACATTTTTGGACA
TAGTTCTTCAAGGGAGTCATGTTCTCCTTCAAAGAGGTCACAAGTTACTGATTCTAAGCTAACTGAAA
GAACATGACAGGCAAACTTCTAGTGAGTAATTGCGAATGGTACTTGTAATCTATGTTCCATCGCGCAA
TCACTATTTTCTGTCCCACATCTTGTATATGAGCTTTAGAGATATGCTTTAGCAACTGAGATGAAGAA
AAGTAAATTTTGAGTTTTGATGAATATGATCACCATATTGATATATCTCATATTGGCAAATATAGCAC
TTCATAT
```

FIG. 18

Nitab4.5_0003151g0080.2 amino acid sequence (SEQ ID NO. 16):

```
MDKHLHQLPLTKSTSRQRYNEWVFRDVPSDITIEVDGGIFSLHKFPLVSRSGRIRKLVAEHRDSDISR
IELVSLPGGAESFELAAKFCYGVNFEITAANVAQLCCVSDYLEMSEDYSKNNLGSRAEEYLDSIVCKN
LEMCVEVLRQCENLLPLADELKVVSRCIDAVASKACVEQIASSFSRLEYSSSGGRLHMNKQANCELDW
WIEDISVLRIDLYQRVITAMKFRGVRPESIAASLVNYAQRELIQKSLSGSNIQEKLVVETIVSLMPVE
KFVVPLTFLFGLLRSAVMLDCTVACRLDLERRIGSQLDTATLDDILIPSFRHAGDTLFDVDTVHRILV
NFSQQEGDSDEDMEDVSVFESDSPTTTPSQTALFKVSKLVDNYLAEIAPDANLKLNKFIAVAETLPAH
ARTVHDGLYRAIDVYLKAHQTLSDPDKRRLCKLIDFQKLSQEAGAHAAQNERLPLQSIVQVLYFEQLR
LRNALFCSYPDDDIKPMHQSWRINSGALSAAMSPKDNYASLRRENRELKLELARMRMRLNDLEKDHVC
MKRNMQKSSSRRFMKSFSKRIGKKFNIFGHSFSRDSNSPSSQSERTESKITERT
```

FIG. 19

Nitab4.5_0003151g0080.2 coding sequence (SEQ ID NO. 17):

```
ATGGACAAGCACCTCCACCAACTACCTCTAACCAAGTCTACTTCACGGCAGCGTTATAACGAATGGGT
ATTTCGAGATGTTCCTAGTGATATAACAATAGAAGTGGATGGTGGCATATTTTCATTACACAAGTTTC
CCCTTGTTTCGAGAAGCGGACGAATCCGGAAGCTAGTAGCAGAGCACAGGGATTCTGATATATCAAGA
ATTGAGCTTGTTAGTCTACCAGGTGGAGCAGAATCATTTGAGCTAGCAGCCAAATTCTGTTATGGTGT
CAACTTTGAGATCACAGCAGCAAATGTTGCTCAGCTTTGTTGTGTATCCGATTACCTCGAGATGTCAG
AGGACTACTCAAAAAACAATCTTGGCTCCAGAGCTGAAGAATATCTTGACAGCATTGTTTGCAAGAAT
CTTGAAATGTGTGTTGAAGTCTTGAGACAATGTGAAAACTTACTTCCACTTGCTGATGAGCTGAAAGT
TGTGAGCCGCTGTATCGATGCTGTAGCCTCCAAAGCTTGTGTCGAGCAAATCGCCTCAAGTTTCTCGC
GATTGGAGTATAGTAGCTCAGGTGGAAGACTACATATGAATAAACAAGCCAATTGTGAATTGGACTGG
TGGATTGAGGATATTTCTGTTCTTCGTATCGACTTGTACCAACGTGTCATAACCGCGATGAAGTTTCG
TGGGGTTAGGCCTGAGAGTATTGCTGCATCACTAGTGAACTATGCACAGAGGGAATTGATACAAAAAT
CCCTTTCTGGTTCAAATATCCAAGAAAAACTCGTGGTTGAGACGATCGTGAGCCTAATGCCTGTTGAA
AAATTCGTCGTGCCCTTGACCTTTCTTTTTGGATTGTTGCGAAGTGCAGTGATGTTAGATTGCACGGT
TGCTTGTAGGCTTGATCTTGAGAGGCGGATAGGATCTCAATTGGATACGGCTACTCTGGACGATATCC
TGATTCCTTCCTTTCGACATGCTGGTGATACATTGTTTGATGTTGACACAGTGCATAGAATCTTGGTT
AACTTTTCACAGCAAGAGGGCGATAGCGATGAAGATATGGAAGATGTCTCGGTTTTTGAATCCGATAG
CCCTACTACGACGCCATCACAAACTGCATTGTTCAAAGTATCAAAGCTGGTTGACAATTATCTAGCTG
AAATTGCACCAGATGCAAATCTAAAGCTGAACAAGTTCATTGCTGTTGCAGAAACATTACCAGCACAT
GCGCGTACTGTCCACGATGGACTTTATCGAGCAATCGATGTTTACCTCAAAGCTCATCAAACCTTATC
AGATCCAGACAAGAGGAGACTATGCAAATTGATTGATTTCCAAAAGCTCTCACAGGAAGCTGGTGCAC
ATGCTGCACAAAACGAACGCCTTCCCCTCCAATCGATAGTTCAAGTTCTTTATTTCGAGCAATTGAGG
CTTCGAAACGCCTTGTTTTGTTCGTACCCTGATGATGACATCAAACCAATGCACCAATCTTGGAGGAT
CAATAGTGGTGCTCTTAGTGCTGCAATGTCTCCTAAGGACAATTATGCTTCGTTGAGACGAGAAAATA
GGGAGCTAAAACTTGAACTAGCGCGGATGAGGATGAGATTAAACGACTTGGAAAAAGACCATGTTTGT
ATGAAGAGGAATATGCAAAAATCTAGCTCGCGACGATTCATGAAATCCTTCTCCAAAAGGATTGGCAA
AAAGTTTAATATTTTCGGACATAGTTTTTCCAGGGATTCTAATTCTCCCTCAAGTCAGTCAGAAAGAA
CTGAATCTAAAATAACTGAAAGAACGTGA
```

FIG. 20

Nitab4.5_0003151g0080.2 genomic sequence (SEQ ID NO. 18):

```
TTGAAAACAAAAAGGTTTGACAAAAAAATGGCCAAAGAACTACTCAACAAACAGCAAAATCTCTCCTA
TTGTGTCTCTGTCCCCTTATTTTCTTGTCTTCTTTAACAAACCTTTCACATTCTTGTTTCTTCTTTCT
CTAAAGATTTCAAATCTTTTCCCCTGGCTTTTCTTCACCATATTTGCCATGGACAAGCACCTCCACCA
ACTACCTCTAACCAAGTCTACTTCACGGCAGCGTTATAACGAATGGTTTGTATTCTGCAGTACGTAGT
TATATACAATGACAATGTAAAAAGATTTTGTAGCATCAATGCGATTTAATATGCTATAGTTGGTTAAA
TGTTTATTATACTTAGTTATACGTGTCATAACTCGTTCTCTCAACTCAGAATCCACAGCTTCTATCTA
AATTCTTGATCCGCTACTACTAGCTCGTATGCTCGTATGTCATAACTCAAAATGTTTGAAAGTTTTAAAGCATTTT
GTTTTTTGGCTTGTCTGTGAATCTACCTACCTTCACAGGGTAGGATTAAGATATGCGTACACATTATT
CTTCTCAGTACTCACTTGTGGGACTATACTGGGTATGTTGGTGCTAGTGGTAGTGAACCTGCATAATT
GTGTCATACTTTTACGTGCAGTTCAAAATCAGTTGGGGCTTTGGTTACATGCATCTTAGTAAAACTTT
TGATGAATTTTTGTGTACACATATAGTCCGAGCCTTCTTTCCTTGAGTCGAGAGTCTATCTGAAATAA
CCTTATTCTACCTTCACAAGGTAGGGATAAGGTCTGCGTACATAATACACTTTCCAGACCTTACTTGT
GGAGTTACATTGGGTATGTTGTCGTTGTTGTTGTACACATAGTCCGAGCCTAAGACAGTGAATGCACG
TGCTACCACTACCTCTATGTTAAATCTTACCCTAGAAGAGAAAGATCAAAATGTTAGTCTTTCTGCTA
ATTGGTTGATTTGTATGTTATAGGGTATTTCGAGATGTTCCTAGTGATATAACAATAGAAGTGGATGG
TGGCATATTTTCATTACACAAGGTAATTCTCTCCATTCTCTATTATCTTATAATCAATTTGGCCAAGC
TTCTCCAATCCTAGAAATACTTTTTTTCAAAGTTTAATTGTTTGGCAATCTTTTGTAAGGAAAAAAAT
TGTTTTTGATGAGAATCAGAAGCTTTTTTTGGAAAAGCAGAAAAAGTAGGCTCTCCATAAAACACT
TTTTTAAAGCACTTTTGATAAAAAAAATATATTTACGAGCAGTTTTTAAAAGTTTGGCCAAATACTAA
TTGTTGCTCAGAAATGTTTTTCAAATTAATTAGCCAAACACAAACTCTTTCTTGCCAAAAGTACGTTT
GAAAAAGCACTTTTGAGAAAAACGCTTATCAAAATAAGCTGATTTTTGCAGCTGCCGTACCCGTATCA
```

FIG. 20 (Continued)

Nitab4.5_0003151g0080.2 genomic sequence (SEQ ID NO. 18):

```
GATTATTCAAAAATGCACTACTTTTAGTGGATCAAACATGCATGTGTTGGCATTTCTGAAGAGCATGA
ACAACATAAACTGCTTAGTAGTATTGCTCACTATGTCTTGTTTTCACACATTTTATATTGAAGTGTTT
GAAATTTTTAAAATTTCATGCCTATGAGTTAGTTCAGAGACCATAATGTAATAGAAAATTCCCTAACA
TAGAATAATTATGATGCAGTTTCCCCTTGTTTCGAGAAGCGGACGAATCCGGAAGCTAGTAGCAGAGC
ACAGGGATTCTGATATATCAAGAATTGAGCTTGTTAGTCTACCAGGTGGAGCAGAATCATTTGAGCTA
GCAGCCAAATTCTGTTATGGTGTCAACTTTGAGATCACAGCAGCAAATGTTGCTCAGCTTTGTTGTGT
ATCCGATTACCTCGAGATGTCAGAGGACTACTCAAAAAACAATCTTGGCTCCAGAGCTGAAGAATATC
TTGACAGCATTGTTTGCAAGAATCTTGAAATGTGTGTTGAAGTCTTGAGACAATGTGAAAACTTACTT
CCACTTGCTGATGAGCTGAAAGTTGTGAGCCGCTGTATCGATGCTGTAGCCTCCAAAGCTTGTGTCGA
GCAAATCGCCTCAAGTTTCTCGCGATTGGAGTATAGTAGCTCAGGTGGAAGACTACATATGAATAAAC
AAGCCAATTGTGAATTGGACTGGTGGATTGAGGATATTTCTGTTCTTCGTATCGACTTGTACCAACGT
GTCATAACCGCGATGAAGTTTCGTGGGGTTAGGCCTGAGAGTATTGCTGCATCACTAGTGAACTATGC
ACAGAGGGAATTGATACAAAAATCCCTTTCTGGTTCAAATATCCAAGAAAAACTCGTGGTTGAGACGA
TCGTGAGCCTAATGCCTGTTGAAAAATTCGTCGTGCCCTTGACCTTTCTTTTTGGATTGTTGCGAAGT
GCAGTGATGTTAGATTGCACGGTTGCTTGTAGGCTTGATCTTGAGAGGCGGATAGGATCTCAATTGGA
TACGGCTACTCTGGACGATATCCTGATTCCTTCCTTTCGACATGCTGGTGATACATTGTTTGATGTTG
ACACAGTGCATAGAATCTTGGTTAACTTTTCACAGCAAGAGGGCGATAGCGATGAAGATATGGAAGAT
GTCTCGGTTTTTGAATCCGATAGCCCTACTACGACGCCATCACAAACTGCATTGTTCAAAGTATCAAA
GCTGGTTGACAATTATCTAGCTGAAATTGCACCAGATGCAAATCTAAAGCTGAACAAGTTCATTGCTG
TTGCAGAAACATTACCAGCACATGCGCGTACTGTCCACGATGGACTTTATCGAGCAATCGATGTTTAC
CTCAAAGTATGTATTACTAACTTACTTGAAATATGTTCAAAAACGTTTTGCTGGTTTGAATGAGAGTT
CTTCAAAATTTCACAACAGGAGAAATATCATATGGTGCTTATGATTCCCTTTATAGAGCTATATGTCC
TCCTTTGATTAGAGAAAATGATCAAATTACCACGTCTACTATACGAAATATTTTAACTTTACCCTCCG
TTATATTTTGAGGTCATTCATATTCTTGTGGTTAGCAAATTATCCTGTATTCACCCATGACCCTAACG
GAGCTCCAACCAAAGTATAACGAAGGGTAATCTTTAACAATAGTACAAAGTACAGAGGGTAAATTTGGA
CCTTTCTCCTTAAGTATTTTGGCACCTGGATCCATCCAATCCGCGATGGAGCTATATTAAAGTGAAGG
ACAGATACGATATATATTCTAATGGACCTCACGCTTCAATTATGCTATCACCCTGTTACCTTATCACT
TTATCTTGTTGTCGTTACTACTTATTATGCCTGCTTCCTTTACTTTTACCTTGAGTCGGGAGTTTATC
GGAAACAGTCTCTCTACCTTCACAAGGTAGTAAGGTCCGTGTACACTCTACTCCTCCCAGACCCCACT
TTGTGGGATTACAATGGGTTTGTTGTTGTTGTTGTTAATGGTATGAATGACGTCAAAGTATAACATTG
AGATATTTCGTATGCTATATGGGTAAATTTGGACCTTTCAACCATTAACTAAGCTAATAGAGTTTCTC
ATCTCAGATTCCTATTTTTTCATTTAACTAACCATAACATTGTTCATGAATGCATATTCCAGGCTCAT
CAAACCTTATCAGATCCAGACAAGAGGAGACTATGCAAATTGATTGATTTCCAAAAGCTCTCACAGGA
AGCTGGTGCACATGCTGCACAAAACGAACGCCTTCCCCTCCAATCGATAGTTCAAGTTCTTTATTTCG
AGCAATTGAGGCTTCGAAACGCCTTGTTTTGTTCGTACCCTGATGATGACATCAAACCAATGCACCAA
TCTTGGAGGATCAATAGTGGTGCTCTTAGTGCTGCAATGTCTCCTAAGGACAATTATGCTTCGTTGAG
ACGAGAAAATAGGGAGCTAAAACTTGAACTAGCGCGGATGAGGATGAGATTAAACGACTTGGAAAAAG
ACCATGTTTGTATGAAGAGGAATATGCAAAAATCTAGCTCGCGACGATTCATGAAATCCTTCTCCAAA
AGGATTGGCAAAAAGTTTAATATTTTCGGACATAGTTTTTCCAGGGATTCTAATTCTCCCTCAAGTCA
GTCAGAAAGAACTGAATCTAAAATAACTGAAAGAACGTGACAATCGATCTTCCAGGTACATCAAATTA
CTCGGATAATTTTGCTGATTCTGCTGAGTAACTGCAAGTCTGTCAATATGAGCTGCAGTCTCATATT
TTCTCCCAAATGTTTGTATATGAGATGCAGTCTGATATGCTTCCGGAGGCAGAGGGATTTCAAGCTTA
TGGGTTCGGCATTCTAATCATTTTATGTTACTGGGTTCTAAATTAGTAATTTATACATATTCAATGAA
TTGTTTAAGATAAATCCATGATTCGAACCAAATTACTGGGTTTGACCGAACCCGCTCCCGGCACTCTA
GC
```

FIG. 21

Nitab4.5_0002641g0190.2 amino acid sequence (SEQ ID NO. 19):

```
MDKHHHQLPLTKSTSRQRYNEWVFRDVPSDITIEVDGGIFSLHKFPLVSRSGRIRRLVAEHRDSDISR
IELVSLPGGTESFELAAKFCYGVNFEITAANVAQLCCVSDYLEMSEDYSKNNLGSRAEEYLDSIVCKN
LEMCVEVLRQCENLLPLADELKIVSRCIDAVASKACVEQIASSFSRLEYSSSGGRLHMIKQANCELDW
WIEDISMLRIDLYQRVITAMKFRGVRPESIAASLVNYAQKELIQKSLSGSNIQEKLVVETIVSLMPVE
KFVVPLSFLFGLLRSAVMLDCTVASRLDLERRIGSQLDTATLDDILIPSFRHAGDTLFDVDTVHRILV
NFSQQEGDSDDDMEDVSVFESDSPTTTPSQNALFKVSKLVDNYLAEIAPDANLKLSKFIAVAETLPAH
```

FIG. 21 (Continued)

Nitab4.5_0002641g0190.2 amino acid sequence (SEQ ID NO. 19):

```
ARTVHDGLYRAIDVYLKAHQTLADPDKRRLCKLIDFQKLSQEAGAHAAQNERLPLQSIVQVLYFEQLR
LRNALFCSYPDDDIKPMHQSWRINSGALSAAMSPKDNYASLRRENRELKLELARMRMRLNDLEKDHVC
MKRNMQKSSSRRFMKSFSKRIGKKFNIFGHNFSRDCSSPSSQSERTESKITERT
```

FIG. 22

Nitab4.5_0002641g0190.2 coding sequence (SEQ ID NO. 20):

```
ATGGACAAACACCACCATCAACTACCACTAACCAAGTCTACTTCGAGGCAGCGTTATAACGAATGGGT
ATTTCGAGATGTTCCTAGTGATATAACAATAGAAGTGGATGGTGGCATATTTTCACTCCACAAGTTTC
CCCTTGTTTCGAGAAGCGGACGAATCCGGAGGCTAGTAGCAGAGCACAGGGATTCAGATATATCAAGA
ATTGAGCTTGTTAGTCTACCAGGTGGAACAGAATCATTTGAGCTAGCAGCCAAATTCTGTTATGGTGT
CAACTTTGAGATCACAGCAGCAAATGTTGCTCAGCTTTGTTGCGTATCCGATTATCTCGAGATGTCGG
AGGACTACTCGAAAAATAATCTTGGTTCAAGAGCTGAAGAATATCTTGACAGCATTGTTTGCAAGAAT
CTTGAAATGTGTGTTGAAGTCTTGAGACAATGTGAAAACTTACTTCCACTTGCTGATGAGCTGAAAAT
TGTTAGCCGGTGTATCGATGCTGTAGCCTCGAAAGCTTGTGTCGAGCAAATCGCCTCAAGTTTCTCAC
GATTAGAGTATAGTAGCTCTGGAGGAAGACTACATATGATTAAACAAGCCAATTGTGAATTGGACTGG
TGGATTGAGGATATTTCAATGCTTCGTATCGACTTGTACCAACGCGTCATAACCGCGATGAAGTTTCG
TGGGGTTAGGCCTGAGAGTATTGCTGCATCACTAGTGAACTATGCACAAAAAGAGTTGATACAAAAT
CCCTTTCTGGTTCAAATATCCAAGAAAAACTCGTGGTTGAGACGATCGTGAGCCTGATGCCTGTTGAA
AAATTCGTCGTGCCCTTGAGCTTTCTTTTTGGATTGTTGCGAAGTGCAGTGATGTTAGATTGCACGGT
TGCTAGTAGGCTTGATCTCGAGAGGCGGATAGGATCTCAATTGGATACGGCTACCCTGGACGATATTC
TGATTCCTTCCTTTCGACATGCTGGTGATACATTGTTTGATGTTGACACAGTGCATAGAATCTTGGTT
AACTTTTCACAGCAAGAGGGGAGTAGTGATGATGATATGGAAGATGTATCGGTTTTTTGAATCCGATAG
CCCTACTACGACGCCATCACAAAATGCATTGTTCAAAGTATCAAAGCTGGTTGACAATTACCTAGCTG
AAATTGCACCAGATGCAAATCTAAAGCTGAGCAAGTTCATTGCTGTTGCAGAAACATTACCAGCACAT
GCGCGTACTGTCCACGATGGACTTTATCGAGCAATCGACGTTTACCTCAAGGCTCATCAAACCTTAGC
AGATCCAGACAAGAGAAGACTATGCAAATTGATAGATTTCCAAAAGCTCTCACAGGAAGCTGGTGCAC
ACGCTGCACAAAACGAGCGCCTTCCTCTCCAATCCATCGTTCAAGTTCTTTATTTCGAGCAATTGAGG
CTACGAAACGCCTTGTTTGTTCATACCCTGATGATGACATTAAGCCAATGCACCAATCCTGGAGGAT
CAATAGTGGTGCTCTTAGTGCTGCAATGTCTCCCAAGGACAATTATGCTTCGTTGAGACGAGAAAATA
GAGAGCTAAAACTTGAACTAGCGCGGATGAGGATGAGATTAAACGACTTGGAAAAAGACCATGTTTGT
ATGAAGAGGAATATGCAAAAATCTAGCTCGCGACGATTCATGAAATCATTCTCCAAAAGGATAGGCAA
AAAGTTCAATATTTTCGGACATAATTTTTCCAGGGATTGTAGTTCTCCCTCAAGCCAGTCAGAAAGAA
CTGAATCTAAAATAACTGAAAGAACTTGA
```

FIG. 23

Nitab4.5_0002641g0190.2 genomic sequence (SEQ ID NO. 21):

```
CAAAATCTCTCCTATTGTGTCTCTGTCCCCTTATTTTCTTGTCTTCTTTAACAAACCTTTCACATTCT
TCTTTATTTAGAGATTTTCAATCTTTTCCCTTGGCTTTTCTTCACCATATTGGCCATGGACAAACACC
ACCATCAACTACCACTAACCAAGTCTACTTCGAGGCAGCGTTATAACGAATGGTTTGTATTTTGCAGT
ACGTAGTTATATACATCGACAGTGTAAAAAGATTAATTTTGTAGCATCAATGTGATTTAATATGCTAT
AGTTGATTAAAAAAATGTGTACTTGGTTATACGTGTCATAACTCGTTCTCTCAACTCAGAATCCACAG
CTTCTAAATTCTTGATCTCGTATATGCAATGCCAAAATGTTTGAAAGTTTTAAAGCATTTTTTTTGGC
TTGTTTGTGAACCTACGTACCTTCCCAAGTTAGAGGTAAGGTCTGCGTACACATTATTCTTCCCAGAA
TTCACTTGTGGGACAATACTGGGTATGTTGTTGCTGGTGGTGATGAACCTGCATATTGTGTCATACTT
TTACGTGCAGTTCAAAATCACTTGGGGCTTTAGTTACATGCATCTTAGTAAAACTTTTGATGAATTTT
TGTACACACATATAGTCCGAGTGCTCTTTCCTTGAGCCGATGGTCTACCGGAAACAACCTTCTACCTT
CACAAGGTACAAGGTAGGGGTAAGGTCTGTGTATATACTACCCTCTCCAGAGTCCACTTGTGGGATTA
CATTGGATATGTTGTCGTTGTTGTTGTACTACACATAGTCCGAGCCTAAGACAGTGAGTGCACGTGCT
CCTACTACCTCTATGTTAAATCTTCCCCTAGAAGAGAAGATCAAAATTTTAGTCTTTCTGCTTATTA
TTGGCTAATTTATATGTTATAGGGTATTTCGAGATGTTCCTAGTGATATAACAATAGAAGTGGATGGT
GGCATATTTTCACTCCACAAGGTAAATGCTCTTCATTCTCTATTATTGATGCTCGAACTCTTCAAAAA
TATTGCCACACCCGTATTCAGGGGCGGAACTAGAGTGGCGAAATGGGGTTCAACCGAATCAACTTCGC
```

FIG. 23 (Continued)

Nitab4.5_0002641g0190.2 genomic sequence (SEQ ID NO. 21):

```
CAAAAAATTATAGAGTATATATAAGGTTAAATTTATTTTTATGCATAAATAGTAAATGTTCAATCCCC
TTGGCATGTTCGTAAGTTTACCTTTTAATATTTCGAATCCCCTTGGTAAAAGTCCTAGCTCTGCTACT
GCCCGTGTCGGACCATTCAAAATGAACTACTTTTGGAGGATCCGACACTCAGGTCAGCATTTTTGAAG
AGTTCGAACAACATAGAATTCTTAGCACTATTCCTCTATATGACTTCTTATCTCACATATTATATTGA
AATGTTTGAAATTTTTTAAATTTCATGCCTATGAGTAAGTTTAGAGACTATAATGTAATAGAAAATTC
CCTAACATAAGATAATTATGATGTAGTTTCCCCTTGTTTCGAGAAGCGGACGAATCCGGAGGCTAGTA
GCAGAGCACAGGGATTCAGATATATCAAGAATTGAGCTTGTTAGTCTACCAGGTGGAACAGAATCATT
TGAGCTAGCAGCCAAATTCTGTTATGGTGTCAACTTTGAGATCACAGCAGCAAATGTTGCTCAGCTTT
GTTGCGTATCCGATTATCTCGAGATGTCGGAGGACTACTCGAAAAATAATCTTGGTTCAAGAGCTGAA
GAATATCTTGACAGCATTGTTTGCAAGAATCTTGAAATGTGTGTTGAAGTCTTGAGACAATGTGAAAA
CTTACTTCCACTTGCTGATGAGCTGAAAATTGTTAGCCGGTGTATCGATGCTGTAGCCTCGAAAGCTT
GTGTCGAGCAAATCGCCTCAAGTTTCTCACGATTAGAGTATAGTAGCTCTGGAGGAAGACTACATATG
ATTAAACAAGCCAATTGTGAATTGGACTGGTGGATTGAGGATATTTCAATGCTTCGTATCGACTTGTA
CCAACGCGTCATAACCGCGATGAAGTTTCGTGGGGTTAGGCCTGAGAGTATTGCTGCATCACTAGTGA
ACTATGCACAAAAGAGTTGATACAAAAATCCCTTTCTGGTTCAAATATCCAAGAAAAACTCGTGGTT
GAGACGATCGTGAGCCTGATGCCTGTTGAAAAATTCGTCGTGCCCTTGAGCTTTCTTTTTGGATTGTT
GCGAAGTGCAGTGATGTTAGATTGCACGGTTGCTAGTAGGCTTGATCTCGAGAGGCGGATAGGATCTC
AATTGGATACGGCTACCCTGGACGATATTCTGATTCCTTCCTTTCGACATGCTGGTGATACATTGTTT
GATGTTGACACAGTGCATAGAATCTTGGTTAACTTTTCACAGCAAGAGGGAGATAGTGATGATGATAT
GGAAGATGTATCGGTTTTTGAATCCGATAGCCCTACTACGACGCCATCACAAAATGCATTGTTCAAAG
TATCAAAGCTGGTTGACAATTACCTAGCTGAAATTGCACCAGATGCAAATCTAAAGCTGAGCAAGTTC
ATTGCTGTTGCAGAAACATTACCAGCACATGCGCGTACTGTCCACGATGGACTTTATCGAGCAATCGA
CGTTTACCTCAAGGTATGTATTGACAATTTAATTGAAATATGTTCAAAAATGTTTTGCTGGTTTGGAT
GAGAGTTACTTCAAAATTTCACAACAGGAGAAATATCATATGGTGCTTATTTTTGATAAAACTATATA
GATTGCTAATGACTTAATTGAATATGGTAGTTCTAGAATAAGTCCATCAAGAGTATTAAGGTTCTTTA
CCTTGAGATAATCATAATTATTCCCATTACAGAGTAATATGTCCTCCTTTGATTAGTGAAAATGGTTA
AATTACCCTTCTATTATACGAAATATCTTAACTTTACACTCTGTTATATTTTGGAGTCATTCATATTC
TTGTGGTTGGGTCATGGTTTATATCGATGTGACCTATGTGATCTATAGGTCATGGGTACGACCGTGGG
ATCAACCACTTATGTTTGTATTAGGGTGGGTTCCCTACATTACACCCCCTTTGGGTTGTGGCCCTTCC
CCAAATCCCCCGTGAACGTGGGATGTTTTGTGCACCAGACTGCCCTTTGTTCATTTCTTGTGGTTAG
CAAATTATCTTGTATTCGCCGATGACCCTAACTGAGCACCAACCAAAAGTACGATTAAAGGTAATCTT
AACCATAGTAAAAACTGGAGAGGTAAATTTGGACCTTTTTCCTTAAGTGTTTTGACACGCGGAATCCA
TCCAATCCGCAATGGAGCTTCGTTAAAGTGAAGGACGAATACAAGATATTTGCTAACAGCAAGGGTAT
GTATAACGTCAAAGTGTAACAGAGGGTAAATTGAGATATTATGTATGGTATAGGAGTAAACTATGTTG
TGTGGACTCTCCAAAATGCTGTCGCAGCATTATCAGATCCTCCAAAAATGCACTATTTTTGGAGTATC
AGACACGCACCCGATGATATTTCGGAGAGTCCGAGCAACATAGGGGGGTAAATTTGGACCTTTTCAC
CTTTTGTTAAGCTGATAGAGCTTCTCATCTCAATTCCTATTTTTTCATATAACTAACCATAACATTGT
TCATGAATGCATATTCCAGGCTCATCAAACCTTAGCAGATCCAGACAAGAGAAGACTATGCAAATTGA
TAGATTTCCAAAAGCTCTCACAGGAAGCTGGTGCACACGCTGCACAAAACGAGCGCCTTCCTCTCCAA
TCCATCGTTCAAGTTCTTTATTTCGAGCAATTGAGGCTACGAAACGCCTTGTTTTGTTCATACCCTGA
TGATGACATTAAGCCAATGCACCAATCCTGGAGGATCAATAGTGGTGCTCTTAGTGCTGCAATGTCTC
CCAAGGACAATTATGCTTCGTTGAGACGAGAAATAGAGAGCTAAAACTTGAACTAGCGCGGATGAGG
ATGAGATTAAACGACTTGGAAAAAGACCATGTTTGTATGAAGAGGAATATGCAAAAATCTAGCTCGCG
ACGATTCATGAAATCATTCTCCAAAAGGATAGGCAAAAAGTTCAATATTTTCGGACATAATTTTTCCA
GGGATTGTAGTTCTCCCTCAAGCCAGTCAGAAAGAACTGAATCTAAAATAACTGAAAGAACTTGACAA
TCGATGAAGGGGAGCCTTGGCGTAACTGATAAAGTTGTTGCTATGCGACCATGAGGTCACGGATTCGA
GCCGTGGAAACAGCCTCTTGCAGAAATGCAGGGTAAGACTCGTACAATAGACCGTTGTGGTCCGGCC
CTTCTCCGGACCCCGCGCATAGCGGGAGCTTAGTGCACTGGGCTGTCCTTTTTTGAACGTGACAATCG
ATCTTCCAGGTACATCAAATTACTCGGGTAATTTTGGCTGATTCTGTTGTTGAGTGTAACTGCAAGTT
TTTCAGTTGTAATCTTTTTGTTCCATTCTACAACACCTTATTTTCTCCCCAAATGTTTGTATATGAGC
TGCAGTGAGATATGCTTTTCATTGACATGATATATAGAGTTTTTATGACTTTGAGTTGGTAAAG
```

FIG. 24

Nitab4.5_0001876g0030.2 amino acid sequence (SEQ ID NO. 22):

```
MVSPYNSFTTRTIFSEVAGDITIAANGESFLLHKFPLVSLSGKIRKMVADANDPNLSELDLNHVPGGP
ETFELAAKFCYGMNFEITTTNVARLRCVAEYLEMTEDYREENLIARTETFLDEVVSPSLEKSVQVLSS
CEALLPTAEEVGIPDRCIDAIARNACQEQLVSSLSRLDCDSGSLELKDRCLEWWVEDFSVLSIDFYRR
VIMAMGHAGVHIDSIIASLMHYAQVSLKGIGKPQIWNPARSYPCKGEKGQRTIIETLVSLLPPEKSSS
VPLNFLFGMLRIGIMVDATLACRLEIERRIAFRLEMVLLDDLLIPSVQTTGDSLFDVDTVKRILIHFL
QRIDQEENEDCGYESEGIDSPSHGALLKVGRLIDTYLAEIAPDPYLSLDKFTAMISMLPDYARVIDDG
LYRAIDVYLKAHPTLSEHGAKKLCKFIDCQKLSQEACNHAAQNERLPVQMTVRVLYFEQLRLKNALSG
SCGDTFVSQKISSGLTSAAMSPRDTYASLRRENRELKLEISRMRVRLSDLEKEQVFMKQGMMDKTGHG
KTFLTSLSRGIGRIGIFGSPSGEKHHKSGRKSRTSEGKTGRSRRYSLS
```

FIG. 25

Nitab4.5_0001876g0030.2 coding sequence (SEQ ID NO. 23):

```
ATGGTGTCTCCTTACAACTCATTTACCACTCGCACTATATTCTCTGAAGTTGCTGGGGATATTACAAT
TGCTGCAAATGGAGAGTCTTTCCTACTGCATAAGTTTCCCCTGGTATCTTTGAGTGGAAAGATCCGGA
AGATGGTGGCAGATGCCAACGATCCAAATCTCTCAGAATTGGATTTGAATCACGTACCAGGAGGACCT
GAAACATTTGAACTGGCTGCAAAGTTTTGTTATGGCATGAACTTTGAGATCACAACCACAAACGTAGC
ACGTTTGCGCTGTGTGCGCAGAATACTTGGAAATGACAGAAGATTATCGTGAAGAGAATCTCATTGCAA
GAACAGAAACTTTCCTTGATGAAGTTGTCTCTCCAAGTCTTGAAAAATCCGTGCAAGTACTTTCTTCC
TGTGAAGCTCTTCTTCCTACTGCAGAGGAGGTTGGTATTCCAGATAGATGCATTGATGCCATTGCCAG
GAATGCTTGTCAAGAGCAACTTGTATCCAGTCTATCTCGTTTAGATTGTGATAGTGGATCTTTGGAAC
TTAAGGACAGGTGTCTTGAATGGTGGGTCGAAGATTTTTCTGTTCTGAGTATTGATTTTTATCGCAGA
GTTATCATGGCAATGGGACATGCTGGGGTACACATAGACAGCATTATTGCGTCCTTGATGCATTATGC
CCAGGTCTCTCTAAAGGGTATTGGGAAACCGCAAATTTGGAATCCAGCCAGATCGTATCCTTGTAAGG
GAGAAAAGGGGCAGAGAACAATAATAGAAACTCTTGTTAGTCTATTGCCTCCAGAAAAGAGTTCATCT
GTTCCTCTGAATTTTCTTTTTGGGATGTTGAGGATAGGTATCATGGTGGATGCCACGCTAGCCTGCAG
GCTTGAAATTGAGAGGAGGATTGCCTTCCGGCTGGAAATGGTCTTACTTGATGATTTGCTTATACCAT
CTGTCCAGACTACAGGTGATTCTTTGTTTGATGTTGACACGGTCAAGCGGATATTGATACATTTCCTC
CAAAGGATTGACCAGGAAGAAAATGAAGATTGTGGATATGAATCAGAAGGTATTGATTCTCCAAGCCA
TGGCGCTCTATTGAAAGTTGGACGGCTGATAGACACATATCTTGCTGAAATAGCTCCTGATCCATATT
TGAGTCTCGACAAATTCACTGCTATGATATCAATGTTGCCTGATTATGCTCGTGTAATTGATGACGGA
CTTTACAGAGCTATTGATGTTTATTTGAAGGCCCATCCAACGCTAAGTGAGCATGGCGCGAAGAAGCT
GTGCAAGTTCATAGATTGCCAGAAGCTCTCTCAAGAAGCATGCAATCATGCAGCACAGAATGAGAGAC
TCCCAGTTCAAATGACTGTCCGAGTTCTCTACTTTGAGCAGCTCCGCCTTAAGAATGCTCTATCTGGA
AGTTGTGGAGATACTTTTGTATCACAAAGATCAGTAGTGGTCTTACAAGTGCAGCTATGTCGCCTAG
AGATACTTACGCTTCTTTAAGGAGAGAGAACCGAGAACTGAAGCTGGAGATATCAAGAATGAGGGTAA
GGCTCAGTGACCTGGAGAAGGAACAAGTGTTCATGAAACAAGGTATGATGGATAAAACAGGACATGGG
AAAACATTCTTAACTTCCCTTTCTAGAGGCATAGGAAGAATTGGTATATTTGGCAGTCCTTCTGGAGA
AAAACATCACAAGTCGGGTCGCAAATCCAGGACATCAGAAGGTAAAACTGGTAGGAGTAGGAGGTATT
CTCTTTCCTAG
```

FIG. 26

Nitab4.5_0001876g0030.2 genomic sequence (SEQ ID NO. 24):

```
ATAAGATCAAGCCTTTCCTTGATTTTAATAATATTAGAATAGAATTAAGCAAAGCATGCACATACCTT
CCAATATTTTACTACTCAATCAAATAACTAGGTTTTAATCCTGAATTAGTTAGATGATTATCTATATC
TGCTTCACTTGACTCTACTAATGTTTAAAAGAATTCATCAAAATTTGATACTAGTAGATTATAGTTTC
GATAATGGTGAATAGGATGACATATTGGTAAGGTAGAGACAAAGGAATTAAAAGACAAAAGGGGAAAA
GGTATTTTGTGTTGCAGTAGAACACTTCACATGGCCACCCATTTCTGTATTCTTTAGCTTTTTCTCTT
TGCATTATTTATGTATCACCATTCCTATGTCACACTTTCCCTTTTAGGTCTTCTTATTGTTGCTTGTA
TTGGGATTTGACTGCAAGAGTGCTTCATCAGATGGTGCTGCTGCTCTAAAGTCTAAAGTGAAGCTCAT
ACAAGAATGGTGTCTCCTTACAACTCATTTACCACTCGGTAATCTCCATCTTCTGGGCTACACATATA
TAACTGTTGATCAAGAATTATTCGGTTACAGTATCAAAGACAGTTTTTTTACTGCGAATTATGTGTTG
GCCTTGGTTTTTGATCATCATATTCTGAATGACATGTTTGATGAATGTACATTTTCAATGAATTTAGT
CTTTCAGCTTGATTTGAGCTACCCCACCCCCTCCAGCAGCCCATCTTGGCTGCCCTGCTTGATGATTC
```

FIG. 26 (Continued)
Nitab4.5_0001876g0030.2 genomic sequence (SEQ ID NO. 24):

```
ATGCTATGATTATATTGTTTCCTCTCTCCAATTATTATTTTTTCAGTACGCATTGCACCTTACAAACA
TTATCCTTATAGGGATTACTTAACATTATCCTTTCCAAATTCCCTCCAGTGAATAGTTACAGGAAGGC
CTTGTTAGAGTAACTCTTTCTTCTGACATTTGAAGGGTAGCCTTGGCGCAATTGGTAAAGTTGCTTCC
ATGTGACCATGAGGTCACGGGTTCGAGCCGTGGAAACAGCCTCTTGCAGAAATGCAGGGTAAGACTGC
GAACGATAGACCCTTCCCCGGACCCGCGCATAGTGGGAGCTTAGTTCACCGGACCACCCTTTTTTCT
TCTGACATTTATATGCTTTCTTTGCGTATGTCATACTCTCTTAGTATACTATTTCACATAATTTGTC
AAACATGTCAAAGTGCTACTACTGTGAACTTGAGTATTGGTGTCCTTTCTTATCATCTTCTTCGTTTT
CATCGATAAACTTGATCTGTCATGTCAGTAGGAGGAAATGCATCACTTTACCCCCCAACACTTCCTAA
TTCATCTGTTATTTCATGAATAATGAACAAAACACCATAAAAGCGTTAATACTTTTTATGACATGGTA
AATTTATTAAGGCAAATAAATACTTTGTCATGTCAAAATCATTGCGATAAATCAACTTATTCGTGATG
ATATTGATCAGCACTATATTCTCTGAAGTTGCTGGGGATATTACAATTGCTGCAAATGGAGAGTCTTT
CCTACTGCATAAGGTACTTTCCTGTTTTCAGAAACTTTCTGCCTTTGGATAATTTAAGAACGTTTGAA
CTTCAAATAAGGTTAGAAATATATATAAATTATCAGGATCATGCTAAAGGTTCAAGATCATGCATAGT
GGGAGAGGGTGGGGTTTTGTTTAAAGACACTTGTTTCTTTCGTCTTGGTTACTAACTAGATAGATTGA
GATTGTGATGGTGGTAAAATTTGAAATTCAGAGGATTATCAGACTTGGTTGAGAATGTTCCTGTAGTT
TGATAGATTATTAAGATTGAAAAACCAAAGTTTCCATTAATGGTGTATTTGGCTATCAAGAAAAAAAA
AGCAACAATTGTTGTAGTGATGGTATACGTAATGTAAGCTAACTTTAAGATCACAATTCTGGAACACA
TTGTAGTTTGAAAAGAACTCCATCTGGGCATGTAATGCAGCTAAAAATAATGACAGTGAAGTCTGTCA
TATTAAGGATACTTTAGCAAATGATTGAAATGGTCATTCTTCTAGGAGTAGCATTGCGACAAATGCTT
TCCAGAAATCAATTTTATGATTATAACATGTGAATCTTAGCCTTGTCTAGGCGTTTCATCGTGAACTA
TTTAATAATTAACTTATCTCTTCCTTATTCGACATTATACTTCATTCTTGAAGTTGATAATTATGTGA
TGTTTACAATAGTTTCCCCTGGTATCTTTGAGTGGAAAGATCCGGAAGATGGTGGCAGATGCCAACGA
TCCAAATCTCTCAGAATTGGATTTGAATCACCGTACCAGGAGGACCTGAAACATTTGAACTGGCTGCAA
AGTTTTGTTATGGCATGAACTTTGAGATCACAACCACAAACGTAGCACGTTTGCGCTGTGTGGCAGAA
TACTTGGAAATGACAGAAGATTATCGTGAAGAGAATCTCATTGCAAGAACAGAAACTTTCCTTGATGA
AGTTGTCTCTCCAAGTCTTGAAAAATCCGTGCAAGTACTTTCTTCCTGTGAAGCTCTTCTTCCTACTG
CAGAGGAGGTTGGTATTCCAGATAGATGCATTGATGCCATTGCCAGGAATGCTTGTCAAGAGCAACTT
GTATCCAGTCTATCTCGTTTAGATTGTGATAGTGGATCTTTGGAACTTAAGGACAGGTGTCTTGAATG
GTGGGTCGAAGATTTTTCTGTTCTGAGTATTGATTTTTATCGCAGAGTTATCATGGCAATGGGACATG
CTGGGGTACACATAGACAGCATTATTGCGTCCTTGATGCATTATGCCCAGGTCTCTCTAAAGGGTATT
GGGAAACCGCAAATTTGGAATCCAGCCAGATCGTATCCTTGTAAGGGAGAAAAGGGGCAGAGAACAAT
AATAGAAACTCTTGTTAGTCTATTGCCTCCAGAAAAGAGTTCATCTGTTCCTCTGAATTTTCTTTTTG
GGATGTTGAGGATAGGTATCATGGTGGATGCCACGCTAGCCTGCAGGCTTGAAATTGAGAGGAGGATT
GCCTTCCGGCTGGAAATGGTCTTACTTGATGATTTGCTTATACCATCTGTCCAGACTACAGGTGATTC
TTTGTTTGATGTTGACACGGTCAAGCGGATATTGATACATTTCCTCCAAAGGATTGACCAGGAAGAAA
ATGAAGATTGTGGATATGAATCAGAAGGTATTGATTCTCCAAGCCATGGCGCTCTATTGAAAGTTGGA
CGGCTGATAGACACATATCTTGCTGAAATAGCTCCTGATCCATATTTGAGTCTCGACAAATTCACTGC
TATGATATCAATGTTGCCTGATTATGCTCGTGTAATTGATGACGGACTTTACAGAGCTATTGATGTTT
ATTTGAAGGTGAATTTTCAAGTTTTTAGTTATAGACCTGTATATTGTTCTAGCAATGCCTTCTAATGA
TAACATGTTCTTTATATTGGTGGTTTGAATATTCTTCTTTGCGCATATAATGTTGTGTTTAACCCTGA
AAGCTGTTTAATGCTTTTAGTAAAATCACATCTCAACCCCTTATAAACATAGTTTTAGTTGAATCTGC
CATTTATCTCTTTGTGAACTTTACTAGGCCCATCCAACGCTAAGTGAGCATGGCGCGAAGAAGCTGTG
CAAGTTCATAGATTGCCAGAAGCTCTCTCAAGAAGCATGCAATCATGCAGCACAGAATGAGAGACTCC
CAGTTCAAATGACTGTCCGAGTTCTCTACTTTGAGCAGCTCCGCCTTAAGAATGCTCTATCTGGAAGT
TGTGGAGATACTTTTGTATCACAAAGATCAGTAGTGGTCTTACAAGTGCAGCTATGTCGCCTAGAGA
TACTTACGCTTCTTTAAGGAGAGAGAACCGAGAACTGAAGCTGGAGATATCAAGAATGAGGGTAAGGC
TCAGTGACCTGGAGAAGGAACAAGTGTTCATGAAACAAGGTATGATGGATAAAACAGGACATGGGAAA
ACATTCTTAACTTCCCTTTCTAGAGGCATAGGAAGAATTGGTATATTTGGCAGTCCTTCTGGAGAAAA
ACATCACAAGTCGGGTCGCAAATCCAGGACATCAGAAGGTAAAACTGGTAGGAGTAGGAGGTATTCTC
TTTCCTAGAAAAGGTTGTATGCCACAATGTAAANNNNNNNNNNNNNNNNNNNNNNNNNNNNNN
```

FIG. 27

Nitab4.5_0000048g0280.2 amino acid sequence (SEQ ID NO. 25):

```
MAMHPSAKCAHFCINSLAFSLCIIYHSHFPFLVFFQRLLLLVLGFDCKSAADGAAALKSKVKLKFLTT
HTRMVSPYNSFTTRTIFSEVAGDITIAANGESFLLHKFPLVSLSGKIQKMVADANDPNLPELDLTHVP
GGPETFELAAKFCYGMNFEITTTNVARLRCVAEYLEMTEDYREENLIARTETFLDEVVSPSLEKSVQV
LSSCEALLPTAEEVGIPDRCIDAIARNACQEQLVSGLSRLDCDTGSLELKDRCLEWWVEDLSALSIDF
YRRVIMAMGHVGVHIDSIIASLMHYAQVSLKGIGKPQIWNPARSYPCKGEKGQRTIIETLVSLLPPEK
SSSVPLNFLFGVLRIGIMVDATLACRLEIERRIAFRLEMVLLDDLLIPSVQTTGDSLFDVDTVKRILI
HFLQRIDQEENEDCGYESQGIDSPSHGALLKVGRLIDTYLAEIAPDPYLSLDKFTAMISVLPEYARVI
DDGLYRAIDVYLKAHPTLSEHEAKKLCKFIDCQKLSQEACNHAARNDRLPVQMTVRVLYFEQLRLKNA
LSGSCGDTFVSQKISSGLTSAAMSPRDTYASLRRENRELKLEISRMRVRLSDLEKEQVFMKQGMMDKT
GHGKTFLTSLSRGIGRIGIFSSPSGEKHHKSGRKSRTSEGKTGRSRKYSLS
```

FIG. 28

Nitab4.5_0000048g0280.2 coding sequence (SEQ ID NO. 26):

```
ATGGCCATGCACCCTTCTGCCAAATGTGCCCATTTCTGTATTAATTCTTTAGCTTTTTCTCTTTGTAT
TATTTATCACTCACATTTCCCCTTTTTGGTCTTCTTTCAACGCTTATTGTTGCTTGTCTTGGGATTTG
ACTGCAAGAGTGCTGCAGATGGTGCTGCTGCTCTAAAGTCTAAAGTGAAGCTCAAGTTTCTTACAACT
CATACAAGAATGGTGTCTCCTTACAACTCATTTACCACTCGCACTATATTCTCTGAAGTTGCTGGGGA
TATTACAATTGCTGCAAATGGAGAGTCTTTCCTACTGCATAAGTTTCCCCTGGTATCTTTGAGTGGAA
AGATCCAGAAGATGGTGGCGGATGCCAACGATCCAAATCTCCCAGAATTGGATTTGACTCACGTACCA
GGAGGACCTGAAACATTTGAACTGGCTGCAAAGTTTTGTTATGGCATGAACTTTGAGATCACAACCAC
AAACGTAGCACGTTTGCGCTGTGTGGCAGAATACTTGGAAATGACAGAAGATTATCGTGAAGAGAATC
TCATTGCAAGAACAGAAACTTTCCTTGATGAAGTTGTCTCTCCAAGTCTTGAAAAATCCGTGCAAGTA
CTTTCTTCCTGTGAAGCCCTGCTTCCTACTGCAGAGGAGGTTGGTATTCCAGATAGATGCATTGATGC
CATTGCCAGGAATGCTTGTCAGGAGCAACTTGTATCCGGTCTATCTCGTTTAGATTGTGATACTGGAT
CTTTGGAACTTAAGGACAGGTGTCTTGAATGGTGGGTCGAAGATCTATCTGCTCTGAGTATTGATTTT
TATCGCAGAGTTATCATGGCAATGGGACATGTTGGGGTACACATCGACAGCATTATTGCGTCCTTGAT
GCATTACGCCCAGGTCTCTCTAAAGGGTATTGGGAAACCGCAAATTTGGAATCCAGCCAGATCGTATC
CTTGTAAGGGAGAAAAGGGGCAGAGAACAATAATAGAAACTCTTGTTAGTCTATTGCCTCCAGAAAAG
AGTTCATCTGTTCCGCTGAATTTTCTTTTTGGGGTGTTGAGGATAGGTATCATGGTGGATGCCACGCT
AGCCTGCAGGCTTGAAATTGAGAGGAGGATTGCCTTCAGGCTGGAAATGGTCTTACTTGATGATTTGC
TTATACCATCTGTCCAGACTACAGGTGATTCTTTGTTTGATGTTGACACTGTCAAGCGGATATTGATA
CATTTCCTCCAAAGGATTGACCAGGAAGAAAATGAAGATTGTGGATATGAATCAACAAGGTATTGATTC
TCCAAGCCATGGCGCTCTATTGAAAGTTGGACGGCTGATAGACACATATCTTGCTGAAATAGCTCCTG
ATCCATATTTGAGTCTTGACAAATTCACTGCTATGATATCAGTGTTGCCTGAGTATGCTCGTGTAATT
GATGACGGACTTTACAGAGCTATTGATGTTTATTTGAAGGCCCATCCAACGCTAAGTGAGCATGAAGC
GAAGAAGCTGTGCAAGTTCATAGATTGCCAGAAGCTCTCTCAAGAAGCATGCAATCATGCAGCACGGA
ATGACAGACTCCCAGTTCAAATGACTGTCCGAGTTCTCTACTTTGAGCAGCTCCGCCTTAAGAATGCT
CTATCCGGAAGTTGTGGAGATACTTTTGTATCACAAAAGATCAGTAGTGGTCTTACAAGTGCAGCTAT
GTCGCCTAGAGATACTTATGCTTCTTTAAGGAGAGAGAACCGAGAACTAAAGCTGGAGATATCAAGAA
TGAGGGTAAGGCTCAGTGACCTGGAGAAGGAACAAGTGTTCATGAAACAAGGTATGATGGATAAAACA
GGACATGGAAAAACATTCTTAACTTCCCTTTCAAGAGGTATAGGAAGAATTGGTATATTTAGCAGTCC
TTCTGGAGAAAAACATCACAAGTCGGGTCGCAAATCCAGGACATCAGAAGGTAAAACTGGTAGGAGTA
GGAAGTATTCTCTTTCCTAG
```

FIG. 29

Nitab4.5_0000048g0280.2 genomic sequence (SEQ ID NO. 27):

```
CAATTAACTACGTTTTAATCCTAAAATAGTTGGATGATTATATGAATTATCTATATCTGCTTCACTCT
AGCTACTAATGTGTAAAGAATTCATCAAAATTTGATACTAGTCTACTAGTATTAGACTAAGTAGATTA
GAGTTTCGATAATATAATGATGATATAAACATTGGTAAGGTAGAGACAAAGGAATAAAAAGCAAAAGG
GGAAAAGGTATTTTGTGTTGCAGTAAAACACTTCACATGGCCATGCACCCTTCTGCCAAATGTGCCCA
TTTCTGTATTAATTCTTTAGCTTTTTCTCTTTGTATTATTTATCACTCACATTTCCCCTTTTTGGTCT
TCTTTCAACGCTTATTGTTGCTTGTCTTGGGATTTGACTGCAAGAGTGCTGCAGATGGTGCTGCTGCT
CTAAAGTCTAAAGTGAAGCTCAAGTTTCTTACAACTCATACAAGAATGGTGTCTCCTTACAACTCATT
```

FIG. 29 (Continued)

Nitab4.5_0000048g0280.2 genomic sequence (SEQ ID NO. 27):

```
TACCACTCGGTAATCTCCATCTTCATGTCTCTATGTGGTACACATGACTGTTGATCATCCCTTTAGAA
TTTCAAGAATTATTCGGCTACAGTAATAAATAGTTTAACAGAGTAATTTGTTTGGATAAATAGTTTAA
AAGACCTATTTACTGCAAATTATGAGTTGGCCATGGTTTTTGATCATCATATTCTGAATGTCCATTTT
CAATGAATTTAGTCTTTGAGCTTGATTTGAGCTACCCCACCTCCTCCAGTAGCCCATCTTGGCTGCCC
TGCTTGATGATTCATGCTATGATTATATTGTTTCCTCACTCCAATTATTATATTTTCAGTATTCATTG
CACCTTACGAAAATCTCTCTTTTGTTTTTTTTCCACGGAATATTACTTATAGGGATTACTTAACATTA
TCCTTTCCAAATTCCCTCCTGTGAATAGTTACAGGAAGGCCTTGCTTATGGAAGTAACTCTTTCTTCT
GACATTTATATGCTTTCTTTGAGTATGTCATTGTCTCTTTAGTATGCTATTTCACATAATTTGAAAGT
GCTACTACTGTGAACTTGAATATTTGTGTCCTATCTTATCATCTTCTTCATTTTCACCGATAAACTTG
ATCTGTCATTAGGAGGAAATGCATCACTTTACCCAAGACTTCCTAATTCATCTGTTATTTCATGAATA
ATTAATAAAATACCACAAATTTATGACATGGTAAATTTATTATGGCAAATCAATACTTTGTCATGTCA
AAATCATTGCGTAATAAATAAACTTATTCGTGATGATATTGATCAGCACTATATTCTCTGAAGTTGCT
GGGGATATTACAATTGCTGCAAATGGAGAGTCTTTCCTACTGCATAAGGTACTTTCCTGTCTTCACTT
TCTCCAGTCTTTCTTTCAGAAACTTTGTGCCTTTGGATAATTTATGAAGGTTTGAACTTCAAATAAGG
TTAGCAATATATATAAATCATCAGGATATAATATGTGTTCAAGATCATGCATAGTAGGAGAGGGTGGG
GCTTTGTTTAAAGACACTTGTTTGTTTCCTCTTGGTTGCTAACTAGATAGATTGAGATTGTGATGGTG
GTAAAATTTGAAATTCAGAGGATTATCAGAGTTGGTTGACAATGTTCCTGTAGTTTGATGGATTATTA
AGATTGGAAAACCAAAGTTTCCATTAATGGTGTATTTGACTATCAAAAAAAGCTACAATACAATTGTT
GTAGTGATGGTATACGTAATGTAAGCTAACTTTAAGATCACAATTTTGGAACAAATTGAAGTTTGAAA
AGAACTCCAGCTGGCATGTAATGCAGCTAAAAATAATTCTGTATCTAGAAGCAAGCCCCTTGTAACTT
GTTGTTGTCTTTAGACCAACTTTATCATGCCTCGTCAAGGGCACTACTAGATGAGATGACGCATCTTA
TACATTGAAACTTTTAATTCAAGCACCCAGTGGTAATGACAGTGAAGTCTGTCATATTAAGGACACTT
TAGCAAATGATTGAAATGGTCATTCTTTTAGGAGTAGCATTGCGACAAATGCTTTCCAGAAATCAATT
TTATGATTATAACATGTGAATCTTAGCCTTGTCTGGGCGTTTCATCATGAACTATTTAATAATTAACT
TATCTCTTCCTTATTCGACATTATTAGTTAATTGCATACATCATTCTTGAAGTTGATAATTATGTGAT
GTTTACAATAGTTTCCCCTGGTATCTTTGAGTGGAAAGATCCAGAAGATGGTGGCGGATGCCAACGAT
CCAAATCTCCCAGAATTGGATTTGACTCACGTACCAGGAGGACCTGAAACATTTGAACTGGCTGCAAA
GTTTTGTTATGGCATGAACTTTGAGATCACAACCACAAACGTAGCACGTTTGCGCTGTGTGGCAGAAT
ACTTGGAAATGACAGAAGATTATCGTGAAGAGAATCTCATTGCAAGAACAGAAACTTTCCTTGATGAA
GTTGTCTCTCCAAGTCTTGAAAAATCCGTGCAAGTACTTTCTTCCTGTGAAGCCCTGCTTCCTACTGC
AGAGGAGGTTGGTATTCCAGATAGATGCATTGATGCCATTGCCAGGAATGCTTGTCAGGAGCAACTTG
TATCCGGTCTATCTCGTTTAGATTGTGATACTGGATCTTTGGAACTTAAGGACAGGTGTCTTGAATGG
TGGGTCGAAGATCTATCTGCTCTGAGTATTGATTTTTATCGCAGAGTTATCATGGCAATGGGACATGT
TGGGGTACACATCGACAGCATTATTGCGTCCTTGATGCATTACGCCCAGGTCTCTCTAAAGGGTATTG
GGAAACCGCAAATTTGGAATCCAGCCAGATCGTATCCTTGTAAGGGAGAAAAGGGGCAGAGAACAATA
ATAGAAACTCTTGTTAGTCTATTGCCTCCAGAAAAGAGTTCATCTGTTCCGCTGAATTTTCTTTTTGG
GGTGTTGAGGATAGGTATCATGGTGGATGCCACGCTAGCCTGCAGGCTTGAAATTGAGAGGAGGATTG
CCTTCAGGCTGGAAATGGTCTTACTTGATGATTTGCTTATACCATCTGTCCAGACTACAGGTGATTCT
TTGTTTGATGTTGACACTGTCAAGCGGATATTGATACATTTCCTCCAAAGGATTGACCAGGAAGAAAA
TGAAGATTGTGGATATGAATCACAAGGTATTGATTCTCCAAGCCATGGCGCTCTATTGAAAGTTGGAC
GGCTGATAGACACATATCTTGCTGAAATAGCTCCTGATCCATATTTGAGTCTTGACAAATTCACTGCT
ATGATATCAGTCGTTGCCTGAGTATGCTCGTGTAATTGATGACGGACTTTACAGAGCTATTGATGTTTA
TTTGAAGGTGAATTTTCAAGTTTTTAGTTATAGACCTGTATATTATTCTAGCAATCCCTGCTAATGAT
AACATGTTCTTTATATTGGTGGTCTGAATATTCTTCTTTGCGCATATAAAGTGCACAAAAAGAATATG
TTGTGTTTTAACCCTGCAAGCTGTTTAATGCTTTAAGTAAAATCACATCTCAACCCCTTATAAACATA
GTTTTAGTTGATTCTGCCATTTATCTCTTTGTGAACTTCACTAGGCCCATCCAACGCTAAGTGAGCAT
GAAGCGAAGAAGCTGTGCAAGTTCATAGATTGCCAGAAGCTCTCTCAAGAAGCATGCAATCATGCAGC
ACGGAATGACAGACTCCCAGTTCAAATGACTGTCCGAGTTCTCTACTTTGAGCAGCTCCGCCTTAAGA
ATGCTCTATCCGGAAGTTGTGGAGATACTTTTGTATCACAAAAGATCAGTAGTGGTCTTACAAGTGCA
GCTATGTCGCCTAGAGATACTTATGCTTCTTTAAGGAGAGAGAACCGAGAACTAAAGCTGGAGATATC
AAGAATGAGGGTAAGGCTCAGTGACCTGGAGAAGGAACAAGTGTTCATGAAACAAGGTATGATGGATA
AAACAGGACATGGAAAAACATTCTTAACTTCCCTTTCAAGAGGTATAGGAAGAATTGGTATATTTAGC
AGTCCTTCTGGAGAAAAACATCACAAGTCGGGTCGCAAATCCAGGACATCAGAAGGTAAAACTGGTAG
GAGTAGGAAGTATTCTCTTTCCTAGAAAAGCTTGTATGCCACAATGTAAATTAATGCATGACTCAAGA
GTTTTGCAAAAGTGGCTAATTATTGGTGAGTGCTCGTTTAATTTCTTGCTGTCCTAGCCAATCTCTTA
GATATCATGCTTCACATTGTTGAACTTGTT
```

FIG. 30

Nitab4.5_0002006g0070.2 amino acid sequence (SEQ ID NO. 28):

```
MGVVTVSELKPSISGKRSFRPSSSARHITEWPISDVSSDLTIEVGAASFALHKFPLVSRSGRIRKLLL
EAKDTKISRLNLTGLPGGSDAFELAAKFCYGVNVEITISNVAMLRCASKFMEMNEDISEKNLEIRTEV
FLKDTVFTNISNSISVLHRCETLLPVSEEVNLVSRLINAIANNACKEQLTSGLSKLEHNFPPKPVQSL
DSETPIDWWGKSLTVLNLDFFQRVVSVVKSKGLKQDIISRILINYAKNSLQGLFIKDPQLVKGSFLDL
DLQKRQRVIVETIASLLPTQSRKSTVPMAFLSSLLKSAIAASASTSCRSDLERRIGLQLDQAILEDIL
IPANPHGNNHSPLYDIDSILRIFSFFLNLDEDDEEDNTLRDESEMVYDFDSPGSPKHSSIVKVSKLLD
NYLAEVALDSNLTPSKYIALAELLPDHARLVYDGLYRAVDIFLKVHPNIKDSERYRLCKTIDCQKLSQ
EACSHAAQNERLPVQMAVQVLYFEQIRLRNAMNGGHNQFFGMNNQFPQRSGSGAGSGCISPRDNYASV
RRENRELKLEVARMRMRLTDLEKDHVSMKQELVKSHPANKLFKSFTKKLSKLNALFRIKDLKPIGGKA
NSESRLLFQKRRRHSVS
```

FIG. 31

Nitab4.5_0002006g0070.2 coding sequence (SEQ ID NO. 29):

```
ATGGGAGTTGTCACTGTTTCTGAACTGAAGCCAAGCATATCTGGGAAAAGGTCTTTTCGTCCAAGTTC
CAGTGCCAGACATATTACTGAATGGCCAATATCTGATGTTTCTAGTGATCTTACAATAGAAGTAGGAG
CTGCCAGTTTTGCTCTTCACAAGTTTCCTCTAGTTTCCCGAAGCGGAAGAATTAGAAAGCTGCTGCTA
GAGGCAAAGGATACAAAGATTTCAAGACTCAATCTTACCGGTCTTCCTGGCGGATCTGATGCATTTGA
ACTTGCTGCTAAGTTCTGTTATGGCGTGAACGTTGAGATTACCATATCAAACGTGGCGATGCTAAGAT
GTGCATCCAAGTTCATGGAAATGAACGAAGACATCTCCGAGAAAAACCTGGAAATTCGTACTGAAGTA
TTCCTTAAAGATACAGTATTCACAAACATATCCAACTCGATATCTGTTCTTCATCGCTGTGAAACACT
ACTACCGGTATCTGAAGAAGTCAATCTCGTTAGTCGATTAATCAATGCAATTGCAAACAATGCTTGTA
AAGAGCAACTAACATCTGGTTTGTCAAAGCTGGAGCATAACTTCCCACCCAAACCTGTTCAAAGCCTT
GATTCTGAGACACCAATAGACTGGTGGGGAAAATCATTGACTGTGCTAAATCTAGATTTTTTCCAGAG
AGTTGTATCTGTAGTGAAGTCAAAAGGTCTTAAACAAGACATTATCAGCAGAATTTTGATAAATTATG
CCAAAAATTCACTTCAGGGACTTTTCATCAAGGATCCTCAGTTGGTTAAAGGAAGTTTCTTGGATTTG
GATTTGCAGAAAAGGCAAAGGGTTATCGTCGAAACAATAGCTAGCTTACTACCAACACAATCCAGGAA
AAGTACAGTCCCAATGGCTTTTCTTTCAAGTTTGTTAAAATCTGCAATAGCAGCATCAGCATCCACTT
CTTGCAGATCTGATCTAGAGAGGCGCATTGGTCTGCAGCTAGATCAGGCAATTCTAGAAGATATTCTC
ATACCTGCAAATCCACATGGGAACAACCACAGCCCTCTCTACGACATAGATTCTATTTTGAGGATCTT
TTCCTTTTTCTTGAATTTGGATGAGGATAGTATTCTGAGGGACGAGTCTGAGATGGTGTATGACTTTG
ATTCACCAGGATCTCCAAAGCATAGCTCAATTGTTAAGGTGTCAAAGTTATTGGAC
AATTATCTAGCAGAAGTTGCACTCGATTCTAACCTCACGCCATCGAAGTATATAGCACTGGCTGAGTT
ACTTCCAGACCACGCGCGTCTAGTTTATGATGGATTATATCGAGCTGTAGATATTTTCCTCAAGGTTC
ATCCCAACATTAAGGACTCGGAACGCTATCGTCTCTGTAAAACTATTGATTGCCAGAAACTATCACAA
GAAGCTTGCAGTCATGCAGCACAAAATGAACGGTTGCCTGTGCAAATGGCGGTCCAAGTGCTATACTT
CGAACAAATCAGGCTGAGAAATGCGATGAACGGGGGACATAACCAATTCTTTGGAATGAATAATCAGT
TCCCCCAGCGTTCAGGCAGCGGAGCAGGAAGCGGATGCATCTCTCCGAGAGATAACTACGCATCAGTC
AGGAGAGAAATAGAGAACTGAAGCTCGAGGTTGCAAGAATGAGAATGAGGCTTACAGATTTAGAGAA
AGATCATGTTTCCATGAAACAGGAGCTAGTAAAGTCACATCCTGCCAATAAGTTATTCAAGTCATTTA
CAAAGAAATTAAGCAAGCTGAATGCACTATTCCGAATAAAAGATTTAAAACCAATAGGAGGGAAAGCT
AACTCAGAAAGCCGGTTACTTTTTCAGAAGAGAAGGCGCCATTCGGTTTCTTGA
```

FIG. 32

Nitab4.5_0002006g0070.2 genomic sequence (SEQ ID NO. 30):

```
GGAGTGGTTAATGGTTTTGGGGAAGTTGAGATTCTGCTGAGAGAAGATGGGAGTTGTCACTGTTTCTG
AACTGAAGCCAAGCATATCTGGGAAAAGGTCTTTTCGTCCAAGTTCCAGTGCCAGACATATTACTGAA
TGGTATATTTACTCTCTCTTCTATCTCACCAACAACTGCTACTTTCACATTACTAATATTTTATGCC
CAGCTTTTCATTTGTGTCATATTTTCTTAAAGAATTTACATGGATAGTACTGTAAGGATATTCCACA
GACCATTTTGATGATGTATCAATTTCTACAATTAATATTTCCTACAACACTTAAGACGTGGAAAAGTC
```

FIG. 32 (Continued)

Nitab4.5_0002006g0070.2 genomic sequence (SEQ ID NO. 30):

```
CATATTGGTATAGCTAGATGATAGCATGAATTCTTGTTAGTTGGGTACTTGTGATTGTCAATTATGCT
GAGTTCTAATAAAAGGCTCAGTCCTAGACAAAGGATACATCTTTTCTTTTGGCATAGTAAAATTAGCT
AACTTGGTTCCCCCCCCCCCCCCAGATACTAATACTATGAGATTATAAAAAGGGAGTTTCTGCAATT
TATCACTAAAAGTTCCACTTAGAGGAAGAAGTTTACTGGTAACAACTAAATGGATCATAGAAGAATTA
ATGCAAGGAAAAAACTAAACTCTTCAACCACCAAAGTATCTGAATTTATGAGTTAGGTGATTGGACAG
AATTTAGTTTCCAACATTTATGACAAACCATGTTCAGGTGCTGACTAAGTGGAAATGGCAATATACTT
ATAGCTTTAGAAATTGATTGTGATGGAACTTATCTTAAAATCTAAGAATCTAAAGTTATTATCAGATC
CTAAAGTAAATAAAAGAAAACAGCAGAGTATGAGTATACATGAGCAGTTTCTAGGGCTGCAATCATTG
AAAATGACAAATCAAATATTTGACTTTTTTACCACCTACAACAAATGATAGTGGCCCTGATTCCAATGT
GTTCAAGTTTCTTGTTTCAACATGTGGTGTGAACGGTGTAGACAGCTACTCCCTCCGTTTCAATTTAT
GTGAACCCATTTGAGTGGGCACGAAATTTAAGAAAAGAGAGAACTTTTAAACTGTGTTGTAAAATGAG
GGCACATATATTTTGTGTGGCTATAAATCATTGCATAAAGGTAAATAAACGGAGGTAGTATATTATTT
CCCTAGTTTTCAACATATGTATCTAATGAGGGCCCTCTACCAAGTACAGATGAGTCCTGCAATTATCT
GTTNNNNNNNNNNNNNNNAAAANGNCACATATATTTTGTGTGGCTATAAATCATTGCATAAAGGTAAATT
GTTTCCAAATAAGGAAAGGTGTCATTCTTTTTGGCACGGACCAAAAAGGAAATAAGTTCACATAAATT
GAAACGGAGGTAGTATATTATTTCCCTAGTTTTCAACATATGTATCTAATGAGGGCCCTCTACCAAGT
ACAGATGAGTCCTGCAATTATCTGTTAGATTACTACAGACCACAAGATAAATCACAACCAGGAATAAA
TTTCAAAGAAACCAGAATATGACTACCACTTGCTATGTTGGATCTAAACACATTGAATAATCTTTGTA
TCCATTCAAGATATTTGTTTTGAGCTTTTCCACTCATAGTGTCCTATGATACTTTTGGTCGTAAATTG
TGGCCGTATGTACAAGCGCTAGAGCACGATAACATATGCTCCCCGAACCGTTAAGGTTTCATCCGCTT
GAATTTGGATAGCTTTAAGGTTCCAATATCCAGCATTACAGTGTTGAGATGTAAGTTGCACCATGTAT
TGAAACTTAGGCTAAAAATATAAACAGAGAAGTTTATTAGTATATGTTTTTTTCTCGACACATTTCCT
GTTTCCGGCTTTTAATCATTGACCATATATTCTATTGCAGGCCAATATCTGATGTTTCTAGTGATCTT
ACAATAGAAGTAGGAGCTGCCAGTTTTGCTCTTCACAAGGTACAAATATGAAGTATTAGATCATTCGT
CTTCTCGTGTATTTTGATCTACCAATCTTTTCAAAATTGGAATGCTCAAGTCTATCAAAAGCATAAAT
TTTGCAAAGAAATGGCTGTCTAATGTAGCTGAAAATGATTTATAAGTTAGCTGTTATAAGTAGGCAA
CTGATATTAGGACAGTCGTGTCCACATCGGAATTTATTTCATGGTGTCAAAATAGGGAGGGAAAAGAA
AAGTAAAAAGGCAGATGTAAAAACAGAACTTAAGCATCAGTCTGAAGGTCAGAAACAACAGCTGAAGT
TGTTTCAATGTAGTGGATCTTAGACTAAGTTATGTGCTTCCTGTTAAAATTAAGAAAAATGAAGGAAG
AATACCTTGGAAACATTTCTAATGTGATTGCTAATATCACACTGTTTGCAGTTTCCTCTAGTTTCCCG
AAGCGGAAGAATTAGAAAGCTGCTGCTAGAGGCAAAGGATACAAAGATTTCAAGACTCAATCTTACCG
GTCTTCCTGGCGGATCTGATGCATTTGAACTTGCTGCTAAGTTCTGTTATGGCGTGAACGTTGAGATT
ACCATATCAAACGTGGCGATGCTAAGATGTGCATCCAAGTTCATGGAAATGAACGAAGACATCTCCGA
GAAAAACCTGGAAATTCGTACTGAAGTATTCCTTAAAGATACAGTATTCACAAACATATCCAACTCGA
TATCTGTTCTTCATCGCTGTGAAACACTACTACCGGTATCTGAAGAAGTCAATCTCGTTAGTCGATTA
ATCAATGCAATTGCAAACAATGCTTGTAAAGAGCAACTAACATCTGGTTTGTCAAAGCTGGAGCATAA
CTTCCCACCCAAACCTGTTCAAAGCCTTGATTCTGAGACACCAATAGACTGGTGGGGAAAATCATTGA
CTGTGCTAAATCTAGATTTTTTCCAGAGAGTTGTATCTGTAGTGAAGTCAAAAGGTCTTAAACAAGAC
ATTATCAGCAGAATTTTGATAAATTATGCCAAAAATTCACTTCAGGGACTTTTCATCAAGGATCCTCA
GTTGGTTAAAGGAAGTTTCTTGGATTTGGATTTGCAGAAAAGGCAAAGGGTTATCGTCGAAACAATAG
CTAGCTTACTACCAACACAATCCAGGAAAAGTACAGTCCCAATGGCTTTTCTTTCAAGTTTGTTAAAA
TCTGCAATAGCAGCATCAGCATCCCACTTCTTGCAGATCTGATCTAGAGAGGCGCATTGGTCTGCAGCT
AGATCAGGCAATTCTAGAAGATATTCTCATACCTGCAAATCCACATGGGAACAACCACAGCCCTCTCT
ACGACATAGATTCTATTTTGAGGATCTTTTCCTTTTTCTTGAATTTGGATGAGGATGATGAAGAGGAC
AACACACTAAGAGATGAAAGCGAAATGGTTTACGACTTTGATAGTCCTGGATCTCCCAAACATAGCTC
AATTGTTAAGGTGTCAAAGTTATTGGACAATTATCTAGCAGAAGTTGCACTCGATTCTAACCTCACGC
CATCGAAGTATATAGCACTGGCTGAGTTACTTCCAGACCACGCGCGTCTAGTTTATGATGGATTATAT
CGAGCTGTAGATATTTTCCTCAAGGTAAGCTGCTTAACCTCATCCACATTATCTCACTCACCTGTTCA
AAACAATTAGTATTTCTCATATGAGTAGTCTAACAATGGAAACTACACATATACTATTTTTTATACTT
TTCGTATAAATAATAGCCGACAAAATATATATTTTTTATATATTAACATGTAATATACATGTTTTATA
CATAATTAGTATATACTTTTCGTATATTTGGTTAGTCATAAAGTTGCTGCCATGTGACCAGGAGATCA
CGGGTTCGAGCCGTGGAAGCAACCTCTTGCAGAAATGCAGGGCAAGGCTGTGTACAATAGACCCTTGT
GGTCCGGCCCTTTTCCAGACCTTGCGCGTAGCGGGAGCTTAACTGCCCTTTTTATATTTAGCTAGCGG
ATGTAATTATTTTTGGCTGATCGGCCAAATGTGTTTAATACAATGCATGACATTCTCACGGCAGGTT
CATCCCAACATTAAGGACTCGGAACGCTATCGTCTCTGTAAAACTATTGATTGCCAGAAACTATCACA
AGAAGCTTGCAGTCATGCAGCACAAAATGAACGGTTGCCTGTGCAAATGGCGGTCCAAGTGCTATACT
```

FIG. 32 (Continued)

Nitab4.5_0002006g0070.2 genomic sequence (SEQ ID NO. 30):

TCGAACAAATCAGGCTGAGAAATGCGATGAACGGGGGACATAACCAATTCTTTGGAATGAATAATCAG
TTCCCCCAGCGTTCAGGCAGCGGAGCAGGAAGCGGATGCATCTCTCCGAGAGATAACTACGCATCAGT
CAGGAGAGAAAATAGAGAACTGAAGCTCGAGGTTGCAAGAATGAGAATGAGGCTTACAGATTTAGACA
AAGATCATGTTTCCATGAAACAGGAGCTAGTAAAGTCACATCCTGCCAATAAGTTATTCAAGTCATTT
ACAAAGAAATTAAGCAAGCTGAATGCACTATTCCGAATAAAAGATTTAAAACCAATAGGAGGGAAAGC
TAACTCAGAAAGCCGGTTACTTTTTCAGAAGAGAAGGCGCCATTCGGTTTCTTGATGCTCTACTCTAA
TGTGAATAAGAAAGAGTATACAGTGTTTCACATTGCTGAATTTGGATGTGTTGAGAGTGAAGTTATTG
CTTTGCGTTTTGATCGTATCCTTGAAAGAAGAGACTCACTCAAACTTTTACTATAAAGGTATATAAAC
AAGTGTGAGTTTTTTTAGCTTCATGTAGTTTGCACTACACGATCATCGAGAAAATTTTACAATTGCTC
TTTCCCAATATTTCTTGTACTCATTTG

FIG. 33

Amino acid sequence of a BTB/POZ homodimerization domain SEQ ID NO. 31

SQEIPSDVTVNAGGSAFSLHKFPLVSKSGYIRKIISESNDADVSIVEIPDIPGGSDAFELAAKFCYGI
NFEISTENIALLRCTAEYLEMTEDYAVGNL

FIG. 34

Amino acid sequence of an NPH3 domain SEQ ID NO. 32

DWWAEDLAVLRIDFFQRVLIAMMGRGFKQYALGPILMLYAQKSLRGLEIFGKGRKKIEPKQEHEKRVV
LETIVSLLPREKNALSVSFLSMLLRAAIYLETTVACRLDLEKRMALQLGQAVLDDLLIPSYSFTGDTL
FDVETVQRIIMNFLDNEMDGSRLGDEEYVSPSLSDMERVGKLMENYLAEIASDRNLSVSKFISLAEVI
PEQAKITEDGMYRAIDIYLKAHPALSDMERKKVCGVMDCQKLSREACAHAAQNDRLPVQTVVQVLYYE
QQR

FIG. 36

Nitab4.5_0000842g0110.2 amino acid sequence (SEQ ID NO. 33)

```
MASSAIFHFLPSSSSSLTSLSFRNSRTHLSQTPNFYKPLLVKASTSVNFSSPSKSPTLTKNNNWLWKY
KDNSVNIYYEEHDKGSDEPCKNVLLIPTISDVSTVEEWRSVAKDIAGRSGKVNYRTTIVDWPGLGYSD
RPKLDYNADVMEKFLADFINAPNSPVNNSDKDLVVFGGGHAATIAVRAAKKGLVKPTAIAAIAPTWAG
PLPIVFGRDSSMETRYGLLRGTLRAPAVGWMMYNVLVSNEKSIQSQYKSHVYSDPEKVTPDIIESRYA
LTKRQGARYVPAAFLTGLLDPVKSREEFVQLFAELEGRIPVLVLATAGSPKRSKAEMEALMEAKGVSK
YIEVPGALLPQEEYPEIVAEQLYRFLQEKFELQA
```

FIG. 37

Nitab4.5_0000842g0110.2 coding sequence (SEQ ID NO. 34)

```
ATGGCATCCTCTGCTATTTTCCACTTTCTTCCATCATCATCTTCTTCCTTGACTTCTCTTTCCTTCAG
AAACAGCAGAACCCATCTTTCTCAAACCCCAAATTTTTACAAACCCCTTTTAGTAAAAGCTTCTACTT
CTGTCAATTTTTCTTCCCCCTCCAAATCACCTACATTGACAAAGAATAATAACTGGCTATGGAAATAC
AAGGACAATTCTGTGAATATTTATTACGAGGAACACGATAAGGGAAGCGATGAGCCTTGTAAGAACGT
TTTGCTGATTCCTACTATTTCAGATGTTAGTACTGTGGAGGAATGGAGATCAGTGGCTAAAGACATTG
CTGGACGAAGTGGTAAAGTTAATTACAGAACTACCATTGTAGATTGGCCTGGTTTAGGCTACTCTGAT
AGACCAAGCTTGATTACAATGCTGATGTCATGGAAAAATTCTTGGCCGACTTCATTAATGCTCCTAA
TAGTCCAGTGAACAATTCGGATAAGGACTTGGTGGTGTTCGGAGGAGGACATGCTGCTACAATAGCAG
TTCGTGCTGCAAAGAAGGGCTTGGTGAAGCCAACAGCGATTGCTGCTATTGCTCCCACCTGGGCTGGT
CCACTTCCTATTGTTTTTGGAAGAGATTCCAGCATGGAAACGAGGTATGGTCTCCTTAGAGGGACCTT
AAGGGCCCCTGCTGTTGGTTGGATGATGTATAATGTACTTGTCAGCAATGAGAAATCAATACAATCAC
AATATAAGTCCCATGTTTATTCAGATCCCGAAAAGGTAACTCCAGATATCATCGAGAGCCGATACGCA
CTCACAAAGCGGCAAGGTGCTCGCTATGTGCCTGCTGCTTTCTTGACTGGTTTGCTTGACCCGGTAAA
GTCCAGGGAAGAATTTGTCCAACTATTTGCTGAGTTAGAGGGTAGGATACCAGTTCTAGTTCTGGCAA
CAGCAGGTTCTCCGAAGAGGTCAAAAGCAGAGATGGAAGCACTTATGGAGGCCAAAGGGGTGAGCAAG
TATATCGAAGTGCCAGGTGCTCTCCTTCCCCAGGAAGAGTATCCTGAAATAGTTGCAGAACAGCTTTA
CAGGTTTCTGCAAGAGAAGTTTGAGCTTCAGGCTTAA
```

FIG. 38

Nitab4.5_0000842g0110.2 genomic sequence (SEQ ID NO. 35)

```
GAGATTTCACAAAAATATCCGGAAAAAAAAAAGTTTCTCCAAAAATCATTTAATTATTTATCTAAGAA
CTTTCCTACCTACAATTTAAGCTAGAACAGGAAAATAAAAATAAAAAGAAAAAATCAACACCAGCGG
CTTCTCTCTTTCACACATACACAAAGTCGCATACCCAGAAAAAAGAAACAATTTTTGTGTTGCAGAA
GTTAAGGTAAAGCTTCCATAATTCACACAATACACAGAGCCTCCATTAATCATTCAATTCATGGCATC
CTCTGCTATTTTCCACTTTCTTCCATCATCATCTTCTTCCTTGACTTCTCTTTCCTTCAGAAACAGCA
GAACCCATCTTTCTCAAACCCCAAATTTTTACAAACCCCTTTTAGTAAAAGCTTCTACTTCTGTCAAT
TTTTCTTCCCCCTCCAAATCACCTACATTGACAAAGGTAAGACTTAAAATTAGTGAACTGTTTATCT
CAAAATCAATTTTTTGAATTTTTTCATATTTTGTTTTTGCAGAATAATAACTGGCTATGGAAATACAA
GGACAATTCTGTGAATATTTATTACGAGGAACACGATAAGGGAAGCGATGAGCCTTGTAAGAACGTTT
TGCTGATTCCTACTATTTCAGATGTTAGTACTGTGGAGGAATGGAGATCAGTGGCTAAAGACATTGCT
GGACGAAGTGGTAAAGTTAATTACAGAACTACCATTGTAGATTGGCCTGGTTTAGGCTACTCTGATGA
ACCCAAGCTTGATTACAATGCTGATGTCATGGAAAAATTCTTGGCCGACTTCATTAATGCTCCTAATA
GTCCAGTGAACAATTCGGGTAAGCTAAAAGAGCCTTCTTGATATATTTTCTGGATAAATTAGAGTACA
ATTTCTAATTTTGCACTCTTTGCATAAACTATTGATATAGTGAATTAATCTGTTTGTCTGTGGACAT
AGGCCAAATCATATATATTATGGTATCACTATTTTTGTTGTTGTTGTTGTTGTTGATGTCATATG
TTGTTGTTCTACATAAATCAAGAGTACTACAGAAATTTCTTTGGAGTTAAATCGTTAGGTACTCTCTT
GGGAAGAAGATCCAAGGAGCGATTCTCAAGGAAATGTAGCCAAACTCTAGGTGTAAATCCAGAAATAG
AGATGTTGAACTTATGAGTGCTAGGACATATTTCCAAAAAATTTGTGAAGTTGGTAAAAATGATGAAC
TGGAGAAGAGACCACAACTATGATCAAGATGTTGAAGAGAAGGATAACGCCAATCTTCTTTTTGTGAT
GGATGATTGTGCTTGATTGGATGATGAATGAATCATAGATATAGGTTGTTCGTACTATATGTCTCCTT
ATTGATACTGGTTTAGCCAATATGAATCTGTTAGTAGCGTCAAAATTTTTCTGGGAAACAACATCCCA
```

FIG. 38 (Continued)

Nitab4.5_0000842g0110.2 genomic sequence (SEQ ID NO. 35)

```
ACCAAAACTATTACGGATTAATATGGTGAGAATATTGACGAGAGTTTGACATATTTTCGGACCCAACG
AAAGATTTCATCTATCTGGATACCCTTGATTCTAATAGGTGCAAGTTTTCGGCCAAAGGTTGTGTGAT
GGTCATGAAGGAGGACTTATTCATGATGAAGGCCAGAAAAGTCGAAAGTTTAATTATTTTATAACGTA
CCCGTGTTATATGAATTGCTGCAGGCTTTTCTTCTATACCTGATTATGAAATTATAACATTGGGATAT
ATGAGGTTCAGACATATGAGCACGAAGGGGCTAATTATGTTGACCAAATGTGAACTTCTTTGCGAGCA
AATTACAAGAAAGGTAGAGCTTTGCGAGCTGTGCATCTGAAAATCAAGGGAGTCCTAATTTTAGTATT
AGTATTCATAAAACAAAAGGTATGCTAGACCACATCGGAGACCTGCAAGTGTTTCATGTAAAGGTAGA
ACGCAATATTTGCTAACCTTTTATATGATTGCTCAACAGGAAAGAAAAGTTTACGTATATCTTCAGA
AACACTAATATGAAGCTCTGGACACTTTTAAGAAGTGAAAGACCTTAATTGAGAAGTCTGGGAAGCAA
TCAAAAGGCTTTGATCCATTAATTTTGTGTAAGTGATTTCAATAAATGCCATGAGGATCATGAAATTG
GCAGACACGTAATGCTATAAAAGTTTATAACAGAGTGACGTTGTTGAACACATTAATATAACCTAATT
GGAGAAAGAAAGGTGTATGCTGTCAAATGTTCGTCTGCAAAGGTTTCTGAGCTAAAAGCTGTCTTTAT
AGCATATTACTTGGTGAACTGCTTACTGTTCACGGGTGTTGAGTTCAAAACTTAAAGAGGTATGGTTT
GGTCTATCGGGATTATTCAAATTTGAAAACCTTGGTTGTCCTGCTTAGATGGATGTTAGCGGAGGAAA
GCTAGAACCAAGAACCAAAAATTGTAGTTTCTTTGGTTATGTATTTTGGGGTGGGAGGGCTGACGAGC
GCAAAACACAACACGAAATTTATGCTTGCTAGTCAAAGATAGTGTAGTTAAGTGATCGTCTCCACAGG
AAATGGATTTAAACAGTGTTCGAATAATCTTTAGTTAATTACTATCCAAGAAAATTAATACTTGATTC
AATGATTATCAACTACGATTAGCTACTAAAAATTAAGCAATTAATAATTGATTACGGAAGACACGGTT
ACAACAACAACAAACCCAGTTTGATCTCATAAATGGGGTCTGGGGAGGGGAGGGTAGTGTGTACGCAG
ACCTTACCCCTAGCTCATAAAGATAGAGAGGTTGTTTCCGATAGACCCTCGGCTCAAGGAACATTGAA
GATAAAGCAACGAAGTAGCAAAGAATATTAGCAGCAATGTAACATGGTAACGGGAGTGAATGCCACAA
CATGCATAATAAAGAACAATAAATAGGAAATTACAAAGATAGTCCTAGTACTACTGGTCGGCCTAGGA
GGAACACATTACGGAAGACACGGTTGAGCAACAAAAAAATATCAATGAGGGAAATAAGGGTAATTGAC
TAGACAGGTACACGACAATTGACTCGGGATCCAATTCTTGAATTTGTTCACTCTATAATACTGTTGAT
TCTCACGAATTCAACGGATAATTAGATTACACTTGAAGTTAATGTTCCTCTTTCGATTAAACATTAAT
TTCAGTAATTAATCCAATTGAATCACAGTGAACAATTGCAACAAATAAAATGACGGTTTTAGTCTTAA
GGGTAACTTCTCACGAATATTTTCCTATTTTCTAGTTCAATTAATAATTCAAGAGGCTTTTTCGATTA
CCTAGTTGAATCACTAATTTAAACTAGAGCATAAGATGTAAAGAAATTCAATATAAAGCTTCTCTTCC
GATTAAGCAAAATAATAAATAACTTCACAATACGATTTAAAACTCCATCAATTAATTCAAACAATTGT
CAAGAATCTAATCCCTAATCAAGTTGTCAATACACCATATCTGTCAACACTCTAAGGGAAATTACTCC
ATAGCAATGGAAAAAGTCATCTCAATAAGGTTTAAAAACATAGAAAACATCAATGCTAATAATTCGAT
ACAAACTCCCGTATTGCACCGATTGTTGGTTGAAATCTTGATGAATTCTTGTGTCTTCTTGCCTTAGT
TGTTCTCAATTCTTTTGTAGGTCAAAAGTCCCTTCAAAAACGTATTTTTGGTGTATTTATACCATGT
AGAAGTGGACCCGGACAAAACTACCCCTTTCAAGCTGAAACAGAAAATACGCTGGGAAAATTGCACA
GGCGCGCCGCGCCGCGCCTCGCGTCGCACCATGCGGCGCGCTTGTGGGAATTATCAGAGGCTTGTCAA
TTTTGTTAGCAGGCGCATTATACACTGCCGCACCACGTCTCGCGGCGCCCCATGCGGTGCGGTAGTGC
TTATTTCTTAGAGTAATATCTTTCTTCTACTTTATGACATCCCGACTTGGTCCTCGACCCCCGAACGC
GATCCCGGCTTAATTTCTTGGGCTTTACTCAGATGTCAAAGCTCCAATTTGTTCGATTCAGCTCCAAA
TTAACTTCTTACCTCAGAATCACTTCCTGCAAGGCATAAAACACGTAATAAGTGTAATTCATTGCAGT
AATTAGAGTGTAAAACGCGCTAAATCATGAGTTTCTAGCCTACCATCAAGGGCATAGCTTGCGGTGTC
CTGGTCCTATATCTCCAATTTTGTTAAGATTAGAAATGTTATGTTAGTTTTGCTAAATCTCTTAAGGT
GACCCGGAGCGGGGTTCATCTATTGCCTTTTGAGACCTATCAGGTAGATAGTTTATCAAAGAAAGTGG
AGATTGAAGTTTACAATCCACAGCTTTCATGAACAGCAAAAGGGGTCGTCAGTTGGGGTGACCAGTGC
CAGGGGGTTGTCCATTGCACCGAGAAACTTGTAAAGTAACATGGACACATCCAAAGCGCCGTGAGCCA
TAATTGGAAATGGAAAGTAGGCCATCCTATATCTACTGTTTTCCCCTCCCTCGTTCTGCTGCTAACTC
TCTGTTTTTTTTTTTTTTTTTTTTTGTGTGTGTGTGTGCTTGTGAGATGTTTCAGTTTTGTTTGCTCTC
TGCATCTGGAAATGATGTTCCAAGTTCCTTTATTTTGGTAAAGATATCTCATCTTACATTTTCTTGGA
AGTTCTCTTGTTAATAATTTCAAATGAATAAATTAGATAAGGACTTGGTGGTGTTCGGAGGAGGACAT
GCTGCTACAATAGCAGTTCGTGCTGCAAAGAAGGGCTTGGTGAAGCCAACAGCGATTGCTGCTATTGC
TCCCACCTGGGCTGGTCCACTTCCTATTGTTTTTGGAAGAGATTCCAGCATGGAAACGAGGTACGCAT
AGATCTTTCCTTCCGTTGCACTTTTCTTGACCTTTTTATTTAACTAAGAGCTCTGCAGCTTGCTAAAT
AATACCCATTGCAGGGCTAGGTCCAATATAGAGAACAAAAGGACTACAAGATTCGGAAGTTTTAAGCA
GACATTAATTCAGTTTTTGTAGGAAAGAAGCAAATGACATGAGAGTCTCCTGCATAGTAATGCATTGG
ATAACACAATCAGCAATCCACCTTTCAAAATATGAAATTTTCATCCGAAAAAAATAACAATAGTATTC
AAGATTTTCACCGTATTTGCAGAAATGATATTACCCTACTTCGTGATTGATATTTCCTTCTCATTTTC
TACAGGTATGGTCTCCTTAGAGGGACCTTAAGGGCCCCTGCTGTTGGTTGGATGATGTATAATGTACT
```

FIG. 38 (Continued)

Nitab4.5_0000842g0110.2 genomic sequence (SEQ ID NO. 35)

```
TGTCAGCAATGAGAAATCAATACAATCACAATATAAGTCCCATGTTTATTCAGATCCCGAAAAGGTAA
CTCCAGATATCATCGAGAGCCGATACGCACTCACAAAGCGGCAAGGTGCTCGCTATGTGCCTGCTGCT
TTCTTGACTGGTTTGCTTGACCCGGTAAAGTCCAGGGAAGAATTTGTCCAACTATTTGCTGAGTTAGA
GGGTAGGATACCAGTTCTAGTTCTGGCAACAGCAGGTTCTCCGAAGAGGTCAAAAGCAGAGATGGAAG
CACTTATGGAGGCCAAAGGGGTGAGCAAGTATATCGAAGTGCCAGGTGCTCTCCTTCCCCAGGAAGAG
TATCCTGAAATAGTTGCAGAACAGCTTTACAGGTTTCTGCAAGAGAAGTTTGAGCTTCAGGCTTAAAA
ATGGTTATCAGCTCAAGACCTAAGTAGTCAAAGGTACAGAATTTTCCCATGGGCAACAGTGAGGTTAA
GTGGTTAAATTTGAAAGTATGAGATGACACTGGAAGTGGCTTTATATATGATAATTCAGGTGATTAAT
GTATGAATTTTTATCTATATTGATAGAGGTTTTCCTTCTCTTAAACCAGACCTAGAATCACAGAAAGT
TGAGTGCTAAACCGATTTATGACAAACGATGTTCTTATTCAATTTGCTGCTATGGCAGTTTTATAGTT
TTTTTTAATTTATTATTACAGATATATTGGTTATTTAGCTGCTCTTCATGGCTTTCTATGAGGAGCTG
AATGTTACATTGATCTTTTGGTTCATCATACCATCGAGGTCAATTTTGATATTTAGCAGGTCAGTTTG
ACTTG
```

FIG. 39

Nitab4.5_0001620g0100.2 amino acid sequence (SEQ ID NO. 36)

```
MGFAYCLWQPNASHCGEALNYRILDRKNSCDVGLNHKLLGNARVLCKNRLGKRLKRSVACSDNSLAYS
RIRFNCALWKSDSSGNLMRRKASRGVKLPRCQGNDSVAFIDGNGRNVESSESAEDGALSANTNGIAEI
SCAIELEEDKEEETEGDNLDELRELLQKALKDLEVAQLNSTMFEEKAQKISEAAIALKDEAANAWDDV
NKQLDSVQEIVSEEMVAKEAVQKATMALSFAEARLQVALDSVQAAKQRIMSSETSEDSKGEDSTSLME
EEAALLAAQEDIKECLDRFGSCEAELRRLQNKKEELQKEVDRLNELAEQAQNNALKAEEDVANIMLLA
EQAVAYELEATQRVSDAEIALQKAEKNLAVSIVDSPETSVLQNGSSTQGQVLVDGTLSEDEVLPRNSV
DSVIEIDREVQLEDAWAASGPLSTEESRISDESDEEDRKLVLDSSKDSDSDTEKPKSVQSLRQEVNKE
SARDSSLNAPKALLKKSSRFLPASFFSFPTDGEEFTPASVFHNLMESARKQLPKLVVGSLLMGAGIAF
YVNRSERISQSFQQPDIITTSIDEVSTNARPLVRQIRKLPKKLKTLMEMLPHQEINEEEASLFDMLWL
LLASVIFVPIFQKIPGGSPVLGYLAAGILIGPYGLSIIRHVHGTKAIAEFGVVFLLFNIGLELSVERL
SSMKKYVFGLGTAQVLVTAVVGLVAHFVAGQAGPAAIVIGNGLALSSTAVVLQVLQERGESTSRHGR
ATFSVLLFQDLAVVVLLILIPLISPNSSKGGVGFRAIAEALGLAAVKAIVAITAIIAGGRLLLRPIYK
QIAENQNAEIFSANTLLVILGTSLLTARAGLSMALGAFLAGLLLAETEFSLQVESDIAPYRGLLLGLF
FMTVGMSIDPKLLLSNFPVIMGSLGLLIGGKTILVALVGKLFGISIVSAIRVGLLLAPGGEFAFVAFG
EAVNQGIMSPHLSSLLFLVVGISMALTPYLAAGGQLIASRFELHDVRSLLPVESETDDLQDHIIICGF
GRVGQIIAQLLSERLIPFVALDVRSERVAVGRALDLPVYFGDAGSREVLHKVGAERACAAAITLDTPG
ANYRTVWALSKYFPNVKTFVRAHDVDHGLNLEKAGATAVVPETLEPSLQLAAAVLAQAKLPMSEIAAT
INEFRSRHLSELTELCETSGSSLGYGFSRVVNKGKVQPPDSSDENQVSEGTLAI
```

FIG. 40

Nitab4.5_0001620g0100.2 coding sequence (SEQ ID NO. 37)

```
ATGGGCTTTGCTTACTGTTTATGGCAGCCGAATGCTTCACATTGTGGTGAAGCTTTGAACTACAGGAT
ATTAGATAGGAAAAACAGCTGTGATGTAGGGTTGAATCATAAATTGCTTGGAAATGCTAGGGTTTTAT
GTAAGAATAGGCTGGGGAAAAGGTTGAAACGGAGTGTGGCCTGTAGTGATAATAGTTTAGCATATTCA
AGGATACGATTTAATTGTGCTTTGTGGAAGTCCGATTCAAGTGGGAATTTGATGCGCCGTAAGGCTTC
TAGGGGAGTGAAATTGCCTCGGTGTCAGGGAAATGATTCAGTTGCGTTTATCGATGGTAATGGTAGAA
ATGTGGAGTCCAGTGAGAGTGCTGAAGATGGAGCTCTGAGTGCTAATACTAATGGAATCGCGGAAATT
AGTTGCGCAATTGAGTTGGAGGAAGATAAAGAAGAAGAAACAGAAGGAGATAATTTGGATGAACTAAG
GGAGTTGTTGCAGAAGGCACTCAAGGATTTGGAAGTTGCACAGCTGAACAGCACAATGTTTGAGGAA
AAGCACAGAAGATATCAGAAGCTGCTATAGCGTTAAAAGATGAAGCGGCTAATGCCTGGGATGATGTA
AACAAACAACTTGATAGTGTTCAAGAGATTGTAAGTGAAGAGATGGTCGCTAAAGAAGCAGTTCAAAA
AGCAACAATGGCCCTTTCTTTTGCTGAGGCAAGGCTTCAGGTTGCTCTTGATTCAGTACAAGCTGCAA
AACAAAGAATTATGTCTTCAGAAACGTCTGAAGATAGCAAAGGGGAAGATTCAACTTCATTGATGGAG
GAAGAGGCAGCACTCTTAGCTGCTCAGGAAGATATAAAGGAGTGTCTGGACCGTTTTGGAAGTTGTGA
GGCTGAGTTGAGGCGTCTGCAGAATAAAAAAGAAGAGCTGCAAAAGGAGGTTGACAGACTGAATGAGC
TAGCTGAGCAAGCACAAAACAATGCTTTAAAAGCCGAGGAAGATGTTGCAAACATAATGCTTTTAGCT
GAACAAGCTGTTGCTTATGAGCTGGAGGCTACTCAAAGGGTCAGTGACGCGGAGATCGCTTTGCAGAA
```

FIG. 40 (Continued)

Nitab4.5_0001620g0100.2 coding sequence (SEQ ID NO. 37)

```
AGCCGAGAAGAACCTAGCTGTGTCAATTGTTGACTCCCCAGAAACTTCAGTTTTACAGAATGGATCAT
CTACTCAAGGGCAAGTGTTGGTCGATGGGACCCTTAGCGAGGATGAGGTACTCCCTAGAAATTCAGTC
GATAGTGTTATTGAAATAGATAGGGAGGTACAACTGGAGGATGCTTGGGCGGCAAGTGGGCCTTTGTC
AACTGAGGAGTCACGTATCTCTGATGAGAGTGATGAAGAAGATAGAAAGTTAGTTCTAGACTCCTCAA
AAGATTCTGATTCTGATACAGAAAAACCAAAAGTGTTCAAAGTCTGAGGCAGGAGGTCAACAAGGAA
TCAGCTAGGGACAGTTCACTTAATGCTCCCAAAGCATTATTGAAGAAATCATCCCGTTTCTTGCCTGC
ATCTTTCTTCTCATTTCCCACAGATGGTGAAGAGTTCACACCTGCTTCAGTTTTCCACAATCTCATGG
AGTCTGCAAGGAAGCAATTGCCCAAGCTGGTGGTTGGCTCATTACTGATGGGAGCAGGAATTGCCTTT
TACGTCAATCGATCAGAGCGAATTTCTCAGTCGTTTCAGCAGCCAGACATCATTACCACCAGCATTGA
TGAGGTTTCAACAAATGCAAGACCTCTGGTTCGACAAATAAGAAAACTGCCCAAGAAACTTAAGACAC
TAATGGAGATGCTTCCTCATCAAGAGATAAATGAGGAGGAAGCTTCTCTTTTTGACATGTTATGGCTA
TTGCTCGCAAGTGTTATCTTTGTGCCGATCTTCCAGAAAATTCCAGGAGGAAGTCCTGTTCTTGGGTA
TTTGGCTGCTGGAATCTTGATTGGACCCTATGGTCTTTCTATCATACGTCATGTACATGGGACCAAGG
CTATAGCTGAATTTGGAGTTGTCTTCCTGCTATTTAACATTGGCCTAGAGCTTTCCGTTGAGAGACTA
AGTTCAATGAAGAAATACGTTTTTGGGTTGGGTACTGCTCAGGTCTTAGTGACAGCTGTTGTGGTCGG
GTTAGTTGCTCATTTTGTTGCCGGGCAGGCTGGACCTGCTGCAATAGTGATTGGGAATGGTCTTGCCT
TATCTTCCACTGCGGTTGTCCTCCAGGTATTGCAGGAGCGAGGTGAGAGCACATCACGGCATGGACGA
GCGACATTTTCTGTATTACTCTTTCAGGATCTGGCGGTGGTTGTTCTACTCATACTGATACCACTAAT
TTCACCAAATTCATCAAAAGGAGGGGGTTGGTTTCAGAGCCATAGCTGAGGCCCTTGGTTTGGCTGCTG
TAAAGGCAATTGTAGCCATCACTGCCATTATTGCTGGAGGACGTCTGCTGCTGCGGCCTATTTATAAG
CAGATTGCAGAAAACCAAAATGCAGAAATATTTTCGGCAAATACGCTTCTTGTTATCCTTGGGACTAG
TCTTCTGACAGCCAGGGCTGGCCTCTCAATGGCTTTAGGTGCATTTTTAGCTGGTTTGCTTCTGGCAG
AAACTGAATTTTCATTGCAAGTTGAATCAGATATTGCTCCATATCGTGGACTCCTATTGGGTCTCTTT
TTCATGACGGTTGGAATGTCCATTGATCCCAAGCTTCTTCTTTCAAACTTTCCAGTTATTATGGGCTC
ATTGGGACTTCTAATTGGTGGCAAGACCATCTTGGTTGCATTAGTTGGTAAACTGTTTGGTATTTCAA
TTGTATCGGCAATAAGAGTTGGTCTTCTAGCTTGCTCCTGGTGGAGAGTTTGCCTTTGTAGCTTTTGGT
GAAGCTGTTAACCAGGGTATAATGTCTCCTCACTTGTCATCTCTGCTATTTCTTGTGGTTGGAATTTC
AATGGCCCTCACGCCATATCTAGCTGCTGGAGGCCAATTAATAGCATCTCGTTTTGAGCTGCACGATG
TGCGAAGTTTATTGCCTGTGGAAAGTGAGACAGATGATTTGCAGGATCATATCATTATTTGTGGATTT
GGTCGTGTTGGCCAGATCATTGCCCAACTTCTCTCCGAGCGACTGATTCCGTTTGTTGCACTTGATGT
GCGAAGTGAACGAGTTGCAGTTGGTCGTGCACTTGACCTTCCTGTATACTTTGGTGATGCTGGTAGCC
GAGAGGTTCTACATAAAGTTGGAGCTGAAAGAGCATGTGCTGCCGCAATAACATTAGATACTCCCGGT
GCAAATTACAGAACTGTTTGGGCCTTGAGCAAGTACTTTCCCAATGTGAAAACATTGTACGTGCTCA
TGATGTGGATCATGGCCTCAATCTAGAAAAGGCTGGAGCAACAGCGGTTGTGCCTGAGACCTTGGAAC
CAAGCCTGCAGTTGGCCGCTGCTGTCCTTGCACAAGCTAAGCTGCCAATGTCAGAGATAGCGGCAACA
ATCAACGAGTTTAGGTCCCGCCACCTCTCTGAGCTTACAGAGCTATGTGAAACTAGTGGAAGTTCTCT
AGGCTATGGATTTTCTCGTGTGGTGAATAAAGGCAAAGTTCAGCCTCCAGATTCTTCGGATGAGAACC
AAGTCAGTGAAGGAACACTAGCAATATGA
```

FIG. 41

Nitab4.5_0001620g0100.2 genomic sequence (SEQ ID NO. 38)

```
GAAGTTTCCATCAAAACAATAAGAAGAAGGGTAATTGTGTAAATGCAGAAAATGGAATATCCACCAAT
AAACCCTCTAATCCAATTTTGTCATGTTCCCCAAATGGAGGGAGAAAACAAAACCTGAAAAGAAAAA
AAAGAAAAGATTTCTTCTCATTATTTCAACTTTTCAAGTAACCGCAGAGTCGCAAACGAAAGGTTGTT
CTTCGGACAAAGCTATAAAAAATCAAAACTGATAGGAAGAGCCAATAAGCAAAGTCAATCCAATCATT
TTCTGACCTAATTTTCCGCCATAGATATTCTTCTCTCAGAACTTGAAACTGTCACTTCTATCGGTATA
TTCAAACTTCTCTCTTCTGTTTTACTTCATTTTCACTACTGTCAACTTTAACTTCAGTATATGTATCG
AAACGGAATGTTGATTAATCGCGAAATCACTTTCAGTTTTTTCAGCTTGCAAATATTTGTTGTGGTGA
TTTTAACTGATTGTTTGTGGCTCCTATGAATTAATTTTCACTTGTTTGTTGATTGAAGTTGAAAACTT
GCTTTATTTGTTTTTTAGGGGTTTGATTTTGAGGTAATGAGAATTGGCGGCATTGTTTTGGTGTATTT
TTGACGTTTAGTGTGTTAGAGGAGAGGAGGATGGGCTTTGCTTACTGTTTATGGCAGCCGAATGCTTC
ACATTGTGGTGAAGCTTTGAACTACAGGATATTAGATAGGAAAACAGCTGTGATGTAGGGTTGAATC
ATAAATTGCTTGGAAATGCTAGGGTTTTATGTAAGAATAGGCTGGGGAAAAGGTTGAAACGGAGTGTG
GCCTGTAGTGATAATAGTTTAGCATATTCAAGGATACGATTTAATTGTGCTTTGTGGAAGTCCGATTC
```

FIG. 41 (Continued)

Nitab4.5_0001620g0100.2 genomic sequence (SEQ ID NO. 38)

```
AAGTGGGAATTTGATGCGCCGTAAGGCTTCTAGGGGAGTGAAATTGCCTCGGTGTCAGGGAAATGATT
CAGTTGCGTTTATCGATGGTAATGGTAGAAATGTGGAGTCCAGTGAGAGTGCTGAAGATGGAGCTCTG
AGTGCTAATACTAATGGAATCGCGGAAATTAGTTGCGCAATTGAGTTGGAGGAAGATAAAGAAGAAGA
AACAGAAGGAGATAATTTGGATGAACTAAGGGAGTTGTTGCAGAAGGCACTCAAGGATTTGGAAGTTG
CACAGCTGAACAGCACAATGTTTGAGGAAAAAGCACAGAAGATATCAGAAGCTGCTATAGCGTTAAAA
GATGAAGCGGCTAATGCCTGGGATGATGTAAACAAACAACTTGATAGTGTTCAAGAGATTGTAAGTGA
AGAGATGGTCGCTAAAGAAGCAGTTCAAAAAGCAACAATGGCCCTTTCTTTTGCTGAGGCAAGGCTTC
AGGTTGCTCTTGATTCAGTACAAGCTGCAAAACAAGAATTATGTCTTCAGAAACGTCTGAAGATAGC
AAAGGGGAAGATTCAACTTCATTGATGGAGGAAGAGGCAGCACTCTTAGCTGCTCAGGAAGATATAAA
GGAGTGTCTGGACCGTTTTGGAAGTTGTGAGGCTGAGTTGAGGCGTCTGCAGAATAAAAAAGAAGAGC
TGCAAAAGGAGGTTGACAGACTGAATGAGCTAGCTGAGCAAGCACAAAACAATGCTTTAAAAGCCGAG
GAAGATGTTGCAAACATAATGCTTTTAGCTGAACAAGCTGTTGCTTATGAGCTGGAGGCTACTCAAAG
GGTCAGTGACGCGGAGATCGCTTTGCAGAAAGCCGAGAAGAACCTAGCTGTGTCAATTGTTGACTCCC
CAGAAACTTCAGTTTTACAGAATGGATCATCTACTCAAGGGCAAGTGTTGGTCGATGGGACCCTTAGC
GAGGATGAGGTACTCCCTAGAAATTCAGTCGATAGTGTTATTGAAATAGATAGGGAGGTACAACTGGA
GGATGCTTGGGCGGCAAGTGGGCCTTTGTCAACTGAGGAGTCACGTATCTCTGATGAGAGTGATGAAG
AAGATAGAAAGTTAGTTCTAGACTCCTCAAAAGATTCTGATTCTGATACAGAAAAACCAAAAAGTGTT
CAAAGTCTGAGGCAGGAGGTCAACAAGGAATCAGCTAGGGACAGTTCACTTAATGCTCCCAAAGCATT
ATTGAAGAAATCATCCCGTTTCTTGCCTGCATCTTTCTTCTCATTTCCCACAGATGGTGAAGAGTTCA
CACCTGCTTCAGTTTTCCACAATCTCATGGAGTCTGCAAGGAAGCAATTGCCCAAGCTGGTGGTTGGC
TCATTACTGATGGGAGCAGGGTACAACTACTATAAAACTGTTCATTCTTTGTTGCTTTTGAAAGATGA
AGCTATTTCTTTCTAGCTGCATGTATAAGTGCCTCGTTAGGATACAATCTTTGTACCATTAGATTGGT
ATAGCTTGTTTATGGTACTTGATATGCTTTTGACGTCTGTCACAGAATTGCCTTTTACGTCAATCGAT
CAGAGCGAATTTCTCAGTCGTTTCAGCAGCCAGACATCATTACCACCAGCATTGATGAGGTTTCAACA
AATGCAAGACCTCTGGTTCGACAAATAAGAAAACTGCCCAAGAAACTTAAGCACACTAATGGAGATGCT
TCCTCATCAAGAGGCATGCTTCTTTAACTCCCTTTAGTTTAACGCCTGCAATCACCATTTGTTAGGA
AGGGGCTTTACTTCTACTTGCTAATGGTGTTGTTGCTCATTTCAGATAAATGAGGAGGAAGCTTCTCT
TTTTGACATGTTATGGCTATTGCTCGCAAGTGTTATCTTTGTGCCGATCTTCCAGAAAATTCCAGGAG
GTAATTGAATTTTGCTACCTTCTTTTATCGCATGAGGACAGTGACTAGGGGCTTCTTATGTTAAATTG
TTCACCAAACTTGTTCTTGATGTAAAGGTTTCCTCGTAGGTCTTTCCTTGAACATGTTCTAAAAATTG
AAAAATGATATTTGATTATTAGACACTTAGTTTTCGGTGACCTTGATGTATGTCACAGATATGTGCCC
TTTGCTCCTCTGTGACAGACGTACTCTTGTTTCTTGTTAATGGTTCATCTTCTGTCTGCTATAATGTG
TAGGAAGTCCTGTTCTTGGGTATTGGCTGCTGGAATCTTGATTGGACCCTATGGTCTTTCTATCATA
CGTCATGTACATGGGACCAAGGCTATAGCTGAATTTGGAGTTGTCTTCCTGCTATTTAACATTGGCCT
AGAGGTACAGTCTAGGAAAATTGACTAGTTTATTTCTTTCTGAATGTGTTACAAATACTGCCTTAATA
ACCTCTGTTTGTATTCTCTTTGACAGCTTTCCGTTGAGAGACTAAGTTCAATGAAGAAATACGTTTTT
GGGTTGGGTACTGCTCAGGTAATTGAAAAAAATTGAGCACTTGGGAGTTGTTAAGCCCCCTCCATAAT
GCTTATAGAGTATGGTCTCAACGTTTTAGGTTTCCACACTAATTATTAATATATTCAAATGAACGCAG
GTCTTAGTGACAGCTGTTGTGGTCGGGTTAGTTGCTCATTTTGTTGCCGGGCAGGCTGGACCTGCTGC
AATAGTGATTGGGAATGGTCTTGCCTTATCTTCCACTGCGGTTGTCCTCCAGGTAAATCCTTCTATAT
ATTTAGCAGGTCTTCCTTGCTGGATGAATGATGGGCGATTTAGCTGGATGAATGATGGGCGATTTAGC
GTTTGAGTAATTTGTTGTACTCATTAAGTACGTTGATTTGGTGACCGTTTCAACACTCTAATTAAAGT
TAATGCTTAAGCAGGCAATATTATTATGCTATGTTCCCCAAAAGTCCAGAAGCTATAATGCTAGATAA
GGGTTGATGCCGAGATATCAAATCAGCATTGGAGTTTTTCTTATCATTTCCTTGTTGATTCACCATAT
TTACTACAATCAAGGAATTGTAGTTTATCTATAATTGGCTTTGTCTATGTGCCTGTGACCCTCCCTCT
TCGAAAAATGAAACTTTAGTAATTAATTTATTATGTTGCATATCTGCAGGTATTGCAGGAGCGAGGTG
AGAGCACATCACGGCATGGACGAGCGACATTTTCTGTATTACTCTTTCAGGTATCTGCATAGAGACAG
TACAAAATTGTCGCATCTTTCTCCTGAGATGGGTGAAACTTGGAATATTATGTGTATCTATGCATACA
CGCGAATCACATATATTTACTTGCCATCACATATAGGCTGCTCTCATGCACTTGAAATGATGACAGTC
AGTGCTGCGGTACTTTTAGATTTTTCTTTCTGATATGATTAACCAAATTCTTCCCTTTATCCTCCAGG
ATCTGGCGGTGGTTGTTCTACTCATACTGATACCACTAATTTCACCAAATTCATCAAAAGGAGGGGTA
TAGACTCTTGTTACCGTCTTGTCTTCTGGAAAAATTATTTAAAATTTTTGTGTTTATTATAATTACGA
TTCCAGCTATGTGAACTGGACCTGTAATATTCACCAAACTGAGAGCCAATAGCTAATCCCCTAAAGTC
ACACGTGAAAACAACATTCTTTGCTTTTGATAGCTGTGAGTTACACTATAGCTGTTTTCTCAAACTGC
CATTATTATAACAGAACTTATTTCTTCTTAGGTTGGTTTCAGAGCCATAGCTGAGGCCCTTGGTTTGG
CTGCTGTAAAGGCAATTGTAGCCATCACTGCCATTATTGCTGGAGGACGTCTGGTAAGGTGTTTGTTC
```

FIG. 41 (Continued)

Nitab4.5_0001620g0100.2 genomic sequence (SEQ ID NO. 38)

```
ATGTAGAATCACTTCCAATATTATAAATGCTTCTGATTAGTATATAATTTTTAAGTTCTAACTACATC
TCTTACGATATTTTGGACTTTAGTCTTTCATTTGCTTTTGTCTATACATTATTAAAGTAGGGTTTGAT
ATTTATCTATTGCAAAATATAAATAGGTTTTAATTCCGTTTTTCACTTTGCAAGTCTTGTAAGATACA
TTGCTGTAATGTGAGGACGTTAATATTTTTGTTCTCTATTCCAATTTCAGCTGCTGCGGCCTATTTAT
AAGCAGATTGCAGAAAACCAAAATGCAGAAATATTTTCGGCAAATACGCTTCTTGTTATCCTTGGGAC
TAGTCTTCTGACAGCCAGGGTACTTATGATCACATTGTTATGTGTTCATGAATACTGCCCAATTCTG
TTAGAACTGTTATCTTGTTAACGCTATGATGTGTTATCTGATGTAAATAATTCAGGCTGGCCTCTCAA
TGGCTTTAGGTGCATTTTTAGCTGGTTTGCTTCTGGCAGAAACTGAATTTTCATTGCAAGTTGAATCA
GATATTGCTCCATATCGTGGACTCCTATTGGGTCTCTTTTTCATGACGGTAGGTGACAATCTTGTTTA
TTGTACAATGTGAATGCTATTTTCTAATCCTACAATTTGTCATTGGAGTTAAGGTAGGATAGGTCTT
GGTAAGGTGCTATTTACATTTAAAGATTCTCACTCTGCAATCTCTAGCACCAACTTGTAGACCTTAGT
TGTCTCTCCTGAGTTGTTCTCTTTGAATGAATGTACTTCTCAGTAACATTTTATCTATTTTAATCAAC
TTTTATCCAGGCTGAAGGGAGAATCGTTTATGAATAAATTATTATAACTAGTGCTACTTTGTGACTTC
AAAACTGAACAATTATCATCTGGTTGCAGGTTGGAATGTCCATTGATCCCAAGCTTCTTCTTTCAAAC
TTTCCAGTTATTATGGGCTCATTGGGACTTCTAATTGGTGGCAAGACCATCTTGGTTGCATTAGTTGG
TAAACTGTTTGGTATTTCAATTGTATCGGCAATAAGAGTTGGTCTTCTACTTGCTCCTGGTGGAGAGT
TTGCCTTTGTAGCTTTTGGTGAAGCTGTTAACCAGGTTTATCTCTGATAGCTTTAACCTATTACAAGC
AATTCTGAGCCGTTAATAAAATTCTTTTATTCCATTTCTTTTTCTCCGTTCTATTGCTATGCTGTTCA
AACAGCATCTTCCTTTATCAAGGAATTGTGGACCTTTTCTACAATTGACCTGTGTGCTGAAATCAAAT
GTTGAGCTAGTGAGATCCTGTTATTGGGGAAGTGGAGACAAACTACCATCAAATCCTTCCAGTTTCTA
TCTATGGCCGCTGTCTTACTTCTATTTTACAAATCCTCTTAGAGACTTGTTCTTTCTCATAGCTACCC
TTAAATAGATTCAGAGCTGCAACATATCTGAACAGTACAATGCTAAGCTCTCTGAGGATCTTTGCCCC
ATGATAAAAATATATCTTATTAGAATAAGTTTATTATCTTATTTAATTAAATTTTCTCCATGATTTTG
CTTTTCTTTTTCCAGGGTATAATGTCTCCTCACTTGTCATCTCTGCTATTTCTTGTGGTTGGAATTTC
AATGGCCCTCACGCCATATCTAGCTGCTGGAGGCCAATTAATAGCATCTCGTTTTGAGCTGCACGATG
TGCGAAGTTTATTGCCTGTGGAAAGTGAGGTATAGTCTCCTACTTGGGGGCACAATCTCTCTTCTTTG
GTTTTAAGCGAGAATAAACCATTTACATGTTCGTAAAATCTTATTTTTTGACAGTTTGGTTTCAGGTT
GTCAATAGTAACAGGGTATTGGAATTAAAGGATTAAGGTTAAGGGGTCTTAATAGTTAATACTATTGT
TAAAAAAAAAACAGTTGTGGAGACTAGGAAAACTGGAATTTTGGTGATAGAAAGCTTCCTTTTTCT
CCTCTTCCCTACCTCAAATTTCTTCATCTTCATTCTTCATCCCTGTCTGCTTTCTCCTTTCAGTGCCT
TTCTTTGATCCTGGTTCATCTCTTAAGTTTTGTGCTCTACTTTGTTGTTGCTATTTAAGTCCCATGCC
TCAGTGTTATGGTACTAAGCCTTTTGGACCCTCGCAGTTTCTCTATGCAAAGATTTTTTTTTCCTTGA
AAATATTGTCTATTGAATTATAGCTTCATATCATCATCTGATTAGGTTTCCGCTGAACCTTATGCCTC
ACTTTGTTTTCCTTCCGAGCTTATTTAACATAATTTTTTTCTTCTTCTAATTTTAAGTGTTCAATACT
TAATTTGTTCTTTAACTTATTGCTTCTTTGCTTTAAATTTAATTGCTATTGGTAATGTCAGCCTTTAT
TACGAAGATCATTTGTCTGAGAAGTAACAGATATTCAGTTACCAAAGCTCATTACTTGAAGGACTACA
TCATTTAATGATATCTTTCTGGATTATTACCTTCGTAAATGTAATGAAGATTCACTGACTTAAATTT
ATTGCATAATAAAAGGTGTAGACTGATAGTACCTTTTTTCCTTCGCAGACAGATGATTTGCAGGATCA
TATCATTATTTGTGGATTTGGTCGTGTTGGCCAGGTTTTGCCCCGTGCTTCATGAATTGGTTAAATTG
ATCATTTGACAGAATGATTTTCAAACTTTGGAACAATGAAGCTATTTCCATCTTCTGCCTGTTGAATT
AGTTTTCATCTTAACAGATCATTGCCCAACTTCTCTCCGAGCGACTGATTCCGTTTGTTGCACTTGAT
GTGCGAAGGTATGATTCTCTTTTTACTCACATTCAACTGATTTCAGCTCCTGTAGGTTCAGTGAAGAT
TTCATCTGCTGTTTGTTAAGCTGACATAGAATTTTTTCTTCCATAGTGTCATTTCCTGATATGGTGGT
TCTAAAATTTTATATTTTTTCGTAAAAGAAAAGAAAAAAAGCAGGAGGAAGAACTTATATCTTTTGAGG
TGTAAGTGACTTTCTGCCTCAGATCTCTATATTCCTATGCCGTGCTTAAGTTTTCTCACCACTATGGT
TCTTTTCACAACTTACGAAGCAGCACCTCCACTATCAACTACTCTTAAAAGCCACCAGATCTTTATAG
CTGACCAAATGCAAGAAATGGTTTTTCTTTATAAGATATTATATAGTTTGTTAATTGTGAGTCATCA
GTCATTATCAACCTTTAGGATATTAAAGTAAAAGTTTTTGTTTTTCTATCTAAATAAAATGTTCAT
ATTCATGCATGCATCCAAGGGATGACAGTGAAAGAGAAGCAGATGATGGTTTTCCTGTAAGAGTGCCA
GTGCCAAGCCAGAGAACTGAGGAAACTGGTCTAGAACAGAGAAGTCCTTAATTGAACTTGTTAAATAG
TTATGTGTAAATAGTCCTAGTCCCATATGTAGGAGTAGAATATGTATCATATATAGAGTTCATTGCAG
TGTTTTAAAAAGCGATCGATCTTTAAGCGAGAAGGGACGCGAAGCGATGGCTGCTCGCTTTTCCATGC
CTGAGGCGACNNNNNNNNNNNNNNNNNNNNNNNNNNNTATATATGTGTGTGTGTGTGTGTGCGTGTGT
GTGTTATATTTTAGTTTATTTGATTTTTTTAATATGTATTTCAGTTATAAAATTAATTATTATATAT
ATTATAGTAGCTTTGATTTTGCTTTTCCTATGGTTTGTGGAGGATTGGTGGTACCTACTTTTGAGTT
TTTAAATTGAACTTTTTGATTATTTATATTGTGTCTTTGCAAGGTTTACATTATATTTTTTAAGAATT
```

FIG. 41 (Continued)

Nitab4.5_0001620g0100.2 genomic sequence (SEQ ID NO. 38)

```
GCGCTTCACTTCAATGAAGCGTGCGCTTCGCTTTTGAAGCGAGGGGAGCCTCTGTCGCTTTTTTGCGC
TTCTCACTCTCAAAAACACTGGCTCATTGCATCATTGTTAAAAAATAGATTTTTCTTCCGTGCATTCT
CGCATGGTATCAGAGCTTCAGTGAGAATTATCGTTGTGCGTCATTCCAACGACATTCGGGAAGAAAGA
TCTCATTGCCGTGCAATTTTCCGGCAATTTCGTCTTGTTCCCAGGGTTCATCACTGCTACAATGGTAC
TATGCATATACCAGTACCACCATCAGATCTGAAACCCTTGTGCGACCAAACCCTAAAAATTCCAGTCC
CATCGGAACAGAAAAGTCAGTAACCGTGCGTCTTTCCGGTTGACGATTCAAGATTGATTTGCGTTATC
TCCTCATTGGTAAGTGTTGTGCGAAAACCAACACTATCACCTTGTTCGGAAAAGTAAGACGACAAAAC
CCCAGTCAATCGCTCCGGCAGAAAGTCACGTGCCGCCAGAACTAGGGTTTCGGCGAGCTACATTAACT
TTTCCGGCGCGTGTGAGCCATCCCGGCCCATTTTTTGACAAAACTTCTCAGGACAACTTACTCGTCCAG
TGATTCCGAACCTACCCATATAAATTACATCAAATTCTGACAACTTTTATTTTTTTGCGACATGAACA
GTGGTTTTCCGGCATGAACAGTAATTCCAGAAAAAGTTTGTGTATTCTGGTGGTGTTTTAGAATCTAT
TTTGTAGTGTGGAATTCGGCTTAGTCTCACTATTTTCAAATTTTTCCGGCAACTGTTCGGCCAACTTT
TGTTTATCAGCAACCACCTGGTTTTGTTGCTCAGGGGGAGTCTAGTGGCCTTGTATGTCGAATGATCA
GCTTGCAGATATTTTCACCAAGTCCCTCATTGGTCCTCATATTAGTTACATATGTAACAACCTCGGTA
CATATGATTTGTATGCACCGGCTTGAGGGAGAGTGTTAGATAGTTATGTGTAAATAGTCTTAGTCCTA
TATGTAGTAGGAGTAGAATATGTATTATATATAGAGCTCATTGCATCATTGTTAAAAAATAGATTTTT
CTTCCGTTCATTCTCACAGAACTTTTAGATTATTTCACAAATCAGCTATGTTGCGCGGACTCCTCATT
TCAGCCCGCACCCGTGTCTACATGACACTAGTAAGGGTAAGGGTGTGAGATTCATACCGAATGTGGTC
AACCCGACATCAGATACTTTGACCACAATCCATGGACAAGTTTGAGGAAAAAAATGGGACTTTGATTT
CTCAAGATAAAAGTTAGTACATATTTGAAGACATGGGAAATGGCATAACTTCAATAGTCGACCCGTAT
TCGTGAAATGTGTATCCGTATCTGGATCTTCACACCTGATGATTTAGGATATTTTTATAAATCTATCT
TTAGAATTTTGAATTATTTTTCGCCGAATCCCCTCACCCGTATCTGGATCCCGTATCCCCAAATCTTT
TAGATTATGAAGGATCCGACCTTTGGATCCGCACCCGGATCGGATACCCGCACCCGAGTCCGAGCAAC
ATAGCAAATCAGATATGAATTAGAATCAAAGTTGGTTCCCATCCAAAGCTTGTAATGTTGCTCTCTAT
AGTACTCTTTAACTAAGATGGATTGTGTGGCGTTGCAGTATCTTATGTAGACACGGTTACATGAAT
TTCTCAAAAACATAAAAGGTACTAGAGTTTCCTTATATGCTGGAGCTTTGATTGTAAGTGGATCGTG
ACTATCATCATATTGCTCTAGAGTACTTTGATATTCAGCAGTTGATTATTAGAGCATCAACAAGTATT
AACTTGATTACTGCATCTATAAGAAAGGTTTCTTTGTGGTGGTGGGGGCGGAGGGTGCAGGAAATGTT
GCTTTCACTTAAATTTTCCAATTGTTATCAGTTATCATGAATATCCTGAGGCTCATCTTAATAGATGT
TTCTATAATAAATGCAGTGAACGAGTTGCAGTTGGTCGTGCACTTGACCTTCCTGTATACTTTGGTGA
TGCTGGTAGCCGAGAGGTAAAGCAAATTCCTGAACTTAAGATTATCATTTCGGATATTTTATTTTGAC
ATTCTGTGTTCCGATTACTAGGTTCTACATAAAGTTGGAGCTGAAAGAGCATGTGCTGCCGCAATAAC
ATTAGATACTCCCGGTGCAAATTACAGAACTGTTTGGGCCTTGAGCAAGTACTTTCCCAATGTGAAAA
CATTTGTACGTGCTCATGATGTGGATCATGGCCTCAATCTAGAAAAGGCTGGAGCAACAGCGGTATCT
TTCTTATTCTAATTTCTGCTATTGATCTTTTCGTTGGAAACTCGTTCATATTTTTTCACTTAGCATTC
TGTATATCTCTTGATAACATTTGGATTCTGAGTCTTGAAAATTTTGTTTTATTGCTGGTGTATTATGT
TGTGCTATGGTAAAATTTTGTAGTTGTAACATATCATGCATAAAGAGGAAATAGTTGCACATTTGAT
GGTTGGATAAATGATGAACAATGCATTAACTGAGGTGGATAAAAACTTTTACAGGTTGTGCCTGAGAC
CTTGGAACCAAGCCTGCAGTTGGCCGCTGCTGTCCTTGCACAAGTAAGTGGATTTGATAAGCACCACT
TCATCAAAAAAGTAGATTTGATAAGCACCTCAGTTAGGAAAAAGAAAAGAAAAGAAAAGAAAATTGAT
GGCCCTTGTTTGTCTCATTTTGACTGATTTAGTTTTTAAGCTGGTAAGTAATTGATCAGTATAACCAA
ATTCTAATTTGAGAAGTTTCGTCCCAATACTGTAGAGTGATATGGATGATGATTCAATAGCTTATCAT
CATGTATCATTCTACACTAGTCCTTCAGAATGGTATAGCATATGGCTTTCTCAAGGTATAGCATATGG
CTTTCAGAATGGTATACTTTAACATTCTTGACGGAAAGGACCAATTGTTGGATCTTCTGATGCAATAA
TCTTGCTGCGCACTGCATTTTGCGTCTCGACCTCCTTGTAGTCTACTTTTGGCAATCTATAACCATCA
TGAAGCAAATAAAATTCTAAGAATATATTGTGTCTTCTAGGCTAAGCTGCCAATGTCAGAGATAGCGG
CAACAATCAACGAGTTTAGGTCCCGCCACCTCTCTGAGCTTACAGAGGTAAATTATACATGCACTACT
TGTCTTAGCTTTTGGAACGTTGTACGAGGTTCATAGTTCAGATTTTGTCAGATATTTTATGCTGCCC
ACGGGATTTTGTTTTGCAGCTATGTGAAACTAGTGGAAGTTCTCTAGGCTATGGATTTTCTCGTGTGG
TGAATAAAGGCAAAGTTCAGCCTCCAGATTCTTCGGATGAGAACCAAGTCAGTGAAGGAACACTAGCA
ATATGATTACCATTAGAAGAAACAGGGATTTGCGTTGATTGGACCCAAAAAAGAAGAAGAAGGAATTG
AGAAGGGAAGATACTCCTGATAAGTGTATAGTGTTTTACTTAACCCCCTGTTCTTGAAAATTGTACA
GAAGAAATATAGTACGTAGCAAGCAACAAGCTATGCAGGAGAGCAAATCTATTGGCATAACCCAAGGG
CAGCTCAAGGGGAGGCTGGTTAAGCCTTTGCTTTAGGCTCCCAAAATTTTGGGGCCCAGAAAACTTTT
AAGGGCAAAAGCGTTTTTGATCCCTGAATTATTATTTTATTCTGATTTTAGTCCTCAATTTAAATGTG
TGATATTGCTCCTTTAACTTTGACATATGTTAATAATTAACTTTAGTACTGTTAGTTGAAGAAGTAAA
```

FIG. 41 (Continued)

Nitab4.5_0001620g0100.2 genomic sequence (SEQ ID NO. 38)

```
AGGGGGAGAAAGGATACTAGATCCATTGCTTCAACCTGATCATCACCATTACTGATTTAAGATTTACT
TTTAAATATACCATCTAATAAGGGAGAATGCGCATCCTAG
```

FIG. 42

Nitab4.5_0001200g0070.2 amino acid sequence (SEQ ID NO. 39)

```
MATKFGFTITSPRLFHGPFRKKPIFSSSSASLEDVSFCSSNLKLINFAGRKLAIKHRVLVLSPKATTD
QPGQLNEDEVEDSKIMQYCSIDGKGKKSLGEMEQEFLQALQSFYYEGKATMSNEEFDNLKEELMWEGS
SVVMLSTDEQKFLEASMAYVSGNPIMTDKEYDKLKMKLKRDGSDIVVEGPRCSLRSRKVYSDLSVDYL
KMFLLNVPAAVVALGLFFFLDDLTGFEITYLLELPEPFSFIFTWFAALPLILYLSFTITNVVVKDFLI
LKGPCPNCGAENTSFFGTILSVSSGGSTNKIKCSGCGTDLVYDSDTRLITLPEGISG
```

FIG. 43

Nitab4.5_0001200g0070.2 coding sequence (SEQ ID NO. 40)

```
ATGGCCACTAAATTTGGATTTACTATAACTAGCCCTCGCCTTTTTCATGGCCCTTTCAGGAAAAAACC
AATATTTTCTTCATCTTCAGCTTCTTTAGAAGATGTTTCATTCTGTTCTTCAAATCTCAAATTAATTA
ATTTTGCTGGAAGAAAGTTAGCTATAAAACATAGGGTATTGGTTCTCTCTCCTAAGGCCACAACTGAC
CAGCCAGGTCAGCTCAATGAGGATGAGGTTGAAGACAGTAAAATCATGCAATATTGTAGCATTGACGG
GAAAGGAAAGAAATCTTTAGGAGAAATGGAGCAAGAGTTTCTTCAAGCACTGCAATCATTCTATTATG
AAGGAAAGGCGACCATGTCAAATGAAGAATTTGATAACCTTAAGGAAGAATTAATGTGGGAAGGGAGC
AGCGTCGTCATGCTAAGCACTGATGAACAGAAGTTTCTGGAAGCTTCTATGGCTTATGTATCTGGGAA
TCCAATTATGACTGATAAAGAGTATGACAAGCTGAAGATGAAACTTAAGAGGGATGGCAGTGATATTG
TGGTTGAGGGTCCTCGGTGCAGTCTTCGAAGTAGAAAGGTTTATAGCGATCTTTCTGTTGATTATCTG
AAGATGTTCTTGTTAAATGTCCCTGCTGCTGTTGTTGCTCTTGGATTGTTCTTTTTCCTTGACGATTT
AACTGGATTTGAGATCACTTATCTTTTGGAGCTTCCAGAGCCTTTCAGTTTCATTTTCACATGGTTTG
CTGCTTTGCCTTTGATATTGTATCTATCGTTTACAATCACAAACGTCGTTGTTAAAGATTTTCTGATC
TTAAAGGGCCCTTGTCCGAATTGTGGAGCAGAAAATACTTCCTTCTTTGGTACCATATTATCAGTATC
TAGTGGTGGTTCTACCAACAAAATAAAATGCTCAGGTTGTGGGACGGATTTGGTCTATGATTCAGACA
CGCGTTTGATCACGTTGCCTGAAGGAATTAGTGGATGA
```

FIG. 44

Nitab4.5_0001200g0070.2 genomic sequence (SEQ ID NO. 41)

```
TCAAAAAACAGTTAAAACCGGGAAACGATTTTCTTGAATTCAAAAAAATCAAGACAAAAGCTTTTCAA
CATTCAACACTCTCCACACATTCATACACATAACCTTATCTTCATCTCTTATCAAAACTCATCAAATT
CTCCATTTTTCAGTTTTTTCACAAATGCAATATTCACTTCCACTTCACTCCCTCCACCACCACCACTG
CTGCCGCCGCCGTCGCCGCCGCCGCCACAAATGGCCACTAAATTTGGATTTACTATAACTAGCCCTCG
CCTTTTTCATGGCCCTTTCAGGAAAAAACCAATATTTTCTTCATCTTCAGCTTCTTTAGAAGATGTTT
CATTCTGTTCTTCAAATCTCAAATTAATTAATTTTGCTGGAAGAAAGTTAGCTATAAAACATAGGGTA
TTGGTTCTCTCTCCTAAGGCCACAACTGACCAGCCAGGTAAATCAATGAGTTATCATCTGCATGTCCT
TCTTTATGAAATTACGGATTAATCTTATCGAAAGATTCACATGTAATTTTTTATTAGTGACATGATTG
TGTAAATATTTTTATACTAGTCCATGTATATAACTTAAACTATTTTTTTTCTTCTTTGATCAAAGTT
TGATTAAATTATAAAGGGTTTAAGTTGTGTAAGCTGACGATGTCAAGAATTGTACTCTATCGTTGGA
ATTTGACTAGTTATAGTAGATTATTACTCTATTTTTCATGTTACCATATTAGGTTTGATATGTAGAGT
TGCATATTGTGGGTCAACGTAATCTGATAGTGTAAATATTCTTTAAACTGTTAGTGCACAGAACACAA
GCTCTATTTTGAATATTTTTAACATGTAGTCGGCCTACTATAACACTTCTCCTTTACCGGTTAACGTA
TAGGAAACTCCAATATGTTTAAAAGATAAATCATTATCACTATGGTAATTAAATGTGCTTGAAAAAG
GTGGAATGGATATAGAGAATTCATATAGCAGAACCCAACTAGTTTGAACGGAACGAACCTGAAATGAA
GGGAATGGATACATAGAATTCATACAGCGGACTCCAAGTAGATTGAGATTGAGGAATAGTTGTTGATT
GACATTTGATAAAGTATATTCTTGCTATAGGTAGGCCTGTTAGTTGCTGCTTCTTTTTCTATAACTCA
AAGAAAGCAATTATTATGTATCATTGATTTATTGCAAGGCCAACTTGATGTTGCTGCAAATAATAGTG
ATTTTCTTGGCATAACTAACTAACCGCCCTAAGCTTGACAAAGAAGATGCAATCAATCTTTCCATAAT
CTGTCTCGTGCTTTTGCTATCGATCAATTTACAATGCCTTATTCCCAAACATAGGTTCTTTGTATTCT
TGATGCTTCAATGAAATAACAAACTTCATTGACCCTCAAATGTTGGTTCTATACATGACACAGTCCTA
```

FIG. 44 (Continued)

Nitab4.5_0001200g0070.2 genomic sequence (SEQ ID NO. 41)

```
AGCTCAATGAGGAATCAACAAATGAATAGAGATAGAAAGAAGTAATAAAGTGAGACCAATATAGAGAC
AATCAACAACTGATGTTTTCATATGAACTGAAAAACACTCTTATACCTTCTCTCTCTCTGTGTATGTT
TGCTCTATGTTTGTATGTTTTTTCCTCTTCTCCAATTTCTTCTTTTTATGGTGGCGTATACCACATCA
TTTGAAGACTCACTTTTGCTTTCAGGTCAGCTCAATGAGGATGAGGTTGAAGACAGTAAAATCATGCA
ATATTGTAGCATTGACGGGAAAGGAAAGAAATCTTTAGGAGAAATGGAGCAAGAGTTTCTTCAAGCAC
TGCAAGTAATGAAGCAGAATCAGTTACTAATTCGTCGATTGTTTTCATTCTCATTCTACTAAAGTTAA
CTAACTCTTTCTTGGTTCTGTACCACAGTCATTCTATTATGAAGGAAAGGCGACCATGTCAAATGAAG
AATTTGATAACCTTAAGGAAGAATTAATGTGGGAAGGGAGCAGCGTCGTCATGCTAAGTAAGTAAGAA
TTTCTGTCTGTTTATGTCTCATTGGCACTTAAAATAGGTATAGTAAGAGCAAATTCCTAACAATGCAG
GCACTGATGAACAGAAGTTTCTGGAAGCTTCTATGGCTTATGTATCTGGGAATCCAATTATGACTGAT
AAAGAGTATGACAAGCTGAAGATGAAACTTAAGGTACTTGGTTATTAGCATTATAAAGTCAGACCTCT
CTATAACATAATCGCTATATAACAGTCATTCACTATAAAGTCAAGTTTTTTTATGGAATCAATTTTT
ATATTATACTATAATATATGTTCTCTATAACACCACTTCGTTATATCAACCAATAAAATTCGGAACAA
ATAAGGCTGTTATAGAGAGGTTTGACTGTATTATTTATTGTTCTTGATAAGATAAGAGAAGATCCAAT
AAATGAAAAGATTTGTTATTTTGACAGTTTTTTCAAAAAAAGCAACTGATTTTACTGTATAATACTG
AATGTGTTGTACTTTCTTTTCCTATCACCATTTAATTGGTAGTTTAAGCTTATCAATTTATGAAGTAG
TTGAACTATGTTAGTCATTGCTATTCTTCAACTTATTGCCCTTACAAATATGAACAAATCAAGTTAGT
TGTTACCGTTCTTTCTGTTGCTTTCTTTGTTTCTTATAATATCGCGGACTTATGTAGTTTTTCCTGTA
TTGACATCTCTTAATTTTTCAGAGGGATGGCAGTGATATTGTGGTTGAGGGTCCTCGGTGCAGTCTTC
GAAGTAGAAAGGTTTGTACTACTTTTCTGCTCAATGAGACATTTACTAGCTGGTTAATAGGTACTCAT
CTTTTATATTGCATCTGTGAAAATACTTATTTTGTGCCATCATACATTCGAAGAGGATCCTTGGAGTC
TCCGTGTGACTATAGGTCATGGGTTCGAGCTGTGGAAGCAACCACTAATGCTTGTATTAGAGTAGGTT
GTCTAATACATTAGCTTCAGTCTGCGGCAGATCTGCGGTCTGCAGATCAATTCTGCAACCGCAGAAAC
GCCCTGCACTTCCAAAATTATTTTTCAACTCCCCAACGCACTGTTCAACCCAAAAAGTCGGAACCGAT
TATCAACGCATAAGTCTACCTCGGCATCATGAAACCCGGGTTTAGGTGAAATTTTCGGGGCCTTA
CATCCTCCCCGCTTAGGATCATTCGTCCTCCAATGAGGGTCAAAATTCAGTATTAGCACCCAATGTGA
CTCAGTTGCTATAGCTCACACCGGCAGTTCCAAATTCGAAGAGGATGCTTTGTGCAGCGGGCTGCCCT
TTTTAGCCATCATACATTCGTGCAAGATGTTTATGAGGTTAAGTGGTTAAATGAACTTTACTTGTTGC
AGGTTTATAGCGATCTTTCTGTTGATTATCTGAAGATGTTCTTGTTAAATGTCCCTGCTGCTGTTGTT
GCTCTTGGATTGTGAGTACTACTTAAAACTCTCAGCATTATAAGTTTTCATTTCTTTGTACATTGTCA
TTAGTTTCTCAACCCGGTTATGAAGCAACCAACATTATTATCCTCTAATAGATATGTTTGGCTAATGT
TTGCTAGGTTCTTTTTCCTTGACGATTTAACTGGATTTGAGATCACTTATCTTTTGGAGGTAATCATA
TCTTGTTATCTAGCCTGGTTCTTTATTGTAATCCCTAGATTATCAAGTGGTTATTTGCAAAGATCAG
AGTATTCATTAACCTTTGTCAAATGCTATAATTTTGTCAATTTTGCAGCTTCCAGAGCCTTTCAGTTT
CATTTTCACATGGTTTGCTGCTTTGCCTTTGATATTGTATCTATCGTTTACAATCACAAACGTCGTTG
TTAAAGATTTTCTGATCTTAAAGGTAAGATTTCGGAAACATTGTGCGCGTAGTATTATCTTATATGCT
ATGTGTTTGATATTAACACACAATTTTCAGGGCCCTTGTCCGAATTGTGGAGCAGAAAATACTTCCTT
CTTTGGTACCATATTATCAGTATCTAGTGGTGGTTCTACCAACAAAATAAAATGCTCAGGGTAAGTCC
ATAAGCCTTAGTTTTTAGGTATTTTTCATCTTTCTCTGCTTGATCTGTTCATAGTGTAATCATCGCCA
TGATCTTTCGCAGTTGTGGGACGGATTTGGTCTATGATTCAGACACGCGTTTGATCACGTTGCCTGAA
GGAATTAGTGGATGATTCGAGGTACCTATGCTCTTTAACCTATTTGTAACAGCTCAGCTCACTAATGA
TATTGTCCGCTTTGGTCTTAGGCTCGTACTGCTTTAAACACGCGTTACTAATGTCTTAAGCTTGCTTT
CCTACCAGTATCTTTTCCGTGTTTTGCAGATATAGAATTTGCCTAGGGTGTAACACTATTATTGCTGC
TTGGAAAATTATAGGCGTTTTAGTTGTCATTGCTCACTTATCTTTCAAGGCGACTGCTAATAGAAGCA
TACCTATGTCTAACCTTGAGGGGTCACCCGACCTCGTAAACTTCGGTAGAAATCTTATATTTTACACC
TTGAAAATGATTTAATTTAAATCGCTTGGCTCCCTGAATACTAAAACCTTTAGGGGGCACTAGTTGAA
CAGAATACCGGTGCTCCCCGTCGTGCTAAAGTCCTGGGTCCGCCTCTAACTGCTAATGCTTAGTGTAC
AAAAATAGGACTTAAACCTAAGAATGGTTCCCTTGATCCTTCCCAACAATTTAGATAAACTAATCTA
TGATATTACCTTTCTCATTTCACATAAGACTTCTTTTCGGTTCATATTTGAAAATAGATCCAGCACTT
ACTTTCAAAAAGAAAAATATAGATTTCCAAAATGCAAATTTTCTAGATAAAATTTTAATATTCTTAAC
TCGTTTTATTTTTCTTGAAATGAATTCAAATACTATTGTTCTCCAACCCAAACGCCACATAATAGTTC
ACTTAAGCACCATCTTTTATGTTCTCAGACCTCAATTTACACTATATTACTTAAATATGACCTGCTCT
ACATCCTCGTACCTCTGTTGTCCTTGAGTTACAGACTATGTTGCGCGAACTTTAAAAAATGTTGTTGC
ATCCATGTCGGAACCTCCAAAAATACAGTACTTATGACGGATCCAACACACACTTAGAGACATTTTCA
GAAAGTCCGAGCAACATAGATTACATGTCATTTTCGATCTAGGAAAAAAGAGCTTTTTTCGCAAGTTT
ATCTGTATTTTATCGCTTGTATGGAGAAGTATAACCGGTGAGAACTTTCCTCGTACAGGAAAACCATT
```

FIG. 44 (Continued)

Nitab4.5_0001200g0070.2 genomic sequence (SEQ ID NO. 41)

```
GCCATTTACTAATAACTTGGAGTTGGAGTTGGAGATCTGCACAATAGATTGCACTAGAACAAGTTGCC
TATTGGAAGAGCCAAATAACATACATGAGTCAAGTTTGTAAAAATGGAAAGCACTTTCAGTGTTGAAA
TTGTGAATGTTTTGCTACTTGTATTTTGTCCAATATATTATGTAATGTGTGAGTATAAGTATATCAAT
ACAAAAAATTAACAACCTTTAATCACAGGTGATGAAAGAATATCAAGGTTC
```

FIG. 45

Nitab4.5_0005803g0040.2 amino acid sequence (SEQ ID NO. 42)

```
MIVRVGLVVAASIAAYAVKQINVKPSKPSENGDSLPEKRSDEGDEKEEQLLYSTDGPKEVVDEEEEKE
EVKLMNGIINPAQGNQLDLDDDLFPEFEDLLSGEIEFPLPSDKYDTEREEREKVYQNEMANNEKELER
LRNLVKELEEREVKLEGELLEYYGLKEQESDIIELQKQLRIKSVEIDMLNITINTLQAEKQKLQEEVF
NGTTARKELEAARSKIKELQRQMQLEANQTKAQLLLLKQHVSGLQEKEEDAFKRDVEVDKKLRLVKEL
EVEVMELKRKNKELQHEKRELVIKLDAAESKVANLSNMTENEMVAQVREEVTNLKHTNEDLLKQVEGL
QMNRFSEVEELVYLRWVNACLRFELRNYQTPQGKVSARDLSKNLSPRSQQKAKQLMLEYAGSERGQGD
TDLESNFSQPSSPGSEDFDNASIDSSTSRFSAFSKKPGLIQKLKRWGKSKDDSSVMSSPARSLGGASP
GRTSVSFRSRGPLESLMLRNAGDGVAITSFGTAEQEYDSPETFRLPPIRTQDSSAEPLNSVASSFQLM
SKSVEGVLDEKYPAFKDRHKLAVEREKQIKVKAEQARAARFEKSLPPKLSQLKEKRVSVSASASAPVV
SASGDSVEQSGDSKTDSQAVSKMKPINIEKRPPRTPRPPPTRSAGGPAPAGNNVTGGAPGGPPPPPPP
PGAPPPPPPPGGGAPRPPPPPPGSLMKGGAGGDKVHRAPELVEFYQSLMKREAKKDTSSPLISSTSNTS
DARSNMIGEIENRSTFLLAVKADVESQGEFVESLATEVRAASFTNIEDLVSFVNWLDEELSFLVDERA
VLKHFDWPEGKADALREAAFEYQDLMKLEKHVTSFVDDPNLPCDAALKKMYKLLEKVEQSVYALLRTR
DMAASRYREFGIPTNWLQDSGVVGKIKLSSVQLARKYMKRVASELDAMGGPEKEPNREFLILQGVRFA
FRVHQFAGGFDAESMKAFEELRSRVKSSQTEETTQEQ
```

FIG. 46

Nitab4.5_0005803g0040.2 coding sequence (SEQ ID NO. 43)

```
ATGATAGTCAGGGTAGGTTTAGTGGTTGCTGCTTCTATAGCAGCCTATGCAGTTAAGCAGATAAATGT
AAAACCCTCAAAGCCTTCAGAAAATGGTGACTCATTGCCTGAAAAACGAAGCGATGAAGGGGATGAAA
AGGAGGAGCAGCTTTTGTATTCTACAGATGGCCCCAAAGAAGTGGTTGATGAGGAAGAGGAGAAAGAA
GAAGTGAAATTAATGAATGGAATTATAAATCCAGCACAGGGTAACCAGCTTGATCTTGATGATGATCT
TTTCCCTGAATTCGAAGATCTTTTATCTGGGGAAATTGAATTTCCATTACCAAGTGACAAGTATGATA
CAGAAAGAGAAGAGAGAGAGAAGGTGTACCAAAATGAGATGGCCAACAATGAAAAAGAACTTGAAAGA
TTGCGAAATCTTGTTAAGGAGCTCGAGGAAAGGGAGGTGAAACTTGAAGGGGAGTTGTTGGAATATTA
TGGTTTGAAGGAACAAGAATCAGATATCATCGAGTTACAAAAGCAGCTCAGGATTAAGTCTGTAGAGA
TCGACATGCTCAACATCACTATAAATACTTTACAGGCCGAGAAACAAAAGCTTCAAGAGGAGGTTTTC
AATGGAACTACTGCTCGGAAAGAGCTAGAAGCAGCAAGGAGCAAGATCAAGGAGTTGCAGAGGCAGAT
GCAGCTTGAAGCTAACCAAACGAAAGCTCAGTTGTTGTTGCTGAAGCAACATGTTAGTGGACTTCAAG
AAAAGGAAGAGGATGCTTTCAAGAGAGATGTCGAGGTTGACAAGAAGCTTAGACTTGTGAAGGAATTA
GAAGTGGAGGTTATGGAGCTTAAGAGGAAGAACAAGAACTTCAGCATGAAAAGAGAGAGTTGGTTAT
AAAATTGGATGCCGCTGAATCTAAAGTAGCAAACTTATCCAATATGACAGAGAATGAAATGGTTGCCC
AGGTCAGGGAAGAGGTAACTAATTTGAAGCATACAAATGAGGATCTTCTAAAACAAGTAGAAGGACTT
CAAATGAACAGATTCAGTGAAGTTGAAGAGCTAGTGTATCTTCGTTGGGTCAATGCCATGCTTAAGATT
TGAACTTCGGAACTACCAAACACCTCAAGGAAAGGTATCAGCTCGTGATCTTAGTAAAAACCTGAGCC
CAAGATCTCAACAGAAGCCAAACAGTTGATGTTAGAATACGCGGTCAGAACGTGGCCAAGGAGAT
ACAGATCTTGAAAGCAATTTTTCGCAGCCATCTTCTCCCGGTAGTGAAGACTTTGATAATGCTTCTAT
TGACAGTTCCACAAGCAGATTTAGTGCTTTCAGTAAAAAGCCTGGCCTAATCCAGAAGTTGAAGAGAT
GGGGCAAAAGTAAAGACGATTCCAGTGTTATGTCTTCACCAGCAAGATCTCTTGGGGGAGCATCTCCG
GGCCGGACAAGTGTAAGTTTTAGATCAAGGGGTCCTCTGGAATCACTAATGCTCAGAAATGCAGGTGA
TGGTGTAGCCATCACTAGTTTTGGAACAGCTGAGCAGGAATATGATTCCCCTGAAACACCGCGGCTTC
CACCGATTAGGACACAAGATTCTTCTGCTGAGCCACTGAACTCAGTTGCATCATCCTTCCAGCTAATG
TCTAAATCAGTTGAAGGAGTTCTAGATGAGAAGTATCCTGCATTCAAAGATAGGCATAAGCTGGCAGT
AGAGCGAGAGAAGCAAATTAAGGTAAAGGCCGAGCAAGCAAGAGCAGCAAGGTTTGAGAAGTCCTTGC
CCCCGAAACTTTCTCAATTGAAAGAGAAGCGAGTATCAGTATCAGCATCAGCATCAGCGCCAGTGGTC
TCTGCCTCTGGTGACTCAGTTGAGCAGTCCGGTGATAGCAAAACTGACTCTCAAGCAGTTAGCAAAAT
```

FIG. 46 (Continued)

Nitab4.5_0005803g0040.2 coding sequence (SEQ ID NO. 43)

```
GAAACCAATTAATATTGAGAAAAGACCTCCTAGGACTCCTCGTCCACCTCCTACACGATCAGCAGGTG
GTCCCGCTCCAGCTGGTAATAATGTTACAGGTGGGGCACCTGGTGGTCCACCCCCACCACCTCCTCCG
CCTGGTGCTCCACCACCGCCGCCGCCACCTGGTGGAGGAGCTCCTAGACCACCTCCTCCTCCTGGATC
TCTAATGAAAGGAGGAGCTGGAGGTGATAAGGTCCATCGCGCTCCTGAATTAGTTGAATTCTACCAAT
CATTGATGAAACGCGAGGCGAAGAAGGATACATCATCACCTTTGATATCCTCTACTTCAAACACATCA
GATGCAAGAAGCAACATGATCGGAGAGATAGAGAACAGATCCACATTCCTGTTAGCTGTGAAAGCTGA
TGTGGAAAGTCAAGGTGAATTTGTCGAGTCATTGCAACTGAAGTTCGTGCTGCTTCATTTACCAATA
TCGAGGATCTAGTGTCATTTGTGAACTGGCTAGATGAAGAACTCTCCTTCTTGGTTGATGAACGAGCT
GTCCTCAAGCACTTTGACTGGCCAGAGGGAAAAGCAGATGCACTGAGAGAGGCTGCCTTCGAATACCA
AGATCTAATGAAACTAGAAAAGCATGTAACCTCCTTTGTTGATGACCCAAATCTTCCATGTGATGCTG
CTTTGAAAAGATGTACAAGTTGCTTGAGAAGGTGGAACAAAGTGTTTATGCACTATTGCGTACTCGC
GACATGGCTGCATCAAGATACAGAGAATTTGGCATTCCTACTAATTGGTTGCAAGATTCAGGTGTTGT
TGGCAAGATCAAGCTTTCGTCGGTACAATTGGCGAGGAAGTACATGAAACGTGTAGCATCAGAGCTTG
ATGCCATGGGTGGACCTGAGAAGGAACCAAACAGAGAATTCTTGATTCTACAAGGGGTTCGTTTTGCT
TTTAGAGTTCATCAGTTTGCTGGAGGATTTGATGCTGAAAGCATGAAGGCTTTTGAAGAATTAAGGAG
TCGTGTCAAAAGTTCACAAACAGAAGAGACTACACAAGAACAATGA
```

FIG. 47

Nitab4.5_0005803g0040.2 genomic sequence (SEQ ID NO. 44)

```
AGAATTTCAATCTTGTTTGGACAAAGACTGACCACTCAAGAAATTGGTGGTTCTTGTGCCCTCTATGT
GTTCGACAATTTGTCTATTAGACTTTCTAGTTATCAACAACACTTTGCACATAACCAAACTTTTTTTT
TCTTGATAAGATGATATAGCCATTAAGTTATTCATAGTGTCCACTTTTTAAAGAATTGTCTAAAACTG
ATAATTCTCTTTCAAGAATTGCACCTTTTTTGCCATTTTTGATGAGGCCATGATTTGAGTTTTGAGCT
ATGGGGTTTGAGAAAAAATGGGTGGGGATTATTTTATGTTAGTAAATGATTTGAAGCTTCAATATTTT
CCATTGAAAATACCTACATGATAGTCAGGGTAGGTTTAGTGGTTGCTGCTTCTATAGCAGCCTATGCA
GTTAAGCAGATAAATGTAAAACCCTCAAAGCCTTCAGGTAATTTTCTGTAGTCAGTTGTATTTGGACT
GTTTTATTAAAGTTGCAAATAAGTAAAGAGGCTGCTAAATTAGTATAATTGGTTTTAGACATATTGAT
AAAACAGTGTCTATAAAGTTTCAATTTTTAATGGAGAAAATCATCCAAGTGAGTGACTAGAGTGTTTT
TTTGTGGCTAAATTGTGTTTATCTTATTGTTTTATGAACGTTGGTGAACAGAAAATGGTGACTCATTG
CCTGAAAAACGAAGCGATGAAGGGGATGAAAAGGAGGAGCAGCTTTTGTATTCTACAGATGGCCCCAA
AGAAGTGGTTGTAAGTATTTGTGTATAGAGAAATTTGTGTGCTTTAGAAACAAAAATTTGTTAGTCAT
TTGGAAATTTGTTTAATATATGACAACTTGTAGGATGAGGAAGAGGAGAAAGAAGAAGTGAAATTAAT
GAATGGAATTATAAATCCAGCACAGGGTAACCAGCTTGATCTTGATGATGATCTTTTCCCTGAATTCG
AAGATCTTTTATCTGGGGAAATTGAATTTCCATTACCAAGTGACAAGTATGATACAGAAAGAGAAGAG
AGAGAGAAGGTGTACCAAAATGAGATGGCCAACAATGAAAAAGAACTTGAAAGATTGCGAAATCTTGT
TAAGGAGCTCGAGGAAAGGGAGGTGAAACTTGAAGGGGAGTTGTTGGAATATTATGGTTTGAAGGAAC
AAGAATCAGATATCATCGAGTTACAAAAGCAGCTCAGGATTAAGTCTGTAGAGATCGACATGCTCAAC
ATCACTATAAATACTTTACAGGCCGAGAAACAAAAGCTTCAAGAGGAGGTTTTCAATGGAACTACTGC
TCGGAAAGAGCTAGAAGCAGCAAGGAGCAAGATCAAGGAGTTGCAGAGGCAGATGCAGCTTGAAGCTA
ACCAAACGAAAGCTCAGTTGTTGTTGCTGAAGCAACATGTTAGTGGACTTCAAGAAAAGGAAGAGGAT
GCTTTCAAGAGAGATGTCGAGGTTGACAAGAAGCTTAGACTTGTGAAGGAATTAGAAGTGGAGGTTAT
GGAGCTTAAGAGGAGTAGCAACAAAGAACTTCAGCATGAAAAGAGAGAGTTGGTTATAAAATTGGATGCCG
CTGAATCTAAAGTAGCAAACTTATCCAATATGACAGAGGTAAATTTAACTCCTGATACCAGTATTTTT
CATGTAATTGATCTTTAGGACAATCTTTGTGTGTTTCCTGCGTATAGCTTTTCTTTCTTTAAGCATCT
TCTTTCTACTTTTCAAGTCTGCAAAAATGTTTTGGAAATGTAGAGCCGACTCTGAGCACCTTATTGAC
CCCCTTTTTCTGATTACTTCCCTTTTTACGCCACGCTCATAAGGTAGTTGAGTCCGTTGAATACTCCA
GTGAAACATGCCCACATTATGGTTTCTTGTAATTATCGTAATTGTCATTGCTATGTTTTGCTGTTTAT
TATGCTCATTAAATTTCTTCTATGTTAATTATCGTGTTGAGCTCCCACCACTTAACCATTGGAGATTCT
TAGCTTCTGAAGAGCTTCATTTGGTGATGCGTTTGGTTGGTGTGTGAACTGATGCTATTTAATTACTG
ACTTGTCTTTGGCATGCTGCTTCAGAATGAAATGGTTGCCCAGGTCAGGGAAGAGGTAACTAATTTGA
AGCATACAAATGAGGATCTTCTAAAACAAGTAGAAGGACTTCAAATGAACAGATTCAGTGAAGTTGAA
GAGCTAGTGTATCTTCGTTGGGTCAATGCATGCTTAAGATTTGAACTTCGGAACTACCAAACACCTCA
AGGAAAGGTATCAGCTCGTGATCTCAGTAAAAACCTGAGCCCAAGATCTCAACAGAAGGCCAAACAGT
TGATGTTAGAATACGCAGGATCAGAACGTGGCCAAGGAGATACAGATCTTGAAAGCAATTTTTCGCAG
CCATCTTCTCCCGGTAGTGAAGACTTTGATAATGCTTCTATTGACAGTTCCACAAGCAGATTTAGTGC
```

FIG. 47 (Continued)

Nitab4.5_0005803g0040.2 genomic sequence (SEQ ID NO. 44)

```
TTTCAGTAAAAAGCCTGGCCTAATCCAGAAGTTGAAGAGATGGGGCAAAAGTAAAGACGATTCCAGTG
TTATGTCTTCACCAGCAAGATCTCTTGGGGGAGCATCTCCGGGCCGGACAAGTGTAAGTTTTAGATCA
AGGGGTCCTCTGGAATCACTAATGCTCAGAAATGCAGGTGATGGTGTAGCCATCACTAGTTTTGGAAC
AGCTGAGCAGGAATATGATTCCCCTGAAACACCGCGGCTTCCACCGATTAGGACACAAGATTCTTCTG
CTGAGCCACTGAACTCAGTTGCATCATCCTTCCAGCTAATGTCTAAATCAGTTGAAGGAGTTCTAGAT
GAGAAGTATCCTGCATTCAAAGATAGGCATAAGCTGGCAGTAGAGCGAGAGAAGCAAATTAAGGTAAA
GGCCGAGCAAGCAAGAGCAGCAAGGTTTGAGAAGTCCTTGCCCCCGAAACTTTCTCAATTGAAAGAGA
AGCGAGTATCAGTATCAGCATCAGCGCCAGTGGTCTCTGCCTCTGGTGACTCAGTTGAGCAG
TCCGGTGATAGCAAAACTGACTCTCAAGCAGTTAGCAAAATGAAACCAATTAATATTGAGAAAAGACC
TCCTAGGACTCCTCGTCCACCTCCTACACGATCAGCAGGTGGTCCCGCTCCAGCTGGTAATAATGTTA
CAGGTGGGGCACCTGGTGGTCCACCCCCACCACCTCCTCCGCCTGGTGCTCCACCACCGCCGCCGCCA
CCTGGTGGAGGAGCTCCTAGACCACCTCCTCCTCCTGGATCTCTAATGAAAGGAGGAGCTGGAGGTGA
TAAGGTCCATCGCGCTCCTGAATTAGTTGAATTCTACCAATCATTGATGAAACGCGAGGCGAAGAAGG
ATACATCATCACCTTTGATATCCTCTACTTCAAACACATCAGATGCAAGAAGCAACATGATCGGAGAG
ATAGAAACAGATCCACATTCCTGTTAGCTGTATGTACAACTTCTCTTTTACTCCTTTGAATAATGCA
TGTGCTTATTAACCTATTCTGACTCAATGGAGACTTGTGCAAAACCAGGTGAAAGCTGATGTGGAAAG
TCAAGGTGAATTTGTCGAGTCATTGGCAACTGAAGTTCGTGCTGCTTCATTTACCAATATCGAGGATC
TAGTGTCATTTGTGAACTGGCTAGATGAAGAACTCTCCTTCTTGGTATTTCCTCTTACCATTATACCT
TCAAGTTCCTCTTCCTTAAATAGGACATGAATATACCTATATTCTTAATCATACTTTTATATGAAAAT
TGTTGCTTACATTAATCTTGCTCGAGCGACAAGGACCATGCAGTTTCTGCATTAAATACCTGGAGCAT
TCATTAACATTGTATCCCGTTGATTCTTTTCAAGGTTGATGAACGAGCTGTCCTCAAGCACTTTGACT
GGCCAGAGGGAAAAGCAGATGCACTGAGAGAGGCTGCCTTCGAATACCAAGATCTAATGAAACTAGAA
AAGCATGTAACCTCCTTGTTGATGACCCAAATCTTCCATGTGATGCTGCTTTGAAAAAGATGTACAA
GTTGCTTGAGAAGTAAGTCTCTACTGATATCTTTATCTCTTGTCTTTAAACTAGAGAATTTCAGTCAG
GTAGGATGTGAAAATGGTTGAATCTTAAATCAAACTATTTTCAGACCATATTTAAACTTCCACTTATT
TGGAATTGGTACCCTTTCATTTCATGTGTAGTTGTTCCTTCTTATCATTTCTGTCTTGTCTATCGCTA
GCTCATTTTTTGTTACTCCTAAGTCTTAAACCCTTTAATCTTCGGGATGCCAGGGTGGAACAAAGTGT
TTATGCACTATTGCGTACTCGCGACATGGCTGCATCAAGATACAGAGAATTTGGCATTCCTACTAATT
GGTTGCAAGATTCAGGTGTTGTTGGCAAGGTATGTTCTCATATAGAAACTTTGCTATGTTGTTCTTTG
TGAAATTGCTTGAACCACAATAATAAAAGAAAAAGAAACAAAATAATCACACTGCAAGAAAACCTTAG
AATGTGATGTTTACTTCATATTACTTAGAAATTAGGAAAACTTACCAACCTCTTAACTAACATGTA
CTCCCTCTATTTCAAAAAGAACGAACCTATTTGATTAGGCACCGAGTTTAAAAAGAATGAAAGACTTA
GATATTTGTGCGGCATAAATCATCTTATTAGGGGTAAAATGAAAAGTTTAAAGTTACATTATTTCCAA
ATTTAGAAAGGAGTCAATCTATTTGAATCGAGTTAAAAAGGAAATAGGTTCATTCTTTTTGAAACAGA
GGGAGTAAATATAATTTCTCTTCATCGTACGGACAATAGAAGGAAAAAAAAAGGAAGTGTGCAGAGA
GATGATCTATCTATGGCGTATAAGTATCGCTGTTTTCTTCTGCAGATCAAGCTTTCGTCGGTACAATT
GGCGAGGAAGTACATGAAACGTGTAGCATCAGAGCTTGATGCCATGGGTGGACCTGAGAAGGAACCAA
ACAGAGAATTCTTGATTCTACAGGGGTTCGTTTTGCTTTTAGAGTTCATCAGGTATACACACAGCAC
CTGCATTTTGTTCACTTACCAAATCTAAAAACAATACCAATCTATTTAACAAATTAAACATGTTTTAG
TAGAGTTACAGATTAATGAATTTACAACTTTTTCTTTTTCTTTTCAGTTTGCTGGAGGATTTGATGCT
GAAAGCATGAAGGCTTTTGAAGAATTAAGGAGTCGTGTCAAAAGTTCACAAACAGAAGAGACTACACA
AGAACAATGAGAATATCTGTATTTTGGTTTTGGTCATTGTAAATTTCATCATTTTCTTTTCTCCAAGT
ATAGCAAACTTACTCTATCTTGGACTTCTGTACAATTCAAAAGGTGAATAACTCGAGGAGAATATCAG
ATAGCACAGATTAGTTAAAAGAAAGTTTAAAGGATAAACATTGTATTGGAAAACACAGAGAAAACTAC
ATTAAACAATGAGTGAAATTTGGAACTGCATAATCATGAATTCACGAGAAGGAAAAAATGCAGCAAGT
TGTCAAGGTGTTGGATCATTTGTTCTGCTTTTGGGGCAAAAGTGAAAACCTGTCCCTCTTCTGGGGCC
TAGTTGTACTAGGCAAAAAATCCTCATTTCTGTGAAATTTAAGTATATTCATCCTAGTACATTTCAGG
GTACAAGCATTGTGCAATAGCAAAAAGAAAAGAAGAGAAACTCATAAAACTGAGTGTTCAGCAGCTGC
TGTGAAGTGACTCTCTGTATGCTCGTCGATGAACATGCAGGTGAAGGTTCTTGATTTCATCTGTTATC
GCATTGTAATAATGAGATTTCTGTCTGCAAATTTGGCACCTCCAACCTTCCCTTGAAGTTGAGATGGT
AGACGAATGACACGTCTCTGATCACCAGCCTCTACCAACAACTCAGACCCTCCTCTAAACTGCAATAA
CCAGAATTCTGATTAATTTCACCTTTTAATTTGATT
```

METHOD FOR MODULATING THE ALKALOID CONTENT OF A TOBACCO PLANT

CROSS REFERENCE TO RELATED APPLICATIONS

This is a U.S. National Phase application claiming priority to PCT/GB2020/051602, filed Jul. 3, 2020, which claims priority to British application No. 1909562.9, filed Jul. 3, 2019, the entire contents of which are hereby expressly incorporated by reference in their entirety including, without limitation, the specification, claims, and abstract, as well as any figures, tables, or drawings thereof.

FIELD OF THE INVENTION

The present invention relates to methods of modulating the alkaloid content a plant or part thereof or cell or cell culture. The invention also extends to methods of modulating the expression and/or activity of polypeptides which modulate alkaloid content within plants. Alternatively, the invention provides methods of modulating the expression and/or activity of genes which encode polypeptides which modulate alkaloid content within plants. The invention also extends to constructs, which can be used to modulate the polypeptides. The invention further relates to plant cells and plants modified to achieve a modulation in alkaloid content. The invention also relates to a processed and harvested leaf from such modulated plants and use thereof in a tobacco industry product, including combustible smoking articles.

BACKGROUND

Alkaloids are a group of naturally occurring compounds which mostly contain basic nitrogen atoms and are produced by a large variety of organisms including bacteria, fungi, plants and animals.

Alkaloids may be classified according to the similarity of the carbon skeleton e.g. indole-, isoquinoline- and pyridine-like. Pyridine derivatives are one class of monomeric alkaloids; this class includes simple derivatives of pyridine, polycyclic condensed and noncondensing pyridine derivatives and sesquiterpene pyridine derivatives. Examples are nicotine, nornicotine, pseudooxynicotine, anabasine, myosmine and anatabine.

Most of the known biological functions of alkaloids are related to protection. Neuroactive molecules, such as caffeine, cocaine, morphine, and nicotine, act as defence compounds against invading predators. The accumulation of these alkaloids is the result of signal transduction cascades that monitor gene expression, enzyme activities, and alkaloid concentrations. The fine-tuning of alkaloid content in the plant involves negative feedback loops and degradative pathways.

Nicotine occurs naturally in several varieties of plants but is found at the highest level in the tobacco plant. Cultivated tobacco produces 2-4% alkaloids of total dry weight. Nicotine is produced in wild and cultivated *Nicotiana* species and plays an important role in plant defence against herbivores and insects (Voelckel et al. (2001) Oecologia 127(2): 274-280, incorporated herein by reference). It accounts for ~90% of the total alkaloid content. The remaining 10% of the alkaloid pool is mostly constituted by the structurally related compounds nornicotine, anatabine, anabasine and pseudooxynicotine (PON).

The regulation of alkaloid content in tobacco is complex. Several factors including genotype, environment, fertilization and agronomic practices (e.g. topping) affect alkaloid levels in tobacco plants. Some key regulators of nicotine biosynthesis are well characterized, for example putrescine N-methyltransferase (PMT), which plays a pivotal role in this pathway, is activated by members of the ethylene responsive factor (ERF) superfamily, the largest transcription factor family in the tobacco genome (Rushton et al. (2008) Plant Physiol. 147(1): 280-295 incorporated herein by reference). Other transcription factors that induce alkaloid biosynthesis belong to the MYC2-like basic helix-loop-helix (bHLH) family. MYC2-like bHLHs regulate alkaloid levels directly, through the Gbox-mediated binding and activation of alkaloid structural genes, and indirectly, through the activation of ERFs.

Tobacco pyridine alkaloids are precursors of tobacco-specific nitrosamines (TSNAs) that form during the post-harvest leaf curing. The four primary TSNAs found in cured tobacco leaves are N'-nitrosonornicotine (NNN), N'nitrosoanatabine (NAT), N'-nitrosoanabasine (NAB) and 4-(methyl nitrosamino)-1-(3-pyridyl)-1-butanone (NNK). During the post-harvest leaf curing, reactions between pyridine alkaloids and nitrosating species leads to the formation of tobacco-specific nitrosamines (TSNAs). PON is likely to function as the direct precursor in the synthesis of the TSNA NNK (Bush et al., 2001 incorporated herein by reference). Reducing the production and accumulation of TSNAs is of high importance. The CYP82E family of nicotine demethylase genes is one of the primary regulators of nicotine to nornicotine conversion, and altering their activity or accumulation may result in a decrease in NNN levels. However, no enzymes or genes responsible for producing PON have been identified thus far.

As described in the Examples, the inventors sought to investigate genes responsible for alkaloid and/or TSNA precursor synthesis, with the aim of modulating alkaloid content in plants, e.g. decreasing TSNA content in tobacco.

SUMMARY OF THE INVENTION

It has been surprisingly found that by modulating the activity or expression of a gene encoding a BTB/POZ NPH3 domain-containing protein the alkaloid content and/or TSNA content or precursor of TSNA content of plants can be modulated. The gene(s) as taught herein which encode BTB/POZ NPH3 domain-containing proteins, for example Nitab4.5_0000868g0020.2, are regulators of alkaloid and TSNA precursor content in cultivated tobacco. In particular the gene(s) as taught herein, for example Nitab4.5_0000868g0020.2, is a regulator of alkaloid content in cultivated tobacco. Nitab4.5_0000868g0020.2 encodes a BTB/POZ NPH3 domain-containing protein according to the present invention. Nitab4.5_0000651g0020.2, Nitab4.5_0009137g0040.2, Nitab4.5_0001772g0090.2, Nitab4.5_0003312g0050.2, Nitab4.5_0003151g0080.2, Nitab4.5_0002641g0190.2, Nitab4.5_0001876g0030.2, Nitab4.5_0000048g0280.2 and Nitab4.5_0002006g0070.2 are homologues of Nitab4.5_0000868g0020.2 according to the present invention.

BTB/POZ NPH3 domain-containing proteins according to the present invention contain conserved domains termed a BTB/POZ domain and an NPH3 domain.

According to the present invention, tobacco industry products with modulated alkaloid content and commercially desirable traits sought after by consumers of tobacco industry products can be produced. In some instances, consumers may desire a product with low levels of alkaloid content e.g. low levels of TSNA precursors.

The present invention may be particularly useful in the field of plant molecular farming, where plants (such as tobacco and other *Nicotiana* spp.) are used for the production of proteins, peptides, and metabolites e.g. for the production of therapeutics and pharmaceuticals such as antibiotics, virus like particles, or neutraceuticals or small molecules. Tobacco has been used for the development of an HIV-neutralising antibody in an EU-funded project called PharmPlant and Medicago Inc., Canada have worked on a tobacco-based platform for the production of virus-like particles for flu vaccine manufacture.

Thus, a plant according to the present invention may be used for molecular farming to reduce or eliminate the presence of nicotinic alkaloids. The use of a low nicotine plant or rootsock is beneficial in molecular farming and would reduce downstream processing costs associated with purification.

The present inventors have surprisingly determined a method for modulating (e.g. decreasing) the alkaloid content, of a plant (e.g. a tobacco plant) by modulating (e.g. decreasing) the activity or expression of a gene encoding a BTB/POZ NPH3 domain-containing protein. The alkaloid content (e.g. the content of one or more of PON, nornicotine, anabasine, anatabine or myosmine) of a plant (e.g. tobacco plant) may be decreased by decreasing the activity or expression of a gene encoding a BTB/POZ NPH3 domain-containing protein or may be increased by increasing the activity or expression of gene encoding a BTB/POZ NPH3 domain-containing protein. Prior to the present invention it had not been known that modulation of the activity or expression of a gene encoding a BTB/POZ NPH3 domain-containing protein as described herein could be used to modulate alkaloid content or modulate PON content in particular.

In one aspect, the present invention provides a method of modulating (e.g. decreasing) the alkaloid content of a plant or a part thereof, or a cell, the method comprising modifying said plant by modulating the activity or expression of at least one gene encoding a BTB/POZ NPH3 domain-containing protein.

In another aspect, the present invention provides a method of modulating (e.g. decreasing) the content of a tobacco specific nitrosamine (TSNA) precursor in a tobacco plant or plant part thereof, or cell, the method comprising modifying said plant or cell by modulating the activity or expression of at least one gene encoding a BTB/POZ NPH3 domain-containing protein.

In a further aspect, there is provided the use of at least one gene encoding a BTB/POZ NPH3 domain-containing protein for modulating (e.g. decreasing) alkaloid content of a cell or plant or part thereof.

In another aspect, there is provided a method for producing a plant or part thereof, a cell, a plant propagation material, a leaf, a cut harvested leaf, a processed leaf or a cut and processed leaf which has modulated (e.g. decreased) alkaloid content, the method comprising modifying said plant or cell to modulate the activity or expression of at least one gene encoding a BTB/POZ NPH3 domain-containing protein.

Suitably, the alkaloid content may be modulated (e.g. decreased) in comparison to a plant or cell which has not been modified to modulate the activity or expression of the at least one gene encoding a BTB/POZ NPH3 domain-containing protein.

In one aspect, the present invention provides a plant or part thereof or cell which has been modified to achieve a modulation (e.g. decrease) in alkaloid content in comparison to an unmodified plant, wherein the modification is the modulation of the activity or expression of at least one gene encoding a BTB/POZ NPH3 domain-containing protein from tobacco.

In a further aspect, the present invention provides a plant propagation material obtainable from a plant or cell according to the present invention or from a plant or cell produced by a method according to the present invention.

Suitably, the at least one BTB/POZ NPH3 domain-containing protein may comprise an amino acid sequence as set out in SEQ ID NO. 1, SEQ ID NO. 4, SEQ ID NO. 7, SEQ ID NO. 10, SEQ ID NO. 13, SEQ ID NO. 16, SEQ ID NO. 19, SEQ ID NO. 22, SEQ ID NO. 25, SEQ ID NO. 28 or a functional variant or functional fragment or orthologue thereof, or a sequence which has at least 80% identity to SEQ ID NO. 1, 4, 7, 10, 13, 16, 19, 22, 25 or 28; or the at least one gene encoding BTB/POZ NPH3 domain-containing protein comprises a nucleotide sequence as set out in SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30 or a functional variant or functional fragment or orthologue of SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30, or a sequence which has at least 80% identity to SEQ ID NO. 2, 3, 5, 6, 8, 9, 11, 12, 14, 15, 17, 18, 20, 21, 23, 24, 26, 27, 29 or 30.

Suitably, an additional gene encoding BTB/POZ NPH3 domain-containing protein may be modulated wherein the additional gene is at least one selected from SEQ ID NO. 1, SEQ ID NO. 4, SEQ ID NO. 7, SEQ ID NO. 10, SEQ ID NO. 13, SEQ ID NO. 16, SEQ ID NO. 19, SEQ ID NO. 22, SEQ ID NO. 25, SEQ ID NO. 28 or a functional variant or functional fragment or orthologue thereof or a sequence which has at least 80% identity to SEQ ID NO. 1, 4, 7, 10, 13, 16, 19, 22, 25 or 28; or the at least one gene encoding BTB/POZ NPH3 domain-containing protein comprises a nucleotide sequence as set out in SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30 or a functional variant or functional fragment or orthologue of SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30, or a sequence which has at least 80% identity to SEQ ID NO. 2, 3, 5, 6, 8, 9, 11, 12, 14, 15, 17, 18, 20, 21, 23, 24, 26, 27, 29 or 30.

In one aspect, the present invention provides the use of a plant or part thereof according to the present invention, or of a plant produced by a method according to the present invention to breed a plant.

In one aspect, the present invention provides the use of a plant or part thereof according to the present invention, or of a plant produced by a method according to the present invention for production of a product.

In one aspect, the present invention provides the use of a plant or part thereof according to the present invention, or of a plant produced by a method according to the present invention to grow a crop.

In one aspect, the present invention provides the use of a plant or part thereof according to the present invention, or of a plant produced by a method according to the present invention to produce a leaf.

In another aspect, there present invention provides a harvested leaf of a plant according to the present invention, or obtainable (e.g. obtained) from a plant propagated from a propagation material according to the present invention, or obtainable (e.g. obtained) from a plant obtained by a use according to the present invention, or obtainable (e.g. obtained) from a plant produced by a method according to the present invention.

Suitably, the harvested leaf of a plant may be a cut harvested leaf.

In another aspect, the present invention provides a processed leaf, preferably a processed tobacco leaf, preferably a non-viable processed tobacco leaf:
  obtainable (e.g. obtained) from a plant obtainable (e.g. obtained) from a use according to the present invention;
  obtainable (e.g. obtained) by processing a plant according to the present invention; obtainable from a plant propagated from a plant propagation material according to the present invention; or
  obtainable (e.g. obtained) by processing a harvested leaf of a plant according to the present invention; or
  obtainable (e.g. obtained) from a plant produced by a method according to the present invention.

Suitably, the leaf may be processed by curing, fermenting, pasteurising or a combination thereof, preferably wherein the content of one or more TSNAs selected from 4-(methylnitrosamino)-1-(3-pyridyl)-1-butanone (NNK), N'-nitrosonornicotine (NNN), N'-nitrosoanatabine (NAT) and N-nitrosoanabasine (NAB) is decreased, wherein preferably the content of NNK and/or NNN is modulated (e.g. decreased), wherein more preferably the content of NNK is decreased.

Suitably, the processed leaf may be a cut processed leaf.

In a further aspect, the present invention provides cured tobacco material made from a plant or a part thereof:
  obtainable (e.g. obtained) from a plant obtainable from a use according to the present invention;
  obtainable (e.g. obtained) by processing a plant according to the present invention;
  obtainable (e.g. obtained) from a plant propagated from a plant propagation material according to the present invention; or
  obtainable (e.g. obtained) by processing a harvested leaf of a plant according to the present invention; or
  obtainable (e.g. obtained) from a plant produced by a method according to the present invention.

In another aspect, the present invention provides a tobacco blend comprising cured tobacco material according to the invention.

In another aspect, the present invention provides a tobacco industry product prepared from:
  a plant according to the present invention, or a part thereof according to the present invention, wherein said plant is a tobacco plant;

a tobacco plant or part thereof propagated from a tobacco plant propagation material according to the present invention;
  a harvested leaf of a plant according to the present invention, wherein said plant is a tobacco plant;
  a processed leaf according to the present invention, wherein said plant is a tobacco plant;
  or
  a plant produced by a method to the present invention.

Suitably, the tobacco industry product may be a combustible smoking article.

Suitably, the tobacco industry product may be a smokeless tobacco product.

Suitably, the tobacco product may be a non-combustible aerosol provision system such as a tobacco heating device or an aerosol-generating device.

In another aspect, the present invention provides a combustible smoking article, non-combustible aerosol provisioning system, smokeless tobacco product or tobacco heating device comprising a plant or a part thereof or a cell according to the present invention or an extract (e.g. a tobacco extract) thereof; or a cured tobacco material according to the present invention; or a tobacco blend according to the present invention.

The present invention provides the use of a nucleotide sequence of at least one gene encoding BTB/POZ NPH3 domain-containing protein preferably where the sequence of the at least one BTB/POZ NPH3 domain-containing protein is selected from: SEQ ID NO. 1, SEQ ID NO. 4, SEQ ID NO. 7, SEQ ID NO. 10, SEQ ID NO. 13, SEQ ID NO. 16, SEQ ID NO. 19, SEQ ID NO. 22, SEQ ID NO. 25, SEQ ID NO. 28 or a functional variant or functional fragment or orthologue thereof, or a sequence which has at least 80% identity to SEQ ID NO. 1, 4, 7, 10, 13, 16, 19, 22, 25 or 28; or the at least one gene encoding a BTB/POZ NPH3 domain-containing protein comprises a nucleotide sequence as set out in SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30 or a functional variant or functional fragment or orthologue of SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30, or a sequence which has at least 80% identity to SEQ ID NO. 2, 3, 5, 6, 8, 9, 11, 12, 14, 15, 17, 18, 20, 21, 23, 24, 26, 27, 29 or 30; to select a plant having modulated (e.g. reduced) alkaloid content and/or modulated (e.g. reduced) content of tobacco specific nitrosamine (TSNA) or a precursor of a TSNA.

In another aspect, the present invention provides a mutant of a plant carrying a heritable mutation in a nucleotide sequence of at least one gene encoding BTB/POZ NPH3 domain-containing protein, preferably wherein the gene is selected from: SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30; or a functional variant or functional fragment or orthologue thereof or a sequence which has at least 80% identity to SEQ ID NO. 2, 3, 5, 6, 8, 9, 11, 12, 14, 15, 17, 18, 20, 21, 23, 24, 26, 27, 29 or 30; wherein said heritable mutation modulates (e.g. decreases) the activity or expression of the at least one gene encoding BTB/POZ NPH3 domain-containing protein and wherein the mutant plant has modulated (e.g. decreased) alkaloid content, preferably nicotine content, and/or modulated content of a tobacco specific nitrosamine (TSNA) or a precursor of a TSNA relative to a comparable plant which does not carry said heritable mutation.

In another aspect, the present invention provides progeny or seed of a mutant plant which carries the heritable mutation according to the present invention.

In a further aspect, the present invention provides a harvested leaf, a processed leaf or cured tobacco material produced from a plant comprising a modification in a nucleotide sequence of at least one gene encoding BTB/POZ NPH3 domain-containing protein, wherein the at least one gene is selected from: SEQ ID NO. 2, SEQ ID NO. 3, SEQ ID NO. 5, SEQ ID NO. 6, SEQ ID NO. 8, SEQ ID NO. 9, SEQ ID NO. 11, SEQ ID NO. 12, SEQ ID NO. 14, SEQ ID NO. 15, SEQ ID NO. 17, SEQ ID NO. 18, SEQ ID NO. 20, SEQ ID NO. 21, SEQ ID NO. 23, SEQ ID NO. 24, SEQ ID NO. 26, SEQ ID NO. 27, SEQ ID NO. 29, SEQ ID NO. 30; or; or a functional variant or functional fragment or orthologue thereof, or a sequence which has at least 80% identity to SEQ ID NO. 2, 3, 5, 6, 8, 9, 11, 12, 14, 15, 17, 18, 20, 21, 23, 24, 26, 27, 29 or 30; wherein said modification modulates (e.g. decreases) the activity or expression of the at least one gene encoding BTB/POZ NPH3 domain-containing protein and wherein said plant has modulated (e.g. decreased) alkaloid content, preferably nicotine content, and/or modulated content of a tobacco specific nitrosamine (TSNA) or a precursor of a TSNA relative to a comparable plant which does not carry said modification in the at least one gene encoding BTB/POZ NPH3 domain-containing protein.

The present invention provides a method, a leaf, a plant, a plant propagation material, a harvested leaf, a processed tobacco, a tobacco product, a use or a combination thereof as described herein with reference to the description and drawings.

BRIEF DESCRIPTION OF THE DRAWINGS

Embodiments of the invention will now be described, by way of example only, with reference to the accompanying drawings, in which:

FIG. 3 shows the amino acid sequence of Nitab4.5_0000868g0020.2—SEQ ID NO. 1—a protein from *Nicotiana tabacum* according to the present invention.

FIG. 4 shows the coding sequence of Nitab4.5_0000868g0020.2—SEQ ID NO. 2—encoding a protein from *Nicotiana tabacum* according to the present invention.

FIG. 5 shows the genomic sequence of Nitab4.5_0000868g0020.2—SEQ ID NO. 3—encoding a protein from *Nicotiana tabacum* according to the present invention.

FIG. 6 shows the amino acid sequence of Nitab4.5_0000651g0020.2—SEQ ID NO. 4—a protein from *Nicotiana tabacum* according to the present invention.

FIG. 7 shows the coding sequence of Nitab4.5_0000651g0020.2—SEQ ID NO. 5—encoding a protein from *Nicotiana tabacum* according to the present invention.

FIG. 8 shows the genomic sequence of Nitab4.5_0000651g0020.2—SEQ ID NO. 6—encoding a protein from *Nicotiana tabacum* according to the present invention.

FIG. 9 shows the amino acid sequence of Nitab4.5_0009137g0040.2—SEQ ID NO. 7—a protein from *Nicotiana tabacum* according to the present invention.

FIG. 10 shows the coding sequence of Nitab4.5_0009137g0040.2—SEQ ID NO. 8—encoding a protein from *Nicotiana tabacum* according to the present invention.

FIG. 11 shows the genomic sequence of Nitab4.5_0009137g0040.2—SEQ ID NO. 9—encoding a protein from *Nicotiana tabacum* according to the present invention.

FIG. 12 shows the amino acid sequence of Nitab4.5_0001772g0090.2—SEQ ID NO. 10—a protein from *Nicotiana tabacum* according to the present invention.

FIG. 13 shows the coding sequence of Nitab4.5_0001772g0090.2—SEQ ID NO. 11—encoding a protein from *Nicotiana tabacum* according to the present invention.

FIG. 14 shows the genomic sequence of Nitab4.5_0001772g0090.2—SEQ ID NO. 12—encoding a protein from *Nicotiana tabacum* according to the present invention.

FIG. 15 shows the amino acid sequence of Nitab4.5_0003312g0050.2—SEQ ID NO. 13—a protein from *Nicotiana tabacum* according to the present invention.

FIG. 16 shows the coding sequence of Nitab4.5_0003312g0050.2—SEQ ID NO. 14—encoding a protein from *Nicotiana tabacum* according to the present invention.

FIG. 17 shows the genomic sequence of Nitab4.5_0003312g0050.2—SEQ ID NO. 15—encoding a protein from *Nicotiana tabacum* according to the present invention.

FIG. 18 shows the amino acid sequence of Nitab4.5_0003151g0080.2—SEQ ID NO. 16—protein from *Nicotiana tabacum* according to the present invention.

FIG. 19 shows the coding sequence of Nitab4.5_0003151g0080.2—SEQ ID NO. 17—encoding a protein from *Nicotiana tabacum* according to the present invention.

FIG. 20 shows the genomic sequence of Nitab4.5_0003151g0080.2—SEQ ID NO. 18—encoding a protein from *Nicotiana tabacum* according to the present invention.

FIG. 21 shows the amino acid sequence of Nitab4.5_0002641g0190.2.—SEQ ID NO. 19—a protein from *Nicotiana tabacum* according to the present invention.

FIG. 22 shows the coding sequence of Nitab4.5_0002641g0190.2.—SEQ ID NO. 20—encoding a protein from *Nicotiana tabacum* according to the present invention.

FIG. 23 shows the genomic sequence of Nitab4.5_0002641g0190.2.—SEQ ID NO. 21—encoding a protein from *Nicotiana tabacum* according to the present invention.

FIG. 24 shows the amino acid sequence of Nitab4.5_0001876g0030.2—SEQ ID NO. 22—a protein from *Nicotiana tabacum* according to the present invention.

FIG. 25 shows the coding sequence of Nitab4.5_0001876g0030.2—SEQ ID NO. 23—encoding a protein from *Nicotiana tabacum* according to the present invention.

FIG. 26 shows the genomic sequence of Nitab4.5_0001876g0030.2—SEQ ID NO. 24—encoding a protein from *Nicotiana tabacum* according to the present invention.

FIG. 27 shows the amino acid sequence of Nitab4.5_0000048g0280.2. —SEQ ID NO. 25—a protein from *Nicotiana tabacum* according to the present invention.

FIG. 28 shows the coding sequence of Nitab4.5_0000048g0280.2. —SEQ ID NO. 26—encoding a protein from *Nicotiana tabacum* according to the present invention.

FIG. 29 shows the genomic sequence of Nitab4.5_0000048g0280.2.—SEQ ID NO. 27—encoding a protein from *Nicotiana tabacum* according to the present invention.

FIG. 30 shows the amino acid sequence of Nitab4.5_0002006g0070.2—SEQ ID NO. 28—a protein from *Nicotiana tabacum* according to the present invention.

FIG. 31 shows the coding sequence of Nitab4.5_0002006g0070.2—SEQ ID NO. 29—encoding a protein from *Nicotiana tabacum* according to the present invention.

FIG. 32 shows the genomic sequence of Nitab4.5_0002006g0070.2—SEQ ID NO. 30—encoding a protein from *Nicotiana tabacum* according to the present invention.

FIG. 33 shows SEQ ID NO. 31 which corresponds to the amino acid sequence of a BTB/POZ homodimerization domain (residues 39-136 of SEQ ID NO. 1).

FIG. 34 shows SEQ ID NO. 32 which corresponds to the amino acid sequence of an NPH3 domain (residues 218-492 of SEQ ID NO. 1).

FIG. 35 shows that knock out of Nitab4.5_0000868g0020.2 leads to a significant decrease in alkaloid content. Alkaloid content of three TN90 lines with knocked out Nitab4.5_0000868g0020.2 is shown. Alkaloid content is represented relative to control. Results were analysed by t-test. Values are shown as means±SEM. Asterisks indicate statistical significance of P value≤0.001.

FIG. 36 shows SEQ ID NO. 33; the genomic sequence of Nitab4.5_0000842g0110.2, an interactor of Nitab4.5_0000868g0020.2.

FIG. 37 shows SEQ ID NO. 34; the genomic sequence of Nitab4.5_0000842g0110.2, an interactor of Nitab4.5_0000868g0020.2.

FIG. 38 shows SEQ ID NO. 35; the genomic sequence of Nitab4.5_0000842g0110.2, an interactor of Nitab4.5_0000868g0020.2.

FIG. 39 shows SEQ ID NO. 36; the amino acid sequence of Nitab4.5_0001620g0100.2, an interactor of Nitab4.5_0000868g0020.2.

FIG. 40 shows SEQ ID NO. 37; the coding sequence of Nitab4.5_0001620g0100.2, an interactor of Nitab4.5_0000868g0020.2.

FIG. 41 shows SEQ ID NO. 38; the genomic sequence of Nitab4.5_0001620g0100.2, an interactor of Nitab4.5_0000868g0020.2.

FIG. 42 shows SEQ ID NO. 39; the amino acid sequence of Nitab4.5_0001200g0070.2, an interactor of Nitab4.5_0000868g0020.2.

FIG. 43 shows SEQ ID NO. 40; the coding sequence of Nitab4.5_0001200g0070.2, an interactor of Nitab4.5_0000868g0020.2.

FIG. 44 shows SEQ ID NO. 41; genomic sequence of Nitab4.5_0001200g0070.2, an interactor of Nitab4.5_0000868g0020.2.

FIG. 45 shows SEQ ID NO. 42; the amino acid sequence of Nitab4.5_0005803g0040.2, an interactor of Nitab4.5_0000868g0020.2.

FIG. 46 shows SEQ ID NO. 43; the coding sequence of Nitab4.5_0005803g0040.2, an interactor of Nitab4.5_0000868g0020.2.

FIG. 47 shows SEQ ID NO. 44; the genomic sequence of Nitab4.5_0005803g0040.2, an interactor of Nitab4.5_0000868g0020.2.

SEQUENCE LISTING

Figure 1:
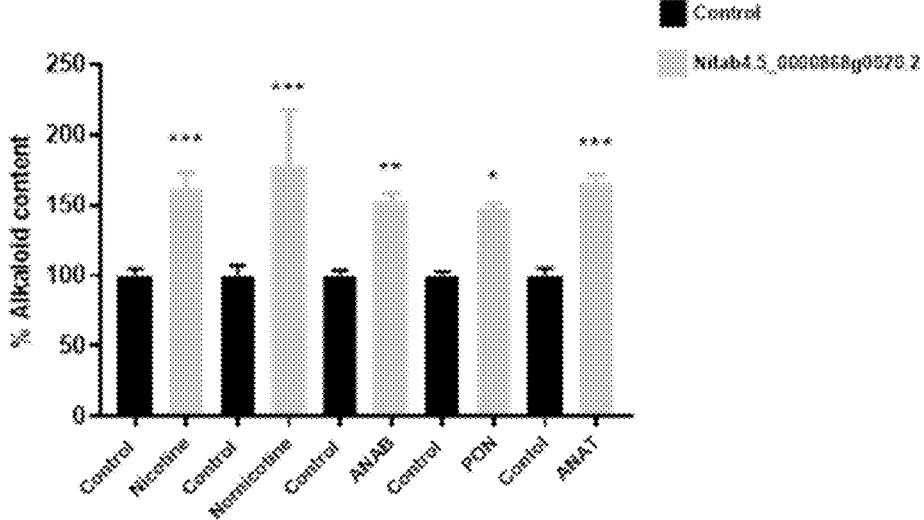
FIG. 1 shows the alkaloid content of 5-week-old tobacco leaves overexpressing Nitab4.5_0000868g0020.2. Alkaloid content is represented relative to a control and is representative of two biological replicates analysed by one-way ANOVA and Tukey's multiple-comparison post-test. Values are shown as means±SEM. Asterisks indicate statistical significance of P value≤0.05.

A summary of sequence identifiers used throughout the subject specification and the corresponding sequence listing is provided wherein:

SEQ ID NO. 1 corresponds to the amino acid sequence of Nitab4.5_0000868g0020.2.

SEQ ID NO. 2 corresponds to the coding sequence of Nitab4.5_0000868g0020.2.

SEQ ID NO. 3 corresponds to the genomic sequence of Nitab4.5_0000868g0020.2.

SEQ ID NO. 4 corresponds to the amino acid sequence of Nitab4.5_0000651g0020.2.

SEQ ID NO. 5 corresponds to the coding sequence of Nitab4.5_0000651g0020.2.

SEQ ID NO. 6 corresponds to the genomic sequence of Nitab4.5_0000651g0020.2.

SEQ ID NO. 7 corresponds to the amino acid sequence of Nitab4.5_0009137g0040.2.

SEQ ID NO. 8 corresponds to the coding sequence of Nitab4.5_0009137g0040.2.

SEQ ID NO. 9 corresponds to the genomic sequence of Nitab4.5_0009137g0040.2.

SEQ ID NO. 10 corresponds to the amino acid sequence of Nitab4.5_0001772g0090.2.

SEQ ID NO. 11 corresponds to the coding sequence of Nitab4.5_0001772g0090.2.

SEQ ID NO. 12 corresponds to the genomic sequence of Nitab4.5_0001772g0090.2.

SEQ ID NO. 13 corresponds to the amino acid sequence of Nitab4.5_0003312g0050.2.

SEQ ID NO. 14 corresponds to the coding sequence of Nitab4.5_0003312g0050.2.

SEQ ID NO. 15 corresponds to the genomic sequence of Nitab4.5_0003312g0050.2.

SEQ ID NO. 16 corresponds to the amino acid sequence of Nitab4.5_0003151g0080.2.

SEQ ID NO. 17 corresponds to the coding sequence of Nitab4.5_0003151g0080.2.

SEQ ID NO. 18 corresponds to the genomic sequence of Nitab4.5_0003151g0080.2.

SEQ ID NO. 19 corresponds to the amino acid sequence of Nitab4.5_0002641g0190.2.

SEQ ID NO. 20 corresponds to the coding sequence of Nitab4.5_0002641g0190.2.

SEQ ID NO. 21 corresponds to the genomic sequence of Nitab4.5_0002641g0190.2.

SEQ ID NO. 22 corresponds to the amino acid sequence of Nitab4.5_0001876g0030.2.

SEQ ID NO. 23 corresponds to the coding sequence of Nitab4.5_0001876g0030.2.

SEQ ID NO. 24 corresponds to the genomic sequence of Nitab4.5_0001876g0030.2.

SEQ ID NO. 25 corresponds to the amino acid sequence of Nitab4.5_0000048g0280.2.

SEQ ID NO. 26 corresponds to the coding sequence of Nitab4.5_0000048g0280.2.

SEQ ID NO. 27 corresponds to the genomic sequence of Nitab4.5_0000048g0280.2.

SEQ ID NO. 28 corresponds to the amino acid sequence of Nitab4.5_0002006g0070.2.

SEQ ID NO. 29 corresponds to the coding sequence of Nitab4.5_0002006g0070.2.

SEQ ID NO. 30 corresponds to the genomic sequence of Nitab4.5_0002006g0070.2.

SEQ ID NO. 31 corresponds to the amino acid sequence of a BTB/POZ homodimerization domain (residues 39-136 of SEQ ID NO. 1).

SEQ ID NO. 32 corresponds to the amino acid sequence of an NPH3 domain (residues 218-492 of SEQ ID NO. 1).

SEQ ID NO. 33 corresponds to the amino acid sequence of Nitab4.5_0000842g0110.2, an interactor of Nitab4.5_0000868g0020.2.

SEQ ID NO. 34 corresponds to the coding sequence of Nitab4.5_0000842g0110.2, an interactor of Nitab4.5_0000868g0020.2.

SEQ ID NO. 35 corresponds to the genomic sequence of Nitab4.5_0000842g0110.2, an interactor of Nitab4.5_0000868g0020.2.

SEQ ID NO. 36 corresponds to the amino acid sequence of Nitab4.5_0001620g0100.2, an interactor of Nitab4.5_0000868g0020.2.

SEQ ID NO. 37 corresponds to the coding sequence of Nitab4.5_0001620g0100.2, an interactor of Nitab4.5_0000868g0020.2.

SEQ ID NO. 38 corresponds to the genomic sequence of Nitab4.5_0001620g0100.2, an interactor of Nitab4.5_0000868g0020.2.

SEQ ID NO. 39 corresponds to the amino acid sequence of Nitab4.5_0001200g0070.2, an interactor of Nitab4.5_0000868g0020.2.

SEQ ID NO. 40 corresponds to the coding sequence of Nitab4.5_0001200g0070.2, an interactor of Nitab4.5_0000868g0020.2.

SEQ ID NO. 41 corresponds to the genomic sequence of Nitab4.5_0001200g0070.2, an interactor of Nitab4.5_0000868g0020.2.

SEQ ID NO. 42 corresponds to the amino acid sequence of Nitab4.5_0005803g0040.2, an interactor of Nitab4.5_0000868g0020.2.

SEQ ID NO. 43 corresponds to the coding sequence of Nitab4.5_0005803g0040.2, an interactor of Nitab4.5_0000868g0020.2.

SEQ ID NO. 44 corresponds the genomic sequence of Nitab4.5_0005803g0040.2, an interactor of Nitab4.5_0000868g0020.2.

Some sequences disclosed herein contain "X" or "N" in nucleotide sequences. "X" or "N" can be any nucleotide or a deletion or insertion of one or more nucleotides. For example, in some cases a string of "X"s or "N"s are shown. The number of "X"s or "N"s does not necessarily correlate with the actual number of nucleotides at that position. There may be more or fewer nucleotides than shown as "X" or "N" in the sequence.

DETAILED DESCRIPTION

For the first time the present inventors have shown that by modulating the activity or expression of at least one gene encoding a BTB/POZ NPH3 domain-containing protein in a plant (e.g. a tobacco plant), the alkaloid and/or TSNA precursor content of the plant (or processed plant) can be modulated.

The present invention provides a method of modulating (e.g. decreasing) the alkaloid content of a plant or a part thereof, the method comprising modifying said plant by modulating (e.g. decreasing) the activity or expression of at least one gene encoding a BTB/POZ NPH3 domain-containing protein.

Also provided is a method of modulating (e.g. decreasing) the content of a tobacco specific nitrosamine (TSNA) precursor in a tobacco plant or plant part thereof, the method comprising modifying said plant by modulating (e.g. decreasing) the activity or expression of at least one gene encoding a BTB/POZ NPH3 domain-containing protein.

The at least one gene encoding a BTB/POZ NPH3 domain-containing protein may be selected from at least one gene encoding a BTB/POZ NPH3 domain-containing protein which comprises an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30.

Suitably, the protein may comprise a BTB/POZ domain and/or an NPH3 domain. Suitably, the protein may comprise a BTB/POZ domain and an NPH3 domain. In one embodiment at least two genes encoding BTB/POZ NPH3 domain-containing proteins are modified selected from the group of genes which encode polypeptides comprising an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30.

In one embodiment at least three, such as at least four, such as at least five, such as at least six, such as at least seven, such as at least eight, such as at least nine, such as ten genes encoding BTB/POZ NPH3 domain-containing proteins are modulated, wherein the genes are selected from those which encode polypeptides comprising an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30. Suitably, the protein may comprise a BTB/POZ domain and/or an NPH3 domain. Suitably, the protein may comprise a BTB/POZ domain and an NPH3 domain. In one aspect, the at least one gene encoding a BTB/POZ NPH3 domain-containing protein encodes a poly-peptide which comprises an amino acid sequence as set out in: SEQ ID NO. 1 or a functional variant or functional fragment or orthologue thereof, or a sequence which has at least 80% identity to SEQ ID NO. 1; or wherein the at least one gene encoding a BTB/POZ NPH3 domain-containing protein comprises a nucleotide sequence as set out in SEQ ID NO. 2 or 3 or a functional variant or functional fragment or orthologue of SEQ ID NO. 2 or 3; or a nucleic acid sequence which has at least 80% identity to SEQ ID NO. 2 or 3. Suitably, the protein may comprise a BTB/POZ domain and/or an NPH3 domain. Suitably, the protein may comprise a BTB/POZ domain and an NPH3 domain.

In one aspect, the activity or expression of at least one further gene is modulated. Suitably, at least two (or at least three or at least four or at least five or at least six or at least seven or at least eight or at least nine) additional genes selected from SEQ ID NO. 2, 3, 5, 6, 8, 9, 11, 12, 14, 15, 17, 18, 20, 21, 23, 24, 27 or 30 or a functional variant or functional fragment or orthologue of SEQ ID NO. 2, 3, 5, 6, 8, 9, 11, 12, 14, 15, 17, 18, 20, 21, 23, 24, 27 or 30 or a nucleic acid sequence which has at least 80% identity to SEQ ID NO. 2, 3, 5, 6, 8, 9, 11, 12, 14, 15, 17, 18, 20, 21, 23, 24, 27 or 30 may also be modulated. Suitably, the protein may comprise a BTB/POZ domain and/or an NPH3 domain. Suitably, the protein may comprise a BTB/POZ domain and an NPH3 domain.

The "expression" of a gene encoding a BTB/POZ NPH3 domain-containing protein may refer to the level of tran-scription, translation i.e. protein expression.

Measurement of the level or amount of a gene product may be carried out by any suitable method, for example comparison of mRNA transcript levels, protein or peptide levels, and/or phenotype of a plant, between a modified plant and comparable plant which has not been modified accord-ing to the present invention.

The term "a comparable product" as defined herein would be one derived from a plant (e.g. a tobacco plant) which had not been modified according to the present invention, but in which all other relevant features were the same (e.g. plant species, growing conditions, method of processing the plant, e.g. tobacco, etc.). The comparable product according to the present invention may mean a plant (e.g. a tobacco plant) or a part thereof, such as a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf) or plant propagation material (e.g. tobacco plant propagation material), or a product comprising said plant or part therefore, e.g. a tobacco industry product or combinations thereof obtainable or obtained from a plant which has not been modified in accordance with the present invention, e.g. to modulate the activity or expression of gene encoding a BTB/POZ NPH3 domain-containing protein. In one embodiment a comparable product is one which does not comprise gene encoding a BTB/POZ NPH3 domain-containing protein whose activity or expression has been modulated.

The term "modifying" or "modified" as used herein means a plant (e.g. a tobacco plant) or nucleic acid sequence that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methane-sulfonate (EMS) mutagenesis and modern population analy-sis approaches.

In one embodiment a natural variant which has a modified gene encoding a BTB/POZ NPH3 domain-containing pro-tein is selected and that trait or gene is bred into a second plant which may have commercially desirable traits.

In one embodiment the plant according to the present invention is a transgenic plant. In one embodiment the plant according to the invention is a non-transgenic plant.

The term "unmodified plant" as defined herein would be a plant (e.g. a tobacco plant) which had not been modified according to the present invention, e.g. to modulate the activity or expression of a gene encoding a BTB/POZ NPH3 domain-containing protein or to modify the nucleic acid sequence of at least one gene encoding a BTB/POZ NPH3 domain-containing protein; and in which all other relevant features were the same (e.g. plant species, growing condi-tions, method of processing tobacco, etc.). In one embodi-ment an unmodified plant is one which does not comprise a gene encoding a BTB/POZ NPH3 domain-containing pro-tein whose activity or expression has been modulated. In one embodiment, an unmodified plant is one which does not comprise a modified nucleic acid sequence which encodes at least one gene encoding a BTB/POZ NPH3 domain-con-taining protein.

BTB/POZ NPH3 Domain-Containing Protein

A "BTB/POZ NPH3 domain-containing protein" as used herein has its usual meaning in the art and refers to a protein which comprises a BTB/POZ domain and an NPH3 domain. An illustrative sequence of a BTB/POZ NPH3 domain-containing protein from tobacco is shown in SEQ ID NO. 1.

A "BTB/POZ domain" as used herein has its usual meaning in the art and refers to the common protein struc-tural domain. The BTB/POZ domain mediates dimerization, such as homomeric dimerization. The BTB/POZ protein comprises a cluster of alpha-helices flanked by short beta-sheets at the top and bottom of the molecule.

BTB is also referred to as bric a brac, Broad-Complex, tramtrack, BR-C, ttk and bab.

POZ is also referred to as Pox virus and Zinc finger.

The BTB domain is a protein-protein interaction motif which participates in cellular functions including transcrip-tional regulation, cytoskeletal dynamics, ion channel assem-bly and gating and targeting proteins for ubiquitination. The BTB fold is structurally well conserved.

An illustrative sequence of a BTB/POZ domain is set forth at amino acids 39-136 of SEQ ID NO. 1 and is also presented as SEQ ID NO. 31.

A BTB/POZ domain may be identified by comparing the protein in question to SEQ ID NO. 31 and/or SEQ ID NO. 1.

Suitably, a BTB/POZ domain as used herein may refer to a sequence set forth in SEQ ID NO. 31 or a sequence which has at least 80% identity thereto. Suitably, a BTB/POZ domain as used herein may refer to a sequence which corresponds to amino acids 39-156 of SEQ ID NO. 1 when aligned with SEQ ID NO. 1.

An "NPH3 domain" as used herein has its usual meaning in the art and refers to a non-phototropic hypocotyl 3 domain. The NPH3 domain may function as an adapter or scaffold protein to a nonphototrophic hypocotyl 1 serine-threonine protein kinase.

The NPH3 domain is a protein-protein interaction motif.

An illustrative sequence of an NPH3 domain is set forth at amino acids 218-492 of SEQ ID NO. 1 and is also presented as SEQ ID NO. 32.

An NPH3 domain may be identified by comparing the protein in question to SEQ ID NO. 32 and/or SEQ ID NO. 1.

Suitably, an NPH3 domain as used herein may refer to a sequence set forth in SEQ ID NO. 32 or a sequence which has at least 80% identity thereto. Suitably, an NPH3 domain as used herein may refer to a sequence which corresponds to amino acids 218-492 of SEQ ID NO. 1 when aligned with SEQ ID NO. 1.

Domains within the amino acid sequence of a protein may be identified using domain prediction software known in the art. Domains are also described in protein databases such as UniprotKB.

Without wishing to be bound by theory, it is hypothesized that modulating content of a BTB/POZ NPH3 domain-containing protein in a plant cell or modulating activity, such as homodimerization or UDP-glycosyltrasnferase activity, of a BTB/POZ NPH3 domain-containing protein in a plant would alter the metabolic pathways producing alkaloids and TSNA precursors such as PON, resulting in modulated alkaloid content.

In one embodiment a BTB/POZ NPH3 domain-containing protein comprises an amino acid sequence shown as SEQ ID NO. 1 or a sequence which has at least 80% identity thereto, or a homologue thereof. The protein comprises a BTB/POZ domain and an NPH3 domain. Suitably, a homologue of SEQ ID NO. 1 may be selected from the group comprising: SEQ ID NO. 4, 7, 10, 13, 16, 19, 22 25 or 28, or a sequence which has at least 80% identity thereto. Suitably, a homologue of SEQ ID NO. 1 may be selected from the group comprising: SEQ ID NO. 4, 7, 10, 13, 16, 19, 22, 25 or 28, wherein said sequence comprises a BTB/POZ domain and an NPH3 domain, or a sequence which has at least 80% identity to SEQ ID NO. 4, 7, 10, 13, 16, 19, 22, 25 or 28 and comprises a BTB/POZ domain and an NPH3 domain.

In one embodiment a BTB/POZ NPH3 domain-containing protein comprises an amino acid sequence shown as SEQ ID NO. 1, 4, 7, 10, 13, 16, 19, 22 25 or 28, or a sequence which has at least 80% identity thereto (preferably at least 85%, at least 90%, at least 95%, at least 96%, at least 97%, at least 98%, or at least 99% identity thereto). In one embodiment a BTB/POZ NPH3 domain-containing protein comprises an amino acid sequence shown as SEQ ID NO. 1, 4, 7, 10, 13, 16, 19, 22 25 or 28, or a sequence which has at least 80% identity thereto (preferably at least 85%, at least 90%, at least 95%, at least 96%, at least 97%, at least 98%, or at least 99% identity thereto) and comprises a BTB/POZ domain and an NPH3 domain.

Suitably, a BTB/POZ NPH3 domain-containing protein according to the present invention may comprise an amino acid sequence shown as SEQ ID NO. 1, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 4, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 7, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 10, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 13, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 16, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 19, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 22, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 25, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, a BTB/POZ NPH3 domain-containing protein according to the present invention may comprise an amino acid sequence shown as SEQ ID NO. 28, or a sequence which has at least 80% identity thereto (preferably at least 85%, preferably at least 90%, preferably at least 93%, preferably at least 95%, at least 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

In one embodiment the BTB/POZ NPH3 domain-containing protein according to the present invention comprises or consists of an amino acid sequence selected from: SEQ ID NO. 1, 4, 7, 10, 13, 16, 19, 22, 25 or 28.

Suitably, the protein may be from *Nicotiana tabacum.*

In one embodiment the at least one BTB/POZ NPH3 domain-containing protein is encoded by a polynucleotide sequence wherein the gene (prior to mutation) comprises the sequence shown as SEQ ID NO. 2, 3, 5, 6, 8, 9, 11, 12, 14, 15, 17, 18, 20, 21, 23, 24, 26, 27, 29 or 30; or a sequence which has at least 80% sequence identity thereto. Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 2, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 3, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 5, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 6, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 8, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 9, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 11, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 12, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 14, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 15, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 17, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 18, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 20, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 21, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 23, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 24, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 26, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 27, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 29, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

Suitably, the BTB/POZ NPH3 domain-containing protein for use according to the present invention may be encoded by a polynucleotide sequence wherein the gene (prior to mutation) comprises the sequence shown as SEQ ID NO. 30, or a sequence which has at least 80% sequence identity thereto (preferably at least 85%, preferably at least 90%, preferably at least 93%, preferably at least 95%, at least, 96%, at least 97%, at least 98%, or at least 99% identity thereto). Suitably, the protein may comprise a BTB/POZ domain and/or an NPH3 domain. Suitably, the protein may comprise a BTB/POZ domain and an NPH3 domain.

In one embodiment the at least one BTB/POZ NPH3 domain-containing protein is encoded by a polynucleotide sequence wherein the gene (prior to mutation) is selected from: SEQ ID NO. 2, 3, 5, 6, 8, 9, 11, 12, 14, 15, 17, 18, 20, 21, 23, 24, 26, 27, 29 or 30.

Suitably, the protein for use according to the present invention may be encoded by a polynucleotide sequence from *Nicotiana tabacum*.

In one aspect the present invention provides a method of decreasing the alkaloid content of a plant or part thereof or cell (e.g. plant cell), the method comprising modifying said plant by decreasing or inhibiting the activity or expression of at least one gene encoding a BTB/POZ NPH3 domain-containing protein.

In one aspect the present invention provides a method of decreasing the alkaloid content of a plant or part thereof or plant cell, the method comprising modifying said plant by decreasing or inhibiting the activity or expression of at least one gene encoding a BTB/POZ NPH3 domain-containing protein comprising the amino acid sequence shown as SEQ ID NO. 1, 4, 7, 10, 13, 16, 19, 22, 25 or 28, or a sequence which has at least 80% identity thereto or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the BTB/POZ NPH3 domain-containing protein may comprise a BTB/POZ domain and/or an NPH3 domain. Suitably, the BTB/POZ NPH3 domain-containing protein may comprise a BTB/POZ domain and an NPH3 domain.

In one aspect the present invention provides a method of decreasing the content of a tobacco specific nitrosamine (TSNA) precursor in a plant or part thereof (e.g. leaf), the method comprising modifying said plant by decreasing or inhibiting the activity or expression of at least one gene encoding BTB/POZ NPH3 domain-containing protein.

In one aspect the present invention provides a method of decreasing the content of a tobacco specific nitrosamine (TSNA) precursor in a plant or part thereof (e.g. leaf), the method comprising modifying said plant by decreasing or inhibiting the activity or expression of at least one gene encoding a BTB/POZ NPH3 domain-containing protein comprising the amino acid sequence shown as SEQ ID NO. 2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the BTB/POZ NPH3 domain-containing protein may comprise a BTB/POZ domain and/or an NPH3 domain. Suitably, the BTB/POZ NPH3 domain-containing protein may comprise a BTB/POZ domain and an NPH3 domain.

In one aspect the present invention provides a method of decreasing the content of a TSNA in a processed leaf, such as a cured leaf, the method comprising:

modifying a plant by decreasing or inhibiting the activity or expression of at least one gene encoding a BTB/POZ NPH3 domain-containing protein;
harvesting a leaf from said plant;
and curing said harvested leaf.

Suitably, the method of decreasing the content of a TSNA in a processed leaf may comprise: modifying said plant by decreasing or inhibiting the activity or expression of at least one gene encoding a BTB/POZ NPH3 domain-containing protein comprising the amino acid sequence shown as SEQ ID NO. 2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the BTB/POZ NPH3 domain-containing protein may comprise a BTB/POZ domain and/or an NPH3 domain. Suitably, the BTB/POZ NPH3 domain-containing protein may comprise a BTB/POZ domain and an NPH3 domain.

The term "decreasing" or "inhibiting" (e.g. inhibiting the activity or expression of gene encoding a BTB/POZ NPH3 domain-containing protein) as used herein means that the activity or expression of the gene encoding the BTB/POZ NPH3 domain-containing protein is lower or decreased compared with the activity or expression of the gene in a comparable product.

In one aspect the present invention provides a method of increasing the alkaloid content of a plant or part thereof or cell (e.g. plant cell), the method comprising modifying said plant by increasing or enhancing the activity or expression of at least one gene encoding a BTB/POZ NPH3 domain-containing protein.

In one aspect the present invention provides a method of increasing the alkaloid content of a plant or part thereof or plant cell, the method comprising modifying said plant by increasing or enhancing the activity or expression of at least one gene encoding a BTB/POZ NPH3 domain-containing protein comprising the amino acid sequence shown as SEQ ID NO. 1, 4, 7, 10, 13, 16, 19, 22, 25 or 28, or a sequence which has at least 80% identity thereto or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30. Suitably, the BTB/POZ NPH3 domain-containing protein may comprise a BTB/POZ domain and/or an NPH3 domain. Suitably, the BTB/POZ NPH3 domain-containing protein may comprise a BTB/POZ domain and an NPH3 domain.

In one aspect the present invention provides a method of increasing the content of a tobacco specific nitrosamine (TSNA) precursor in a plant or part thereof (e.g. leaf), the method comprising modifying said plant by increasing or enhancing the activity or expression of at least one gene encoding a BTB/POZ NPH3 domain-containing protein.

In one aspect the present invention provides a method of increasing the content of a tobacco specific nitrosamine (TSNA) precursor in a plant or part thereof (e.g. leaf), the method comprising modifying said plant by increasing or enhancing the activity or expression of at least one gene encoding a BTB/POZ NPH3 domain-containing protein comprising the amino acid sequence shown as SEQ ID NO.

2, 3, 5, 6, 8, 9, 11, 12, 14, 15, 17, 18, 20, 21, 23, 24, 26, 27, 29 or 30, or a sequence which has at least 80% identity thereto, or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

The term "increasing" or "enhancing" (e.g. increasing the activity or expression of gene encoding a BTB/POZ NPH3 domain-containing protein) as used herein means that the activity or expression of the gene encoding the BTB/POZ NPH3 domain-containing protein is higher or increased compared with the activity or expression of the gene in a comparable product.

According to the present invention, the activity or expression of a gene encoding a BTB/POZ NPH3 domain-containing protein is modulated.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the activity of at least one gene encoding a BTB/POZ NPH3 domain-containing protein.

The term "activity" refers to any functionality of the BTB/POZ NPH3 domain-containing protein encoded by the at least one gene. Examples of activity include the formation of protein:protein interactions, enzymatic activity or localization of the BTB/POZ NPH3 domain-containing protein.

Suitably, the activity may be the ability of the BTB/POZ NPH3 domain-containing protein to interact with another molecule or molecules. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of a BTB/POZ NPH3 domain-containing protein to interact with another molecule.

Suitably, the ability of the BTB/POZ NPH3 domain-containing protein to interact with the other molecule may be the ability to bind the other molecule. The other molecule may be a protein, such as another BTB/POZ NPH3 domain-containing protein. Suitably, the other molecule may be more than one molecule, such as one or more molecules, such as two or more molecules, such as three or more molecules. Where the other molecule is more than one molecule, the other molecules may be the same molecule or may be different molecules.

Suitably, the activity may be the ability of the BTB/POZ NPH3 domain-containing protein to homodimerize. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of a BTB/POZ NPH3 domain-containing protein to homodimerize.

Suitably, the activity may be the ability of the BTB/POZ NPH3 domain-containing protein to function as a UDP-glycosyltransferase. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of a BTB/POZ NPH3 domain-containing protein to function as a UDP-glycosyltransferase.

Modulation of the activity of a gene encoding a BTB/POZ NPH3 domain-containing protein may entail increasing or decreasing the activity of the BTB/POZ NPH3 domain-containing protein.

Increasing the activity of a BTB/POZ NPH3 domain-containing protein refers to enhancing or improving the ability of the BTB/POZ NPH3 domain-containing protein to carry out a particular function in comparison to a BTB/POZ NPH3 domain-containing protein in a plant that has not been modified in accordance with the invention.

Decreasing the activity of a BTB/POZ NPH3 domain-containing protein refers to reducing, inhibiting or disrupting the ability of the BTB/POZ NPH3 domain-containing protein to carry out a particular function in comparison to a BTB/POZ NPH3 domain-containing protein in a plant that has not been modified in accordance with the invention. The activity of a BTB/POZ NPH3 domain-containing protein may be reduced to such an extent that the activity is prevented or eliminated.

In some embodiments the activity of a BTB/POZ NPH3 domain-containing protein may be modulated (i.e. increased or decreased) by at least about 10% 20% 30%, or 40%, suitably at least about 50%, 60%, 70%, more suitably at least about 80%, 90%, 95% or 100% in comparison to the activity of a gene encoding a BTB/POZ NPH3 domain-containing protein in a plant (e.g. a tobacco plant) which has not been modified in accordance with the present invention.

In some embodiments the modulated BTB/POZ NPH3 domain-containing protein exhibits increased or decreased activity compared to an unmodified BTB/POZ NPH3 domain-containing protein. The modulated BTB/POZ NPH3 domain-containing protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased activity compared to an unmodified BTB/POZ NPH3 domain-containing protein.

Techniques are known in the art for measuring protein activities. For example, assays are known for measuring the enzymatic activity of a protein and the localization of a protein can be identified using microscopy techniques.

In particular, the ability of a BTB/POZ NPH3 domain-containing protein to bind another molecule may be measured using techniques known in the art. Examples of such techniques include immunoprecipitation, isothermal calorimetry, surface plasmon resonance and microscale thermophoresis. For example, the ability of a modulated or mutated a BTB/POZ NPH3 domain-containing protein to bind other molecules may be determined for example by performing co-immunoprecipitation experiments using a modulated or mutated a BTB/POZ NPH3 domain-containing protein and a corresponding unmodified or unmutated a BTB/POZ NPH3 domain-containing protein. If the modulation or mutation in the a BTB/POZ NPH3 domain-containing protein reduces, inhibits or eliminates the ability of the a BTB/POZ NPH3 domain-containing protein to bind other molecules, the co-immunoprecipitation will show that the modulated or mutated a BTB/POZ NPH3 domain-containing protein binds fewer other molecules.

The ability of a BTB/POZ NPH3 domain-containing protein to homodimerize may be measured using techniques known in the art. Examples of such techniques include techniques such as gel electrophoresis under native conditions, size exclusion chromatography, diffusion nuclear magnetic resonance (NMR) or analytical ultracentrifugation. According to the present invention, the activity or expression of a BTB/POZ NPH3 domain-containing protein is modulated.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the expression of at least one gene encoding a BTB/POZ NPH3 domain-containing protein.

The "expression" of a gene refers to the degree to which the information encoded in the gene is converted to a functionality. The level of expression of a gene may be equated with the amount of the product of that gene present in a cell or organism. A modification that modulates (i.e. increases or decreases) the expression of a gene is one that increases the amount of the product of that gene in a plant or cell in comparison to an unmodified plant or cell.

In some embodiments the expression of a BTB/POZ NPH3 domain-containing protein is modulated (i.e. increased or decreased) in comparison to the expression of a gene encoding a BTB/POZ NPH3 domain-containing protein in a plant (e.g. a tobacco plant) which has not been modified in accordance with the present invention.

In some embodiments the expression of a BTB/POZ NPH3 domain-containing protein may be modulated (i.e. increased or decreased) by at least about 10% 20% 30%, or 40%, suitably at least about 50%, 60%, 70%, more suitably at least about 80%, 90%, 95% or 100% in comparison to the expression of a gene encoding a BTB/POZ NPH3 domain-containing protein in a plant (e.g. a tobacco plant) which has not been modified in accordance with the present invention.

In some embodiments the modulated a BTB/POZ NPH3 domain-containing protein exhibits increased or decreased expression compared to an unmodified a BTB/POZ NPH3 domain-containing protein. The modulated a BTB/POZ NPH3 domain-containing protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased expression compared to an unmodified a BTB/POZ NPH3 domain-containing protein.

Typically, genes are transcribed to mRNA, which is translated to protein, the final gene product. Proteins may be sequestered in cellular stores and/or degraded. The expression of a gene may be modulated by modulating any or all of these steps. Accordingly, in some embodiments the modification modulates expression of at least one gene encoding a BTB/POZ NPH3 domain-containing protein in one of the following ways:

modulating transcription from the at least one gene encoding a BTB/POZ NPH3 domain-containing protein;

modulating translation of the mRNA from the at least one gene encoding a BTB/POZ NPH3 domain-containing protein;

modulating release of the BTB/POZ NPH3 domain-containing protein from intracellular stores; and/or modulating the rate of degradation of the BTB/POZ NPH3 domain-containing protein.

The expression of specific genes encoding BTB/POZ NPH3 domain-containing proteins can be measured by measuring transcription and/or translation of the gene. Methods for measuring transcription are well known in the art and include, amongst others, northern blot, RNA-Seq, in situ hybridization, DNA microarrays and RT-PCR. Alternatively, the expression of a gene may be measured indirectly by measuring the level of the gene product for example the protein encoded by said gene. For example, the expression of a BTB/POZ NPH3 domain-containing protein may be determined by measuring the presence of the protein using an antibody specific for the BTB/POZ NPH3 domain-containing protein (for example antibodies specific for a BTB/POZ, NPH3 domains) by western blot.

Modifying

The plant or cell may be modified in any way that modulates activity or expression of at least one gene encoding a BTB/POZ NPH3 domain-containing protein. Types of modifications to plants and cells that modulate activity or expression of genes, as well as techniques to achieve those modifications, are known in the art.

In some embodiments the present invention provides a method of decreasing the alkaloid content of a plant or part thereof or cell (e.g. plant cell), the method comprising modifying said plant by decreasing or inhibiting the activity or expression of at least one gene encoding a BTB/POZ NPH3 domain-containing protein.

In some embodiments the present invention provides a method of decreasing the content of a tobacco specific nitrosamine (TSNA) or a precursor of a TSNA in a tobacco plant or plant part thereof, the method comprising modifying said plant or a cell culture by decreasing the activity or expression of at least one gene encoding a BTB/POZ NPH3 domain-containing protein.

Any method known in the art for decreasing or inhibiting the activity or expression of a gene may be used in the methods according to the present invention.

Suitably, the activity or expression of the gene encoding a BTB/POZ NPH3 domain-containing protein may be reduced, partly inactivated, inhibited, eliminated, knocked out or lost such that the protein activity, expression or function of the gene encoding a BTB/POZ NPH3 domain-containing protein is not detectable.

In one aspect, the at least one gene encoding a BTB/POZ NPH3 domain-containing protein is knocked out. In other words, the gene encoding a BTB/POZ NPH3 domain-containing protein has been rendered completely inoperative.

By way of example, the present method may comprise:

providing a mutation in a nucleic acid sequence which encodes a protein comprising the amino acid sequence shown as SEQ ID NO. 1, 4, 7, 10, 13, 16, 19, 22, 25 or 28, or an amino acid sequence which has at least 80% sequence identity thereto;

providing a mutation in a regulatory region (e.g. a promoter or an enhancer) which contributes to controlling the expression of a protein comprising the amino acid sequence shown as SEQ ID NO. 1, 4, 7, 10, 13, 16, 19, 22, 25 or 28, or an amino acid sequence which has at least 80% sequence identity thereto;

providing an antisense RNA, siRNA or miRNA which reduces the level of nucleic acid sequence encoding a protein comprising the amino acid sequence shown as SEQ ID NO. 1, 4, 7, 10, 13, 16, 19, 22, 25 or 28, or an amino acid sequence which has at least 80% sequence identity thereto.

Each of the above approaches results in the reduction or prevention of activity or expression of a protein comprising the amino acid sequence shown as SEQ ID NO. 1, 4, 7, 10, 13, 16, 19, 22, 25 or 28, or an amino acid sequence which has at least 80% sequence identity thereto or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID NO. 1, 4, 7, 10, 13, 16, 19, 22, 25 or 28, or an amino acid sequence which has at least 80% (preferably at least 85%, preferably at least 90%, preferably at least 93%, preferably at least 95%, preferably at least 98%, preferably at least 99%) sequence identity thereto.

In one embodiment the mutation decreases the alkaloid content of a plant. In another embodiment, the mutation decreases the content of at least one TSNA precursor in a plant or part thereof, or leaf such as a harvested or processed leaf. In one embodiment the mutation decreases the content of one or more TSNAs selected from NNK, NNN, NAT, NAB, preferably NNK content is decreased in a processed leaf. Suitably, the TSNA content is reduced in relation to a comparable product.

In one embodiment, a method according to the present invention may comprise providing a nucleic acid sequence to a plant or part thereof or plant cell, wherein said nucleic acid results in the reduction or elimination of the activity or expression of at least one gene encoding a BTB/POZ NPH3 domain-containing protein.

In one embodiment, a method according to the present invention may comprise providing a nucleic acid sequence to a plant or part thereof or plant cell, wherein said nucleic acid results in the modification of the nucleic acid sequence of at least one gene encoding a BTB/POZ NPH3 domain-containing protein.

Suitably said nucleic acid sequence may be introduced to the plant or part thereof or cell. Suitably an endogenous nucleic acid sequence in the plant or part thereof or cell may be modified to encode the polypeptide according to the present invention (e.g. by gene editing). For example, an endogenous nucleotide sequence may be modified to decrease the activity or expression of at least one gene encoding a BTB/POZ NPH3 domain-containing protein.

In a preferred embodiment, each copy of a nucleic acid sequence encoding a protein comprising a sequence shown as SEQ ID NO. 1, 4, 7, 10, 13, 16, 19, 22, 25 or 28, or a sequence which has at least 80% sequence identity thereto or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30 which is present in the plant is modified e.g. mutated as defined herein (e.g. each genomic copy of a gene encoding said protein in a plant is mutated). For example, each copy of the gene in the allotetraploid genome of *Nicotiana tabacum* may be mutated.

In a preferred embodiment, some or all of the homologues of the BTB/POZ NPH3 domain-containing protein described herein are modified e.g. inhibited or mutated. Suitably, some or all of SEQ ID NO. 1, 4, 7, 10, 13, 16, 19, 22, 25 or 28, or corresponding sequences which have at least 80% sequence identity thereto are modified e.g. inhibited or mutated.

In some embodiments the plant or plant cell according to the present invention is homozygous. Suitably, the plant or plant cell may be homozygous for the modification e.g. inhibition or mutation.

In some embodiments the plant or plant cell according to the present invention expresses only the modified e.g. mutated nucleic acid encoding the BTB/POZ NPH3 domain-containing protein. In other words, in some embodiments no endogenous (or endogenous and functional protein) is present in the plant according to the present invention. In other words, if any endogenous protein is present it is preferably in an inactive form.

In one embodiment the present method may comprise providing a mutation in the nucleic acid sequence shown as SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity thereto.

The mutation may alter the plant genome such that a nucleic acid sequence encoding a protein comprising the amino acid sequence shown as SEQ ID NO. 1, 4, 7, 10, 13, 16, 19, 22, 25 or 28, or an amino acid sequence which has at least 80% sequence identity thereto is completely or partially deleted or otherwise modified to inhibit or eliminate the ability of the BTB/POZ NPH3 domain-containing protein to homodimerize. In some embodiments the mutation does not alter the level or expression of the protein but reduces inhibits or eliminates the ability of the BTB/POZ NPH3 domain-containing protein to homodimerize. The expression "inhibits or eliminates" means that the BTB/POZ NPH3 domain-containing protein is predominantly present in monomeric form.

Suitably, the mutation may be in a BTB/POZ domain of the BTB/POZ NPH3 domain-containing protein. Suitably, the mutation may be in an NPH3 domain of the BTB/POZ NPH3 domain-containing protein. Suitably, the BTB/POZ NPH3 domain-containing protein may comprise multiple mutations, each in a different domains. In some embodiments, the mutation in the BTB/POZ domain modifies the ability of BTB/POZ NPH3 domain-containing protein to homodimerize. Suitably, the mutation may prevent or reduce homodimerization Suitably, the mutation in the BTB/POZ domain prevents or reduces homodimerization and reduces activity of the BTB/POZ NOH3 domain-containing protein.

The mutation may be in one or more domains of the BTB/POZ NPH3 domain-containing protein, such as in a BTB/POZ domain and/or an NPH3 domain. In some embodiments, one or more domains of the BTB/POZ NPH3 domain-containing protein, such as in a BTB/POZ domain and/or an NPH3 domain, may be mutated thereby modifying the ability of the BTB/POZ NPH3 to homodimerize. In some embodiments, one or more domains, such as a BTB/POZ domain and/or an NPH3 domain, are deleted from the BTB/POZ NPH3 domain-containing protein.

The mutation may interrupt the nucleic acid sequence which encodes a protein comprising the amino acid sequence shown as SEQ ID NO. 1, 4, 7, 10, 13, 16, 19, 22, 25 or 28, or an amino acid sequence which has at least 80% sequence identity thereto.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutation or a non-tolerated amino acid substitution in the open reading frame.

A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutation inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the method according to the present invention. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID NO. 1, 4, 7, 10, 13, 16, 19, 22, 25 or 28, or a sequence which has at least 80% sequence identity thereto.

In some embodiments, the BTB/POZ domain may contain a mutation which decreases the expression of the at least one gene encoding a BTB/POZ NPH3 domain-containing protein.

In some embodiments, the NPH3 domain may contain a mutation which decreases the expression of the at least one gene encoding a BTB/POZ NPH3 domain-containing protein.

The mutation may be a deletion, a splice mutant or codon encoding a non-tolerated amino acid substitution.

In one embodiment, the nucleic acid sequence encoding the BTB/POZ NPH3 domain-containing protein may be wholly or partially deleted. The deletion may be continuous, or may comprise a plurality of sections of sequence. The deletion preferably removes a sufficient amount of nucleotide sequence such that the nucleic acid sequence no longer encodes a functional BTB/POZ NPH3 domain-containing protein. The deletion may be total, in which case 100% of the coding portion of the nucleic acid sequence is absent, when compared to the corresponding genome of a comparable unmodified plant. The deletion may, for example, remove at least 50, 60, 70, 80 or 90% of the coding portion of the nucleic acid sequence. Suitably, at least part of the protein may be deleted. The deletion may, for example, remove at least 10, 20, 30, 40, 50, 60, 70, 80 or 90% of the coding portion of the protein.

The deletion may remove at least part of a BTB/POZ domain. The deletion may, for example, remove at least 10, 20, 30, 40, 50, 60, 70, 80 or 90% of a BTB/POZ domain. Suitably, the deletion may remove at least 5 amino acids, at least 10 amino acids, at least 15, at least 20, at least 25, at least 30 amino acids of a BTB/POZ domain. Suitably, the deletion may remove at least 5 amino acids, at least 10 amino acids, at least 15, at least 20, at least 25, at least 30 amino acids of a BTB/POZ domain.

The deletion may remove at least part of a NPH3 domain. The deletion may, for example, remove at least 10, 20, 30, 40, 50, 60, 70, 80 or 90% of a NPH3 domain. Suitably, the deletion may remove at least 5 amino acids, at least 10 amino acids, at least 15, at least 20, at least 25, at least 30 amino acids of a NPH3 domain. Suitably, the deletion may remove at least 5 amino acids, at least 10 amino acids, at least 15, at least 20, at least 25, at least 30 amino acids of a NPH3 domain.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described herein may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KEYBASE® or TALENs).

Alternatively, mutagenesis systems such as TILLING (Targeting Induced Local Lesions IN Genomics; McCallum et al. (2000) Nat. Biotech. 18:455, and McCallum et al. (2000) Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds, cells and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the modification. Preferably modified plants are homozygous for the modification.

In one embodiment the method of reducing or preventing the activity or expression of a protein comprising the amino acid sequence shown as SEQ ID NO. 1, 4, 7, 10, 13, 16, 19, 22, 25 or 28, or an amino acid sequence which has at least 80% sequence identity thereto does not comprise treating the plant with a chemical (e.g. an agrochemical).

Other ways of reducing or preventing the expression will be apparent to one skilled in the art and include the use of virus-induced gene silencing (VIGs), micro RNA silencing, RNAi, antisense, tDNA insertions, or dominant negative constructs (or antimorphic mutations).

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by virus-induced gene silencing.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by microRNAs.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by RNAi.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by antisense suppression.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by sense suppression.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by tDNA insertions.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by dominant negative constructs (or antimorphic mutations).

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by a targeted mutagenesis based system.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by CRISPR based system.

In one embodiment the expression of a gene encoding a protein comprising the amino acid sequence shown as SEQ ID NO. 1, 4, 7, 10, 13, 16, 19, 22, 25 or 28, or an amino acid sequence which has at least 80% sequence identity thereto may be reduced or eliminated by zinc finger nuclease, TALENs, meganucleases, mutagenic oligonucleotides or TILLING.

In some embodiments the present invention provides a method of increasing the alkaloid content of a plant or part thereof or cell (e.g. plant cell), the method comprising modifying said plant by increasing or enhancing the activity or expression of at least one gene encoding a BTB/POZ NPH3 domain-containing protein.

Any method known in the art for increasing or enhancing the activity or expression of a gene may be used in the methods according to the present invention.

In some embodiments the method may comprise overexpressing at least one gene encoding a BTB/POZ NPH3 domain-containing protein. Suitably the method may comprise expressing one or more additional copies of the at least one gene encoding a BTB/POZ NPH3 domain-containing protein in the plant or cell. Suitably the method may comprise modifying the endogenous copy of the at least one gene encoding a BTB/POZ NPH3 domain-containing protein such that its expression is increased. The method may comprise mutating the coding sequence of the at least one gene encoding a BTB/POZ NPH3 domain-containing protein. The method may comprise mutating a regulatory sequence that regulates expression of the at least one gene encoding a BTB/POZ NPH3 domain-containing protein.

Suitably the method may comprise transforming a cell of a plant (e.g. a tobacco plant) with a genetic construct which encodes at least one BTB/POZ NPH3 domain-containing protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30; or which comprises a nucleotide sequence which encodes a protein which is capable of promoting or augmenting at least one endogenous BTB/POZ NPH3 domain-containing protein. It will be appreciated that each of these options would result in an increased activity and expression of the polypeptide encoded by the at least one BTB/POZ NPH3 domain-containing protein. The method may comprise regenerating the plant from the transformed cell. There is provided use of genetic construct which is capable of increasing the activity and/or expression of a polypeptide encoded by at least one gene encoding a BTB/POZ NPH3 domain-containing protein for increasing the alkaloid content (e.g. nicotine content) in a plant or part there of or cell transformed with the construct.

The genetic construct may encode a polypeptide comprising the amino acid SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

In another embodiment, the invention relates to a method of increasing the alkaloid content of a plant or part thereof or a cell, comprising modifying said plant or cell by increasing the activity of at least one gene encoding a BTB/POZ NPH3 domain-containing protein.

In one embodiment the activity of at least one gene encoding a BTB/POZ NPH3 domain-containing protein may be increased by introducing (or providing) a mutation to at least one gene encoding a BTB/POZ NPH3 domain-containing protein.

Suitably, the activity of at least one gene encoding a BTB/POZ NPH3 domain-containing protein may be increased by introducing a mutation to at least one gene encoding a BTB/POZ NPH3 domain-containing protein which comprises an amino acid sequence as set out in SEQ ID NO. 1, 4, 7, 10, 13, 16, 19, 22, 25 or 28; or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30, or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

In some embodiments a modification which increases the activity or expression of at least one gene encoding a BTB/POZ NPH3 domain-containing protein and thereby increases alkaloid content by one of the following:

modulating transcription from the at least one gene encoding a BTB/POZ NPH3 domain-containing protein;

modulating translation of the mRNA from the at least one gene encoding a BTB/POZ NPH3 domain-containing protein;

modulating release of the BTB/POZ NPH3 domain-containing protein rom intracellular stores; and/or modulating the rate of degradation of the BTB/POZ NPH3 domain-containing protein.

In one aspect, the activity and or expression of a BTB/POZ NPH3 domain containing protein may be modulated e.g. decreased by modifying the activity or expression of an interactor protein.

Without wishing to be bound by theory, in one aspect the interactor protein may reduce or block the activity and/or expression of a BTB/POZ NPH3 protein. For example the interactor protein may bind to and/or sequester the BTB/POZ NPH3 protein; thus increasing the activity and/or expression of the interactor protein may reduce the activity and/or expression of the BTB/POZ NPH3 domain containing protein.

In an alternative aspect, the interactor protein may increase or enhance the activity and/or expression of a BTB/POZ NPH3 protein. For example the interactor protein may act as a co-factor to the BTB/POZ NPH3 protein; thus decreasing the activity and/or expression of the interactor protein may reduce the activity and/or expression of the BTB/POZ NPH3 domain containing protein.

In one aspect, the activity and/or expression of a BTB/POZ NPH3 protein may be modulated (e.g. reduced) by modifying the activity and/or expression of an interactor protein.

Suitably the interactor protein may be selected from SEQ ID NO. 33, SEQ ID NO. 36. SEQ ID NO. 39, SEQ ID NO. 42 or variants thereof having at least 80% identity thereto (such as at least 85% identity, at least 90% identity, at least 95%, at least 97% identity, at least 98% identity). Suitably the interactor protein may have a coding sequence be selected from SEQ ID NO. 34, SEQ ID NO. 37. SEQ ID NO. 40, SEQ ID NO. 43 or variants thereof having at least 80% identity thereto (such as at least 85% identity, at least 90% identity, at least 95%, at least 97% identity, at least 98% identity).

Suitably the interactor protein may be encoded by a nucleotide sequence selected from SEQ ID NO. 35, SEQ ID NO. 38. SEQ ID NO. 41, SEQ ID NO. 44 or variants thereof having at least 80% identity thereto (such as at least 85% identity, at least 90% identity, at least 95%, at least 97% identity, at least 98% identity).

Alkaloid Content

In one embodiment the present invention provides a method of modulating the alkaloid content of a plant (e.g. a tobacco plant) or a part thereof, the method comprising modifying said plant by modulating the activity or expression of at least one gene encoding a BTB/POZ NPH3 domain-containing protein.

The term "modulating" is used herein to mean either increasing or decreasing.

The term "increasing alkaloid content" is used herein to mean that the alkaloid content in the product of the present invention (e.g. plant, part thereof (e.g. leaf), processed leaf or a product made from the plant (e.g. a tobacco industry product)) is higher compared with a comparable product which has not been modified in accordance with the present invention.

The term "decreasing alkaloid content" is used herein to mean that alkaloid content in the product of the present invention (e.g. plant, part thereof (e.g. leaf), processed leaf or a product made from the plant (e.g. a tobacco industry product)) is lower compared with a comparable product which has not be modified in accordance with the present invention.

In some embodiments, the modulation of alkaloid content refers to an increase in alkaloid content wherein the activity or expression of at least one gene encoding a BTB/POZ NPH3 domain-containing protein is increased (or in other words the protein is overexpressed).

In some embodiments, the modulation of alkaloid content refers to a decrease in alkaloid content wherein the expression of at least one gene encoding a BTB/POZ NPH3 domain-containing protein is decreased or inhibited or eliminated.

In a further aspect, the alkaloid content is measured from leaves. In one aspect the alkaloid content is measured from green leaves. In a further aspect, the alkaloid content is measured from cured leaves, e.g. air-cured, flue-cured, fire-cured or sun-cured leaves. In a further aspect, the alkaloid content is measured from flue-cured leaves. In a further aspect, the alkaloid content is measured from air-cured leaves.

The term "alkaloid content" is used herein to mean the concentration and/or total amount of the entire group of compounds classified as alkaloids or the concentration and/or total amount of one or more compounds classified as alkaloids. Alkaloids typically present in tobacco include nicotine, nornicotine, PON, anatabine, anabasine and myosmine. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is modulated. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is increased. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is decreased. In some embodiments the total alkaloid content of the plant or cell is modulated. In some embodiments the total alkaloid content is increased. In some embodiments the total alkaloid content is increased.

In one embodiment the nicotine content is not substantially decreased but the content of one or more alkaloids selected from PON, nornicotine, anatabine, anabasine and myosmine is modulated.

In one embodiment the nicotine content is not substantially decreased but the content of one or more alkaloids selected from PON, nornicotine, anatabine and anabasine is modulated. Suitably the nicotine content may not be modulated but the content of PON is modulated. Suitably the nicotine content may not be substantially decreased but the content of PON is decreased.

Any method known in the art for determining the concentration and/or total content of alkaloids may be used. One preferred method for analysing alkaloid content involves the analysis by gas chromatography-flame ionization detection method (GC-FID) or by reversed phase high performance liquid chromatography with tandem mass spectrometry (LC-MS/MS).

In one embodiment there is provided a method for producing a plant (e.g. a tobacco plant) or part thereof, a plant propagation material (e.g. a tobacco plant propagation material), a cell (e.g. a tobacco cell), a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf), a cut and processed leaf (e.g. a cut and processed tobacco leaf), a product comprising said plant or part thereof (e.g. a tobacco industry product) or combinations thereof obtainable or obtained by a plant of the invention which has modulated alkaloid content, the method comprising modifying said plant to modulate the activity or expression of a gene encoding a BTB/POZ NPH3 domain-containing protein. The modulated alkaloid content may be determined by comparing the alkaloid content in the plant (e.g. tobacco plant) or part thereof, plant propagation material (e.g. tobacco plant propagation material), a cell (e.g. a tobacco cell), leaf (e.g. tobacco leaf), harvested leaf (e.g. a harvested tobacco leaf), cut harvested leaf (e.g. a cut harvested tobacco leaf), processed leaf (e.g. processed tobacco leaf), cut and processed leaf (e.g. cut and processed tobacco leaf), a product comprising a plant or part thereof of the present invention, e.g. a tobacco industry product, or combinations thereof with a comparable product.

Suitably the alkaloid content may be modulated in a plant, e.g. a tobacco plant e.g. modified tobacco plant. Suitably the alkaloid content may be modulated in a leaf (e.g. a tobacco leaf e.g. a tobacco leaf from a modified tobacco plant). Suitably the alkaloid content may be modulated in a harvested leaf (e.g. a harvested tobacco leaf from a modified tobacco plant). Suitably the alkaloid content may be modulated in a cut harvested leaf (e.g. a cut harvested tobacco leaf from a modified tobacco plant). Suitably the alkaloid content may be modulated in a processed leaf (e.g. a processed tobacco leaf e.g. a processed tobacco leaf from a modified tobacco plant). Suitably the alkaloid content may be modulated in a cut and processed leaf (e.g. a cut and processed tobacco leaf e.g. a cut and processed tobacco leaf from a modified tobacco plant). Suitably the alkaloid content may be modulated in a cured leaf (e.g. cured a tobacco leaf from a modified tobacco plant). Suitably the alkaloid content may be modulated in an extract of a green leaf (e.g. a green tobacco leaf from a modified tobacco plant). Suitably the alkaloid content may be modulated in a product comprising the plant of the present invention or part thereof (e.g. a tobacco industry product, for example a tobacco industry product produced from a modified tobacco plant or part thereof). Suitably the alkaloid content may be modulated in any one of the above products or combinations thereof. Suitably the modulation of alkaloid content described above may be an increase in alkaloid content. Suitably the modulation of alkaloid content described above may be a decrease in alkaloid content (e.g. a decrease in PON content).

In one embodiment the content of one or more alkaloids selected from nornicotine, PON, anatabine and anabasine is decreased. In one embodiment the content of PON is decreased. In one embodiment the content of nornicotine is decreased. In one embodiment the content of anatabine is decreased. In one embodiment the content of anabasine is decreased.

In one embodiment, the content of nicotine is not substantially modulated. Suitably the modulation of alkaloid content described above may be a decrease in the content of one or more alkaloids selected from nornicotine, PON, anatabine and anabasine but not a decrease in the content of nicotine.

In one embodiment the nicotine content of a modified plant (e.g. tobacco plant), plant propagation material (e.g. tobacco plant propagation material), leaf (e.g. tobacco leaf), harvested leaf (e.g. harvested tobacco leaf), cut harvested leaf (e.g. cut harvested tobacco leaf), processed leaf (e.g. processed tobacco leaf), cut and processed leaf (e.g. cut and processed tobacco leaf) or tobacco industry product from a modified tobacco plant is not substantially decreased. Suitably, the nicotine content is at least 85% (such as at least 90%, such as at least 95%, such as at least 98%, such as at least 99%) of the nicotine content of a comparable product.

In one embodiment the alkaloid content of a plant (e.g. tobacco plant) or part thereof may be modulated by at least 0.5, 1.5, 2, 3 or 4 fold when compared to the alkaloid content of a plant (e.g. tobacco plant) or part thereof, respectively, which has not been modified to modulate the activity or expression of at least one gene encoding a BTB/POZ NPH3 domain-containing protein and which has been grown under similar growth conditions. Suitably the alkaloid content may be modulated by about 0.5 fold to about 4 fold. Suitably the alkaloid content may be modulated by about 4 fold. Suitably the modification may be an increase or a decrease in alkaloid content. Suitably the modulation may be of one or more alkaloids selected from nicotine, nornicotine, PON, anatabine, anabasine and myosmine. Suitably the modulation may be of one or more alkaloids selected from nicotine, nornicotine, PON, anatabine and anabasine. Suitably, the nornicotine content may be reduced. Suitably, the PON content may be reduced. Suitably, the anatabine content may be reduced. Suitably, the anabasine content may be reduced.

In one embodiment of the invention the alkaloid content of a plant (e.g. a tobacco plant) or part thereof may be modulated by at least 1%, 2%, 5%, 8%, 10%, 12%, 15%, 20%, 25%, 30%, 40%, 50%, 60%, 70%, 80%, 90% or 100% in comparison to a plant (e.g. a tobacco plant) or part thereof which has not been modified according to the present invention. In one embodiment the alkaloid content may be modulated by at least 30% in comparison to an unmodified plant or part thereof. In one embodiment the alkaloid content may be modulated by at least 40% in comparison to an unmodified plant or part thereof. In one embodiment the alkaloid content may be modulated by at least 50% in comparison to an unmodified plant or part thereof. In one embodiment the alkaloid content may be modulated by at least 60% in comparison to an unmodified plant or part thereof. The modulation may be an increase or a decrease in alkaloid content when compared to an unmodified plant (e.g. a tobacco plant) or part thereof.

Suitably the modulation may be of total alkaloid content. Suitably the modulation may be of one or more alkaloids selected from nicotine, nornicotine, PON, anatabine, anabasine and myosmine. Suitably the modulation may be of one or more alkaloids selected from nicotine, nornicotine, PON, anatabine and anabasine. Suitably the modulation may be of nornicotine content, such as decrease in nornicotine content. Suitably the modulation may be of anabasine content, such as decrease in anabasine content. Suitably the modulation may be of PON content, such as decrease in PON content. Suitably the modulation may be of anatabine content, such as decrease in anatabine content.

Suitably the modulation may be of more than one alkaloid, such as two or more alkaloids, such as three or more alkaloids, such as four or more alkaloids, such as five or more alkaloids, such as all six alkaloids, selected from nicotine, nornicotine, PON, anatabine, anabasine and myosmine.

In some embodiments the alkaloid content of the plant may be modulated by between about 5% and about 100%, by between about 10% and about 90%, by between about 20% and about 80%, by between about 30% and about 70%, by between about 40% and 60%, by between about 40% and 50%, or by between about 50% and 60%.

Tobacco-Specific Nitrosamine (TSNA) Content

In one embodiment the present invention provides a method of decreasing the content of at least one tobacco-specific nitrosamine (TSNA) precursor in a plant (e.g. a tobacco plant) or a part thereof. Suitably, the method may comprise modifying said plant by modulating the activity or expression of at least one gene encoding a BTB/POZ NPH3 domain-containing protein. In one embodiment, the present invention provides a method of producing a processed leaf with decreased TSNA content (e.g. relative to a comparable product). The method of producing a processed leaf with decreased TSNA content may comprise:

modifying a plant by decreasing or inhibiting the activity or expression of at least one gene encoding a BTB/POZ NPH3 domain-containing protein;

harvesting a leaf from said plant;

and curing said harvested leaf.

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco industry products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production.

In one embodiment the TSNA may be one or more of group selected from: N'-nitrosonornicotine (NNN), N'-nitrosoanatabine (NAT), N'-nitrosoanabasine (NAB) and 4-(methyl nitrosamino)-1-(3-pyridyl)-1-butanone (NNK). Suitably the at least one tobacco-specific nitrosamine may be NNK or NNN. In one embodiment the tobacco-specific nitrosamine is NNK.

In one embodiment the precursor of the TSNA is one or more of the group selected from nornicotine, anabasine, anatabine, and an oxidised derivative of nicotine such as pseudooxynicotine (PON).

In one embodiment the TSNA is 4-(methylnitrosamino)-1-(3-pyridyl)-1-butanone (NNK) and/or the precursor is PON. In one embodiment the content of NNK is decreased. In one embodiment the content of PON is decreased. In one embodiment the content of NNK and PON is decreased.

In one embodiment the TSNA is N'nitrosonornicotine (NNN) and/or the precursor is nornicotine.

In one embodiment the TSNA is N'nitrosoanatabine (NAT) and/or the precursor is anatabine.

In one embodiment the TSNA is N'-nitrosoanabasine (NAB) and/or the precursor is anabasine.

The precursor of the TSNA (e.g. NNK, NNN, NAB and/or NAT) may be measured in green tobacco leaf, e.g. prior to processing, e.g. prior to curing. In one embodiment the precursor of the TSNA (e.g. NNK, NNN, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc.).

Any method known in the art for determining the concentration and/or levels of at least one TSNA or precursor thereto may be used. In particular a method such may comprise the addition of deuterium labelled internal standard, an aqueous extraction and filtration, followed by analysis using reversed phase high performance liquid chromatography with tandem mass spectrometry (LC-MS/MS) may be used. Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. (2005) Analytical Chemistry 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified in accordance with present invention.

The concentration and/or total content of the at least one tobacco-specific nitrosamine(s) or precursor thereto may be reduced in a tobacco leaf, harvested leaf, processed tobacco leaf, tobacco industry product or combinations thereof obtainable or obtained from a tobacco plant (or part of a tobacco plant or a tobacco cell culture) of the invention when compared with a tobacco leaf, harvested leaf, processed tobacco leaf, tobacco industry product or combinations thereof obtainable or obtained from a tobacco plant (or part of a tobacco plant or a tobacco cell culture) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40% or at least about 50%. In some embodiments the at least one tobacco-specific nitrosamine or precursor thereto may be reduced by between about 5% and about 50%, by between about 10% and about 50%, by between about 20% and about 50%, by between about 30% and about 50%, or by between about 40% and 50%.

In relation to processed (e.g. cured) tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

Biomass Production

In some instances, it may be desirable to produce plants or biomass with high alkaloid levels e.g. high levels of nicotine content so that nicotine may be purified to produce a pure nicotine product for example for use in devices which utilize liquid containing nicotine (e.g. e-cigarettes) or within tobacco heating devices. For example, the production of nicotine in this way could reduce costs of nicotine extraction for the production of e-liquids for e-cigarettes.

In one aspect, the present invention provides a method of producing a biomass comprising: growing a cell which has been engineered to modulate (e.g. increase) the activity or expression of a gene encoding a BTB/POZ NPH3 domain-containing protein under conditions to produce a biomass. Suitably, the activity or expression of a BTB/POZ NPH3 domain-containing protein may be increased in order to increase the concentration and/or total nicotine content.

In one embodiment, the present invention provides a method of producing a biomass having modified (e.g. increased) concentration and/or total content of nicotine, comprising growing a cell which has been engineered to increase the activity or expression of at least one gene encoding a BTB/POZ NPH3 domain-containing protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30, or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30.

The cell may be engineered by any method known in the art to modify the activity or expression of at least one gene encoding a BTB/POZ NPH3 domain-containing protein. Suitably, the cell may be engineered to express an exogenous gene encoding a BTB/POZ NPH3 domain-containing protein. Suitably, the cell may be engineered to overexpress a gene encoding a BTB/POZ NPH3 domain-containing protein. Suitably, the cell may be engineered to decrease the activity or expression of a gene encoding a BTB/POZ NPH3 domain-containing protein.

Suitably, the biomass may contain a higher concentration and/or total content of nicotine compared with the biomass produced by a comparable cell which has not been modified in accordance with the present invention.

Suitably the cell for use in biomass production may be a plant cell, such as a tobacco cell.

Suitably the cell for use in biomass production may be a yeast cell.

In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell). The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltrans- ferase or S-adenosyl-L-methionine: putrescine N-methyl- transferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification in this way may be taught in US2016032299 for example, which is incorporated herein by reference.

Commercially Desirable Traits

In one embodiment the plants of the present invention have modified (i.e. increased or decreased) total alkaloid content and/or modified (i.e. increased or decreased) content of one or more alkaloids, whilst the flavour characteristics and/or other commercially desirable traits are at least main- tained. Suitably, the plants of the present invention may have decreased total alkaloid content and/or decreased content of one or more alkaloids, whilst the flavour characteristics and/or other commercially desirable traits are at least main- tained.

In one embodiment the plants of the present invention produce leaves of a similar grade and/or quality to plants which have not been modified according to the invention.

In one embodiment the plants of the present invention have reduced nornicotine and/or PON and/or anabasine and/or anatabine content without a significant change in the flavour characteristics of the plant (e.g. compared with the same plant which has not been modified in accordance with the present invention).

In one embodiment, the plants of the present invention have reduced total alkaloid content without a significant change in the nicotine content (e.g. compared with the same plant which has not been modified in accordance with the present invention). In one embodiment, the plants of the present invention have reduced nornicotine and/or PON and/or anabasine and/or anatabine content without a signifi- cant change in the nicotine content (e.g. compared with the same plant which has not been modified in accordance with the present invention).

Suitably, the nicotine content of a plant according to the present invention is at least 85% of the nicotine content present in a comparable plant (e.g. compared with the same plant which has not been modified in accordance with the present invention). Suitably, the nicotine content of a plant according to the present invention is at least 90% of the nicotine content present in a comparable plant. Suitably, the nicotine content of a plant according to the present invention is at least 95% of the nicotine content present in a compa- rable plant. Suitably, the nicotine content of a plant accord- ing to the present invention is at least 98% of the nicotine content present in a comparable plant. Suitably, the nicotine content of a plant according to the present invention is at least 99% of the nicotine content present in a comparable plant.

In one embodiment the plants of the present invention have decreased TSNA precursor content without a signifi- cant change (e.g. decrease) in other commercially desirable traits of the plant (e.g. compared with the same plant which has not been modified in accordance with the present invention). In particular the yield of the modified plant is preferably not reduced compared with the same plant which has not been modified in accordance with the present invention.

Therefore in one embodiment the methods and uses of the present invention relate to decreasing TSNA precursor con- tent whilst maintaining the flavour characteristics and/or other commercially desirable traits (e.g. yield).

The term "commercially desirable traits" as used herein will include traits such as yield, mature plant height, har- vestable leaf number, average node length, cutter leaf length, cutter leaf width, quality (e.g. leaf quality, suitably cured leaf quality), abiotic (for instance drought) stress tolerance, herbicide tolerance and/or biotic (for instance insect, bacte- ria or fungus) stress tolerance.

Leaf quality may be measured based on colour, texture and aroma of the cured leaf, for example according to United States Department of Agriculture (USDA) grades and stan- dards.

Tobacco grades are evaluated based on factors including, but not limited to, the leaf stalk position, leaf size, leaf colour, leaf uniformity and integrity, ripeness, texture, elas- ticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar- Binder Tobacco (U.S. Types 54 and 55), effective Nov. 20, 1969 (34 F.R. 17061); Official Standard Grades for Georgia and Florida ShadeGrown Cigar-Wrapper Tobacco (U.S. Type 62), Effective April 1971. A USDA grade index value can be determined according to an industry accepted grade index. See e.g. Bowman et al. (1988) Tobacco Science, 32:39-40; Legacy Tobacco Document Library (Bates Docu- ment #523267826-523267833, Jul. 1, 1988, Memorandum on the Proposed Burley Tobacco Grade Index); and Miller et al. (1990) Tobacco Intern., 192:55-57 (all foregoing refer- ences are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g. WO 2011/027315 (which is incorporated herein by reference).

In one embodiment, a tobacco plant of the present inven- tion provides tobacco of commercially acceptable grade.

Suitably, the tobacco plant of the present invention pro- vides cured tobacco of commercially acceptable grade.

In one embodiment, a tobacco plant of the present inven- tion is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a plant (e.g. a tobacco plant) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. a tobacco plant) yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions.

In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plant Breeding

In one embodiment the present invention provides a method of producing a plant having a modified alkaloid content and/or modified content of a tobacco specific nitrosamine (TSNA) precursor comprising:

a. crossing a donor plant having modified nicotine content and/or modified content of a tobacco specific nitrosamine (TSNA) precursor and wherein the activity or expression of at least one gene encoding a BTB/POZ NPH3 domain-containing protein according to the present invention has been modulated in the donor plant in accordance with the present invention with a recipient tobacco plant that does not have modified nicotine content or modified content of a tobacco specific nitrosamine (TSNA) precursor and possesses commercially desirable traits;

b. isolating genetic material from a progeny of said donor plant crossed with said recipient plant; and c. performing molecular marker-assisted selection with a molecular marker comprising:

i. identifying an introgressed region comprising a mutation in a polynucleotide sequence encoding a protein defined in a.

Suitably, the activity or expression of a protein comprising an amino acid sequence as set out in SEQ ID NO. 1, 4, 7, 10, 13, 16, 19, 22, 25 or 28, or a functional variant or functional fragment or orthologue thereof, or a sequence which has at least 80% identity to SEQ ID NO. 2, 3, 5, 6, 8, 9, 11, 12, 14, 15, 17, 18, 20, 21, 23, 24, 26, 27, 29 or 30; or a protein encoded by a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30 is modulated in the donor plant when compared to a comparable plant.

The molecular marker assisted selection may comprise performing PCR to identify an introgressed nucleic acid sequence comprising a mutation which modulates the activity or expression of a protein comprising the amino acid sequence shown as SEQ ID NO. 1, 4, 7, 10, 13, 16, 19, 22, 25 or 28 or an amino acid sequence which has at least 80% identity thereto.

Plants

In one embodiment, the present invention relates to methods of modulating (e.g. decreasing) alkaloid content in plants, or parts thereof or plant cells.

Suitable plants according to the invention include the Solanaceae family of plants which include, for example jimson weed, eggplant, mandrake, deadly nightshade (*belladonna*), *capsicum* (paprika, chilli pepper), potato and tobacco.

In one embodiment a suitable genus of Solanaceae is *Nicotiana*, e.g. *Nicotiana tabacum* or *Nicotiana rustica*.

A suitable species of *Nicotiana* may be *Nicotiana tabacum*. Species of *Nicotiana* may be referred to herein as a tobacco plant, or simply tobacco.

Tobacco Plants

The present invention provides methods, uses directed to plants (e.g. tobacco plants) as well as a cell (e.g. a tobacco cell), a plant (e.g. a tobacco plant) and a plant propagation material.

The term "tobacco plant" as used herein refers to a plant in the genus *Nicotiana* that is used in the production of tobacco industry products. Non-limiting examples of suitable "tobacco" plants include *N. tabacum* and *N. rustica* (for example, *N. tabacum* L., LA B21, LN KY171, TI 1406, Basma, *Galpao*, Perique, Beinhart 1000-1, and Petico).

In one aspect, the tobacco plant according to the present invention is a non-naturally occurring tobacco plant. Suitably, the tobacco plant may be a mutant, non-naturally occurring tobacco plant. Suitably, the tobacco plant may be a transgenic tobacco plant.

In one aspect, the tobacco plant according to the present invention comprises a non-naturally occurring mutation which modulates (e.g. decreases) the activity or expression of at least one BTB/POZ NPH3 protein as defined herein. Suitably, the tobacco plant may comprise a mutation which has been introduced.

The tobacco material can be derived or obtained from varieties of *Nicotiana tabacum* types, commonly known as Burley varieties, flue or bright varieties and dark varieties. In some embodiments, the tobacco material is derived from a Burley, Virginia or a dark tobacco plant.

The tobacco plant may be selected from Burley tobacco, rare tobacco, specialty tobacco, expanded tobacco or the like.

Suitably, the plant may not be *Nicotiana benthamiana*.

The use of tobacco cultivars and elite tobacco cultivars is also contemplated herein. The tobacco plant for use herein may therefore be a tobacco variety or elite tobacco cultivar. Particularly useful *Nicotiana tabacum* varieties include Flue-cured Virginia type, Burley type, and Oriental type.

In some embodiments, the tobacco plant may be, for example, selected from one or more of the following varieties: L. cultivar T.I. 1068, AA 37-1, B 13P, Xanthi (Mitchell-Mor), KT D #3 Hybrid 107, Bel-W3, 79-615, Samsun Holmes N N, F4 from cross BU21×Hoja Parado, line 97, KTRDC #2 Hybrid 49, KTRDC #4 Hybrid 1 10, Burley 21, PM016, KTRDC #5 KY 160 SI, KTRDC #7 FCA, KTRDC #6 TN 86 SI, PM021, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, P01, P02, P03, RG 11, RG 17, RG 8, Speight G-28, TN 86, TN 90, VA 509, AS44, Banket A1, Basma Drama B84/31, Basma I Zichna ZP4/B, Basma Xanthi BX 2A, Batek, Besuki Jember, C104, Coker 319, Coker 347, Criollo Misionero, PM092, Delcrest, Djebel 81, DVH 405, Galpao Comum, HBO4P, Hicks Broadleaf, Kabakulak Elassona, PM 102, Kutsage E1, KY 14×L8, KY 171, LA BU 21, McNair 944, NC 2326, NC 71, NC 297, NC 3, PVH 03, PVH 09, PVH 19, PVH 21 10, Red Russian, Samsun, Saplak, Simmaba, Talgar 28, PM132, Wislica, Yayaldag, NC 4, TR Madole, Prilep HC-72, Prilep P23, Prilep PB 156/1, Prilep P12-2/1, Yaka JK-48, Yaka JB 125/3, TI-1068, KDH-960, TI-1070, TW136, PM204, PM205, Basma, TKF 4028, L8, TKF 2002, TN 90, GR141, Basma xanthi, GR149, GR153, and Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC, *Galpao* tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D 94, TN D 950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley, Flue-cured Virginia, or Oriental.

In one embodiment the plant propagation material may be obtainable from a plant (e.g. a tobacco plant) of the invention.

A "plant propagation material" as used herein refers to any plant matter taken from a plant from which further plants may be produced. Suitably, a plant propagation material may be selected from a seed, plant calli and plant clumps. Suitably the plant propagation material may be a seed. Suitably, the plant propagation material may be plant calli. Suitably the plant propagation material may be plant clumps.

In one embodiment the cell (e.g. tobacco cell), tobacco plant and/or plant propagation material may be obtainable (e.g. obtained) by a method according to the invention.

Suitably a tobacco plant according to the present invention may have modulated (e.g. decreased) nicotine content when compared to an unmodified tobacco plant, wherein the tobacco plant has been modified to modulate (e.g. decrease) the activity or expression of at least on one gene encoding a BTB/POZ NPH3 domain-containing protein.

Suitably a tobacco plant according to the present invention may have modulated (e.g. reduced) content of a tobacco specific nitrosamine (TSNA) precursor when compared to an unmodified tobacco plant, wherein the tobacco plant has been modified to modulate (e.g. increase) the activity or expression of at least on one gene encoding a BTB/POZ NPH3 domain-containing protein.

In one embodiment the tobacco plant in accordance with the present invention comprises a tobacco cell of the invention.

In another embodiment the plant propagation material may be obtainable (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided a cell such as a plant cell, such as a tobacco plant cell having modulated activity or expression of at least one gene encoding a BTB/POZ NPH3 protein. Suitably, the cell may be a non-naturally occurring cell. Suitably, the cell may be a mutant cell. Suitably, the cell may be a non-naturally occurring mutant cell. For example the cell may comprise a non-naturally occurring mutation which modulates (e.g. decreases) activity or expression of at least one gene encoding a BTB/POZ NPH3 protein.

In one embodiment there is provided the use of a cell as provided for in the foregoing embodiments for production of a tobacco industry product.

In one embodiment the present invention provides a cell culture (e.g. in in vitro culture).

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The tobacco cells harvested from an in vitro culture may be dried, e.g. freeze-dried, for example to produce a powder.

In one embodiment, the cell culture is a tobacco cell culture. The skilled person will be aware of known methods for establishing in vitro cultures of tobacco cells. By way of example only, the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture or an extract therefrom may be incorporated into tobacco industry products according to the present invention.

In one embodiment, the present invention provides a plant (e.g. tobacco plant) or part thereof for use in molecular farming. Suitably, a plant or part thereof modified in accordance with the present invention may be used in the manufacture of proteins such as therapeutics e.g. antibiotics, virus like particles, neutraceuticals or small molecules.

In one embodiment, the present invention provides a method for the production of proteins (e.g. therapeutic proteins), the method comprising modifying a plant or part thereof capable of producing said protein (e.g. therapeutic protein) by modulating the activity or expression of at least one gene encoding a BTB/POZ NPH3 domain-containing protein having an amino acid sequence as set out in SEQ ID NO. 1, 4, 7, 10, 13, 16, 19, 22, 25 or 28 or a functional variant or functional fragment or orthologue thereof, or a sequence which has at least 80% identity to SEQ ID NO. 1, 4, 7, 10, 13, 16, 19, 22, 25 or 28; or wherein the at least one gene encoding a BTB/POZ NPH3 domain-containing protein comprises a nucleotide sequence as set out in SEQ ID NO. 2, 3, 5, 6, 8, 9, 11, 12, 14, 15, 17, 18, 20, 21, 23, 24, 26, 27, 29 or 30 or a functional variant or functional fragment or orthologue of SEQ ID NO. 2, 3, 5, 6, 8, 9, 11, 12, 14, 15, 17, 18, 20, 21, 23, 24, 26, 27, 29 or 30 or a nucleic acid sequence which has at least 80% identity to SEQ ID NO. 2, 3, 5, 6, 8, 9, 11, 12, 14, 15, 17, 18, 20, 21, 23, 24, 26, 27, 29 or 30; and culturing the plant under conditions sufficient to allow the production of said protein (e.g. therapeutic protein).

Products

The present invention also provides for products obtainable or obtained from plants according to the present invention. Products are provided which are obtainable or obtained from a plant in which the activity or expression of gene encoding a BTB/POZ NPH3 domain-containing protein has been modulated.

In one embodiment, the product may comprise a construct of the invention which modulates the activity or expression of at least one gene encoding a BTB/POZ NPH3 domain-containing protein as defined herein. In one embodiment, the product may comprise a construct of the invention which modifies the nucleic acid sequence of at least one gene encoding a BTB/POZ NPH3 domain-containing protein as defined herein.

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing.

Thus in one embodiment the use of the foregoing embodiment may provide a processed tobacco leaf. Suitably the tobacco leaf may be subjected to curing, fermenting, pasteurising or combinations thereof. In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention.

In a further embodiment the harvested leaf may be obtainable (e.g. obtained) from a tobacco plant propagated from a propagation material of the present invention.

In another embodiment there is provided a harvest leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable from a tobacco plant of the invention. Suitably the processed tobacco leaf may be obtainable from a tobacco plant obtained in accordance with any of the methods and/or uses of the present invention.

Suitably, the processed leaf may comprise reduced content of one or more TSNAs selected from NNK, NNN, NAT and NAB. Preferably, the content of NNK is reduced. Suitably, the reduction in TSNA content is in relation to a comparable product which has not been modified according to the present invention.

In another embodiment the processed tobacco leaf may be obtainable from a tobacco plant propagated form a tobacco plant propagation material according to the present invention.

The processed tobacco leaf of the present invention may be obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low shoulder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco industry product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden Tobacco Control (2003) 12: 349-359, the teaching of which is incorporated herein by reference.

During the production of snus, pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In one embodiment, the use of the foregoing embodiment may provide reconstituted tobacco.

In one embodiment, there is provided reconstituted tobacco.

"Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent; the soluble residue is formed to sheets by extracting the water).

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

Suitably, the cured tobacco may comprise a reduced content of one or more TSNAs selected from NNK, NNN, NAT and NAB. Preferably, the content of NNK is reduced. Suitably, the reduction in TSNA content is in relation to a comparable product which has not been modified according to the present invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably, the cured tobacco material may be air cured. Suitably, the cured tobacco material may be flue cured.

Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product.

In one embodiment the tobacco industry product according to the present invention may be a blended tobacco industry product. Suitably, the tobacco blend may comprise cured tobacco material according to the present invention.

In one embodiment the tobacco industry product may be prepared from a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant.

Delivery System

As used herein, the term "delivery system" is intended to encompass systems that deliver at least one substance to a user, and includes:

combustible aerosol provision systems, such as cigarettes, cigarillos, cigars, and tobacco for pipes or for roll-your-own or for make-your-own cigarettes (whether based on tobacco, tobacco derivatives, expanded tobacco, reconstituted tobacco, tobacco substitutes or other smokable material);

non-combustible aerosol provision systems that release compounds from an aerosol-generating material without combusting the aerosol-generating material, such as electronic cigarettes, tobacco heating products, and hybrid systems to generate aerosol using a combination of aerosol-generating materials; and aerosol-free delivery systems that deliver the at least one substance to a user orally, nasally, transdermally or in another way without forming an aerosol, including but not limited to, lozenges, gums, patches, articles comprising inhalable powders, and oral products such as oral tobacco which includes snus or moist snuff, wherein the at least one substance may or may not comprise nicotine.

According to the present disclosure, a "combustible" aerosol provision system is one where a constituent aerosol-generating material of the aerosol provision system (or component thereof) is combusted or burned during use in order to facilitate delivery of at least one substance to a user.

In some embodiments, the delivery system is a combustible aerosol provision system, such as a system selected from the group consisting of a cigarette, a cigarillo and a cigar.

In some embodiments, the disclosure relates to a component for use in a combustible aerosol provision system, such as a filter, a filter rod, a filter segment, a tobacco rod, a spill, an aerosol-modifying agent release component such as a capsule, a thread, or a bead, or a paper such as a plug wrap, a tipping paper or a cigarette paper.

According to the present disclosure, a "non-combustible" aerosol provision system is one where a constituent aerosol-generating material of the aerosol provision system (or component thereof) is not combusted or burned in order to facilitate delivery of at least one substance to a user.

In some embodiments, the delivery system is a non-combustible aerosol provision system, such as a powered non-combustible aerosol provision system.

In some embodiments, the non-combustible aerosol provision system is an electronic cigarette, also known as a vaping device or electronic nicotine delivery system (END), although it is noted that the presence of nicotine in the aerosol-generating material is not a requirement.

In some embodiments, the non-combustible aerosol provision system is an aerosol-generating material heating system, also known as a heat-not-burn system. An example of such a system is a tobacco heating system.

In some embodiments, the non-combustible aerosol provision system is a hybrid system to generate aerosol using a combination of aerosol-generating materials, one or a plurality of which may be heated. Each of the aerosol-generating materials may be, for example, in the form of a solid, liquid or gel and may or may not contain nicotine. In some embodiments, the hybrid system comprises a liquid or gel aerosol-generating material and a solid aerosol-generating material. The solid aerosol-generating material may comprise, for example, tobacco or a non-tobacco product.

Typically, the non-combustible aerosol provision system may comprise a non-combustible aerosol provision device and a consumable for use with the non-combustible aerosol provision device.

In some embodiments, the disclosure relates to consumables comprising aerosol-generating material and configured to be used with non-combustible aerosol provision devices. These consumables are sometimes referred to as articles throughout the disclosure.

In some embodiments, the non-combustible aerosol provision system, such as a non-combustible aerosol provision device thereof, may comprise a power source and a controller. The power source may, for example, be an electric power source or an exothermic power source. In some embodiments, the exothermic power source comprises a carbon substrate which may be energised so as to distribute power in the form of heat to an aerosol-generating material or to a heat transfer material in proximity to the exothermic power source.

In some embodiments, the non-combustible aerosol provision system may comprise an area for receiving the consumable, an aerosol generator, an aerosol generation area, a housing, a mouthpiece, a filter and/or an aerosol-modifying agent.

In some embodiments, the consumable for use with the non-combustible aerosol provision device may comprise aerosol-generating material, an aerosol-generating material storage area, an aerosol-generating material transfer component, an aerosol generator, an aerosol generation area, a housing, a wrapper, a filter, a mouthpiece, and/or an aerosol-modifying agent.

Suitably, the delivery system may be prepared from (e.g. may comprise) a tobacco plant or a part thereof according to the present invention.

Suitably, the delivery system may be prepared from a tobacco cell culture according to the present invention.

Suitably, the delivery system may be prepared from (e.g. may comprise) a tobacco plant or part thereof propagated from a tobacco plant propagation material according to the present invention.

Suitably, the delivery system may be prepared from (e.g. may comprise) a harvested leaf of a tobacco plant according to the present invention.

Suitably, the delivery system may be prepared from (e.g. may comprise) a processed tobacco leaf according to the present invention.

Suitably, the delivery system may be prepared from (e.g. may comprise) a cured tobacco material according to the present invention.

Suitably, the delivery system may be prepared from (e.g. may comprise) a tobacco blend according to the present invention.

In one embodiment, the delivery system is a combustible smoking article, selected from the group consisting of a cigarette, a cigarillo and a cigar.

In one embodiment, the delivery system comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the delivery system is a non-combustible aerosol provision system.

In one embodiment, the delivery system comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the delivery system is a heating product which releases one or more compounds by heating, but not burning, a substrate material. The substrate material is an aerosolizable material which may be for example tobacco or other non-delivery systems, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the delivery system is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-delivery systems, which may or may not contain nicotine. In one embodiment, the hybrid system comprises a liquid or gel substrate and tobacco.

In another embodiment, the product may comprise a construct of the invention which modulates activity or expression of at least one BTB/POZ NPH3 domain-containing protein and thereby decreases alkaloid content when expressed in a plant (e.g. tobacco plant).

Tobacco Industry Product

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurising.

Suitably the tobacco industry product may comprise a cut tobacco leaf, optionally processed as per the foregoing embodiment.

In another embodiment, the tobacco industry product may be prepared from a tobacco cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco industry product may be a smokeless tobacco industry product.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco.

An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention.

In one embodiment the tobacco heating device may be a hybrid device.

Polynucleotides/Polypeptides/Constructs

In certain embodiments of the present invention, constructs which modulate activity or expression at least gene encoding a BTB/POZ NPH3 domain-containing protein may be transformed into plant cells, suitably under the direction of a promoter.

In certain embodiments of the present invention, constructs which decrease (i.e. inhibit) the activity or expression of at least one gene encoding a BTB/POZ NPH3 domain-containing protein may be transformed into plant cells under the direction of a promoter. For example, the genetic construct may be a gene editing construct or may comprise an RNAi molecule, which may comprise a small interfering RNA (siRNA) molecule, or a short hairpin loop (shRNA) molecule.

In certain embodiments of the present invention, constructs which increase activity or expression of gene encoding a BTB/POZ NPH3 domain-containing protein may be transformed into plant cells, suitably under the direction of a promoter e.g. constructs which encode a gene encoding a BTB/POZ NPH3 domain-containing protein such as an endogenous BTB/POZ NPH3 domain-containing protein.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting gene encoding a BTB/POZ NPH3 domain-containing protein and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application NO. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest, e.g. the gene the promoter is going to direct, for instance a gene encoding a BTB/POZ NPH3 domain-containing protein according to the invention, a coding sequence used in the present invention or may be derived from a different gene, from *Nicotiana tabacum*, or another organism, for example from a plant of the family Solanaceae, or from the subfamily Cestroideae. The expression cassette may be incorporated into a basic plant transformation vector, such as pBIN 19 Plus, pBI 101, pKYLX71:3552, pCAMBIA2300 or other suitable plant transformation vectors known in the art. In addition to the expression cassette, the plant transformation vector will contain such sequences as are necessary for the transformation process. These may include the *Agrobacterium vir* genes, one or more T-DNA border sequences, and a selectable marker or other means of identifying transgenic plant cells.

The term "expression vector or plant transformation vector" means a construct capable of in vivo or in vitro expression. Preferably, the expression vector is incorporated in the genome of the organism. In one embodiment the vector of the present invention expresses a protein e.g. a BTB/POZ NPH3 domain-containing protein as described herein. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27), which are incorporated herein by reference.

Typically, in *Agrobacterium*-mediated transformation a binary vector carrying a foreign DNA of interest, i.e. a construct according to the present invention, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher et al. (1980) *Tissue Culture Methods for Plant Pathologists*, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation and production of fertile transgenic maize plants by silicon carbide whisker-mediated transformation is taught in Frame et al. (1994) The Plant Journal 6(6): 941-948, which is incorporated herein by reference, and viral transformation techniques is taught in, for example, Meyer et al. (1992) Mol. Gen. Genet. 231(3): 345-352, which is incorporated herein by reference. The use of cassava mosaic virus as a vector system for plants is taught in Meyer et al. (1992) Gene 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a tobacco plant. The vector system may comprise one vector, but it may comprise two vectors. In the case of two vectors, the vector system is normally referred to as a binary vector system. Binary vector systems are described in further detail in Gynheung et al. (1980) Binary Vectors, Plant Molecular Biology Manual A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al. (1986) Plant Physiol. 81, 301-305 and Butcher et al. (1980) *Tissue Culture Methods for Plant Pathologists* eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema (1985) The Binary Plant Vector System, Offset-drukkerij Kanters B. B., Amsterdam Chapter V; Fraley et al. Crit. Rev. Plant Sci. 4:1-46; and An et al. (1985) EMBO J 4: 277-284, all incorporated herein by reference.

Plant cells transformed with construct(s) which modulate the activity or expression of at least one gene encoding a BTB/POZ NPH3 domain-containing protein may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the activity or expression of at least one gene encoding a BTB/POZ NPH3 domain-containing protein according to the invention. Accordingly a transgenic plant is a plant which has been transformed with a construct according to the invention. Preferably the transgenic plant exhibits modulated alkaloid content and/or modulated TSNA precursor content according to the present invention. The term "transgenic plant" does not cover native nucleotide coding sequences in their natural environment when they are under the control of their native promoter which is also in its natural environment.

In one aspect, a gene encoding a BTB/POZ NPH3 domain-containing protein, a construct, a plant transformation vector or a plant cell according to the present invention is in an isolated form. The term "isolated" means that the sequence is at least substantially free from at least one other component with which the sequence is naturally associated in nature and as found in nature.

In one aspect, a gene encoding a BTB/POZ NPH3 domain-containing protein, a construct, plant transformation vector or a plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the gene encoding a BTB/POZ NPH3 domain-containing protein, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

The nucleotide sequence for use in the present invention may be present in a vector in which the nucleotide sequence is operably linked to regulatory sequences capable of providing for the expression of the nucleotide sequence by a suitable host organism. The constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced. Vectors may be used in vitro, for example for the production of RNA or used to transfect, transform, transduce or infect a host cell.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of gene encoding a BTB/POZ NPH3 domain-containing protein as described herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes gene encoding a BTB/POZ NPH3 domain-containing protein may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

In some embodiments, a promoter may be operably linked to nucleotide sequence in a construct or vector which is used to modulate the concentration and/or total content of nicotine in a cell or cell culture or tobacco plant or part thereof.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) (CaMV/35S), figwort mosaic virus 35S promoter. The sequence of carnation etched ring virus DNA: comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

A nucleotide sequence encoding either a protein which has the specific properties as gene encoding a BTB/POZ NPH3 domain-containing protein as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a yet further alternative, the nucleotide sequence encoding the BTB/POZ NPH3 domain-containing protein may be prepared synthetically by established standard methods, e.g. the phosphoroamidite method described by Beucage et al. (1981) Tetrahedron Letters 22, 1859-1869 which is incorporated herein by reference, or the method described by Matthes et al. (1984) EMBO J. 3, 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. a gene encoding a BTB/POZ NPH3 domain-containing protein (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the BTB/POZ NPH3 domain-containing gene. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs.

In one embodiment, a homologous sequence is taken to include an amino acid sequence or nucleotide sequence which has one, two or several additions, deletions and/or substitutions compared with the subject sequence.

Sequence Identity

Sequence identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. (1999) Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | |
| --- | --- |
| GAP OPEN | 0 |
| GAP EXTENSION | 0 |

| FOR CLUSTAL | DNA | PROTEIN | |
| --- | --- | --- | --- |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides.

Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-l-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon et al. (1992) PNAS 89(20), 9367-9371 and Horwell (1995) Trends Biotechnol. 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M Na$_3$ citrate pH 7.0}). More preferably, hybridisation is determined under high stringency conditions (e.g. 65° C. and 0.1×SSC {1×SSC=0.15 M NaCl, 0.015 M Na$_3$ citrate pH 7.0}).

A review of the general techniques used for transforming plants may be found in articles such as Potrykus et al. (1991) Annu Rev Plant Physiol. Plant Mol. Biol. 42:205-225 and Christou et al. (1994) Agro-Food-Industry Hi-Tech March/April 17-27, which are incorporated herein by reference. Further teachings on plant transformation may be found in EP-A-0449375, incorporated herein by reference.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

Advantages

It has been surprisingly found that by modulating the activity or expression of at least one gene encoding a BTB/POZ NPH3 domain-containing protein as taught herein which acts as a positive regulator of alkaloid content in tobacco, the alkaloid and/or TSNA precursor content of plants can be modulated. Thereby tobacco industry products with modulated (e.g. reduced) alkaloid content) and/or reduced TSNA precursor content and commercially desirable traits sought after by consumers of tobacco industry products can be produced.

The present inventors have surprisingly determined a method for modulating the alkaloid content and/or TSNA precursor content of a plant (e.g. tobacco plant) by modulating the activity or expression of a gene encoding a BTB/POZ NPH3 domain-containing protein. Alkaloid or TSNA precursor content of a plant (e.g. tobacco plant) may be decreased by decreasing or inhibiting the activity or expression of a gene encoding a BTB/POZ NPH3 domain-containing protein. Prior to the present invention it had not been known that modulation of the activity or expression of a gene encoding a BTB/POZ NPH3 domain-containing protein as described herein could be used to modulate alkaloid (and/or TSNA precursor content of a plant (e.g. a tobacco plant).

The publications discussed herein are provided solely for their disclosure prior to the filing date of the present application. Nothing herein is to be construed as an admission that such publications constitute prior art to the claims appended hereto.

EXAMPLES

Example 1—Transient Overexpression of a BTB/POZ NPH3 Domain-Containing Protein Increases Alkaloid Content in Leaves

Methods and Materials

Cloning a BTB/POZ NPH3 Domain-Containing Expression Vector

The Nitab4.50000868g0020.2 BTB/POZ NPH3 domain-containing protein gene sequence (SEQ ID NO. 3) was amplified from a GATEWAY™ cloning system compatible cDNA library using primers located outside restriction sites flanking the gene sequence.

The resulting plasmid was sequenced and transformed into *Agrobacterium tumefaciens* GV3101pMP90 by heat shock and transiently expressed in tobacco leaves.

Transient Gene Expression

*Agrobacterium tumefaciens* GV3101 strains carrying the construct of interest were grown overnight in Luria-Bertani (LB) medium supplemented with appropriate antibiotics. Cultures were spun down and re-suspended in buffer containing 10 mM MgCl$_2$, 10 mM MES pH 5.6 and 100 µM acetosyringone to OD600=0.6 and incubated for one hour at room temperature. Infiltration was performed with a needle-less syringe into tobacco leaves. Samples are taken 5 days post-infiltration.

Tests were performed in two biological replicates.

Alkaloid Measurement

Relative content of pyridine alkaloids was determined by reversed phase high performance liquid chromatography with tandem mass spectrometry (LC-MS/MS). Chromatographic separation was achieved using a Gemini-NX column (100 mm×3.0 mm, particle size 3 μm, Phenomenex) and gradient chromatographic separation using 6.5 mM ammonium acetate buffer (aq) (pH10) and Methanol.

Mass Spectrometer operates in electrospray (ESI) positive mode using scheduled MRM data acquisition. Two MRM transitions were monitored for each analyte and one for the isotope labelled internal standard.

| Analyte | Precursor Ion | Daughter Ion (quant/confirm) |
|---|---|---|
| Nicotine | 163.1 | 130/106 |
| Nicotine d4 | 167.1 | 134.1 |
| Anabasine | 163.1 | 80/120 |
| Anatabine | 161.1 | 144/80 |
| Nornicotine | 149.1 | 80/130 |
| Nornicotine d4 | 153.1 | 84.1 |
| PON | 176.1 | 106.0/148 |
| PON d4 | 183.1 | 110.0 |

Results

Alkaloid content of 5-week-old tobacco leaves expressing the Nitab4.5_0000868g0020.2 construct is shown in FIG. 1. Alkaloid content is represented relative to control and comprises two biological replicates analysed by one-way t-test. Values are shown as means±SEM. Asterisks indicate statistical significance of P value≤0.001.

Overexpression of Nitab4.5_0000868g0020.2 leads to a significant increase in alkaloid content in leaves.

FIG. 35 shows that knock out of Nitab4.5_0000868g0020.2 leads to a significant decrease in alkaloid content. Alkaloid content of three TN90 lines with knocked out Nitab4.5_0000868g0020.2 is shown. Alkaloid content is represented relative to control. Results were analysed by t-test. Values are shown as means±SEM. Asterisks indicate statistical significance of P value≤0.001.

Conclusions

Nitab4.5_0000868g0020 is a positive regulator of alkaloid content, and is a regulator of pyridine alkaloids in tobacco.

Example 2—Transient Expression of Antisense RNA Targeting Nitab4.5_00008680020.2 Decreases Alkaloid Content in Leaves Materials and Methods The Nitab4.5_0000868g0020.2 coding sequence was cloned in reverse orientation into a plant expression vector driven by the CERV promoter.

Results

Figure 2:
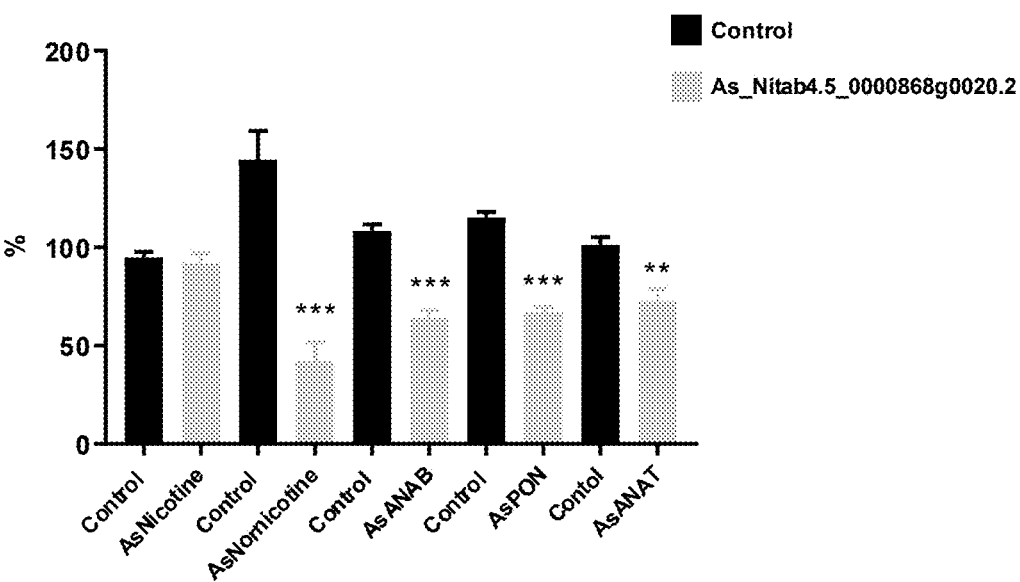
FIG. 2 shows the alkaloid content of 5-week-old tobacco leaves expressing an artificial miRNA targeting Nitab4.5_0000868g0020.2. Alkaloid content is represented relative to control and comprises three biological replicates analysed by one-way ANOVA and Tukey's multiple-comparison post-test. Values are shown as means±SEM. Asterisks indicate statistical significance of P value≤0.001.

Alkaloid content of 5-week-old tobacco leaves expressing Nitab4.5_0000868g0020.2 antisense RNA is shown in FIG. 2. Alkaloid content is represented relative to control and comprises three biological replicates analysed by t-test. Values are shown as means±SEM. Asterisks indicate statistical significance of P value≤0.001

Suppressing Nitab4.5_0000868g0020.2 expression using antisense RNA leads to a decrease in alkaloid content in leaves, in particular a decrease in PON, nornicotine, anabasine and anatabine content.

Conclusions

Nitab4.5_0000868g0020.2 is a positive regulator of alkaloid content, in particular alkaloid content in leaves and is a regulator of pyridine alkaloids in tobacco.

Example 3—Homologue Testing

The effects of the homologues of SEQ ID NO. 3, namely SEQ ID NOs 6, 9, 12, 15, 18, 21, 24, 27 and 30, are tested in assays as described in Examples 1 and 2.

Example 4—Interactome Study of Nitab4.5_00008680020.2

Method

Triplicate co-immunoprecipitation samples of Nitab4.5_0000868g0020.2 were submitted to mass spectrometry analysis. Samples were digested with trypsin and analysed on THERMO SCIENTIFIC™ ORBITRAP FUSION™ mass spectrometer. Data was analysed with Proteome Discoverer 2.1 against the BAT tobacco proteome database and common contaminant databases, using a 5% false discovery rate. Proteins were sorted based on: identification in all replicates of the candidate sample; the number of peptides identified, in the candidate sample; and not present in control (GFP) or the other candidate samples. Using these criteria a list of candidate interactors for Nitab4.5_0000868g0020.2 was generated.

Results and Conclusion

The interactome of Nitab4.5_0000868g0020.2 was characterised (data not shown). The strongest interactors (SEQ ID NOs) are located in the chloroplast or chloroplast membrane, suggesting that, like its closest *Arabidopsis thaliana* homologue (AT5G67385, NCH1), Nitab4.5_0000868g0020.2 is involved in the regulation of Chloroplast movement. Chloroplast signalling pathways are tightly regulated by auxin, which is involved in long-distance signalling in tobacco plants from the shoot and regulates the nicotine synthesis in the root.

These findings give a mechanistic insight on the involvement of Nitab4.5_0000868g0020.2 in the regulation of nicotine and nicotinic alkaloid levels in tobacco.

The invention claimed is:

1. A method of modulating the alkaloid content of a plant or a part thereof, or a cell, the method comprising modifying said plant or cell by modulating the expression or decreasing the activity of at least one gene encoding a BTB/POZ NPH3 domain-containing protein, wherein i) the content of one or more alkaloids selected from nicotine, nornicotine, pseudooxynicotine (PON), anabasine, and anatabine is modulated;

ii) the plant or part thereof, or cell is from the genus *Nicotiana,* iii) modulation of the expression of said at least one gene is achieved by overexpression, mutation, knock out, gene silencing or RNA silencing of said at least one gene;

iv) the BTB/POZ NPH3 domain-containing protein comprises an amino acid sequence:

a) as set out in SEQ ID NO: 1, or b) a functional variant of SEQ ID NO: 1 comprising a BTB/POZ domain with a sequence set forth in SEQ ID NO: 31 or a sequence with at least 98% identity thereto, and a NPH3 domain with a sequence as set forth in SEQ ID NO: 32 or a sequence with at least 98% identity thereof, or c) a sequence which has at least 98% identity to SEQ ID NO: 1; or the at least one gene encoding the BTB/POZ NPH3 domain-containing protein encodes the BTB/POZ NPH3 domain-containing protein as defined in a), b) or c) above and comprises a nucleotide sequence:

a) as set out in SEQ ID NO: 2 or SEQ ID NO: 3, b) a functional variant of SEQ ID NO: 2 or SEQ ID NO: 3 comprising a nucleotide sequence encoding a BTB/POZ domain with a sequence set forth in SEQ ID NO: 31 or a sequence with at least 98% identity thereto, and a NPH3 domain with a sequence as set forth in SEQ ID NO: 32 or a sequence with at least 98% identity thereof, or c) a sequence which has at least 98% identity to SEQ ID NO: 2 or 3; and v) when the plant or cell is modified to increase the expression of the at least one gene encoding a BTB/POZ NPH3 domain-containing protein, the plant or cell exhibits increased alkaloid content in comparison to a plant or cell which has not been modified to modulate the expression of the at least one gene encoding a BTB/POZ NPH3 domain-containing protein, or when the plant or cell is modified to decrease the activity or expression of the at least one gene encoding a BTB/POZ NPH3 domain-containing protein, the plant or cell exhibits decreased alkaloid content in comparison to a plant or cell which has not been modified to modulate the expression or decrease the activity of the at least one gene encoding a BTB/POZ NPH3 domain-containing protein.

2. The method according to claim 1, wherein the alkaloid content is modulated in comparison to a plant or cell which has not been modified to modulate the expression or decrease the activity of the at least one gene encoding a BTB/POZ NPH3 domain-containing protein.

3. A plant or part thereof or cell, or plant propagation material obtained therefrom, which has been modified to achieve a modulation in alkaloid content in comparison to an unmodified plant, wherein the modification is the modulation of the expression or decrease the activity of at least one gene encoding a BTB/POZ NPH3 domain-containing protein from tobacco, wherein i) the content of one or more alkaloids selected from nicotine, nornicotine, pseudooxynicotine (PON), anabasine, and anatabine is modulated;

ii) the plant or part thereof, or cell, or plant propagation material obtained therefrom is from the genus *Nicotiana;* iii) modulation of the expression of said at least one gene is achieved by overexpression, mutation, knock out, gene silencing or RNA silencing of said at least one gene;

iv) the BTB/POZ NPH3 domain-containing protein comprises an amino acid sequence:

a) as set out in SEQ ID NO: 1, or b) a functional variant of SEQ ID NO: 1 comprising a BTB/POZ domain with a sequence set forth in SEQ ID NO: 31 or a sequence with at least 98% identity thereto, and a NPH3 domain with a sequence as set forth in SEQ ID NO: 32 or a sequence with at least 98% identity thereof, or c) a sequence which has at least 98% identity to SEQ ID NO: 1; or the at least one gene encoding the BTB/POZ NPH3 domain-containing protein encodes the BTB/POZ NPH3 domain-containing protein as defined in a), b) or c) above and comprises a nucleotide sequence:

a) as set out in SEQ ID NO: 2 or SEQ ID NO: 3, b) a functional variant of SEQ ID NO: 2 or SEQ ID NO: 3 comprising a nucleotide sequence encoding a BTB/POZ domain with a sequence set forth in SEQ ID NO: 31 or a sequence with at least 98% identity thereto, and a NPH3 domain with a sequence as set forth in SEQ ID NO: 32 or a sequence with at least 98% identity thereof, or c) a sequence which has at least 98% identity to SEQ ID NO: 2 or 3; and v) when the plant or part thereof or cell, or plant propagation material obtained therefrom is modified to increase the expression of the at least one gene encoding a BTB/POZ NPH3 domain-containing protein, the plant or part thereof or cell, or plant propagation material obtained therefrom exhibits increased alkaloid content in comparison to a plant or part thereof or cell, or plant propagation material obtained therefrom which has not been modified to modulate the expression of the at least one gene encoding a BTB/POZ NPH3 domain-containing protein, or when the plant or part thereof or cell, or plant propagation material obtained therefrom is modified to decrease the activity or expression of the at least one gene encoding a BTB/POZ NPH3 domain-containing protein, the plant or part thereof or cell, or plant propagation material obtained therefrom exhibits decreased alkaloid content in comparison to a plant or part thereof or cell, or plant propagation material obtained therefrom which has not been modified to modulate the expression or decrease the activity of the at least one gene encoding a BTB/POZ NPH3 domain-containing protein.

4. The plant or part thereof or cell, or plant propagation material obtained therefrom, according to claim 3, wherein the alkaloid content of the plant or cell is decreased in comparison to a plant or cell which has not been modified to modulate the expression or decrease the activity of at least one gene encoding a BTB/POZ NPH3 domain-containing protein.

5. The plant or part thereof or cell, or plant propagation material obtained therefrom, according to claim 4, wherein the activity or expression of at least one gene encoding a BTB/POZ NPH3 domain-containing protein is decreased in comparison to a plant or cell which has not been modified to modulate the expression or decrease the activity of the at least one gene encoding a BTB/POZ NPH3 domain-containing protein.

6. The plant or part thereof or cell, or plant propagation material obtained therefrom, according to claim 3, wherein the alkaloid content of the plant or cell is increased in comparison to a plant or cell which has not been modified to modulate the expression of the at least one gene encoding a BTB/POZ NPH3 domain-containing protein.

7. The plant or part thereof or cell, or plant propagation material obtained therefrom, according to claim 6, wherein the plant or cell is modified to increase the expression of at least one gene encoding a BTB/POZ NPH3 domain-containing protein and the plant or cell exhibits increased alkaloid content in comparison to a plant or cell which has not been modified to modulate the expression of the at least one gene encoding a BTB/POZ NPH3 domain-containing protein.

8. The plant or part thereof or cell, or plant propagation material obtained therefrom, according to claim 3, wherein the content of one or more alkaloids selected from nornicotine and/or PON and/or anabasine is modulated.

9. The plant or part thereof or cell, or plant propagation material obtained therefrom, according to claim 3, wherein the at least one BTB/POZ NPH3 domain-containing protein comprises an amino acid sequence as set out in SEQ ID NO: 1 or a functional variant of SEQ ID NO: 1 comprising a BTB/POZ domain with a sequence set forth in SEQ ID NO: 31 and a NPH3 domain with a sequence as set forth in SEQ ID NO: 32; or the at least one gene encoding the BTB/POZ NPH3 domain-containing protein comprises a nucleotide sequence as set out in SEQ ID NO: 2 or SEQ ID NO: 3, or a functional variant of SEQ ID NO: 2 or SEQ ID NO: 3 comprising a nucleotide sequence encoding a BTB/POZ domain with a sequence set forth in SEQ ID NO: 31 and a NPH3 domain with a sequence as set forth in SEQ ID NO: 32.

10. The plant or part thereof or cell, or plant propagation material obtained therefrom, according to claim 3, wherein an additional gene encoding a BTB/POZ NPH3 domain-containing protein is modulated wherein the additional gene is at least one selected from SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28; or the at least one gene encoding the BTB/POZ NPH3 domain-containing protein comprises a nucleotide sequence as set out in SEQ ID NO: 5, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 17, SEQ ID NO: 18, SEQ ID NO: 20, SEQ ID NO: 21, SEQ ID NO: 23, SEQ ID NO: 24, SEQ ID NO: 26, SEQ ID NO: 27, SEQ ID NO: 29, SEQ ID NO: 30.

11. A harvested leaf, a cut harvested leaf, a processed leaf, a processed tobacco leaf, a non-viable processed tobacco leaf, or a cut processed leaf of the plant according to claim 3 or a plant propagated from a plant propagation material obtained therefrom, wherein said harvested leaf, a cut harvested leaf, a processed leaf, a processed tobacco leaf, a non-viable processed tobacco leaf, or a cut processed leaf has a modulation of the expression or a decrease in the activity of at least one gene encoding a BTB/POZ NPH3 domain-containing protein from tobacco to achieve a modulation in alkaloid content in comparison to an unmodified harvested leaf, a cut harvested leaf, a processed leaf, a processed tobacco leaf, a non-viable processed tobacco leaf, or a cut processed leaf, wherein the modulation is as defined in claim 6.

12. The processed leaf, a processed tobacco leaf, a non-viable processed tobacco leaf, or cut processed leaf according to claim 11, wherein the leaf is processed by curing, fermenting, pasteurising or a combination thereof.

13. A cured tobacco material, or a tobacco blend comprising the cured tobacco material, made from the plant or part thereof of claim 3 or a plant propagated from a plant propagation material obtained therefrom, wherein said cured tobacco material or tobacco blend has a modulation of the expression or a decrease in the activity of at least one gene encoding a BTB/POZ NPH3 domain-containing protein from tobacco to achieve a modulation in alkaloid content in comparison to an unmodified cured tobacco material or tobacco blend, wherein the modulation is as defined in claim 3.

14. A mutant of a plant carrying a heritable mutation in a nucleotide sequence of at least one gene encoding the BTB/POZ NPH3 domain-containing protein, wherein the BTB/POZ NPH3 domain-containing protein comprises an amino acid sequence:

a) as set out in SEQ ID NO: 1, or b) a functional variant of SEQ ID NO: 1 comprising a BTB/POZ domain with a sequence set forth in SEQ ID NO:31 or a sequence with at least 98% identity thereto, and a NPH3 domain with a sequence as set forth in SEQ ID NO:32 or a sequence with at least 98% identity thereof, or c) a sequence which has at least 98% identity to SEQ ID NO: 1; or the at least one gene encoding the BTB/POZ NPH3 domain-containing protein encodes the BTB/POZ NPH3 domain-containing protein as defined in a), b) or c) above and comprises a nucleotide sequence:

a) as set out in SEQ ID NO: 2 or SEQ ID NO: 3, b) a functional variant of SEQ ID NO: 2 or SEQ ID NO: 3 comprising a nucleotide sequence encoding a BTB/POZ domain with a sequence set forth in SEQ ID NO:31 or a sequence with at least 98% identity thereto, and a NPH3 domain with a sequence as set forth in SEQ ID NO:32 or a sequence with at least 98% identity thereof, or c) a sequence which has at least 98% identity to SEQ ID NO: 2 or 3;

wherein said heritable mutation modulates the expression or decrease the activity of the at least one gene encoding the BTB/POZ NPH3 domain-containing protein by overexpression, mutation, knock out, gene silencing or RNA silencing of said at least one gene; and wherein the mutant plant has modulated alkaloid content relative to a comparable plant which does not carry said heritable mutation, wherein i) the content of one or more alkaloids selected from nicotine, nornicotine, pseudooxynicotine (PON), anabasine, and anatabine is modulated;

ii) the plant is from the genus *Nicotiana*, and iii) when said heritable mutation increases the expression of the at least one gene encoding a BTB/POZ NPH3 domain-containing protein the plant exhibits increased alkaloid content in comparison to a plant which does not carry said heritable mutation, or when said heritable mutation decreases the activity or expression of the at least one gene encoding a BTB/POZ NPH3 domain-containing protein the plant exhibits decreased alkaloid content in comparison to a plant which does not carry said heritable mutation.

15. Progeny or seed of the mutant plant which carries the heritable mutation according to claim 14.

16. A harvested leaf, a processed leaf or cured tobacco material produced from the plant according to claim 14, wherein the harvested leaf, processed leaf or cured tobacco material has modulated alkaloid content relative to a harvested leaf, processed leaf or cured tobacco material from a comparable plant which does not carry said modification in the at least one gene encoding the BTB/POZ NPH3 domain-containing protein.

17. The mutant plant according to claim 14, wherein the modulated alkaloid is nicotine.

18. The method according to claim 1, wherein the BTB/POZ NPH3 domain-containing protein comprises:

a) a functional variant of SEQ ID NO: 1 comprising a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 1; or the at least one gene encoding the BTB/POZ NPH3 domain-containing protein encodes the BTB/POZ NPH3 domain-containing protein as defined in a) or b) above and comprises:

a) a functional variant of SEQ ID NO: 2 or SEQ ID NO: 3 comprising a nucleotide sequence encoding a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 2 or 3.

19. The plant or part thereof or cell, or plant propagation material obtained therefrom, according to claim 3, wherein the BTB/POZ NPH3 domain-containing protein comprises:

a) a functional variant of SEQ ID NO: 1 comprising a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 1; or the at least one gene encoding the BTB/POZ NPH3 domain-containing protein encodes the BTB/POZ NPH3 domain-containing protein as defined in a) or b) above and comprises:

a) a functional variant of SEQ ID NO: 2 or SEQ ID NO: 3 comprising a nucleotide sequence encoding a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 2 or 3.

20. The mutant of a plant carrying a heritable mutation in a nucleotide sequence of at least one gene encoding the BTB/POZ NPH3 domain-containing protein according to claim 14, wherein the BTB/POZ NPH3 domain-containing protein comprises:

a) a functional variant of SEQ ID NO: 1 comprising a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 1; or the at least one gene encoding the BTB/POZ NPH3 domain-containing protein encodes the BTB/POZ NPH3 domain-containing protein as defined in a) or b) above and comprises:

a) a functional variant of SEQ ID NO: 2 or SEQ ID NO: 3 comprising a nucleotide sequence encoding a BTB/POZ domain with a sequence set forth in SEQ ID NO:31 or a sequence with at least 99% identity thereto, and a NPH3 domain with a sequence as set forth in SEQ ID NO:32 or a sequence with at least 99% identity thereof, or b) a sequence which has at least 99% identity to SEQ ID NO: 2 or 3.

* * * * *

SEQUENCE LISTING

<160> NUMBER OF SEQ ID NOS: 44

<210> SEQ ID NO 1
<211> LENGTH: 620

<212> TYPE: PRT
<213> ORGANISM: Artificial Sequence
<220> FEATURE:
<223> OTHER INFORMATION: Nitab4.5_0000868g0020.2 amino acid sequence

<400> SEQUENCE: 1

```
Met Val Asp Leu Asp Ser Glu Gly Thr Glu Gln Pro Ser Thr Val Asn
1               5                   10                  15

Asn Met Ser Thr Lys Lys Lys Glu Leu Leu Ser Thr Ala Met Lys Arg
                20                  25                  30

Thr Ser Asp Trp Ile Phe Ser Gln Glu Ile Pro Ser Asp Val Thr Val
            35                  40                  45

Asn Ala Gly Gly Ser Ala Phe Ser Leu His Lys Phe Pro Leu Val Ser
        50                  55                  60

Lys Ser Gly Tyr Ile Arg Lys Ile Ile Ser Glu Ser Asn Asp Ala Asp
65                  70                  75                  80

Val Ser Ile Val Glu Ile Pro Asp Ile Pro Gly Gly Ser Asp Ala Phe
                85                  90                  95

Glu Leu Ala Ala Lys Phe Cys Tyr Gly Ile Asn Phe Glu Ile Ser Thr
                100                 105                 110

Glu Asn Ile Ala Leu Leu Arg Cys Thr Ala Glu Tyr Leu Glu Met Thr
            115                 120                 125

Glu Asp Tyr Ala Val Gly Asn Leu Val Gly Arg Thr Glu Ala Tyr Leu
        130                 135                 140

Asn Glu Val Ala Leu Lys Ser Leu Ala Gly Ala Val Ser Ile Leu His
145                 150                 155                 160

Ser Ser Glu Ser Leu Leu Pro Ile Ala Glu Lys Val Lys Met Val Ser
                165                 170                 175

Arg Cys Ile Asp Thr Ile Ala Tyr Ile Ala Cys Lys Asp Asn Gln Phe
            180                 185                 190

Cys Thr Ser Gly Arg Ala Glu Ala Gly Thr Asn Gly Leu Asn Ser Ser
            195                 200                 205

Thr Phe Ser Asn Pro Lys Pro Met Val Asp Trp Trp Ala Glu Asp Leu
        210                 215                 220

Ala Val Leu Arg Ile Asp Phe Phe Gln Arg Val Leu Ile Ala Met Met
225                 230                 235                 240

Gly Arg Gly Phe Lys Gln Tyr Ala Leu Gly Pro Ile Leu Met Leu Tyr
                245                 250                 255

Ala Gln Lys Ser Leu Arg Gly Leu Glu Ile Phe Gly Lys Gly Arg Lys
                260                 265                 270

Lys Ile Glu Pro Lys Gln Glu His Glu Lys Arg Val Val Leu Glu Thr
                275                 280                 285

Ile Val Ser Leu Leu Pro Arg Glu Lys Asn Ala Leu Ser Val Ser Phe
        290                 295                 300

Leu Ser Met Leu Leu Arg Ala Ala Ile Tyr Leu Glu Thr Thr Val Ala
305                 310                 315                 320

Cys Arg Leu Asp Leu Glu Lys Arg Met Ala Leu Gln Leu Gly Gln Ala
                325                 330                 335

Val Leu Asp Asp Leu Leu Ile Pro Ser Tyr Ser Phe Thr Gly Asp Thr
                340                 345                 350

Leu Phe Asp Val Glu Thr Val Gln Arg Ile Ile Met Asn Phe Leu Asp
            355                 360                 365

Asn Glu Met Asp Gly Ser Arg Leu Gly Asp Glu Glu Tyr Val Ser Pro
        370                 375                 380
```

```
Ser Leu Ser Asp Met Glu Arg Val Gly Lys Leu Met Glu Asn Tyr Leu
385             390             395             400

Ala Glu Ile Ala Ser Asp Arg Asn Leu Ser Val Ser Lys Phe Ile Ser
            405             410             415

Leu Ala Glu Val Ile Pro Glu Gln Ala Lys Ile Thr Glu Asp Gly Met
            420             425             430

Tyr Arg Ala Ile Asp Ile Tyr Leu Lys Ala His Pro Ala Leu Ser Asp
        435             440             445

Met Glu Arg Lys Lys Val Cys Gly Val Met Asp Cys Gln Lys Leu Ser
        450             455             460

Arg Glu Ala Cys Ala His Ala Ala Gln Asn Asp Arg Leu Pro Val Gln
465             470             475             480

Thr Val Val Gln Val Leu Tyr Tyr Glu Gln Gln Arg Leu Arg Glu Val
            485             490             495

Met Asp Gly Ser Gln Leu Val Ala Thr Glu Pro Pro Ala Leu Ile Pro
            500             505             510

Ser Lys Thr Asn Gln Phe Ser Thr Asp Ile Arg Pro Ile Ser Asp Glu
        515             520             525

Val Ser Ser Leu Lys Arg Glu Asn Gln Glu Leu Lys Phe Glu Leu Leu
        530             535             540

Lys Met Lys Met Arg Leu Lys Glu Ile Glu Lys Pro Ser Asn Lys Ser
545             550             555             560

Ala Thr Ser Ser Pro Leu Val Ile Thr His Pro Ser Ala Asp Lys Pro
            565             570             575

Pro Leu Pro Arg Lys Pro Ser Asn Phe Ile Ser Ser Val Ser Lys Lys
            580             585             590

Leu Gly Lys Phe Ile Arg Ala Asp Gly Leu Thr Ala Asn Lys Gly Arg
        595             600             605

Asn Lys Pro Ser Lys Asp Arg Arg His Ser Ile Ser
    610             615             620
```

```
<210> SEQ ID NO 2
<211> LENGTH: 1863
<212> TYPE: DNA
<213> ORGANISM: Artificial Sequence
<220> FEATURE:
<223> OTHER INFORMATION: Nitab4.5_0000868g0020.2 coding sequence

<400> SEQUENCE: 2
atggtggatc ttgattcaga ggggactgaa caaccctcta ctgttaacaa tatgtccact        60
aaaaagaagg agcttctttc cactgctatg aagaggacct ctgattggat tttctcccaa       120
gagatcccaa gtgatgtaac tgtaaatgca ggcggatccg ccttttcact gcacaagttc       180
cctttagttt caaagagtgg ctacataagg aagattatct cagaatccaa tgatgctgat       240
gtttctatag tcgaaatccc tgatataccc ggtggatcag atgcatttga acttgctgca       300 aaatttgtt atggaataaa ttttgagata agcacagaaa acattgcctt gctgagatgc       360
acagcggaat atcttgagat gacagaagac tatgcagttg ggaatttggt tggaagaact       420
gaggcctact aaatgaagt agctcttaaa agcctagctg gtgcagtttc aatttttgcat       480 tcttcagaaa gccttcttcc cattgcagag aaagtaaaaa tggttagtcg atgcatcgac       540
acaattgcat atattgcatg caaggataac caattctgca catcaggtag agcagaggct       600
ggtactaacg gattgaattc gtccacgttt tcaaacccga agcctatggt tgattggtgg       660
gctgaggatt tagctgtcct tagaattgat ttttccaaa gggttctaat tgcaatgatg       720
```

```
ggaagaggat tcaagcagta tgcacttgga ccaatattaa tgctatatgc acagaagtct     780
cttcgaggtt tggaaatatt tggaaaggga aggaaaaaaa ttgagccaaa acaagaacat     840
gaaaagaggg ttgttttaga aacaattgtt agtcttctgc caagggagaa aaatgcattg     900
tcagttagct ttctgtcaat gctgctccga gctgcaatat atctagaaac cacagttgct     960
tgcaggcttg acttggagaa gaggatggca ttgcagcttg acaggctgt  gttagatgat     1020 ttattgattc cttcatattc cttcacaggg gacacattgt ttgatgttga aaccgtgcag     1080
cgtatcatca tgaatttcct tgacaatgaa atggatggaa gtcgattggg agatgaggag     1140
tatgtgtctc cttcattaag tgacatggag cgggttggga aacttatgga aaattacctt     1200
gctgaaatag cctcagaccg taatctatcc gtttcaaaat tcattagtct agctgaagtc     1260
atcccagagc aagcaaagat cactgaagat gggatgtaca gggcaattga tatttatttg     1320
aaggcacatc cagctctaag tgatatggaa agaaaaaaag tttgcggtgt tatggactgt     1380
caaaagctat ctagagaggc ttgtgctcat gctgctcaaa atgataggct ccctgttcag     1440
acagttgtgc aagtacttta ctacgagcag caacgccttc gtgaggtcat ggacgggagc     1500
caacttgtag caactgaacc tccagctcta attccttcta aaactaatca gttctccact     1560
gatatccgtc ctatttcaga tgaggtctct agtctaaaac gagaaaatca ggagctgaaa     1620
tttgagttgc taaagatgaa aatgaggttg aaagaaattg aaaaaccttc aaacaaatca     1680
gctactagca gcccttttggt catcactcat ccatctgctg ataaacctcc tttgccaaga    1740
aaaccatcta atttcataag ctcagtatcc aaaaagcttg gaaaatttat tcgagcagat     1800
ggactcacag ccaacaaagg ccgaaataaa ccaagtaaag acaggcgtca ttctatatcc     1860
tga     1863
```

<210> SEQ ID NO 3
<211> LENGTH: 6688
<212> TYPE: DNA
<213> ORGANISM: Artificial Sequence
<220> FEATURE:
<223> OTHER INFORMATION: Nitab4.5_0000868g0020.2 genomic sequence
<220> FEATURE:
<221> NAME/KEY: misc_feature
<222> LOCATION: (5212)..(5405)
<223> OTHER INFORMATION: n is a, c, g, or t

<400> SEQUENCE: 3

```
ctgagctaaa tccttttcta ctctatttaa ccccaatcat tcacataata cctttaatac      60
cactcacatt tctgctgtag gggctcctca aacatgatct ttgttctgct aacattaagg     120
cctataatgg gaattgtacc aatgccttga ttgatagtga aagatgataa caataattca     180
attattaggg gccagatact gttgattaaa tgctcagaca ttgaactaac agaagcaaag     240
gaaaagaaca tgtctttctg gttttttgctc cataaggaaa cagcttaaga gaaacctcta     300
ccgtagaccg aatgtgatgg acatggttaa gaccctttaa agtttcaatc atggtggatc     360
ttgattcaga ggggactgaa caaccctcta ctgttaacaa tatgtccact aaaaagaagg     420
agcttctttc cactgctatg aagaggacct ctgattggta tgctctatat atcttgactt     480
cttattgtgc tttgtaaaag tagccagccc cttttatgta ctattattaa tctgtttctc     540
aagatactcg ctggaaggat aggtactgac aagtaaagtt acctatataa tcttaacagg     600
attttctccc aagagatccc aagtgatgta actgtaaatg caggcggatc cgcctttttca     660 ctgcacaagg tgtggtgttc tctatgcttt tgtcataaga agttataact aaacttcact     720
cacaatccaa actgttgttg gttttagtta tattcctatt tggattgagt tatcagccct     780
```

-continued

```
ggtcacacct caatgagaat ctgaatttgg tgattttttc tcttttctga cgattgaatc     840
acaaggttca ataatgattt attgtgtacc atgcagttcc ctttagtttc aaagagtggc     900
tacataagga agattatctc agaatccaat gatgctgatg tttctatagt cgaaatccct     960
gatatacccg gtggatcaga tgcatttgaa cttgctgcaa aattttgtta tggaataaat    1020
tttgagataa gcacagaaaa cattgccttg ctgagatgca cagcggaata tcttgagatg    1080
acagaagact atgcagttgg gaatttggtt ggaagaactg aggcctactt aaatgaagta    1140
gctcttaaaa gcctagctgg tgcagtttca attttgcatt cttcagaaag ccttcttccc    1200
attgcagaga aagtaaaaat ggttagtcga tgcatcgaca caattgcata tattgcatgc    1260
aaggataacc aattctgcac atcaggtaga gcagaggctg gtactaacgg attgaattcg    1320
tccacgtttt caaacccgaa gcctatggtt gattggtggg ctgaggattt agctgtcctt    1380
agaattgatt ttttccaaag ggttctaatt gcaatgatgg aagaggatt caagcagtat     1440 gcacttggac caatattaat gctatatgca cagaagtctc ttcgaggttt ggtgaggcct    1500
tgtcctataa tataatctgg attatttagt taaaatattt acgcagatag taattttttt    1560
gtttatcaca ggaaatattt ggaaagggaa ggaaaaaaat tgagccaaaa caagaacatg    1620
aaaagagggt tgtttagaa acaattgtta gtcttctgcc aagggagaaa aatgcattgt     1680
cagttagctt tctgtcaatg ctgctccgag ctgcaatata tctagaaacc acagttgctt    1740
gcaggcttga cttggagaag aggatggcat tgcagcttgg acaggctgtg ttagatgatt    1800
tattgattcc ttcatattcc ttcacagggg acacattgtt tgatgttgaa accgtgcagc    1860
gtatcatcat gaatttcctt gacaatgaaa tggatggaag tcgattggga gatgaggagt    1920
atgtgtctcc ttcattaagt gacatggagc gggttgggaa acttatggaa aattaccttg    1980
ctgaaatagc ctcagaccgt aatctatccg tttcaaaatt cattagtcta gctgaagtca    2040
tcccagagca agcaaagatc actgaagatg ggatgtacag ggcaattgat atttatttga    2100
aggtatgcgc gatgaaatac ttgattagtt ataaatttat ctatgcatat ttacacatac    2160
aggagcattt tcatagtttt agatcatgtt tagaaaagga gaaaaacttt tgctcccgac    2220
tgctacatgg taattggcat gctaaactta gtaatcttga ttgaaatgcc ttctacaaca    2280
atgtacctct tggtcctagc ataattatga ctgagagaag actttgggaa taaacaaaat    2340
cagaaaatat gtcaccaatg aagaaccagt cattttcaca aaatccttgc tcctcaatta    2400 tttttttttgc aggcattgct cggtccgcct catgattttg acccaagccc atgtcctata    2460
ctcctttacc ctacaaccat tttgtgagac tgatgttgtc tggagtttcg aatctcgttt    2520
cttcccctgt cctgaacatc tatctcatgg tgcatttatc ctgcacctgg tttgaacttt    2580
gaatatgtgt tcaattcaac tcaccgtgtc ttacttagac catatatata tatactagta    2640
gttttagcta agggatatgg tatgttagga agaagaacat tcctcatttc aaatggactt    2700
aaggggaagc tcccttagta tattacttag gtattatagt atgttttgt gaggaataat     2760 ttggagtaaa gagtagctgt gaagcatgtt aaagcacatg actgaggtgg tactttaaat    2820
cgttgtgtcg ctcatcatta gggaatgcca gatcaggctt ttttaatttt tatattctgt    2880
ttccgagtat ataatttctt cttgatacag acggtataac aggacttaat cagggtaatt    2940
aattagtatc tgcacgtgca agatcaattt aaatgtaggt taaatatgtt agtacttagt    3000
accttctcat cattgaagaa attaatagag gacgaacata tatatatata tatatatata   3060
tatatatata tttctctgca cgtgtattgc atgtgtatgc caaattatat aatatctaat    3120
```

-continued

```
tttataacat aatattaata ttattaaaaa aaattccgaa caaataatta tacataaaat   3180
aaggtacaag tatttacgaa ttgatccatg taaatcagca tatattgact ttgaaagttc   3240
gtcccaaaca aacactttta actttgcaac cattcttaca cgaaacaaca taatatgtaa   3300
atgtagcttg gtggctaaac taacaaacca taaactcatt gctaatgtct tcgtaaaaaa   3360
atgtatgtca caaaaccgct taagttggta atttaatatt tcatgaaaag actttgtaag   3420
gctaattaac aaaatattta atttgaatta tcttatttag ggagtagtat ttaattttaa   3480
atattttatt ttgatgttat ttttgcaggt tcttttttct tttgacttaa aagtattaat   3540
tcaatttttc aagattcatc attaaaacac aatttaatag gctattcgag atataggggaa  3600 cttgaatatg aaaataactt ttaaataaga atatgagtag taattattta ttgcgagcga   3660
cacaatttta ttttttttgtt aattttctta aagaaaaaaa gaaagagacc gccacttttg  3720
tataataaat actcttaatc tgattttaaa ttaattataa taattgaagt ttactacttg   3780
tttagtttca aaatctgtct gttaaagaaa aattataact gcttgaattt ggagatgaac   3840
gatctatgtg gaaaatagtt ttttttatttg aatttaaaat aaatgactta tattgcaaca   3900
tgcaaacatt gcgtcgtctt gtctaaagca gccagtagga aagcattgtc taaataaaaa   3960
gccagtagaa aagccgaaaa cagtagataa atacaacaat cattttcttt ctccacttct   4020
taaaataatg atcacccaat agaaaaaaaa atatagattt ttttcgtaag ttaaatactt   4080
tagattatct caatatatgt gcagaatttt agcaccgttt gtgaattaaa atttgaagac   4140
tcgactaaac tttaaataaa aaggtcaaaa gaaaggtatg agtgcaattt aataacaaaa   4200
aaaaggcaca cagcaaaaga agaataccctt tcaatgatga atttttataga attgctgatg  4260 agactaagta atcgggggtgc gttttttaagt cactctctgc ttaactgtaa ataaatacat  4320
acttatttat tatcaagaag ttagaacact cttcgtcttc tattccttta gaatatatct   4380
gtgtgagttt atggaacaaa ggcttttttt tatttgaata gtaagccaat tgtttctcta   4440
tctattctaa aagatgccaa acggttgaaa gacaaaatca aatgggaacc ggtagaaact   4500
attttaagca ttattgacta atatgaaaga tcacatccct tcaaataaat ttggtattta   4560
cttaaaattt ttggtataaa taaaattaaa ttatttagaa aggcatttag gtaattcaac   4620
tttttggtta agagcttcct acatatatat atatatatat atatgtgcgt gtgtgcaaaa   4680
tattatagat attaagtttt gaacccataa tctaaaaaat ctcataacct tgaacccatt   4740
aaatttaaat cttggatccg cctccttttg cattgcatag atcattgcta caatgtggtg   4800
gctcttgttt tctcttgcct atgttgcagg gcttgctgtg cataggtctt catacttgag   4860 gtcttttttct ataatttgac accttaatgt taaccagggt gaaataagga tctggtatct   4920
gctcgttgac ccttcgcttt ctcctttcaa ctgtaggtca aatttgtcat aacatcctaa   4980
agaatcttgt gtgccaatac atacttcgta tatggtatct catccaaaag aagaagctcg   5040
tttatatgct catatatatg caaactgcca ccccccccc cccggttact ctttctaatt   5100
taaaaggtaa gaatagactc aataggtttt tgctacagaa gctctgaatc ttattgctat   5160
tcagtcacgt cacataataa caagatctaa accatgtata ccatttgatc tnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnn nnnnnnnnnn nnnnnnnnnn nnnnnnnnnn   5400 nnnnntttttt tttttttttt tttttttttg cttttggtgc caaagggtat taagtagcat   5460
ccattcattg cgtagtgttt cttgagtaca taatagtaat ctgtttgcct ctaacatctc   5520
```

-continued

```
taagacaatc ataggaagaa atccaaaatg tattatccta gtagactcct tcatcctacc    5580
accaaatttg gctaattgat ttgctacttt tgttctgctc cttgtaatta tgctcaatca    5640
gagggtctcc gagctggctg agaaatgata ttagaataat gtgaaatccc atttgatgat    5700
cttcacatat gttgttagta catcaaatat attcttgaac aatgagttga acttcatcag    5760
aaagtttaag cttttaaaa tgcagaacaa aagtgtggaa cccttaaacc atgctaatga    5820
gcattatctt cataccggtt aaaactactt tcatctttct aatgttttg ctgttgcata    5880 atttgaaggc acatccagct ctaagtgata tggaaagaaa aaagtttgc ggtgttatgg    5940 actgtcaaaa gctatctaga gaggcttgtg ctcatgctgc tcaaaatgat aggctccctg    6000
ttcagacagt tgtgcaagta ctttactacg agcagcaacg ccttcgtgag gtcatggacg    6060
ggagccaact tgtagcaact gaacctccag ctctaattcc ttctaaaact aatcagttct    6120
ccactgatat ccgtcctatt tcagatgagg tctctagtct aaaacgagaa aatcaggagc    6180
tgaaatttga gttgctaaag atgaaaatga ggttgaaaga aattgaaaaa ccttcaaaca    6240
aatcagctac tagcagccct ttggtcatca ctcatccatc tgctgataaa cctcctttgc    6300
caagaaaacc atctaatttc ataagctcag tatccaaaaa gcttggaaaa tttattcgag    6360
cagatggact cacagccaac aaaggccgaa ataaaccaag taaagacagg cgtcattcta    6420
tatcctgatt tgagctagct atatttgtcg ttgggttgaa gaattattac tgcattgtct    6480
gaacatatat gatactggat tcaaatttta gtttttattt tagtcgtgcg agttgtatgg    6540
taaagtataa atttggtcag actttaatcc aaaaattgta tttagatgga cgtggacgac    6600
ttcctgtaca ttatctcatga aagatttta atcttggttt ctcttatatg tatcttgaag    6660
aaagatttgc aatcttgaga tgtacaag                                       6688
```

<210> SEQ ID NO 4
<211> LENGTH: 620
<212> TYPE: PRT
<213> ORGANISM: Artificial Sequence
<220> FEATURE:
<223> OTHER INFORMATION: Nitab4.5_0000651g0020.2 amino acid sequence

<400> SEQUENCE: 4

```
Met Ala Asp Leu Asp Ser Asp Gly Ile Glu Gln Pro Ser Gly Val Asn
1               5                   10                  15

Asn Met Ser Thr Thr Lys Lys Glu Leu Leu Ser Thr Ala Met Lys Arg
            20                  25                  30

Thr Ser Asp Trp Ile Phe Ser Gln Glu Ile Pro Ser Asp Val Thr Val
        35                  40                  45

Asn Ala Gly Gly Ser Ala Phe Ser Leu His Lys Phe Pro Leu Val Ser
    50                  55                  60

Lys Ser Gly Tyr Ile Arg Lys Ile Ile Ser Glu Ser Asn Asp Ala Asp
65                  70                  75                  80

Ala Ser Thr Val Glu Ile Pro Asp Ile Pro Gly Gly Ser Asp Ala Phe
                85                  90                  95

Glu Leu Ala Ala Lys Phe Cys Tyr Gly Ile Asn Phe Glu Ile Ser Thr
            100                 105                 110

Glu Asn Ile Ala Leu Leu Arg Cys Thr Ala Glu Tyr Leu Glu Met Thr
        115                 120                 125

Glu Asp Tyr Ala Val Gly Asn Leu Val Gly Arg Thr Glu Ala Tyr Leu
    130                 135                 140

Asn Glu Val Ala Leu Lys Ser Leu Ala Gly Ala Val Ser Ile Leu His
```

-continued

```
       145                 150                 155                 160

Ser Ser Glu Ser Leu Leu Pro Ile Ala Glu Lys Val Lys Leu Val Ser
                  165                 170                 175

Arg Cys Ile Asp Thr Ile Ala Tyr Ile Ala Cys Lys Asp Asn Gln Phe
                  180                 185                 190

Cys Thr Ser Gly Arg Ala Glu Pro Gly Thr Asn Gly Leu Asn Ser Ser
                  195                 200                 205

Thr Phe Ser Asn Pro Lys Pro Met Val Asp Trp Trp Ala Glu Asp Leu
                  210                 215                 220

Thr Val Leu Arg Ile Asp Phe Phe Gln Arg Val Leu Ile Ala Met Met
225                 230                 235                 240

Gly Arg Gly Phe Lys Gln Tyr Ala Leu Gly Pro Ile Leu Met Leu Tyr
                  245                 250                 255

Ala Gln Lys Ser Leu Arg Gly Leu Glu Ile Phe Gly Lys Gly Arg Lys
                  260                 265                 270

Lys Ile Glu Pro Lys Gln Glu His Glu Lys Arg Val Val Leu Glu Thr
                  275                 280                 285

Ile Val Ser Phe Leu Pro Arg Glu Lys Asn Ala Leu Ser Val Ser Phe
                  290                 295                 300

Leu Ser Met Leu Leu Arg Ala Ala Ile Tyr Leu Glu Thr Thr Val Ala
305                 310                 315                 320

Cys Arg Leu Asp Leu Glu Lys Arg Met Ser Leu Gln Leu Gly Gln Ala
                  325                 330                 335

Val Leu Asp Asp Leu Leu Ile Pro Ser Tyr Ser Phe Thr Gly Asp Thr
                  340                 345                 350

Leu Phe Asp Val Glu Thr Val Gln Arg Ile Ile Met Asn Phe Leu Asp
                  355                 360                 365

Asn Glu Met Asp Gly Ser Arg Leu Gly Asp Glu Glu Tyr Val Ser Pro
                  370                 375                 380

Ser Leu Ser Asp Met Glu Arg Val Gly Lys Leu Met Glu Asn Tyr Leu
385                 390                 395                 400

Ala Glu Ile Ala Ser Asp Arg Asn Leu Ser Val Ser Lys Phe Ile Ser
                  405                 410                 415

Leu Ala Glu Val Ile Pro Glu Gln Ala Lys Ile Thr Glu Asp Gly Met
                  420                 425                 430

Tyr Arg Ala Ile Asp Ile Tyr Leu Lys Ala His Pro Ala Leu Ser Asp
                  435                 440                 445

Met Glu Arg Lys Lys Val Cys Gly Val Met Asp Cys Gln Lys Leu Ser
                  450                 455                 460

Arg Glu Ala Cys Ala His Ala Ala Gln Asn Asp Arg Leu Pro Val Gln
465                 470                 475                 480

Thr Val Val Gln Val Leu Tyr Tyr Glu Gln Gln Arg Leu Arg Glu Val
                  485                 490                 495

Met Asp Gly Ser Gln Leu Val Ala Thr Glu Pro Pro Thr Leu Ile Pro
                  500                 505                 510

Ser Lys Thr Asn His Phe Ser Ile Asp Ile Pro Pro Val Ser Asp Glu
                  515                 520                 525

Val Ser Ser Leu Lys Arg Glu Asn Gln Glu Leu Lys Phe Glu Leu Leu
                  530                 535                 540

Lys Met Lys Met Arg Leu Lys Glu Ile Glu Lys Pro Ser Asn Lys Ser
545                 550                 555                 560

Ala Ala Ser Ser Pro Leu Val Ile Thr His Pro Ser Ala Asp Lys Pro
                  565                 570                 575
```

```
Pro Leu Pro Arg Lys Pro Ser Asn Phe Ile Ser Ser Val Ser Lys Lys
            580                 585                 590

Leu Gly Lys Phe Ile Arg Ala Asp Gly Leu Thr Ala Asn Lys Gly Arg
        595                 600                 605

Asn Lys Pro Ser Lys Asp Arg Arg His Ser Ile Ser
    610                 615                 620
```

```
<210> SEQ ID NO 5
<211> LENGTH: 1863
<212> TYPE: DNA
<213> ORGANISM: Artificial Sequence
<220> FEATURE:
<223> OTHER INFORMATION: Nitab4.5_0000651g0020.2 coding sequence

<400> SEQUENCE: 5
atggcggatc ttgattcaga tgggattgaa caaccctctg gtgttaacaa tatgtccact      60
acaaagaagg agcttctttc cactgctatg aagaggacct ctgattggat tttctcccaa     120
gagatcccaa gtgatgtaac tgtaaatgca ggcggatccg cctttcact gcacaagttc      180 cctttagtct caaagagtgg atacataagg aagattatct cagaatccaa cgatgctgat     240
gcttctacag tcgaaatccc tgatataccc ggtggatcag acgcatttga actggccgca     300
aaattttgtt atggaataaa ttttgagata agcacagaaa acattgcctt gctgagatgc     360
acagcggaat atcttgagat gacagaagac tatgcagttg ggaatttggt tggaagaact     420
gaggcctact taaatgaagt agctcttaaa agcctagctg gcgcagtttc aattttgcat     480
tcttccgaaa gccttcttcc cattgcagag aaagtaaaac tagttagtcg atgcatcgac     540
acaattgcat atattgcatg caaggataac caattctgca catcaggtcg agcagagcct     600
ggtactaacg gattgaattc gtccacgttt tcaaacccga gcctatggt tgattggtgg      660 gctgaggatt taactgtcct tagaattgat tttttccaaa gggttctaat tgcaatgatg     720
ggaagaggat tcaagcagta tgcacttgga ccaatattaa tgctctatgc acagaagtct     780
cttcgaggtt tggaaatatt tggaaaggga aggaaaaaaa ttgagccaaa caagaacat     840 gaaaagaggg ttgtttaga aacaattgtt agttttctgc caagggagaa aaatgcattg      900
tcagttagct ttctgtcaat gctgctccga gctgcaatat atctagaaac cacggttgct     960
tgcagacttg acttggagaa gagaatgtca ttgcagcttg gtcaggctgt attagatgat    1020
ctgttaattc cttcatattc cttcacaggg gatacattgt ttgatgttga aaccgtgcag    1080
cgtatcatca tgaatttcct tgacaatgaa atggatggaa gtcgattggg agatgaggag    1140
tatgtgtctc cttcattaag tgacatggag cgggttggga aacttatgga aaattacctt    1200
gctgaaatag cctcagaccg taatctatcc gtttcaaaat tcattagtct tgctgaagtc    1260
atcccagagc aagcaaagat cactgaagat gggatgtaca gggctattga tatttatttg    1320
aaggcacatc cagctctaag tgacatggaa agaaaaaaag tttgcggtgt tatggactgt    1380
caaaagctat ctagagaggc ttgtgctcat gctgctcaaa atgataggct ccctgttcag    1440
acagttgtgc aagtacttta ctacgagcag caacgccttc gtgaggtcat ggacgggagc    1500
caacttgtag caactgaacc tccaactcta attccttcta aaacgaatca cttctccatt    1560
gatatccctc ctgtttcaga tgaggtctct agtctaaaac gagaaaatca ggagctgaaa    1620
tttgagttgc taaagatgaa aatgaggttg aaagaaattg aaaaaccttc aaacaaatca    1680
gctgctagca gcccttttggt catcactcat ccatctgctg ataaacctcc tttgccaaga   1740
aaaccatcta atttcattag ctcagtatcc aaaaagcttg gaaaatttat tcgagcagat    1800
```

```
ggactcacag ccaacaaagg ccgaaataaa ccaagtaaag ataggcgtca ttctatatcc      1860
tga                                                                    1863

<210> SEQ ID NO 6
<211> LENGTH: 3998
<212> TYPE: DNA
<213> ORGANISM: Artificial Sequence
<220> FEATURE:
<223> OTHER INFORMATION: Nitab4.5_0000651g0020.2 genomic sequence

<400> SEQUENCE: 6
cctacgtcca cacactgaac taaatccttt tccactctat ttaaccccaa tcattcacat        60
aataccttta ataccatgta ggggctcctc acatatgatc tttctcctgc taacattaag       120
gcctataatg ggaattgtac caatgccatg attgatagtg aaagatgata acaataatgc       180
aattattagg ggccagatac tgttgattaa atgctcagac attgaactaa cagaagcaaa       240
ggaaaagaac atatctttct gttttttgct ccataaggaa acagcttaag agaatcctct       300
accatagacc aaatgtgatg gagatggtta agacccttta aagtttcaat catggcggat       360
cttgattcag atgggattga acaaccctct ggtgttaaca atatgtccac tacaaagaag       420
gagcttcttt ccactgctat gaagaggacc tctgattggt atgctctata tatcttgact       480
tcttattgtg ctttctaata gtagcccctt ttatgtacta ttattgaatt attattaatc       540
tgtttctcaa gatactcact ggaaaggtaa ttgtaggtat tgataaatga gttacctgta       600
taatcttgac aggattttct cccaagagat cccaagtgat gtaactgtaa atgcaggcgg       660
atccgccttt tcactgcaca aggtgcgttg cgctctctgc ttttatcata attaagttac       720
aactaactcc gggttcaatc aaaattgttg ttggttttag ttaagttcct atttggattg       780
agttatcagc cctggtcaca cctcaatgag aatatgaatt tggtgatttt ttctcttttc       840
tgacgattga atcacaaggt tcaataatga tttattgtgt tccatgcagt tccctttagt       900
ctcaaagagt ggatacataa ggaagattat ctcagaatcc aacgatgctg atgcttctac       960
agtcgaaatc cctgatatac ccggtggatc agacgcattt gaactggccg caaaattttg      1020
ttatggaata aattttgaga taagcacaga aaacattgcc ttgctgagat gcacagcgga      1080
atatcttgag atgacagaag actatgcagt tgggaatttg gttggaagaa ctgaggccta      1140
cttaaatgaa gtagctctta aaagcctagc tggcgcagtt tcaattttgc attcttccga      1200
aagccttctt cccattgcag agaaagtaaa actagttagt cgatgcatcg acacaattgc      1260
atatattgca tgcaaggata accaattctg cacatcaggt cgagcagagc ctggtactaa      1320
cggattgaat tcgtccacgt tttcaaaccc gaagcctatg gttgattggt gggctgagga      1380
tttaactgtc cttagaattg attttttcca aagggttcta attgcaatga tgggaagagg      1440
attcaagcag tatgcacttg gaccaatatt aatgctctat gcacagaagt ctcttcgagg      1500
tttggtgagg ccttgtccta taatatactc tggattattt ggttaaaatg aaatatttat      1560
gcaaatagta aacttttttg tttatcacag gaaatatttg gaaagggaag gaaaaaaatt      1620
gagccaaaac aagaacatga aaagagggtt gttttagaaa caattgttag ttttctgcca      1680
agggagaaaa atgcattgtc agttagcttt ctgtcaatgc tgctccgagc tgcaatatat      1740
ctagaaacca cggttgcttg cagacttgac ttggagaaga gaatgtcatt gcagcttggt      1800
caggctgtat tagatgatct gttaattcct tcatattcct tcacagggga tacattgttt      1860
gatgttgaaa ccgtgcagcg tatcatcatg aatttccttg acaatgaaat ggatggaagt      1920
```

-continued

```
cgattgggag atgaggagta tgtgtctcct tcattaagtg acatggagcg ggttgggaaa        1980
cttatggaaa attaccttgc tgaaatagcc tcagaccgta atctatccgt ttcaaaattc        2040
attagtcttg ctgaagtcat cccagagcaa gcaaagatca ctgaagatgg gatgtacagg        2100
gctattgata tttatttgaa ggtatgcgcg atgataattt ttctaattat aattttctta        2160
tgcatattta cacatacagg agcattttca tagatttaga tcatgtttag aaaaggagaa        2220
aacctttggg tcctgattgc tacatggtaa ttggcatgct aaacttaatg atcttggttg        2280
ggataccttc tatagaaatg ttgttcttgg tgctaacaca attcagtccg agagatgatt        2340
ttgggaataa gcaaaatcag aaaatatgtc accaatgaag aaccattcgt catcacagaa        2400
tccttgcctt gcaggcattg ctcggccagc cttgtgattt tgacccaatc ccatgtctta        2460
tactccttta ccctacaacc attttatgag gctgatgttg tccggagttt caaatctcat        2520
attttcccct ttcccaaaca tctatctcat ggtgcatcta ttctgtacca gggcagacct        2580
atagttttga acatgggatc aattgaactc acaatttttt ttttaaaaaa aaattataaa        2640
ttttaaggtt tgaacccata atttcaaaaa actaagaaac ttggtagagg ttcatcacta        2700
cagtgtggtg gctttgtttt ctcttgtcta tgtgcaggcc ttgctgttta taggtattca        2760
tacttgaggt cttttctatc atttgaaacc ttaataagga tcttgagttt gcttgttgac        2820
gtggactttt ctcctttcag ttttaggtca aactagtaat aacatcctaa aaaatttggc        2880
atgccaatac atagttcata tatggtatct tatcctaaag aagaagctgt atatataagc        2940
tcatagatat gtaaactgca ctcccctgtt actctctcta atttaaaaaa agagataatg        3000
atggactcaa taggttctcg ctacagaagc tctgaatctt attgctgccc ggtcacgtaa        3060
taacaagatc ttattgtgaa atcccagttg atgatgttca catgtttggt cagtacatca        3120
aatatattct tgaacaaagt ttcaggtcgt taaaatgcag aataaaagtg tggaaccaag        3180
ctaacatgat attggtatca tcaattaaaa tcttgtgtaa tgtttttggt gttgcataat        3240
ttgaaggcac atccagctct aagtgacatg gaaagaaaaa aagtttgcgg tgttatggac        3300
tgtcaaaagc tatctagaga ggcttgtgct catgctgctc aaaatgatag gctccctgtt        3360
cagacagttg tgcaagtact ttactacgag cagcaacgcc ttcgtgaggt catggacggg        3420
agccaacttg tagcaactga acctccaact ctaattcctt ctaaaacgaa tcacttctcc        3480
attgatatcc ctcctgtttc agatgaggtc tctagtctaa aacgagaaaa tcaggagctg        3540
aaatttgagt tgctaaagat gaaaatgagg ttgaaagaaa ttgaaaaacc ttcaaacaaa        3600
tcagctgcta gcagcccttt ggtcatcact catccatctg ctgataaacc tcctttgcca        3660
agaaaaccat ctaatttcat tagctcagta tccaaaaagc ttggaaaatt tattcgagca        3720
gatggactca cagccaacaa aggccgaaat aaaccaagta aagataggcg tcattctata        3780
tcctgatttg agctagctat atttgtcgtt gggttgaaga attttactgc attatattgt        3840
ctgaacatat atgatactgg attcaaattt tagcttttat tttagtcgtg cgagttttat        3900
ggtaaagtat aaatttggtc atgctttaat ccaaaaattg tatttagatg gacgtggacg        3960
acttcctgta cattatctat gaaagatttg taatcttg                              3998
```

```
<210> SEQ ID NO 7
<211> LENGTH: 621
<212> TYPE: PRT
<213> ORGANISM: Artificial Sequence
<220> FEATURE:
<223> OTHER INFORMATION: Nitab4.5_0009137g0040.2 amino acid sequence

<400> SEQUENCE: 7
```

-continued

```
Met Val Asp Leu Gly Ser Asp Glu Thr Ala Gln Pro Ser Thr Thr Val
1               5                   10                  15

Asn Met Phe Thr Lys Lys Lys Glu Leu Leu Ser Asn Val Met Lys Arg
            20                  25                  30

Thr Ser Glu Trp Ile Leu Ser Gln Glu Ile Pro Ser Asp Ile Thr Val
        35                  40                  45

His Val Ala Gly Thr Ser Phe Ala Leu His Lys Phe Pro Leu Val Ser
    50                  55                  60

Lys Cys Gly Tyr Ile Arg Lys Leu Val Ala Lys Ser Asn Asp Ala Asn
65                  70                  75                  80

Leu Ser Val Phe Glu Ile Pro Asp Ile Pro Gly Gly Ala Glu Ala Phe
                85                  90                  95

Glu Phe Ala Ala Lys Phe Cys Tyr Gly Ile Asn Phe Glu Ile Ser Ser
            100                 105                 110

Gly Asn Val Ala Leu Leu Arg Cys Val Ala Glu Tyr Leu Asp Met Thr
        115                 120                 125

Asp Asp Tyr Ala Val Gly Asn Leu Val Gly Leu Ser Glu Ala Tyr Leu
    130                 135                 140

Asn Glu Leu Ala Leu Lys Ser Ile Ala Gly Ala Val Ser Val Leu His
145                 150                 155                 160

Ser Ser Glu Lys Leu Leu Pro Ile Ala Glu Asn Ile Lys Leu Val Asn
            165                 170                 175

Arg Ser Ile Asp Thr Ile Ala Tyr Met Val Cys Lys Asp Ser His Phe
            180                 185                 190

Cys Lys Ser Gly Arg Ile Glu Val Asp Ala Asn Ser Leu Thr Asn Ser
            195                 200                 205

Ser Thr Phe Ser Asn Pro Arg Thr Ile Val Val Asp Trp Trp Ala Glu
    210                 215                 220

Asp Leu Thr Val Leu Arg Ile Asp Phe Phe Gln Arg Val Leu Ile Ala
225                 230                 235                 240

Met Met Ala Arg Gly Tyr Lys Gln Tyr Ala Leu Gly Pro Val Leu Met
            245                 250                 255

Leu Tyr Ser Gln Lys Ser Leu Gln Asn Leu Glu Ile Ser Gly Asn Glu
            260                 265                 270

Arg Lys Met Thr Glu Leu Arg Gln Val His Glu Lys Arg Val Val Val
            275                 280                 285

Glu Thr Ile Val Ser Leu Leu Pro Arg Glu Lys Asn Ala Leu Ser Val
    290                 295                 300

Ser Phe Leu Ser Met Leu Leu Arg Ala Ala Ile Tyr Leu Glu Thr Thr
305                 310                 315                 320

Val Ala Cys Arg Val Asp Leu Glu Arg Arg Ile Ala Leu Gln Leu Gly
            325                 330                 335

Gln Ala Val Leu Asp Asp Leu Leu Ile Pro Ser Tyr Ser Ser Phe Thr
            340                 345                 350

Glu Asp Thr Leu Phe Asp Val Glu Ile Val Gln Arg Ile Met Thr Tyr
            355                 360                 365

Phe Ile Glu Tyr Glu Met Val Glu Asn Gln Phe Gly Phe Asn Asp Glu
    370                 375                 380

Glu Tyr Val Pro Pro Leu Ala Thr Glu Met Glu Lys Val Gly Glu Leu
385                 390                 395                 400

Met Glu Asp Tyr Leu Ala Lys Ile Ala Ser Asp Asn Asn Leu Ser Val
            405                 410                 415
```

-continued

```
Ser Gln Phe Ile Ser Ile Ala Glu Val Ile Pro Glu Lys Ser Arg Ile
        420                 425                 430

Thr Glu Asp Arg Met Tyr Lys Ala Ile Asp Thr Tyr Leu Lys Ala His
        435                 440                 445

Pro Ala Leu Ser Asp Ile Glu Arg Lys Arg Val Cys Ser Val Met Asn
        450                 455                 460

Cys Gln Lys Leu Thr Arg Glu Ala Cys Ala His Ala Ala Gln Asn Glu
465                 470                 475                 480

Arg Leu Pro Val Gln Thr Val Val Gln Val Leu Tyr Phe Glu Gln Gln
                485                 490                 495

Arg Leu Arg Gln Val Met Asp Gly Ser Leu Asp Gly Ala Asp Glu Ser
                500                 505                 510

Ser Thr Asp Asn Asn Pro Val Thr Asp Glu Val Ser Ser Leu Lys Arg
                515                 520                 525

Glu Asn Gln Asp Leu Lys Phe Glu Leu Val Lys Met Lys Thr Arg Leu
        530                 535                 540

Asn Glu Ile Glu Lys Cys Gly Asp Ile Ser Ala Thr Ser Thr Pro Val
545                 550                 555                 560

Glu Ile Thr Thr Pro Ile Ser Ser Asp Lys Pro Arg Leu Arg Arg Lys
                565                 570                 575

Ser Phe Ile Ser Ser Val Ser Glu Thr Leu Gly Lys Leu Tyr Pro Ile
                580                 585                 590

Ser Phe Gly Ala Asp His Val Ile Met Pro Ser Ala Ser Lys Gly Arg
                595                 600                 605

Tyr Lys Pro Ile Ser Arg Asp Arg Arg Tyr Ser Ile Ser
        610                 615                 620
```

<210> SEQ ID NO 8
<211> LENGTH: 1866
<212> TYPE: DNA
<213> ORGANISM: Artificial Sequence
<220> FEATURE:
<223> OTHER INFORMATION: Nitab4.5_0009137g0040.2 coding sequence

<400> SEQUENCE: 8

```
atggttgatc ttggttcaga cgagactgca caaccttcaa ctactgttaa catgttcact       60
aagaaaaaag agcttctttc caatgttatg aaaaggacct ccgaatggat tttatcccag      120
gagatcccaa gtgatataac tgttcatgtt gcaggaactt cctttgctct gcacaagttc      180
ccactagtct caaagtgcgg atatataagg aagttggtcg caaaatccaa tgatgctaat      240
ctttctgtat tcgaaatccc tgacattcct ggtggagcag aggcatttga atttgcagca      300
aaattttgtt atggaataaa ctttgagata agctcaggaa acgtcgcatt gcttagatgt      360
gtagcagaat atcttgatat gacagatgac tatgcagttg aaatttggt aggattatca      420 gaagcctact aaacgagtt agcacttaag agcattgcag gtgcagtttc cgtcttgcac      480
tcttcagaaa aacttcttcc aattgcagaa aatataaaat tggtgaacag aagcatagat      540
acaattgcat acatggtttg caaggatagc cattttttgta agtcaggtag aatagaggtc      600
gacgctaata gtttgacgaa ttcctccaca ttttcaaatc cgaggaccat tgttgttgat      660
tggtgggctg aggattaac tgtccttaga attgattttt tccaaagggt tctaattgct      720
atgatggcta ggggatacaa acagtatgca cttggaccag tattgatgct ctattcgcag      780
aaatcccttc aaaatttgga aatatcagga aatgagagga aaatgactga gctgagacaa      840
gtacatgaaa agagggttgt tgttgaaacc atagttagtc ttctgccaag ggagaaaaat      900
```

-continued

```
gcattgtcag ttagttttct ctcaatgctt cttcgcgctg caatatatct tgaaaccaca     960
gttgcttgta gggttgatct ggagaggaga atcgcgttgc aacttggaca agctgtatta    1020
gatgatttgc taattccttc atattcttcc ttcacagaag acacattatt tgatgttgaa    1080
atcgtgcaac gtatcatgac gtatttcatt gagtatgaaa tggtggaaaa tcagtttggc    1140
ttcaacgatg aagagtatgt gccgccatta gcaactgaaa tggagaaagt tggggaactc    1200
atggaagatt accttgctaa aatagcctca gacaataatc tctctgtttc gcagtttatc    1260
agtattgctg aagtcattcc agagaaatca aggatcacag aagataggat gtacaaggcc    1320
attgacactt atttgaaggc acatccagct ctaagtgaca ttgagagaaa aagagtttgc    1380
agtgttatga actgtcaaaa gctaactcga gaagcttgtg ctcatgctgc tcagaatgag    1440
aggctccctg ttcagactgt tgtgcaagtc ctttactttg aacaacaacg ccttcgccaa    1500
gttatggatg gtagtctaga cggggcagat gagtcatcca ccgacaataa ccctgttaca    1560
gatgaagtct caagtctaaa aagagaaaat caagatctaa aattcgagct agtgaaaatg    1620
aaaacgaggt tgaatgaaat tgaaaaatgt ggtgatatat cagctactag tacccctgtg    1680
gagatcacca ctccaatatc ttctgataaa cctcgtctgc gaagaaaatc tttcataagc    1740
tcagtttccg aaacgcttgg gaaactgtat ccaatatcat ttggagctga tcatgtaatc    1800
atgccatcgg ccagcaaagg aagatatataa ccaattagta gagataggcg ttattcgata    1860
tcatga                                                                1866
```

```
<210> SEQ ID NO 9
<211> LENGTH: 4169
<212> TYPE: DNA
<213> ORGANISM: Artificial Sequence
<220> FEATURE:
<223> OTHER INFORMATION: Nitab4.5_0009137g0040.2 genomic sequence

<400> SEQUENCE: 9
ctatatccta atatatttaa ccccagtacc ttcacataaa catatgtaac actactcgtg      60
tcatgtgtct agtagaggct cactcgtaca caatctttcc actgccaact ttctggccta     120
taatgggaat tctgcaatct tatgattgat actggctgct gacagtaata tataatgcag     180
tttacggacc aacactgaag ttgtacttat tccctaactg ttgatctctt attctttgt      240 gggtgaaaga gaattaatta aagaagcagg ggaaaggaca tagtacatac tagttttttgc     300 tttatcaaga attatataat aggccaatat ggttgatctt ggttcagacg agactgcaca     360
accttcaact actgttaaca tgttcactaa gaaaaaagag cttctttcca atgttatgaa     420
aaggacctcc gaatggtacg tagtctatct tcagttattt ctctctcttt tgttgtttcc     480
agcgtacttt tacgcgtctt tatgcaattt ttccgtgtaa catgatcagt agtggagggt     540
aaaatgtagg cattgatgaa tgagtgacct ttatattatc tgcaggattt tatcccagga     600
gatcccaagt gatataactg ttcatgttgc aggaacttcc tttgctctgc acaaggtaca     660
acctttttcc ttgttctaag aagttcctaa tatatttcaa ctagaacaca aatcaagatt     720
gttcttttca gtaactagtt acacttatta tggcagttac ctatagtcat ctaaaattat     780
tttatactgt cagtaagtag aagttaaact cttaactaaa aggtgaagtc tttgataatg     840
agtactttta tgttccatgc agttcccact agtctcaaag tgcggatata taaggaagtt     900
ggtcgcaaaa tccaatgatg ctaatctttc tgtattcgaa atccctgaca ttcctggtgg     960
agcagaggca tttgaatttg cagcaaaatt ttgttatgga ataaactttg agataagctc    1020
aggaaacgtc gcattgctta gatgtgtagc agaatatctt gatatgacag atgactatgc    1080
```

```
agttggaaat ttggtaggat tatcagaagc ctacttaaac gagttagcac ttaagagcat    1140
tgcaggtgca gtttccgtct tgcactcttc agaaaaactt cttccaattg cagaaaatat    1200
aaaattggtg aacagaagca tagatacaat tgcatacatg gtttgcaagg atagccattt    1260
ttgtaagtca ggtagaatag aggtcgacgc taatagtttg acgaattcct ccacatttc    1320 aaatccgagg accattgttg ttgattggtg ggctgaggat ttaactgtcc ttagaattga    1380
ttttttccaa agggttctaa ttgctatgat ggctagggga tacaaacagt atgcacttgg    1440
accagtattg atgctctatt cgcagaaatc ccttcaaaat ttggtgagtc ctcatcccat    1500
gagtttagat tatttggtta gagataataa caacaacaat aacaacaata acaacagtgg    1560
agtctgggga aggtaatacg tacgcagacc ttatccctac cctcagggag gattatttgg    1620
ttagagaaag taacataaat agtgatcttt tatgttaatc aaaattgaac acctatggcc    1680
gctgttatat ttaatacaca aaatgtgcgc agttttttt tttaacacga aggactaaac    1740
ctgctcagtt gaatagttaa aggattattt tagaccaagg ctcaaacata agaaagtatt    1800
ttaggcatgt gctcaatttg gataattgaa atatttatgc atatgatttt cttgttattc    1860
caggaaatat caggaaatga gaggaaaatg actgagctga gacaagtaca tgaaaagagg    1920
gttgttgttg aaaccatagt tagtcttctg ccaagggaga aaaatgcatt gtcagttagt    1980
tttctctcaa tgcttcttcg cgctgcaata tatcttgaaa ccacagttgc ttgtagggtt    2040
gatctggaga ggagaatcgc gttgcaactt ggacaagctg tattagatga tttgctaatt    2100
ccttcatatt cttccttcac agaagacaca ttatttgatg ttgaaatcgt gcaacgtatc    2160
atgacgtatt tcattgagta tgaaatggtg gaaaatcagt ttggcttcaa cgatgaagag    2220
tatgtgccgc cattagcaac tgaaatggag aaagttgggg aactcatgga agattacctt    2280
gctaaaatag cctcagacaa taatctctct gtttcgcagt ttatcagtat tgctgaagtc    2340
attccagaga aatcaaggat cacagaagat aggatgtaca aggccattga cacttatttg    2400
aaggtatgca cgttgaatca ttcgcccggt ggagcaattt ttctatgtgc actagtacac    2460
ctacaagggc atgatcgtat atttaggtca tactaaatgt ttaatttaat atgtattata    2520
agcattcatt aactcctcca aaaacaaatc tttgaagcca actgctaaat agtaatggct    2580
taatcaactg ctttagtacc ttgattgaaa tatcaaattc tttaatgaca tatttttgat    2640
aggttgcacc taaacagtgg aaatattgtg gcttgggatg ttaagtggta tttgaatcct    2700
tatgatctct tgcataaatc cattaaaggc ataattcagt taagtgaaga tgttttttca    2760
atatacaagt gaaactaagg gttgaatttt acttctctgc tacagaagcc atcttatgtt    2820
agaattgccc tgcatcttag gttacgatat cacgtgtttc tgcctatgca tttacaggat    2880
attaaacatg ttatatgttg atgttctttc aagtgtgtca tctttagatc aaatgtacag    2940
tttaacaaac agttacattt gataataagc aggtttatag ctaagcagct tgtcatactg    3000
tggcaagaaa gactttttgaa acttcagatc atgcttagtt gatcttcgtc ataaataaag    3060
gattttaggt catatacact catagaaggg gagccttggc gtaactggta aagttactgc    3120
catgtgacca agaagtcatg ggttcgagcc gtgaaaatag cctcttgcag aatgtagggt    3180
aaggttacgc acaatagacc ctagtggtcc ggcccttccc cagaccccgc atatagcggg    3240
agcttagtgc accgggctgc ccttttata cactcatagc ctaaaaatct ttcatactct    3300
catctcaatt taatcggaaa taccaggtta ttactctatt ttttaggtta ctatatcagg    3360
cttgctatga atagctatct actggtctat gtcattttga cttgataatg taaaagaatt    3420
```

-continued

```
atgtaccgtt agtgtacaga acttactctt aaataataat aaatttaccg gagaatagtt    3480
gtctaatctt ctagcttttt caaaatttga aggcacatcc agctctaagt gacattgaga    3540
gaaaaagagt ttgcagtgtt atgaactgtc aaaagctaac tcgagaagct tgtgctcatg    3600
ctgctcagaa tgagaggctc cctgttcaga ctgttgtgca agtgctttac tttgaacaac    3660
aacgccttcg ccaagttatg gatggtagtc tagacggggc agatgagtca tccaccgaca    3720
ataaccctgt tacagatgaa gtctcaagtc taaaaagaga aaatcaagat ctaaaattcg    3780
agctagtgaa aatgaaaacg aggttgaatg aaattgaaaa atgtggtgat atatcagcta    3840
ctagtacccc tgtggagatc accactccaa tatcttctga taaacctcgt ctgcgaagaa    3900
aatctttcat aagctcagtt tccgaaacgc ttgggaaact gtatccaata tcatttggag    3960
ctgatcatgt aatcatgcca tcggccagca aaggaagata taaaccaatt agtagagata    4020
ggcgttattc gatatcatga tgcggctaaa tttgccataa agctgttggt tttggctgaa    4080
gtatttgaat ctttgggaaa gcagtaatgg atttagctat atttctgtct tttgttctcc    4140
tttgttttat gttatataag tgttttaac                                     4169
```

```
<210> SEQ ID NO 10
<211> LENGTH: 594
<212> TYPE: PRT
<213> ORGANISM: Artificial Sequence
<220> FEATURE:
<223> OTHER INFORMATION: Nitab4.5_0001772g0090.2 amino acid sequence

<400> SEQUENCE: 10

Met Phe Thr Lys Lys Lys Glu Leu Leu Ser Asn Val Met Lys Arg Thr
1               5                   10                  15

Ser Glu Trp Ile Leu Ser Gln Glu Ile Pro Ser Asp Ile Thr Val His
            20                  25                  30

Val Ala Gly Thr Ser Phe Ala Leu His Lys Phe Pro Leu Val Ser Lys
        35                  40                  45

Cys Gly Tyr Ile Arg Lys Leu Val Ala Lys Ser Asn Asp Ala Asn Leu
    50                  55                  60

Ser Glu Ile Glu Ile Pro Asp Ile Pro Gly Gly Ala Glu Ala Phe Glu
65                  70                  75                  80

Phe Ala Ala Lys Phe Cys Tyr Gly Ile Asn Phe Glu Ile Ser Ser Gly
                85                  90                  95

Asn Ile Ala Leu Leu Arg Cys Val Ala Glu Tyr Leu Asp Met Thr Asp
            100                 105                 110

Asp Tyr Ala Val Gly Asn Leu Val Gly Leu Ser Glu Ser Tyr Leu Asn
        115                 120                 125

Glu Val Ala Leu Lys Ser Ile Ala Gly Ala Val Ser Val Leu His Ser
    130                 135                 140

Ser Glu Lys Leu Leu Pro Ile Ala Glu Asn Ile Lys Leu Val Asn Arg
145                 150                 155                 160

Ser Ile Asp Thr Ile Ala Tyr Ile Val Cys Lys Asp Ser His Phe Cys
                165                 170                 175

Lys Ser Gly Arg Ile Glu Val Asp Ala Asn Ser Leu Met Asn Ser Ser
            180                 185                 190

Thr Leu Ser Asn Pro Arg Pro Ile Val Val Asp Cys Trp Ala Glu Asp
            195                 200                 205

Leu Thr Val Leu Arg Ile Asp Phe Phe Gln Arg Val Leu Ile Ala Met
    210                 215                 220

Met Ala Arg Gly Cys Lys Gln Tyr Ala Leu Gly Pro Val Leu Met Leu
```

```
225             230             235             240

Tyr Ser Gln Lys Ser Leu Gln Asn Leu Glu Ile Ser Gly Lys Glu Arg
            245             250             255

Lys Leu Thr Glu Gln Arg Gln Val His Glu Lys Arg Val Val Val Glu
            260             265             270

Thr Ile Val Ser Leu Leu Pro Arg Glu Lys Asn Ala Leu Ala Val Ser
            275             280             285

Phe Leu Ser Met Leu Leu Arg Ala Ala Ile Tyr Leu Glu Thr Thr Val
    290             295             300

Ala Cys Arg Val Asp Leu Glu Arg Arg Ile Ala Leu Gln Leu Gly Glu
305             310             315             320

Ala Val Leu Asp Asp Leu Leu Ile Pro Ser Tyr Ser Ser Phe Thr Lys
            325             330             335

Asp Thr Leu Phe Asp Val Glu Ile Val Gln Arg Ile Met Thr Asn Phe
            340             345             350

Ile Glu Tyr Glu Met Val Glu Asn Arg Leu Gly Phe Asn Asp Glu Glu
            355             360             365

Tyr Ala Ser Pro Val Gly Glu Leu Met Glu Asp Tyr Leu Ala Lys Ile
    370             375             380

Ala Ser Asp Asn Asn Leu Ser Val Ser Gln Phe Ile Ser Ile Ala Glu
385             390             395             400

Val Ile Pro Glu Gln Cys Glu Asp Arg Met Tyr Lys Ala Ile Asp Thr
            405             410             415

Tyr Leu Lys Ala His Pro Ala Leu Ser Asp Asn Glu Arg Lys Arg Val
            420             425             430

Cys Ser Val Met Asn Cys Gln Lys Leu Thr Arg Glu Ala Cys Ala His
            435             440             445

Ala Ala Gln Asn Glu Arg Leu Pro Val Gln Thr Val Val Gln Val Leu
    450             455             460

Tyr His Glu Gln Gln Arg Leu Arg Gln Val Met Asp Gly Ser Leu Ala
465             470             475             480

Asp Ala Asp Gln Ser Ser Ala Asp Asn Asn Pro Val Thr Asp Glu Phe
            485             490             495

Ser Ser Leu Lys Arg Glu Asn Gln Asp Leu Lys Phe Glu Leu Val Lys
            500             505             510

Met Lys Thr Arg Leu Lys Glu Ile Glu Lys Cys Gly Asp Lys Ser Ala
            515             520             525

Ala Ser Thr Pro Leu Glu Ile Thr Thr Pro Ile Ser Ser Asp Lys Pro
    530             535             540

Arg Leu Arg Arg Lys Ser Phe Ile Ser Ser Val Tyr Glu Lys Leu Gly
545             550             555             560

Lys Leu Tyr Pro Ile Ser Phe Gly Ala Asp His Val Val Met Pro Ser
            565             570             575

Ala Ser Lys Gly Arg Tyr Lys Pro Ile Asn Arg Tyr Arg Arg Tyr Ser
            580             585             590

Ile Ser
```

<210> SEQ ID NO 11
<211> LENGTH: 1785
<212> TYPE: DNA
<213> ORGANISM: Artificial Sequence
<220> FEATURE:
<223> OTHER INFORMATION: Nitab4.5_0001772g0090.2 coding sequence

<400> SEQUENCE: 11

-continued

```
atgttcacta agaaaaaaga gcttctttcg aatgttatga aaaggacctc cgaatggatt        60
ttatcccagg agatcccaag tgatataact gttcatgttg caggaacttc ctttgctctg       120
cacaagttcc cactagtctc aaagtgcgga tatataagga agttggtcgc aaaatccaat       180
gatgctaatc tttctgaaat tgaaatccct gacattcctg gtggagcaga ggcatttgaa       240
tttgcagcaa aattttgtta tggaataaac tttgagataa gctcaggaaa catcgcattg       300
cttagatgtg tagcagaata tcttgatatg acagatgact atgcagttgg aaatttggta       360
ggattatcag aatcctactt aaatgaagta gcacttaaga gcattgcagg tgcagtttcc       420
gttctgcact cttcagaaaa acttcttccc attgcagaaa atataaaatt ggtgaacaga       480
agcatagata caattgcata catagtttgc aaggatagcc atttttgtaa gtcaggtaga       540
atagaggtcg acgctaatag cttgatgaat tcctctacat tatcaaatcc gaggcctatt       600
gttgttgact gctgggctga ggatttaact gtccttagaa ttgatttttt ccaaagggtt       660
ctaattgcta tgatggctag gggatgcaaa cagtatgcgc ttggaccagt attgatgctc       720
tattcacaga aatcccttca aaatttggaa atatcaggaa aggaaaggaa attgactgag       780
caaagacaag tacatgaaaa gagggttgtt gttgaaacca ttgttagtct tttgccaagg       840
gagaaaaatg cattggcagt tagttttctc tcaatgcttc ttcgcgctgc tatatatctc       900
gaaaccacag ttgcttgtag agttgatctg gagaggagaa tcgcgttgca acttggagag       960
gctgtattag atgatttgtt gattccttca tattcttcct tcacaaaaga cacattattt      1020
gatgttgaaa tcgtgcaacg tatcatgacg aatttcattg agtatgaaat ggtggaaaat      1080
cggttgggct tcaacgatga agagtatgcg tctccagtag gggaactcat ggaagattac      1140
cttgctaaaa tagcctctga caataatctc tctgtttcgc agtttattag tattgctgaa      1200
gtgattccag agcaatgtga agataggatg tacaaggcca ttgacactta tttgaaggca      1260
catccagctc taagtgataa tgagagaaaa agagtttgca gtgttatgaa ctgtcaaaag      1320
ctaactcgag aagcttgtgc tcatgctgct cagaatgaga ggctccctgt tcagactgtt      1380
gtgcaagtgc tttaccatga acaacaacgc cttcgccaag ttatggatgg tagtctagcc      1440
gatgcagatc agtcatccgc cgacaataac cctgttacag atgaattctc aagtctaaaa      1500
agagaaaatc aagatctaaa attcgagcta gtgaaaatga aaacgagatt gaaagaaata      1560
gaaaaatgtg tgtgacaaatc agctgctagc accccttttgg agatcaccac tccaatatct      1620
tctgataaac ctcgtttgcg aagaaaatct ttcataagct cagtttacga aaagcttggg      1680
aaactgtatc caatatcatt tggagctgat catgtagtca tgccatcagc cagcaaagga      1740
agatataaac caattaatag atataggcgt tattctatat catga                      1785
```

```
<210> SEQ ID NO 12
<211> LENGTH: 4142
<212> TYPE: DNA
<213> ORGANISM: Artificial Sequence
<220> FEATURE:
<223> OTHER INFORMATION: Nitab4.5_0001772g0090.2 genomic sequence

<400> SEQUENCE: 12
```

```
cctatttaac ccccgtatgt aacactactc gtgtcgtgtg tctactagag gctcactcgt        60
acacaatctt tccacttcca actttctggc ctatagcggg aattctgcca atcttatgat       120
tgatcgtggc tgctgacgat aagttgataa tatataatgc agtttacggt ccaacactga       180
ggctgtactt attccccaac tgttgatcac ttattctttt gttggttgaa agagaattaa       240
```

-continued

```
ttaaagaagc tagcaacgga accaaaagaa gcaggggaaa ggacatagta cattctagtt    300
tttgctttat caagaattat ataataggcc aatatgatgg atcttggttc ataggagact    360
gcacaacctt caactactgt taacatgttc actaagaaaa aagagcttct ttcgaatgtt    420
atgaaaagga cctccgaatg gtacgtagtc catcttcagt tatttttctt tctcttttgt    480
tgtttctcag cgtccttttc cacgtcttta tgcaatgagt gaccttttta atatctgcag    540
gattttatcc caggagatcc caagtgatat aactgttcat gttgcaggaa cttcctttgc    600
tctgcacaag gtacaacctt tttccttgtt ctaagaagtt tctaatataa tttcaactag    660
aacaccaatc aagattgttc tttaactagt tacacttatt atggcagtta cctatagtca    720
tcttaaatta atttgacact gtcagtgagt agaaattaaa ctcttaacta aaaggtgcaa    780
tctttgataa tgagtacttt atgtcccatg cagttcccac tagtctcaaa gtgcggatat    840
ataaggaagt tggtcgcaaa atccaatgat gctaatcttt ctgaaattga aatccctgac    900
attcctggtg gagcagaggc atttgaattt gcagcaaaat tttgttatgg aataaacttt    960
gagataagct caggaaacat cgcattgctt agatgtgtag cagaatatct tgatatgaca   1020
gatgactatg cagttggaaa tttggtagga ttatcagaat cctacttaaa tgaagtagca   1080
cttaagagca ttgcaggtgc agtttccgtt ctgcactctt cagaaaaact tcttcccatt   1140
gcagaaaata taaaattggt gaacagaagc atagatacaa ttgcatacat agtttgcaag   1200
gatagccatt tttgtaagtc aggtagaata gaggtcgacg ctaatagctt gatgaattcc   1260
tctacattat caaatccgag gcctattgtt gttgactgct gggctgagga tttaactgtc   1320
cttagaattg attttttcca aagggttcta attgctatga tggctagggg atgcaaacag   1380
tatgcgcttg gaccagtatt gatgctctat tcacagaaat cccttcaaaa tttggtgagt   1440
ccttatccca tgagtttgga ttatttggtt agagaaaata acaaagttat ggtcgctgtt   1500
atatttaaca cacaaaatgt gcgcagtttt tatgaacatg aaggactaaa actgctcagc   1560
tgtatagtta aaggattatt ttatacaaac gctcaaacat aagaaactat tttggtcatg   1620
tgctctattt gtccaaatga aatatttatg catatgattt tcttgtcatt ccaggaaata   1680
tcaggaaagg aaaggaaatt gactgagcaa agacaagtac atgaaaagag ggttgttgtt   1740
gaaaccattg ttagtctttt gccaagggag aaaaatgcat tggcagttag ttttctctca   1800
atgcttcttc gcgctgctat atatctcgaa accacagttg cttgtagagt tgatctggag   1860
aggagaatcg cgttgcaact tggagaggct gtattagatg atttgttgat tccttcatat   1920
tcttccttca caaaagacac attatttgat gttgaaatcg tgcaacgtat catgacgaat   1980
ttcattgagt atgaaatggt ggaaaatcgg ttgggcttca cgatgaaga gtatgcgtct    2040 ccagtagggg aactcatgga agattacctt gctaaaatag cctctgacaa taatctctct   2100
gtttcgcagt ttattagtat tgctgaagtg attccagagc aatgtgaaga taggatgtac   2160
aaggccattg acacttattt gaaggtatgc acgttgaatc attcgcccgg tggagcaatt   2220
tttctgtaca ctagtacacc tacaagggca tgatcgtata tttaggtcat actatatgtt   2280
taatttaata agtattataa gcattcatta actccataaa caaatctttg atgccaactg   2340
cgaaatagta atggcttaat caactgcttt agtaccttga ttgaaatatc aacttcttta   2400
atgacataat ttgataggtt gcacctgaac agtggaaatg ttgtggcttg ggatgttaag   2460
tggtatttga accattatga tctcttgcat aaatccatta aaggcttaat ttagttaagt   2520
gaaaatatgt ttcaatatac aagtgaaact aaggggttgaa ttttactttt ctgttagaga   2580
agccatctta tcttagaatt gccctgcatc ttaggttatg atatcacgtg tttttgccta   2640
```

-continued

```
tgcatttaca ggattttaaa catgttctat gttgatgttc tctcaagtgt gtcatcttta    2700
gatcaaatgt acagtttaac aaacagttac atttgataat aagcaggttt atagctaagc    2760
agctcatctt cagaccatgc ttagttgatc ttcaacataa ataaaggatt ttaagtcata    2820
tacactcata gcctaaaaat cttttcatact ctcatatcag cctaaactat tttttttaggt   2880 tactatatca ggcttgctac gaatagctac ctacttctgt atgtcatttt gacttgaaaa    2940
tgcaaaagaa ttacgtacta tcagtgtaca gaacttactc ttatcaggtt actcttaata    3000
gctggagcaa cctttcccct gtaaatgatt aaattccatt tcaagatttt attagctctc    3060
tgtctttggc ttgattgcca accttaggct tctggttagc tcccggtgct tctggttagc    3120
tccctggtca gaactgcatt tttgtgtaaa tggagctaac caacctcttt tctaatgttt    3180
tgcatctttt tgatgccagt tatatagcat cttacttcat caaaaaaaga acttactctt    3240
aaataaacaa ctctaccaga gatagttgct ctgatggtaa gcaccctcca cttccaacca    3300
agaggttgtg agttcgaatt accccaagag caaggtgggg agtttttgga gggaaggatg    3360
ccgagggtct attggaaaca gcctctctac cccagggtag gggtaaggtc tgcgtataca    3420
ttaccctccc cagacccccac tagtgggatt atactttttt gttgttattg ttgttgttgt    3480
tgtaccagag atagttgtct aatcttgtag cttttgcaaa atttgaaggc acatccagct    3540
ctaagtgata atgagagaaa aagagtttgc agtgttatga actgtcaaaa gctaactcga    3600
gaagcttgtg ctcatgctgc tcagaatgag aggctccctg ttcagactgt tgtgcaagtg    3660
ctttaccatg aacaacaacg ccttcgccaa gttatggatg gtagtctagc cgatgcagat    3720
cagtcatccg ccgacaataa ccctgttaca gatgaattct caagtctaaa aagagaaaat    3780
caagatctaa aattcgagct agtgaaaatg aaaacgagat tgaaagaaat agaaaaatgt    3840
ggtgacaaat cagctgctag cacccctttg gagatcacca ctccaatatc ttctgataaa    3900
cctcgtttgc gaagaaaatc tttcataagc tcagtttacg aaaagcttgg gaaactgtat    3960
ccaatatcat ttggagctga tcatgtagtc atgccatcag ccagcaaagg aagatataaa    4020
ccaattaata gatataggcg ttattctata tcatgatgca gtaaaatttg ccattaagct    4080
gttggttttg gcagaagtag attgcactat ttgaactttt gggaaagcag taatgaattt    4140
ag                                                                   4142
```

<210> SEQ ID NO 13
<211> LENGTH: 606
<212> TYPE: PRT
<213> ORGANISM: Artificial Sequence
<220> FEATURE:
<223> OTHER INFORMATION: Nitab4.5_0003312g0050.2 amino acid sequence

<400> SEQUENCE: 13

```
Met Asp Lys His His Ser Gln Leu Pro Leu Ala Lys Cys Ser Arg Gln
1               5                   10                  15

Arg Tyr Ser Glu Trp Val Phe Arg Asp Val Pro Ser Asp Ile Thr Ile
            20                  25                  30

Glu Val Asp Gly Gly Thr Phe Ser Leu His Lys Phe Pro Leu Val Ser
        35                  40                  45

Arg Ser Gly Arg Ile Arg Lys Leu Val Ala Gly His Arg Asp Ser Asp
    50                  55                  60

Ile Ser Arg Ile Glu Leu Leu Ser Leu Pro Gly Gly Val Glu Ser Phe
65                  70                  75                  80

Glu Leu Ala Ala Lys Phe Cys Tyr Gly Val Asn Phe Glu Ile Thr Ala
```

```
                    85                    90                    95

Ala Asn Val Ala Gln Leu Cys Cys Val Ser Asp Tyr Leu Glu Met Thr
                100                   105                   110

Glu Asp Tyr Ser Lys Asn Asn Leu Gly Ser Arg Ala Glu Glu Tyr Leu
                115                   120                   125

Asp Ile Val Ala Cys Lys Asn Leu Glu Met Cys Val Glu Val Leu Lys
                130                   135                   140

Gln Cys Glu Asn Leu Leu Pro Leu Ala Asp Glu Leu Lys Ile Val Thr
145                   150                   155                   160

Arg Cys Ile Asp Ala Ile Ala Ser Lys Ala Cys Ala Glu Gln Ile Ala
                165                   170                   175

Ser Ser Phe Ser Arg Leu Glu Tyr Ser Ser Ser Gly Arg Leu His Met
                180                   185                   190

Asn Arg Gln Ala Lys Cys Glu Gly Asp Trp Trp Ile Glu Asp Leu Ser
                195                   200                   205

Val Leu Arg Ile Asp Leu Tyr Gln Arg Val Ile Thr Ala Met Lys Cys
                210                   215                   220

Arg Gly Val Arg Pro Glu Ser Ile Ala Ala Ser Leu Val Asn Tyr Ala
225                   230                   235                   240

Gln Lys Glu Leu Thr Lys Lys Ser Ser Ser Trp Asn Gln Ser Ser Gln
                245                   250                   255

Pro Lys Val Asp Val Val Ser Gly Ser Asn Gly His Glu Lys Val Val
                260                   265                   270

Val Glu Thr Ile Val Ser Leu Met Pro Val Glu Lys Leu Val Val Pro
                275                   280                   285

Ile Thr Phe Leu Phe Gly Leu Leu Arg Ser Ala Val Met Leu Asp Cys
                290                   295                   300

Thr Val Ala Cys Arg Leu Asp Leu Glu Arg Arg Ile Gly Ser Gln Leu
305                   310                   315                   320

Asp Ile Ala Thr Leu Asp Asp Leu Leu Ile Pro Phe Phe Arg Asn Ala
                325                   330                   335

Gly Asp Thr Leu Phe Asp Val Asp Thr Val His Arg Ile Leu Val Asn
                340                   345                   350

Phe Phe Gln Gln Glu Asp Ser Asp Glu Asp Met Asp Asp Val Ser Val
                355                   360                   365

Phe Glu Ser Gly Ser Pro Thr Ser Pro Ser Gln Thr Ala Leu Phe Lys
                370                   375                   380

Val Ala Lys Leu Val Asp Asn Tyr Leu Ala Glu Ile Ala Pro Asp Ala
385                   390                   395                   400

Asn Leu Lys Leu Asn Lys Phe Ile Ala Ile Ala Glu Ser Leu Pro Ala
                405                   410                   415

His Ala Arg Thr Val His Asp Gly Leu Tyr Arg Ser Ile Asp Val Tyr
                420                   425                   430

Leu Lys Ala His Gln Ala Leu Ser Asp Pro Asp Arg Arg Arg Leu Cys
                435                   440                   445

Lys Leu Ile Asp Phe Gln Lys Leu Ser Gln Glu Ala Gly Ser His Ala
                450                   455                   460

Ala Gln Asn Glu Arg Leu Pro Leu Gln Ser Ile Val Gln Val Leu Tyr
465                   470                   475                   480

Phe Glu Gln Leu Arg Leu Arg Asn Ala Leu Phe Cys Ser Tyr His Asp
                485                   490                   495

Asp Asp His Lys Pro Thr His Gln Ser Trp Arg Ile Asn Ser Gly Ala
                500                   505                   510
```

```
Leu Ser Ala Ala Met Ser Pro Arg Asp Asn Tyr Ala Ser Leu Arg Arg
        515             520             525

Glu Asn Arg Glu Leu Lys Leu Glu Leu Thr Arg Met Arg Met Arg Leu
    530             535             540

Asp Asp Leu Glu Lys Asp His Val Cys Met Lys Lys Asn Met Glu Lys
545             550             555             560

Ser Asn Ser Gly Gly Phe Met Ser Asn Phe Ser Lys Lys Ile Gly Lys
            565             570             575

Leu Asn Ile Phe Gly His Ser Ser Ser Arg Glu Ser Cys Ser Pro Ser
            580             585             590

Lys Arg Ser Gln Val Thr Asp Ser Lys Leu Thr Glu Arg Thr
        595             600             605
```

```
<210> SEQ ID NO 14
<211> LENGTH: 1821
<212> TYPE: DNA
<213> ORGANISM: Artificial Sequence
<220> FEATURE:
<223> OTHER INFORMATION: Nitab4.5_0003312g0050.2 coding sequence

<400> SEQUENCE: 14
atggacaaac accattcgca attgcctctc gccaagtgtt cacggcagcg ttatagtgaa      60
tgggtgtttc gggatgttcc aagtgatata acgatagaag tagatggtgg cacatttca     120 ttgcacaagt ttcctctagt ctcgagaagt gggcgaatcc ggaagcttgt agcagggcac     180
agggattctg atatatcaag gatagagcta cttagcctac caggcggagt tgaatcattt     240
gagctggcag caaaattctg ctacggcgtt aactttgaga ttacagctgc aaatgttgct     300
cagctttgtt gtgtatcaga ttatcttgag atgactgagg actattcaaa gaacaatctt     360
ggttcccgag ctgaagaata tcttgatatt gttgcttgca agaatcttga aatgtgtgtt     420
gaagtcctga acaatgcgaa aatctactt cctttggctg atgagctgaa aatagttacc     480
cgatgcattg atgctatagc atctaaggct tgcgcggagc aaattgcctc aagtttctcg     540
cgcttggaat acagtagttc tggtagactt catatgaacc gccaagccaa gtgtgaagga     600
gactggtgga tagaggattt gtcagttctt cgtattgact tgtatcaacg agtcataaca     660
gcgatgaaat gtcgtggtgt taggcctgaa agtattgcag catcactagt gaactacgca     720
cagaaggagt tgacaaagaa gtccagttcc tggaatcaat cgagccaacc caaagttgac     780
gtggtttctg gttcaaacgg ccatgaaaag gttgtggtcg aaacaattgt tagccttatg     840
cctgttgaga aattggttgt tccaataacc tttcttttg ggttgctgag aagtgcagtg     900
atgcttgact gcacagttgc ttgtagactt gatcttgaga ggcggatagg atctcaatta     960
gacatagcta ctctcgatga tcttctaatt ccattctttc gcaatgctgg tgacacatta    1020
tttgacgttg acacagtgca tagaatcttg gttaatttt ttcagcagga ggatagtgat    1080
gaagatatgg acgatgtctc agtgttcgag tctggtagcc ctacttcgcc atcccaaact    1140
gcattattca aagtcgcaaa actggtggac aattaccttg ctgaaattgc acctgatgca    1200
aacctaaagc tgaacaagtt catagcaatt gccgaaagct taccagcaca tgctcgtact    1260
gtccatgatg gactttatcg atcaatcgat gtctacctca agctcatca ggcgttatca    1320 gatccagata ggagaagact atgcaagctg attgattttc agaagctctc acaagaagct    1380
ggatcacacg ctgcacaaaa cgaacgcctc ccactccaat caatcgtgca ggttctatat    1440
ttcgagcaac tgaggcttcg aaatgcctta ttttgttctt atcatgatga tgatcataag    1500
```

| | | |
|---|---|---|
| ccaacgcacc aatcgtggag gatcaatagt ggtgctttaa gtgcagctat gtctccccgg | 1560 | |
| gataattatg cttctctaag acagagaaat agggaactaa aacttgaact aacacgaatg | 1620 | |
| aggatgagat tgaatgacct ggagaaagat catgtttgta tgaagaaaaa tatggaaaaa | 1680 | |
| tctaattccg ggggattcat gagtaacttc tcgaaaaaga ttggcaagtt aaacattttt | 1740 | |
| ggacatagtt cttcaaggga gtcatgttct ccttcaaaga ggtcacaagt tactgattct | 1800 | |
| aagctaactg aaagaacatg a | 1821 | |

```
<210> SEQ ID NO 15
<211> LENGTH: 4019
<212> TYPE: DNA
<213> ORGANISM: Artificial Sequence
<220> FEATURE:
<223> OTHER INFORMATION: Nitab4.5_0003312g0050.2 genomic sequence

<400> SEQUENCE: 15
```

| | | |
|---|---|---|
| ctcatcttta gctgactgtt ttcttgactt tctctgtttc gactgaacca aagtttgcta | 60 | |
| aacttgttcc tttttggca cccctttatc tgctgctaaa catttatccc actcaaattt | 120 | |
| tataacttca ttatacagca ataagaatat ataaaatgct acagaaagag agttaatggt | 180 | |
| gggtatttta attattggta ctatcaagga catgacccac aaaagtggcc cattggtttg | 240 | |
| gacaagtgta atctatgatt tgagcacaaa cagtttgact caaaaatggc caaagaagta | 300 | |
| gaccaacacc aatattttcc actgtgtctt tgtcccccct tattacttgg cttctttaac | 360 | |
| aaccttcacg ttctcctgtt ctgcttctca gaatttgcag ttttttcctc tggattttct | 420 | |
| tcactacagc catggacaaa caccattcgc aattgcctct cgccaagtgt tcacggcagc | 480 | |
| gttatagtga atggtttgta tttaatagtt ctattttttt tttggtctat ctggtcgctc | 540 | |
| tggttcattt gtagttttgt atttggttta actgtacttt agtgattttt ttgtctctag | 600 | |
| gaactggaag tgtaaaacag ggttcatttg ttgttatgta tttggtttat ctgtaattct | 660 | |
| ttatgaattc ttttctgtg ggaattgcga agtgcagtcg gttcagatac cacaatagaa | 720 | |
| gtgggacgag atagccatag actttgtctt tggattgctg aagatggcaa agcaagatga | 780 | |
| tggccgttcg gggtgattat tgattggctg gccattagct cacttcctgc cgatgagtat | 840 | |
| gacttacttt acgacaagt taatcccata tatatatata tatgggttgg cttttgaggg | 900 | |
| gaggaggtgg gggacttcca ttcttttcct ctattatggt ttgttcataa aaagatagtt | 960 | |
| tggtgcacaa aactctcgct acgtgcagga tcagggaagg attggaccat attgggtcta | 1020 | |
| ttgtatgcag cgtacctgca atggcttatt tccacaactt gaactaggga cttcctggtc | 1080 | |
| gcacgatgac tactcttacc attgcgttaa ggctcccttc tcatagctac cataggcaag | 1140 | |
| gtgaaaatgt ttcaactttt aaaggattgt tgaagtggta ggggaagaca tgtagttaaa | 1200 | |
| aaacacttga agctgtaggg acatctgaat gcatcatttt tgcttcagat tttaacagta | 1260 | |
| gtagaaatct tattggcaat aatcgtttgg gtgtttttat gtgctccttt tttcatgttt | 1320 | |
| cttctgcagt tttctttccc cactcctctt tcgtgctctg aattatagcc attagtatac | 1380 | |
| ttaccaaaca taatgatttt ctagttgtga gcaatgttta aacgtggcat aaatgcttag | 1440 | |
| atatctgctt ttataacttg ttgctgtctt atatttaatc aactattttg atctggtata | 1500 | |
| gggtgtttcg ggatgttcca agtgatataa cgatagaagt agatggtggc acattttcat | 1560 | |
| tgcacaaggt aaatctgtca attctcttat ttgcccactg cgaactggtg atagattttg | 1620 | |
| cggagtaatt cgcattgtag aggtaatgaa acataacgaa aaaaagactt cttttggaga | 1680 | |
| ggggattcgt gttagtccct ttcatactgt tatagctaag ccttcagaaa atgttaattt | 1740 | |

```
catgcctatg agcaagttca gagactataa tgtagcagag ctcctaacat agagacgtga    1800
tgtgatgcag tttcctctag tctcgagaag tgggcgaatc cggaagcttg tagcagggca    1860
cagggattct gatatatcaa ggatagagct acttagccta ccaggcggag ttgaatcatt    1920
tgagctggca gcaaaattct gctacggcgt taactttgag attacagctg caaatgttgc    1980
tcagctttgt tgtgtatcag attatcttga gatgactgag gactattcaa agaacaatct    2040
tggttcccga gctgaagaat atcttgatat tgttgcttgc aagaatcttg aaatgtgtgt    2100
tgaagtcctg aaacaatgcg aaaatctact tcctttggct gatgagctga aaatagttac    2160
ccgatgcatt gatgctatag catctaaggc ttgcgcggag caaattgcct caagtttctc    2220
gcgcttggaa tacagtagtt ctggtagact tcatatgaac cgccaagcca agtgtgaagg    2280
agactggtgg atagaggatt tgtcagttct tcgtattgac ttgtatcaac gagtcataac    2340
agcgatgaaa tgtcgtggtg ttaggcctga aagtattgca gcatcactag tgaactacgc    2400
acagaaggag ttgacaaaga agtccagttc ctggaatcaa tcgagccaac ccaaagttga    2460
cgtggtttct ggttcaaacg gccatgaaaa ggttgtggtc gaaacaattg ttagccttat    2520
gcctgttgag aaattggttg ttccaataac ctttcttttt gggttgctga gaagtgcagt    2580
gatgcttgac tgcacagttg cttgtagact tgatcttgag aggcggatag gatctcaatt    2640
agacatagct actctcgatg atcttctaat tccattcttt cgcaatgctg gtgacacatt    2700
atttgacgtt gacacagtgc atagaatctt ggttaatttt tttcagcagg aggatagtga    2760
tgaagatatg gacgatgtct cagtgttcga gtctggtagc cctacttcgc catcccaaac    2820
tgcattattc aaagtcgcaa aactggtgga caattacctt gctgaaattg cacctgatgc    2880
aaacctaaag ctgaacaagt tcatagcaat tgccgaaagc ttaccagcac atgctcgtac    2940
tgtccatgat ggactttatc gatcaatcga tgtctacctc aaagtatgta ctacaaattt    3000
cttgaaagat gttttagaaa aagcattaat ggtttgagtt aaagttttaa acttaaatgt    3060
caggagaaaa ctcatggtac ttgtcttttc gaaaaataac ctgtttgcta atggcttaaa    3120
tgaatatggt acccttatat gaggaggatt aagtacttta cattgagttt gattttgcct    3180
ttaatagaat cttctaacct aaatccatat ttctaaggaa gtaataaagc ttccttaggc    3240
atttccttaa gttaatactt ttgactaatc atcgacgttc attcatggaa attccaggct    3300
catcaggcgt tatcagatcc agataggaga agactatgca agctgattga tttttcagaag    3360 ctctcacaag aagctggatc acacgctgca caaaacgaac gcctcccact ccaatcaatc    3420
gtgcaggttc tatatttcga gcaactgagg cttcgaaatg ccttattttg ttcttatcat    3480
gatgatgatc ataagccaac gcaccaatcg tggaggatca atagtggtgc tttaagtgca    3540
gctatgtctc cccgggataa ttatgcttct ctaagacgaa aaaataggga actaaaactt    3600
gaactaacac gaatgaggat gagattgaat gacctggaga aagatcatgt ttgtatgaag    3660
aaaaatatgg aaaaatctaa ttccgggyga ttcatgagta acttctcgaa aaagattggc    3720
aagttaaaca tttttggaca tagttcttca agggagtcat gttctccttc aaagaggtca    3780
caagttactg attctaagct aactgaaaga acatgacagg caaacttcta gtgagtaatt    3840
gcgaatggta cttgtaatct atgttccatc gcgcaatcac tattttctgt cccacatctt    3900
gtatatgagc tttagagata tgctttagca actgagatga agaaaagtaa attttgagtt    3960
ttgatgaata tgatcaccat attgatatat ctcatattgg caaatatagc acttcatat     4019
```

```
<210> SEQ ID NO 16
```

<211> LENGTH: 598
<212> TYPE: PRT
<213> ORGANISM: Artificial Sequence
<220> FEATURE:
<223> OTHER INFORMATION: Nitab4.5_0003151g0080.2 amino acid sequence

<400> SEQUENCE: 16

Met Asp Lys His Leu His Gln Leu Pro Leu Thr Lys Ser Thr Ser Arg
1               5                   10                  15

Gln Arg Tyr Asn Glu Trp Val Phe Arg Asp Val Pro Ser Asp Ile Thr
            20                  25                  30

Ile Glu Val Asp Gly Gly Ile Phe Ser Leu His Lys Phe Pro Leu Val
        35                  40                  45

Ser Arg Ser Gly Arg Ile Arg Lys Leu Val Ala Glu His Arg Asp Ser
    50                  55                  60

Asp Ile Ser Arg Ile Glu Leu Val Ser Leu Pro Gly Gly Ala Glu Ser
65                  70                  75                  80

Phe Glu Leu Ala Ala Lys Phe Cys Tyr Gly Val Asn Phe Glu Ile Thr
                85                  90                  95

Ala Ala Asn Val Ala Gln Leu Cys Cys Val Ser Asp Tyr Leu Glu Met
            100                 105                 110

Ser Glu Asp Tyr Ser Lys Asn Asn Leu Gly Ser Arg Ala Glu Glu Tyr
        115                 120                 125

Leu Asp Ser Ile Val Cys Lys Asn Leu Glu Met Cys Val Glu Val Leu
    130                 135                 140

Arg Gln Cys Glu Asn Leu Leu Pro Leu Ala Asp Glu Leu Lys Val Val
145                 150                 155                 160

Ser Arg Cys Ile Asp Ala Val Ala Ser Lys Ala Cys Val Glu Gln Ile
                165                 170                 175

Ala Ser Ser Phe Ser Arg Leu Glu Tyr Ser Ser Ser Gly Gly Arg Leu
            180                 185                 190

His Met Asn Lys Gln Ala Asn Cys Glu Leu Asp Trp Trp Ile Glu Asp
        195                 200                 205

Ile Ser Val Leu Arg Ile Asp Leu Tyr Gln Arg Val Ile Thr Ala Met
    210                 215                 220

Lys Phe Arg Gly Val Arg Pro Glu Ser Ile Ala Ala Ser Leu Val Asn
225                 230                 235                 240

Tyr Ala Gln Arg Glu Leu Ile Gln Lys Ser Leu Ser Gly Ser Asn Ile
                245                 250                 255

Gln Glu Lys Leu Val Val Glu Thr Ile Val Ser Leu Met Pro Val Glu
            260                 265                 270

Lys Phe Val Val Pro Leu Thr Phe Leu Phe Gly Leu Leu Arg Ser Ala
        275                 280                 285

Val Met Leu Asp Cys Thr Val Ala Cys Arg Leu Asp Leu Glu Arg Arg
    290                 295                 300

Ile Gly Ser Gln Leu Asp Thr Ala Thr Leu Asp Asp Ile Leu Ile Pro
305                 310                 315                 320

Ser Phe Arg His Ala Gly Asp Thr Leu Phe Asp Val Asp Thr Val His
                325                 330                 335

Arg Ile Leu Val Asn Phe Ser Gln Gln Glu Gly Asp Ser Asp Glu Asp
            340                 345                 350

Met Glu Asp Val Ser Val Phe Glu Ser Asp Ser Pro Thr Thr Thr Pro
        355                 360                 365

Ser Gln Thr Ala Leu Phe Lys Val Ser Lys Leu Val Asp Asn Tyr Leu
    370                 375                 380

```
Ala Glu Ile Ala Pro Asp Ala Asn Leu Lys Leu Asn Lys Phe Ile Ala
385                 390                 395                 400

Val Ala Glu Thr Leu Pro Ala His Ala Arg Thr Val His Asp Gly Leu
            405                 410                 415

Tyr Arg Ala Ile Asp Val Tyr Leu Lys Ala His Gln Thr Leu Ser Asp
            420                 425                 430

Pro Asp Lys Arg Arg Leu Cys Lys Leu Ile Asp Phe Gln Lys Leu Ser
        435                 440                 445

Gln Glu Ala Gly Ala His Ala Ala Gln Asn Glu Arg Leu Pro Leu Gln
    450                 455                 460

Ser Ile Val Gln Val Leu Tyr Phe Glu Gln Leu Arg Leu Arg Asn Ala
465                 470                 475                 480

Leu Phe Cys Ser Tyr Pro Asp Asp Asp Ile Lys Pro Met His Gln Ser
            485                 490                 495

Trp Arg Ile Asn Ser Gly Ala Leu Ser Ala Ala Met Ser Pro Lys Asp
            500                 505                 510

Asn Tyr Ala Ser Leu Arg Arg Glu Asn Arg Glu Leu Lys Leu Glu Leu
        515                 520                 525

Ala Arg Met Arg Met Arg Leu Asn Asp Leu Glu Lys Asp His Val Cys
    530                 535                 540

Met Lys Arg Asn Met Gln Lys Ser Ser Ser Arg Arg Phe Met Lys Ser
545                 550                 555                 560

Phe Ser Lys Arg Ile Gly Lys Lys Phe Asn Ile Phe Gly His Ser Phe
            565                 570                 575

Ser Arg Asp Ser Asn Ser Pro Ser Ser Gln Ser Glu Arg Thr Glu Ser
        580                 585                 590

Lys Ile Thr Glu Arg Thr
        595
```

<210> SEQ ID NO 17
<211> LENGTH: 1797
<212> TYPE: DNA
<213> ORGANISM: Artificial Sequence
<220> FEATURE:
<223> OTHER INFORMATION: Nitab4.5_0003151g0080.2 coding sequence

<400> SEQUENCE: 17

```
atggacaagc acctccacca actacctcta accaagtcta cttcacggca gcgttataac      60
gaatgggtat ttcgagatgt tcctagtgat ataacaatag aagtggatgg tggcatattt     120
tcattacaca agtttcccct tgtttcgaga agcggacgaa tccggaagct agtagcagag     180
cacagggatt ctgatatatc aagaattgag cttgttagtc taccaggtgg agcagaatca     240
tttgagctag cagccaaatt ctgttatggt gtcaactttg agatcacagc agcaaatgtt     300
gctcagcttt gttgtgtatc cgattacctc gagatgtcag aggactactc aaaaaacaat     360
cttggctcca gagctgaaga atatcttgac agcattgttt gcaagaatct tgaaatgtgt     420
gttgaagtct tgagacaatg tgaaaactta cttccacttg ctgatgagct gaaagttgtg     480
agccgctgta tcgatgctgt agcctccaaa gcttgtgtcg agcaaatcgc ctcaagtttc     540
tcgcgattgg agtatagtag ctcaggtgga agactacata tgaataaaca agccaattgt     600
gaattggact ggtggattga ggatatttct gttcttcgta tcgacttgta ccaacgtgtc     660
ataaccgcga tgaagtttcg tggggttagg cctgagagta ttgctgcatc actagtgaac     720
tatgcacaga gggaattgat acaaaaatcc ctttctggtt caaatatcca agaaaaactc     780
```

```
gtggttgaga cgatcgtgag cctaatgcct gttgaaaaat tcgtcgtgcc cttgaccttt    840 cttttttggat tgttgcgaag tgcagtgatg ttagattgca cggttgcttg taggcttgat    900
cttgagaggc ggataggatc tcaattggat acggctactc tggacgatat cctgattcct    960
tcctttcgac atgctggtga tacattgttt gatgttgaca cagtgcatag aatcttggtt   1020 aactttttcac agcaagaggg cgatagcgat gaagatatgg aagatgtctc ggttttttgaa   1080 tccgatagcc ctactacgac gccatcacaa actgcattgt tcaaagtatc aaagctggtt   1140
gacaattatc tagctgaaat tgcaccagat gcaaatctaa agctgaacaa gttcattgct   1200
gttgcagaaa cattaccagc acatgcgcgt actgtccacg atggacttta tcgagcaatc   1260
gatgtttacc tcaaagctca tcaaaccttca tcagatccag acaagaggag actatgcaaa   1320
ttgattgatt tccaaaagct ctcacaggaa gctggtgcac atgctgcaca aaacgaacgc   1380
cttcccctcc aatcgatagt tcaagttctt tatttcgagc aattgaggct tcgaaacgcc   1440
ttgttttgtt cgtaccctga tgatgacatc aaaccaatgc accaatcttg gaggatcaat   1500
agtggtgctc ttagtgctgc aatgtctcct aaggacaatt atgcttcgtt gagacgagaa   1560
aatagggagc taaaacttga actagcgcgg atgaggatga gattaaacga cttggaaaaa   1620
gaccatgttt gtatgaagag gaatatgcaa aaatctagct cgcgacgatt catgaaatcc   1680
ttctccaaaa ggattggcaa aaagtttaat attttcggac atagttttttc cagggattct   1740 aattctccct caagtcagtc agaaagaact gaatctaaaa taactgaaag aacgtga    1797
```

```
<210> SEQ ID NO 18
<211> LENGTH: 4422
<212> TYPE: DNA
<213> ORGANISM: Artificial Sequence
<220> FEATURE:
<223> OTHER INFORMATION: Nitab4.5_0003151g0080.2 genomic sequence

<400> SEQUENCE: 18
```

```
ttgaaaacaa aaaggtttga caaaaaaatg gccaaagaac tactcaacaa acagcaaaat     60
ctctcctatt gtgtctctgt cccccttattt tcttgtcttc tttaacaaac ctttcacatt    120
cttgtttctt ctttctctaa agatttcaaa tcttttcccc tggctttttct tcaccatatt    180 tgccatggac aagcacctcc accaactacc tctaaccaag tctacttcac ggcagcgtta    240
taacgaatgg tttgtattct gcagtacgta gttatataca atgacaatgt aaaaagattt    300
tgtagcatca atgcgattta atatgctata gttggttaaa tgtttattat acttagttat    360
acgtgtcata actcgttctc tcaactcaga atccacagct tctatctaaa ttcttgatcc    420
gctactacta gctcgtatgt gcaataccaa aatgtttgaa agttttaaag cattttgttt    480
tttggcttgt ctgtgaatct acctaccttc acagggtagg attaagatat gcgtacacat    540
tattcttctc agtactcact tgtgggacta tactgggtat gttggtgcta gtggtagtga    600
acctgcataa ttgtgtcata cttttacgtg cagttcaaaa tcagttgggg ctttggttac    660
atgcatctta gtaaaacttt tgatgaattt ttgtgtacac atatagtccg agccttcttt    720
ccttgagtcg agagtctatc tgaaataacc ttattctacc ttcacaaggt agggataagg    780
tctgcgtaca taatacactt tccagacctt acttgtggag ttacattggg tatgttgtcg    840
ttgttgttgt acacatagtc cgagcctaag acagtgaatg cacgtgctac cactacctct    900
atgttaaatc ttaccctaga agagaaagat caaaatgtta gtctttctgc taattggttg    960
atttgtatgt tatagggtat ttcgagatgt tcctagtgat ataacaatag aagtggatgg   1020
tggcatattt tcattacaca aggtaattct ctccattctc tattatctta taatcaattt   1080
```

```
ggccaagctt ctccaatcct agaaatactt tttttcaaag tttaattgtt tggcaatctt      1140
ttgtaaggaa aaaaattgtt tttgatgaga atcagaagct ttttttggaa aagcagaaaa      1200
aagtaggctc tccataaaaa cacttttttta aagcactttt gataaaaaaa atatatttac      1260
gagcagtttt taaaagtttg gccaaatact aattgttgct cagaaatgtt tttcaaatta      1320
attagccaaa cacaaactct ttcttgccaa aagtacgttt gaaaaagcac tttttgagaaa      1380 aacgcttatc aaaataagct gattttttgca gctgccgtac ccgtatcaga ttattcaaaa      1440
atgcactact tttagtggat caaacatgca tgtgttggca tttctgaaga gcatgaacaa      1500
cataaactgc ttagtagtat tgctcactat gtcttgtttt cacacatttt atattgaagt      1560
gtttgaaatt tttaaaattt catgcctatg agttagttca gagaccataa tgtaatagaa      1620
aattccctaa catagaataa ttatgatgca gtttcccctt gtttcgagaa gcggacgaat      1680
ccggaagcta gtagcagagc acagggattc tgatatatca agaattgagc ttgttagtct      1740
accaggtgga gcagaatcat ttgagctagc agccaaattc tgttatggtg tcaactttga      1800
gatcacagca gcaaatgttg ctcagctttg ttgtgtatcc gattacctcg agatgtcaga      1860
ggactactca aaaaacaatc ttggctccag agctgaagaa tatcttgaca gcattgtttg      1920
caagaatctt gaaatgtgtg ttgaagtctt gagacaatgt gaaaacttac ttccacttgc      1980
tgatgagctg aaagttgtga gccgctgtat cgatgctgta gcctccaaag cttgtgtcga      2040
gcaaatcgcc tcaagtttct cgcgattgga gtatagtagc tcaggtggaa gactacatat      2100
gaataaacaa gccaattgtg aattggactg gtggattgag gatatttctg ttcttcgtat      2160
cgacttgtac caacgtgtca taaccgcgat gaagtttcgt ggggttaggc ctgagagtat      2220
tgctgcatca ctagtgaact atgcacagag ggaattgata caaaaatccc tttctggttc      2280
aaatatccaa gaaaaactcg tggttgagac gatcgtgagc ctaatgcctg ttgaaaaatt      2340
cgtcgtgccc ttgacctttc tttttggatt gttgcgaagt gcagtgatgt tagattgcac      2400
ggttgcttgt aggcttgatc ttgagaggcg gataggatct caattggata cggctactct      2460
ggacgatatc ctgattcctt cctttcgaca tgctggtgat acattgtttg atgttgacac      2520
agtgcataga atcttggtta acttttcaca gcaagagggc gatagcgatg aagatatgga      2580
agatgtctcg gttttttgaat ccgatagccc tactacgacg ccatcacaaa ctgcattgtt      2640
caaagtatca aagctggttg acaattatct agctgaaatt gcaccagatg caaatctaaa      2700
gctgaacaag ttcattgctg ttgcagaaac attaccagca catgcgcgta ctgtccacga      2760
tggactttat cgagcaatcg atgtttacct caaagtatgt attactaact tacttgaaat      2820
atgttcaaaa acgtttttgct ggtttgaatg agagttcttc aaaatttcac aacaggagaa      2880
atatcatatg gtgcttatga ttccctttat agagctatat gtcctccttt gattagagaa      2940
aatgatcaaa ttaccacgtc tactatacga aatattttaa ctttacccctc cgttatattt      3000 tgaggtcatt catattcttg tggttagcaa attatcctgt attcacccat gaccctaacg      3060
gagctccaac caaagtataa cgaagggtaa tctttaacaa tagtacaaag tacagaggta      3120
aatttggacc tttctcctta agtattttgg cacctggatc catccaatcc gcgatggagc      3180
tatattaaag tgaaggacag atacgatata tattctaatg gacctcacgc ttcaattatg      3240
ctatcaccct gttaccttat cactttatct tgttgtcgtt actacttatt atgcctgctt      3300
cctttacttt tacctttgagt cgggagttta tcggaaacag tctctctacc ttcacaaggt      3360
agtaaggtcc gtgtacactc tactcctccc agacccccact ttgtgggatt acaatgggtt      3420
```

```
tgttgttgtt gttgttaatg gtatgaatga cgtcaaagta taacattgag atatttcgta      3480
tgctatatgg gtaaatttgg acctttcaac cattaactaa gctaatagag tttctcatct      3540
cagattccta ttttttcatt taactaacca taacattgtt catgaatgca tattccaggc      3600
tcatcaaacc ttatcagatc cagacaagag gagactatgc aaattgattg atttccaaaa      3660
gctctcacag gaagctggtg cacatgctgc acaaaacgaa cgccttcccc tccaatcgat      3720
agttcaagtt ctttatttcg agcaattgag gcttcgaaac gccttgtttt gttcgtaccc      3780
tgatgatgac atcaaaccaa tgcaccaatc ttggaggatc aatagtggtg ctcttagtgc      3840
tgcaatgtct cctaaggaca attatgcttc gttgagacga gaaaataggg agctaaaact      3900
tgaactagcg cggatgagga tgagattaaa cgacttggaa aaagaccatg tttgtatgaa      3960
gaggaatatg caaaaatcta gctcgcgacg attcatgaaa tccttctcca aaaggattgg      4020
caaaaagttt aatattttcg gacatagttt ttccagggat tctaattctc cctcaagtca      4080
gtcagaaaga actgaatcta aaataactga aagaacgtga caatcgatct tccaggtaca      4140
tcaaattact cggataattt tggctgattc tgctgagtaa ctgcaagtct gtcaatatga      4200
gctgcagtct catattttct cccaaatgtt tgtatatgag atgcagtctg atatgcttcc      4260
ggaggcagag ggatttcaag cttatgggtt cggcattcta atcattttat gttactgggt      4320
tctaaattag taatttatac atattccatg aattgtttaa gataaatcca tgattcgaac      4380
caaattactg ggtttgaccg aacccgctcc cggcactcta gc                        4422
```

```
<210> SEQ ID NO 19
<211> LENGTH: 598
<212> TYPE: PRT
<213> ORGANISM: Artificial Sequence
<220> FEATURE:
<223> OTHER INFORMATION: Nitab4.5_0002641g0190.2 amino acid sequence

<400> SEQUENCE: 19

Met Asp Lys His His His Gln Leu Pro Leu Thr Lys Ser Thr Ser Arg
1               5                   10                  15

Gln Arg Tyr Asn Glu Trp Val Phe Arg Asp Val Pro Ser Asp Ile Thr
            20                  25                  30

Ile Glu Val Asp Gly Gly Ile Phe Ser Leu His Lys Phe Pro Leu Val
        35                  40                  45

Ser Arg Ser Gly Arg Ile Arg Arg Leu Val Ala Glu His Arg Asp Ser
    50                  55                  60

Asp Ile Ser Arg Ile Glu Leu Val Ser Leu Pro Gly Gly Thr Glu Ser
65                  70                  75                  80

Phe Glu Leu Ala Ala Lys Phe Cys Tyr Gly Val Asn Phe Glu Ile Thr
                85                  90                  95

Ala Ala Asn Val Ala Gln Leu Cys Cys Val Ser Asp Tyr Leu Glu Met
            100                 105                 110

Ser Glu Asp Tyr Ser Lys Asn Asn Leu Gly Ser Arg Ala Glu Glu Tyr
        115                 120                 125

Leu Asp Ser Ile Val Cys Lys Asn Leu Glu Met Cys Val Glu Val Leu
        130                 135                 140

Arg Gln Cys Glu Asn Leu Leu Pro Leu Ala Asp Glu Leu Lys Ile Val
145                 150                 155                 160

Ser Arg Cys Ile Asp Ala Val Ala Ser Lys Ala Cys Val Glu Gln Ile
                165                 170                 175

Ala Ser Ser Phe Ser Arg Leu Glu Tyr Ser Ser Ser Gly Gly Arg Leu
            180                 185                 190
```

```
His Met Ile Lys Gln Ala Asn Cys Glu Leu Asp Trp Trp Ile Glu Asp
        195                 200                 205

Ile Ser Met Leu Arg Ile Asp Leu Tyr Gln Arg Val Ile Thr Ala Met
        210                 215                 220

Lys Phe Arg Gly Val Arg Pro Glu Ser Ile Ala Ala Ser Leu Val Asn
225                 230                 235                 240

Tyr Ala Gln Lys Glu Leu Ile Gln Lys Ser Leu Ser Gly Ser Asn Ile
                245                 250                 255

Gln Glu Lys Leu Val Val Glu Thr Ile Val Ser Leu Met Pro Val Glu
                260                 265                 270

Lys Phe Val Val Pro Leu Ser Phe Leu Phe Gly Leu Leu Arg Ser Ala
                275                 280                 285

Val Met Leu Asp Cys Thr Val Ala Ser Arg Leu Asp Leu Glu Arg Arg
        290                 295                 300

Ile Gly Ser Gln Leu Asp Thr Ala Thr Leu Asp Asp Ile Leu Ile Pro
305                 310                 315                 320

Ser Phe Arg His Ala Gly Asp Thr Leu Phe Asp Val Asp Thr Val His
                325                 330                 335

Arg Ile Leu Val Asn Phe Ser Gln Gln Glu Gly Asp Ser Asp Asp Asp
                340                 345                 350

Met Glu Asp Val Ser Val Phe Glu Ser Asp Ser Pro Thr Thr Thr Pro
                355                 360                 365

Ser Gln Asn Ala Leu Phe Lys Val Ser Lys Leu Val Asp Asn Tyr Leu
        370                 375                 380

Ala Glu Ile Ala Pro Asp Ala Asn Leu Lys Leu Ser Lys Phe Ile Ala
385                 390                 395                 400

Val Ala Glu Thr Leu Pro Ala His Ala Arg Thr Val His Asp Gly Leu
                405                 410                 415

Tyr Arg Ala Ile Asp Val Tyr Leu Lys Ala His Gln Thr Leu Ala Asp
                420                 425                 430

Pro Asp Lys Arg Arg Leu Cys Lys Leu Ile Asp Phe Gln Lys Leu Ser
        435                 440                 445

Gln Glu Ala Gly Ala His Ala Ala Gln Asn Glu Arg Leu Pro Leu Gln
        450                 455                 460

Ser Ile Val Gln Val Leu Tyr Phe Glu Gln Leu Arg Leu Arg Asn Ala
465                 470                 475                 480

Leu Phe Cys Ser Tyr Pro Asp Asp Ile Lys Pro Met His Gln Ser
                485                 490                 495

Trp Arg Ile Asn Ser Gly Ala Leu Ser Ala Ala Met Ser Pro Lys Asp
                500                 505                 510

Asn Tyr Ala Ser Leu Arg Arg Glu Asn Arg Glu Leu Lys Leu Glu Leu
                515                 520                 525

Ala Arg Met Arg Met Arg Leu Asn Asp Leu Glu Lys Asp His Val Cys
        530                 535                 540

Met Lys Arg Asn Met Gln Lys Ser Ser Ser Arg Arg Phe Met Lys Ser
545                 550                 555                 560

Phe Ser Lys Arg Ile Gly Lys Lys Phe Asn Ile Phe Gly His Asn Phe
                565                 570                 575

Ser Arg Asp Cys Ser Ser Pro Ser Ser Gln Ser Glu Arg Thr Glu Ser
                580                 585                 590

Lys Ile Thr Glu Arg Thr
        595
```

129                                                                 130

-continued

<210> SEQ ID NO 20
<211> LENGTH: 1797
<212> TYPE: DNA
<213> ORGANISM: Artificial Sequence
<220> FEATURE:
<223> OTHER INFORMATION: Nitab4.5_0002641g0190.2 coding sequence

<400> SEQUENCE: 20

```
atggacaaac accaccatca actaccacta accaagtcta cttcgaggca gcgttataac      60
gaatgggtat ttcgagatgt tcctagtgat ataacaatag aagtggatgg tggcatattt     120
tcactccaca agtttcccct tgtttcgaga agcggacgaa tccggaggct agtagcagag     180
cacagggatt cagatatatc aagaattgag cttgttagtc taccaggtgg aacagaatca     240
tttgagctag cagccaaatt ctgttatggt gtcaactttg agatcacagc agcaaatgtt     300
gctcagcttt gttgcgtatc cgattatctc gagatgtcgg aggactactc gaaaaataat     360
cttggttcaa gagctgaaga atatcttgac agcattgttt gcaagaatct tgaaatgtgt     420
gttgaagtct tgagacaatg tgaaaactta cttccacttg ctgatgagct gaaaattgtt     480
agccggtgta tcgatgctgt agcctcgaaa gcttgtgtcg agcaaatcgc ctcaagtttc     540
tcacgattag agtatagtag ctctggagga agactcacata tgattaaaca agccaattgt     600
gaattggact ggtggattga ggatatttca atgcttcgta tcgacttgta ccaacgcgtc     660
ataaccgcga tgaagtttcg tggggttagg cctgagagta ttgctgcatc actagtgaac     720
tatgcacaaa aagagttgat acaaaaatcc ctttctggtt caaatatcca agaaaaactc     780
gtggttgaga cgatcgtgag cctgatgcct gttgaaaaat tcgtcgtgcc cttgagcttt     840 cttttttggat tgttgcgaag tgcagtgatg ttagattgca cggttgctag taggcttgat     900
ctcgagaggc ggataggatc tcaattggat acggctaccc tggacgatat tctgattcct     960
tcctttcgac atgctggtga tacattgttt gatgttgaca cagtgcatag aatcttggtt    1020
aacttttcac agcaagaggg agatagtgat gatgatatgg aagatgtatc ggtttttgaa    1080
tccgatagcc ctactacgac gccatcacaa aatgcattgt tcaaagtatc aaagctggtt    1140
gacaattacc tagctgaaat tgcaccagat gcaaatctaa agctgagcaa gttcattgct    1200
gttgcagaaa cattaccagc acatgcgcgt actgtccacg atggactta tcgagcaatc     1260 gacgtttacc tcaaggctca tcaaacctta gcagatccag acaagagaag actatgcaaa    1320
ttgatagatt tccaaaagct ctcacaggaa gctggtgcac acgctgcaca aaacgagcgc    1380
cttcctctcc aatccatcgt tcaagttctt tatttcgagc aattgaggct acgaaacgcc    1440 ttgtttttgtt cataccctga tgatgacatt aagccaatgc accaatcctg gaggatcaat    1500
agtggtgctc ttagtgctgc aatgtctccc aaggacaatt atgcttcgtt gagacgagaa    1560
aatagagagc taaaacttga actagcgcgg atgaggatga gattaaacga cttggaaaaa    1620
gaccatgttt gtatgaagag gaatatgcaa aaatctagct cgcgacgatt catgaaatca    1680
ttctccaaaa ggataggcaa aaagttcaat attttcggac ataattttc cagggattgt     1740 agttctccct caagccagtc agaaagaact gaatctaaaa taactgaaag aacttga      1797
```

<210> SEQ ID NO 21
<211> LENGTH: 4552
<212> TYPE: DNA
<213> ORGANISM: Artificial Sequence
<220> FEATURE:
<223> OTHER INFORMATION: Nitab4.5_0002641g0190.2 genomic sequence

<400> SEQUENCE: 21

-continued

```
caaaatctct cctattgtgt ctctgtcccc ttattttctt gtcttcttta acaaaccttt      60
cacattcttc tttatttaga gattttcaat cttttccctt ggcttttctt caccatattg     120
gccatggaca aacaccacca tcaactacca ctaaccaagt ctacttcgag gcagcgttat     180
aacgaatggt ttgtattttg cagtacgtag ttatatacat cgacagtgta aaaagattaa     240
ttttgtagca tcaatgtgat ttaatatgct atagttgatt aaaaaaatgt gtacttggtt     300
atacgtgtca taactcgttc tctcaactca gaatccacag cttctaaatt cttgatctcg     360
tatatgcaat gccaaaatgt ttgaaagttt taaagcattt tttttggctt gtttgtgaac     420
ctacgtacct tcccaagtta gaggtaaggt ctgcgtacac attattcttc ccagaattca     480
cttgtgggac aatactgggt atgttgttgc tggtggtgat gaacctgcat attgtgtcat     540
acttttacgt gcagttcaaa atcacttggg gctttagtta catgcatctt agtaaaactt     600
ttgatgaatt tttgtacaca catatagtcc gagtgctctt tccttgagcc gatggtctac     660
cggaaacaac cttctacctt cacaaggtac aaggtagggg taaggtctgt gtatatacta     720
ccctctccag agtccacttg tgggattaca ttggatatgt tgtcgttgtt gttgtactac     780
acatagtccg agcctaagac agtgagtgca cgtgctccta ctacctctat gttaaatctt     840
cccctagaag agaaagatca aaattttagt cttttctgctt attattggct aatttatatg     900
ttatagggta tttcgagatg ttcctagtga tataacaata gaagtggatg gtggcatatt     960
ttcactccac aaggtaaatg ctcttcattc tctattattg atgctcgaac tcttcaaaaa    1020
tattgccaca cccgtattca ggggcggaac tagagtggcg aaatggggtt caaccgaatc    1080
aacttcgcca aaaaattata gagtatatat aaggttaaat ttatttttat gcataaatag    1140
taaatgttca atccccttgg catgttcgta agtttacctt ttaatatttc gaatcccctt    1200
ggtaaaagtc ctagctctgc tactgcccgt gtcggaccat tcaaaatgaa ctacttttgg    1260
aggatccgac actcaggtca gcatttttga agagttcgaa caacatagaa ttcttagcac    1320
tattcctcta tatgacttct tatctcacat attatattga aatgtttgaa attttttaaa    1380
tttcatgcct atgagtaagt ttagagacta taatgtaata gaaaattccc taacataaga    1440
taattatgat gtagtttccc cttgtttcga gaagcggacg aatccggagg ctagtagcag    1500
agcacaggga ttcagatata tcaagaattg agcttgttag tctaccaggt ggaacagaat    1560
catttgagct agcagccaaa ttctgttatg gtgtcaactt tgagatcaca gcagcaaatg    1620
ttgctcagct ttgttgcgta tccgattatc tcgagatgtc ggaggactac tcgaaaaata    1680
atcttggttc aagagctgaa gaatatcttg acagcattgt ttgcaagaat cttgaaatgt    1740
gtgttgaagt cttgagacaa tgtgaaaact acttccact tgctgatgag ctgaaaattg    1800
ttagccggtg tatcgatgct gtagcctcga aagcttgtgt cgagcaaatc gcctcaagtt    1860
tctcacgatt agagtatagt agctctggag gaagactaca tatgattaaa caagccaatt    1920
gtgaattgga ctggtggatt gaggatattt caatgcttcg tatcgacttg taccaacgcg    1980
tcataaccgc gatgaagttt cgtggggtta ggcctgagag tattgctgca tcactagtga    2040
actatgcaca aaaagagttg atacaaaaat ccctttctgg ttcaaatatc caagaaaaac    2100
tcgtggttga gacgatcgtg agcctgatgc ctgttgaaaa attcgtcgtg cccttgagct    2160 ttcttttttgg attgttgcga agtgcagtga tgttagattg cacggttgct agtaggcttg    2220
atctcgagag gcggatagga tctcaattgg atacggctac cctggacgat attctgattc    2280
cttcctttcg acatgctggt gatacattgt ttgatgttga cacagtgcat agaatcttgg    2340
```

```
ttaactttttc acagcaagag ggagatagtg atgatgatat ggaagatgta tcggtttttg      2400
aatccgatag ccctactacg acgccatcac aaaatgcatt gttcaaagta tcaaagctgg      2460
ttgacaatta cctagctgaa attgcaccag atgcaaatct aaagctgagc aagttcattg      2520
ctgttgcaga aacattacca gcacatgcgc gtactgtcca cgatggactt tatcgagcaa      2580
tcgacgttta cctcaaggta tgtattgaca atttaattga aatatgttca aaaatgtttt      2640
gctggtttgg atgagagtta cttcaaaatt tcacaacagg agaaatatca tatggtgctt      2700 attttttgata aaactatata gattgctaat gacttaattg aatatggtag ttctagaata      2760
agtccatcaa gagtattaag gttctttacc ttgagataat cataattatt cccattacag      2820
agtaatatgt cctcctttga ttagtgaaaa tggttaaatt acccttctat tatacgaaat      2880
atcttaactt tacactctgt tatattttgg agtcattcat attcttgtgg ttgggtcatg      2940
gtttatatcg atgtgaccta tgtgatctat aggtcatggg tacgaccgtg ggatcaacca      3000
cttatgtttg tattagggtg ggttccctac attacacccc ctttgggttg tggcccttcc      3060
ccaaatcccc cgtgaacgtg ggatgttttg tgcaccagac tgcccttttg ttcatttctt      3120
gtggttagca aattatcttg tattcgccga tgaccctaac tgagcaccaa ccaaaagtac      3180
gattaaaggt aatcttaacc atagtaaaaa ctggagaggg aaatttggac cttttttcctt      3240 aagtgttttg acacgcggaa tccatccaat ccgcaatgga gcttcgttaa agtgaaggac      3300
gaatacaaga tatttgctaa cagcaagggg atgtataacg tcaaagtgta acagagggta      3360
aattgagata ttatgtatgg tataggagta aactatgttg tgtggactct ccaaaatgct      3420
gtcgcagcat tatcagatcc tccaaaaatg cactattttt ggagtatcag acacgcaccc      3480
gatgatattt tcggagagtc cgagcaacat aggggggtaa atttggacct tttcacctttt      3540 tgttaagctg atagagcttc tcatctcaat tcctattttt tcatataact aaccataaca      3600
ttgttcatga atgcatattc caggctcatc aaaccttagc agatccagac aagagaagac      3660
tatgcaaatt gatagatttc caaaagctct cacaggaagc tggtgcacac gctgcacaaa      3720
acgagcgcct tcctctccaa tccatcgttc aagttcttta tttcgagcaa ttgaggctac      3780
gaaacgcctt gttttgttca taccctgatg atgacattaa gccaatgcac caatcctgga      3840
ggatcaatag tggtgctctt agtgctgcaa tgtctcccaa ggacaattat gcttcgttga      3900
gacgagaaaa tagagagcta aaacttgaac tagcgcggat gaggatgaga ttaaacgact      3960
tggaaaaaga ccatgtttgt atgaagagga atatgcaaaa atctagctcg cgacgattca      4020
tgaaatcatt ctccaaaagg ataggcaaaa agttcaatat tttcggacat aatttttcca      4080
gggattgtag ttctccctca agccagtcag aaagaactga atctaaaata actgaaagaa      4140
cttgacaatc gatgaagggg agccttggcg taactgataa agttgttgct atgcgaccat      4200
gaggtcacgg attcgagccg tggaaacagc ctcttgcaga aatgcagggt aagactgcgt      4260
acaatagacc gttgtggtcc ggcccttctc cggaccccgc gcatagcggg agcttagtgc      4320
actgggctgt cctttttttga acgtgacaat cgatcttcca ggtacatcaa attactcggg      4380
taattttggc tgattctgtt gttgagtgta actgcaagtt tttcagttgt aatctttttg      4440
ttccattcta caacacctta ttttctcccc aaatgtttgt atatgagctg cagtgagata      4500
tgcttttcat tgacatgata tatagagttt ttatgacttt gagttggtaa ag              4552
```

<210> SEQ ID NO 22
<211> LENGTH: 592
<212> TYPE: PRT
<213> ORGANISM: Artificial Sequence
<220> FEATURE:
<223> OTHER INFORMATION: Nitab4.5_0001876g0030.2 amino acid sequence

<400> SEQUENCE: 22

```
Met Val Ser Pro Tyr Asn Ser Phe Thr Thr Arg Thr Ile Phe Ser Glu
1               5                   10                  15

Val Ala Gly Asp Ile Thr Ile Ala Ala Asn Gly Glu Ser Phe Leu Leu
            20                  25                  30

His Lys Phe Pro Leu Val Ser Leu Ser Gly Lys Ile Arg Lys Met Val
        35                  40                  45

Ala Asp Ala Asn Asp Pro Asn Leu Ser Glu Leu Asp Leu Asn His Val
    50                  55                  60

Pro Gly Gly Pro Glu Thr Phe Glu Leu Ala Ala Lys Phe Cys Tyr Gly
65                  70                  75                  80

Met Asn Phe Glu Ile Thr Thr Thr Asn Val Ala Arg Leu Arg Cys Val
                85                  90                  95

Ala Glu Tyr Leu Glu Met Thr Glu Asp Tyr Arg Glu Glu Asn Leu Ile
            100                 105                 110

Ala Arg Thr Glu Thr Phe Leu Asp Glu Val Val Ser Pro Ser Leu Glu
        115                 120                 125

Lys Ser Val Gln Val Leu Ser Ser Cys Glu Ala Leu Leu Pro Thr Ala
    130                 135                 140

Glu Glu Val Gly Ile Pro Asp Arg Cys Ile Asp Ala Ile Ala Arg Asn
145                 150                 155                 160

Ala Cys Gln Glu Gln Leu Val Ser Ser Leu Ser Arg Leu Asp Cys Asp
            165                 170                 175

Ser Gly Ser Leu Glu Leu Lys Asp Arg Cys Leu Glu Trp Trp Val Glu
        180                 185                 190

Asp Phe Ser Val Leu Ser Ile Asp Phe Tyr Arg Arg Val Ile Met Ala
        195                 200                 205

Met Gly His Ala Gly Val His Ile Asp Ser Ile Ile Ala Ser Leu Met
    210                 215                 220

His Tyr Ala Gln Val Ser Leu Lys Gly Ile Gly Lys Pro Gln Ile Trp
225                 230                 235                 240

Asn Pro Ala Arg Ser Tyr Pro Cys Lys Gly Glu Lys Gly Gln Arg Thr
            245                 250                 255

Ile Ile Glu Thr Leu Val Ser Leu Leu Pro Pro Glu Lys Ser Ser Ser
            260                 265                 270

Val Pro Leu Asn Phe Leu Phe Gly Met Leu Arg Ile Gly Ile Met Val
        275                 280                 285

Asp Ala Thr Leu Ala Cys Arg Leu Glu Ile Glu Arg Arg Ile Ala Phe
    290                 295                 300

Arg Leu Glu Met Val Leu Leu Asp Asp Leu Leu Ile Pro Ser Val Gln
305                 310                 315                 320

Thr Thr Gly Asp Ser Leu Phe Asp Val Asp Thr Val Lys Arg Ile Leu
            325                 330                 335

Ile His Phe Leu Gln Arg Ile Asp Gln Glu Glu Asn Glu Asp Cys Gly
            340                 345                 350

Tyr Glu Ser Glu Gly Ile Asp Ser Pro Ser His Gly Ala Leu Leu Lys
        355                 360                 365

Val Gly Arg Leu Ile Asp Thr Tyr Leu Ala Glu Ile Ala Pro Asp Pro
    370                 375                 380

Tyr Leu Ser Leu Asp Lys Phe Thr Ala Met Ile Ser Met Leu Pro Asp
385                 390                 395                 400
```

```
Tyr Ala Arg Val Ile Asp Asp Gly Leu Tyr Arg Ala Ile Asp Val Tyr
            405                 410                 415

Leu Lys Ala His Pro Thr Leu Ser Glu His Gly Ala Lys Lys Leu Cys
            420                 425                 430

Lys Phe Ile Asp Cys Gln Lys Leu Ser Gln Glu Ala Cys Asn His Ala
            435                 440                 445

Ala Gln Asn Glu Arg Leu Pro Val Gln Met Thr Val Arg Val Leu Tyr
    450                 455                 460

Phe Glu Gln Leu Arg Leu Lys Asn Ala Leu Ser Gly Ser Cys Gly Asp
465                 470                 475                 480

Thr Phe Val Ser Gln Lys Ile Ser Ser Gly Leu Thr Ser Ala Ala Met
            485                 490                 495

Ser Pro Arg Asp Thr Tyr Ala Ser Leu Arg Arg Glu Asn Arg Glu Leu
            500                 505                 510

Lys Leu Glu Ile Ser Arg Met Arg Val Arg Leu Ser Asp Leu Glu Lys
            515                 520                 525

Glu Gln Val Phe Met Lys Gln Gly Met Met Asp Lys Thr Gly His Gly
    530                 535                 540

Lys Thr Phe Leu Thr Ser Leu Ser Arg Gly Ile Gly Arg Ile Gly Ile
545                 550                 555                 560

Phe Gly Ser Pro Ser Gly Glu Lys His His Lys Ser Gly Arg Lys Ser
            565                 570                 575

Arg Thr Ser Glu Gly Lys Thr Gly Arg Ser Arg Arg Tyr Ser Leu Ser
            580                 585                 590
```

<210> SEQ ID NO 23
<211> LENGTH: 1779
<212> TYPE: DNA
<213> ORGANISM: Artificial Sequence
<220> FEATURE:
<223> OTHER INFORMATION: Nitab4.5_0001876g0030.2 coding sequence

<400> SEQUENCE: 23

```
atggtgtctc cttacaactc atttaccact cgcactatat tctctgaagt tgctggggat      60
attacaattg ctgcaaatgg agagtctttc ctactgcata agtttcccct ggtatctttg     120
agtggaaaga tccggaagat ggtggcagat gccaacgatc caaatctctc agaattggat     180
ttgaatcacg taccaggagg acctgaaaca tttgaactgg ctgcaaagtt ttgttatggc     240
atgaactttg agatcacaac cacaaacgta gcacgtttgc gctgtgtggc agaatacttg     300
gaaatgacag aagattatcg tgaagagaat ctcattgcaa gaacagaaac tttccttgat     360
gaagttgtct ctccaagtct tgaaaaatcc gtgcaagtac tttcttcctg tgaagctctt     420
cttcctactg cagaggaggt tggtattcca gatagatgca ttgatgccat tgccaggaat     480
gcttgtcaag agcaacttgt atccagtcta tctcgtttag attgtgatag tggatctttg     540
gaacttaagg acaggtgtct tgaatggtgg gtcgaagatt tttctgttct gagtattgat     600
ttttatcgca gagttatcat ggcaatggga catgctgggg tacacataga cagcattatt     660
gcgtccttga tgcattatgc ccaggtctct ctaaagggta ttgggaaacc gcaaatttgg     720
aatccagcca gatcgtatcc ttgtaaggga gaaaaggggc agagaacaat aatagaaact     780
cttgttagtc tattgcctcc agaaaagagt tcatctgttc ctctgaattt tcttttgggg     840
atgttgagga taggtatcat ggtggatgcc acgctagcct gcaggcttga aattgagagg     900
aggattgcct tccggctgga aatggtctta cttgatgatt tgcttatacc atctgtccag     960
```

-continued

```
actacaggtg attctttgtt tgatgttgac acggtcaagc ggatattgat acatttcctc      1020
caaaggattg accaggaaga aaatgaagat tgtggatatg aatcagaagg tattgattct      1080
ccaagccatg gcgctctatt gaaagttgga cggctgatag acacatatct tgctgaaata      1140
gctcctgatc catatttgag tctcgacaaa ttcactgcta tgatatcaat gttgcctgat      1200
tatgctcgtg taattgatga cggactttac agagctattg atgtttattt gaaggcccat      1260
ccaacgctaa gtgagcatgg cgcgaagaag ctgtgcaagt tcatagattg ccagaagctc      1320
tctcaagaag catgcaatca tgcagcacag aatgagagac tcccagttca aatgactgtc      1380
cgagttctct actttgagca gctccgcctt aagaatgctc tatctggaag ttgtggagat      1440
acttttgtat cacaaaagat cagtagtggt cttacaagtg cagctatgtc gcctagagat      1500
acttacgctt cttaaggag agagaaccga gaactgaagc tggagatatc aagaatgagg      1560
gtaaggctca gtgacctgga gaaggaacaa gtgttcatga acaaggtat gatggataaa      1620 acaggacatg ggaaaacatt cttaacttcc ctttctagag gcataggaag aattggtata      1680
tttggcagtc cttctggaga aaaacatcac aagtcgggtc gcaaatccag gacatcagaa      1740
ggtaaaactg gtaggagtag gaggtattct ctttcctag                             1779
```

```
<210> SEQ ID NO 24
<211> LENGTH: 4139
<212> TYPE: DNA
<213> ORGANISM: Artificial Sequence
<220> FEATURE:
<223> OTHER INFORMATION: Nitab4.5_0001876g0030.2 genomic sequence
<220> FEATURE:
<221> NAME/KEY: misc_feature
<222> LOCATION: (4114)..(4139)
<223> OTHER INFORMATION: n is a, c, g, or t

<400> SEQUENCE: 24
```

```
ataagatcaa gcctttcctt gattttaata atattagaat agaattaagc aaagcatgca        60
cataccttcc aatattttac tactcaatca aataactagg ttttaatcct gaattagtta       120
gatgattatc tatatctgct tcacttgact ctactaatgt ttaaaagaat tcatcaaaat       180
ttgatactag tagattatag tttcgataat ggtgaatagg atgacaatat tggtaaggta       240
gagacaaagg aataaaaagc aaaaggggaa aaggtatttt gtgttgcagt agaacacttc       300
acatggccac ccattctgt attctttagc tttttctctt tgcattattt atgtatcacc       360
attcctatgt cacactttcc cttttaggtc ttcttattgt tgcttgtatt gggatttgac       420
tgcaagagtg cttcatcaga tggtgctgct gctctaaagt ctaaagtgaa gctcatacaa       480
gaatggtgtc tccttacaac tcatttacca ctcggtaatc tccatcttct gggctacaca       540
tatataactg ttgatcaaga attattcggt tacagtatca aagacagttt ttttactgcg       600
aattatgtgt tggccttggt ttttgatcat catattctga atgacatgtt tgatgaatgt       660
acattttcaa tgaatttagt ctttcagctt gatttgagct accccacccc ctccagcagc       720
ccatcttggc tgccctgctt gatgattcat gctatgatta tattgtttcc tctctccaat       780 tattatttt tcagtacgca ttgcacctta caaacattat ccttataggg attacttaac        840
attatccttt ccaaattccc tccagtgaat agttacagga aggccttgtt agagtaactc       900
tttcttctga catttgaagg gtagccttgg cgcaattggt aaagttgctt ccatgtgacc       960
atgaggtcac gggttcgagc cgtggaaaca gcctcttgca gaaatgcagg gtaagactgc      1020
gaacgataga cccttccccg gacccgcgca tagtgggagc ttagttcacc ggaccaccct      1080
ttttttcttc tgacatttat atgctttctt tgcgtatgtc atactctctt tagtatacta      1140
```

```
tttcacataa tttgtcaaac atgtcaaagt gctactactg tgaacttgag tattggtgtc      1200
ctttcttatc atcttcttcg ttttcatcga taaacttgat ctgtcatgtc agtaggagga      1260
aatgcatcac tttaccccccc aacacttcct aattcatctg ttatttcatg aataatgaac      1320
aaaacaccat aaaagcgtta atactttta tgacatggta aatttattaa ggcaaataaa       1380
tactttgtca tgtcaaaatc attgcgataa atcaacttat tcgtgatgat attgatcagc      1440
actatattct ctgaagttgc tggggatatt acaattgctg caaatggaga gtctttccta      1500
ctgcataagg tactttcctg ttttcagaaa ctttctgcct ttggataatt taagaacgtt      1560
tgaacttcaa ataaggttag aaatatatat aaattatcag gatcatgcta aaggttcaag      1620
atcatgcata gtgggagagg gtggggtttt gtttaaagac acttgtttct ttcgtcttgg      1680
ttactaacta gatagattga gattgtgatg gtggtaaaat ttgaaattca gaggattatc      1740
agacttggtt gagaatgttc ctgtagtttg atagattatt aagattgaaa aaccaaagtt      1800
tccattaatg gtgtatttgg ctatcaagaa aaaaaaagca acaattgttg tagtgatggt      1860
atacgtaatg taagctaact ttaagatcac aattctggaa cacattgtag tttgaaaaga      1920
actccatctg ggcatgtaat gcagctaaaa ataatgacag tgaagtctgt catattaagg      1980
atactttagc aaatgattga aatggtcatt cttctaggag tagcattgcg acaaatgctt      2040
tccagaaatc aattttatga ttataacatg tgaatcttag ccttgtctag gcgtttcatc      2100
gtgaactatt taataattaa cttatctctt ccttattcga cattatactt cattcttgaa      2160
gttgataatt atgtgatgtt tacaatagtt tcccctggta tctttgagtg gaaagatccg      2220
gaagatggtg gcagatgcca acgatccaaa tctctcagaa ttggatttga atcacgtacc      2280
aggaggacct gaaacatttg aactggctgc aaagttttgt tatggcatga actttgagat      2340
cacaaccaca aacgtagcac gtttgcgctg tgtggcagaa tacttggaaa tgacagaaga      2400
ttatcgtgaa gagaatctca ttgcaagaac agaaactttc cttgatgaag ttgtctctcc      2460
aagtcttgaa aaatccgtgc aagtactttc ttcctgtgaa gctcttcttc ctactgcaga      2520
ggaggttggt attccagata gatgcattga tgccattgcc aggaatgctt gtcaagagca      2580
acttgtatcc agtctatctc gtttagattg tgatagtgga tctttggaac ttaaggacag      2640
gtgtcttgaa tggtgggtcg aagatttttc tgttctgagt attgatttt atcgcagagt        2700 tatcatggca atgggacatg ctggggtaca catagacagc attattgcgt ccttgatgca      2760
ttatgcccag gtctctctaa agggtattgg gaaaccgcaa atttggaatc cagccagatc      2820
gtatccttgt aagggagaaa aggggcagag aacaataata gaaactcttg ttagtctatt      2880
gcctccagaa aagagttcat ctgttcctct gaatttttctt tttgggatgt tgaggatagg      2940
tatcatggtg gatgccacgc tagcctgcag gcttgaaatt gagaggagga ttgccttccg      3000
gctggaaatg gtcttacttg atgatttgct tataccatct gtccagacta caggtgattc      3060
tttgtttgat gttgacacgg tcaagcggat attgatacat ttcctccaaa ggattgacca      3120
ggaagaaaat gaagattgtg gatatgaatc agaaggtatt gattctccaa gccatggcgc      3180
tctattgaaa gttggacggc tgatagacac atatcttgct gaaatagctc ctgatccata      3240
tttgagtctc gacaaattca ctgctatgat atcaatgttg cctgattatg ctcgtgtaat      3300
tgatgacgga ctttacagag ctattgatgt ttatttgaag gtgaattttc aagttttttag      3360 ttatagacct gtatattgtt ctagcaatgc cttctaatga taacatgttc tttatattgg      3420
tggtttgaat attcttcttt gcgcatataa tgttgtgttt aaccctgaaa gctgtttaat      3480
```

-continued

```
gcttttagta aaatcacatc tcaacccctt ataaacatag ttttagttga atctgccatt      3540
tatctctttg tgaactttac taggcccatc caacgctaag tgagcatggc gcgaagaagc      3600
tgtgcaagtt catagattgc cagaagctct ctcaagaagc atgcaatcat gcagcacaga      3660
atgagagact cccagttcaa atgactgtcc gagttctcta ctttgagcag ctccgcctta      3720
agaatgctct atctggaagt tgtggagata cttttgtatc acaaaagatc agtagtggtc      3780
ttacaagtgc agctatgtcg cctagagata cttacgcttc tttaaggaga gagaaccgag      3840
aactgaagct ggagatatca agaatgaggg taaggctcag tgacctggag aaggaacaag      3900
tgttcatgaa acaaggtatg atggataaaa caggacatgg gaaaacattc ttaacttccc      3960
tttctagagg cataggaaga attggtatat ttggcagtcc ttctggagaa aaacatcaca      4020
agtcgggtcg caaatccagg acatcagaag gtaaaactgg taggagtagg aggtattctc      4080
tttcctagaa aaggttgtat gccacaatgt aaannnnnnn nnnnnnnnnn nnnnnnnnn       4139
```

```
<210> SEQ ID NO 25
<211> LENGTH: 663
<212> TYPE: PRT
<213> ORGANISM: Artificial Sequence
<220> FEATURE:
<223> OTHER INFORMATION: Nitab4.5_0000048g0280.2 amino acid sequence

<400> SEQUENCE: 25

Met Ala Met His Pro Ser Ala Lys Cys Ala His Phe Cys Ile Asn Ser
1               5                   10                  15

Leu Ala Phe Ser Leu Cys Ile Ile Tyr His Ser His Phe Pro Phe Leu
            20                  25                  30

Val Phe Phe Gln Arg Leu Leu Leu Leu Val Leu Gly Phe Asp Cys Lys
        35                  40                  45

Ser Ala Ala Asp Gly Ala Ala Ala Leu Lys Ser Lys Val Lys Leu Lys
    50                  55                  60

Phe Leu Thr Thr His Thr Arg Met Val Ser Pro Tyr Asn Ser Phe Thr
65                  70                  75                  80

Thr Arg Thr Ile Phe Ser Glu Val Ala Gly Asp Ile Thr Ile Ala Ala
                85                  90                  95

Asn Gly Glu Ser Phe Leu Leu His Lys Phe Pro Leu Val Ser Leu Ser
            100                 105                 110

Gly Lys Ile Gln Lys Met Val Ala Asp Ala Asn Asp Pro Asn Leu Pro
        115                 120                 125

Glu Leu Asp Leu Thr His Val Pro Gly Gly Pro Glu Thr Phe Glu Leu
    130                 135                 140

Ala Ala Lys Phe Cys Tyr Gly Met Asn Phe Glu Ile Thr Thr Thr Asn
145                 150                 155                 160

Val Ala Arg Leu Arg Cys Val Ala Glu Tyr Leu Glu Met Thr Glu Asp
                165                 170                 175

Tyr Arg Glu Glu Asn Leu Ile Ala Arg Thr Glu Thr Phe Leu Asp Glu
            180                 185                 190

Val Val Ser Pro Ser Leu Glu Lys Ser Val Gln Val Leu Ser Ser Cys
        195                 200                 205

Glu Ala Leu Leu Pro Thr Ala Glu Glu Val Gly Ile Pro Asp Arg Cys
    210                 215                 220

Ile Asp Ala Ile Ala Arg Asn Ala Cys Gln Glu Gln Leu Val Ser Gly
225                 230                 235                 240

Leu Ser Arg Leu Asp Cys Asp Thr Gly Ser Leu Glu Leu Lys Asp Arg
            245                 250                 255
```

-continued

```
Cys Leu Glu Trp Trp Val Glu Asp Leu Ser Ala Leu Ser Ile Asp Phe
            260                 265                 270

Tyr Arg Arg Val Ile Met Ala Met Gly His Val Gly Val His Ile Asp
            275                 280                 285

Ser Ile Ile Ala Ser Leu Met His Tyr Ala Gln Val Ser Leu Lys Gly
            290                 295                 300

Ile Gly Lys Pro Gln Ile Trp Asn Pro Ala Arg Ser Tyr Pro Cys Lys
305                 310                 315                 320

Gly Glu Lys Gly Gln Arg Thr Ile Ile Glu Thr Leu Val Ser Leu Leu
                325                 330                 335

Pro Pro Glu Lys Ser Ser Ser Val Pro Leu Asn Phe Leu Phe Gly Val
                340                 345                 350

Leu Arg Ile Gly Ile Met Val Asp Ala Thr Leu Ala Cys Arg Leu Glu
                355                 360                 365

Ile Glu Arg Arg Ile Ala Phe Arg Leu Glu Met Val Leu Leu Asp Asp
            370                 375                 380

Leu Leu Ile Pro Ser Val Gln Thr Thr Gly Asp Ser Leu Phe Asp Val
385                 390                 395                 400

Asp Thr Val Lys Arg Ile Leu Ile His Phe Leu Gln Arg Ile Asp Gln
                405                 410                 415

Glu Glu Asn Glu Asp Cys Gly Tyr Glu Ser Gln Gly Ile Asp Ser Pro
                420                 425                 430

Ser His Gly Ala Leu Leu Lys Val Gly Arg Leu Ile Asp Thr Tyr Leu
            435                 440                 445

Ala Glu Ile Ala Pro Asp Pro Tyr Leu Ser Leu Asp Lys Phe Thr Ala
            450                 455                 460

Met Ile Ser Val Leu Pro Glu Tyr Ala Arg Val Ile Asp Asp Gly Leu
465                 470                 475                 480

Tyr Arg Ala Ile Asp Val Tyr Leu Lys Ala His Pro Thr Leu Ser Glu
                485                 490                 495

His Glu Ala Lys Lys Leu Cys Lys Phe Ile Asp Cys Gln Lys Leu Ser
            500                 505                 510

Gln Glu Ala Cys Asn His Ala Ala Arg Asn Asp Arg Leu Pro Val Gln
            515                 520                 525

Met Thr Val Arg Val Leu Tyr Phe Glu Gln Leu Arg Leu Lys Asn Ala
            530                 535                 540

Leu Ser Gly Ser Cys Gly Asp Thr Phe Val Ser Gln Lys Ile Ser Ser
545                 550                 555                 560

Gly Leu Thr Ser Ala Ala Met Ser Pro Arg Asp Thr Tyr Ala Ser Leu
                565                 570                 575

Arg Arg Glu Asn Arg Glu Leu Lys Leu Glu Ile Ser Arg Met Arg Val
                580                 585                 590

Arg Leu Ser Asp Leu Glu Lys Glu Gln Val Phe Met Lys Gln Gly Met
                595                 600                 605

Met Asp Lys Thr Gly His Gly Lys Thr Phe Leu Thr Ser Leu Ser Arg
            610                 615                 620

Gly Ile Gly Arg Ile Gly Ile Phe Ser Ser Pro Ser Gly Glu Lys His
625                 630                 635                 640

His Lys Ser Gly Arg Lys Ser Arg Thr Ser Glu Gly Lys Thr Gly Arg
                645                 650                 655

Ser Arg Lys Tyr Ser Leu Ser
                660
```

-continued

<210> SEQ ID NO 26
<211> LENGTH: 1992
<212> TYPE: DNA
<213> ORGANISM: Artificial Sequence
<220> FEATURE:
<223> OTHER INFORMATION: Nitab4.5_0000048g0280.2 coding sequence

<400> SEQUENCE: 26

```
atggccatgc acccttctgc caaatgtgcc catttctgta ttaattcttt agctttttct      60
ctttgtatta tttatcactc acatttcccc tttttggtct tctttcaacg cttattgttg     120
cttgtcttgg gatttgactg caagagtgct gcagatggtg ctgctgctct aaagtctaaa     180
gtgaagctca agtttcttac aactcataca agaatggtgt ctccttacaa ctcatttacc     240
actcgcacta tattctctga agttgctggg gatattacaa ttgctgcaaa tggagagtct     300
ttcctactgc ataagtttcc cctggtatct ttgagtggaa agatccagaa gatggtggcg     360
gatgccaacg atccaaatct cccagaattg gatttgactc acgtaccagg aggacctgaa     420
acatttgaac tggctgcaaa gttttgttat ggcatgaact ttgagatcac aaccacaaac     480
gtagcacgtt tgcgctgtgt ggcagaatac ttggaaatga cagaagatta tcgtgaagag     540
aatctcattg caagaacaga aactttcctt gatgaagttc tctctccaag tcttgaaaaa     600
tccgtgcaag tactttcttc ctgtgaagcc ctgcttccta ctgcagagga ggttggtatt     660
ccagatagat gcattgatgc cattgccagg aatgcttgtc aggagcaact tgtatccggt     720
ctatctcgtt tagattgtga tactggatct ttggaactta aggacaggtg tcttgaatgg     780
tgggtcgaag atctatctgc tctgagtatt gatttttatc gcagagttat catggcaatg     840
ggacatgttg gggtacacat cgacagcatt attgcgtcct tgatgcatta cgcccaggtc     900
tctctaaagg gtattgggaa accgcaaatt tggaatccag ccagatcgta tccttgtaag     960
ggagaaaagg ggcagagaac aataatagaa actcttgtta gtctattgcc tccagaaaag    1020
agttcatctg ttccgctgaa ttttcttttt ggggtgttga ggataggtat catggtggat    1080
gccacgctag cctgcaggct tgaaattgag aggaggattg ccttcaggct ggaaatggtc    1140
ttacttgatg atttgcttat accatctgtc cagactacag gtgattcttt gtttgatgtt    1200
gacactgtca agcggatatt gatacatttc ctccaaagga ttgaccagga agaaaatgaa    1260
gattgtggat atgaatcaca aggtattgat tctccaagcc atggcgctct attgaaagtt    1320
ggacggctga tagacacata tcttgctgaa atagctcctg atccatattt gagtcttgac    1380
aaattcactg ctatgatatc agtgttgcct gagtatgctc gtgtaattga tgacggactt    1440
tacagagcta ttgatgttta tttgaaggcc catccaacgc taagtgagca tgaagcgaag    1500
aagctgtgca agttcataga ttgccagaag ctctctcaag aagcatgcaa tcatgcagca    1560
cggaatgaca gactcccagt tcaaatgact gtccgagttc tctactttga gcagctccgc    1620
cttaagaatg ctctatccgg aagttgtgga gatacttttg tatcacaaaa gatcagtagt    1680
ggtcttacaa gtgcagctat gtcgcctaga gatacttatg cttctttaag gagagagaac    1740
cgagaactaa agctggagat atcaagaatg agggtaaggc tcagtgacct ggagaaggaa    1800
caagtgttca tgaaacaagg tatgatggat aaaacaggac atggaaaaac attcttaact    1860
tccctttcaa gaggtatagg aagaattggt atatttagca gtccttctgg agaaaaacat    1920
cacaagtcgg tcgcaaatc caggacatca gaaggtaaaa ctggtaggag taggaagtat    1980
tctctttcct ag                                                        1992
```

<210> SEQ ID NO 27
<211> LENGTH: 4246
<212> TYPE: DNA
<213> ORGANISM: Artificial Sequence
<220> FEATURE:
<223> OTHER INFORMATION: Nitab4.5_0000048g0280.2 genomic sequence

<400> SEQUENCE: 27

```
caattaacta cgttttaatc ctaaaatagt tggatgatta tatgaattat ctatatctgc     60
ttcactctag ctactaatgt gtaaagaatt catcaaaatt tgatactagt ctactagtat    120
tagactaagt agattagagt ttcgataata taatgatgat ataaacattg gtaaggtaga    180
gacaaaggaa taaaaagcaa aaggggaaaa ggtattttgt gttgcagtaa aacacttcac    240
atggccatgc acccttctgc caaatgtgcc catttctgta ttaattcttt agcttttttct    300 ctttgtatta tttatcactc acatttcccc tttttggtct tctttcaacg cttattgttg    360
cttgtcttgg gatttgactg caagagtgct gcagatggtg ctgctgctct aaagtctaaa    420
gtgaagctca agtttcttac aactcataca agaatggtgt ctccttacaa ctcatttacc    480
actcggtaat ctccatcttc atgtctctat gtggtacaca tgactgttga tcatcccttt    540
agaatttcaa gaattattcg gctacagtaa taaatagttt aacagagtaa tttgtttgga    600
taaatagttt aaaagaccta tttactgcaa attatgagtt ggccatggtt tttgatcatc    660
atattctgaa tgtccatttt caatgaattt agtctttgag cttgatttga gctaccccac    720
ctcctccagt agcccatctt ggctgccctg cttgatgatt catgctatga ttatattgtt    780
tcctcactcc aattattata ttttcagtat tcattgcacc ttacgaaaat ctctcttttg    840
ttttttttcc acggaatatt acttataggg attacttaac attatccttt ccaaattccc    900
tcctgtgaat agttacagga aggccttgct tatggaagta actctttctt ctgacattta    960
tatgctttct ttgagtatgt cattgtctct ttagtatgct atttcacata atttgaaagt   1020
gctactactg tgaacttgaa tatttgtgtc ctatcttatc atcttcttca ttttcaccga   1080
taaacttgat ctgtcattag gaggaaatgc atcactttac ccaagacttc ctaattcatc   1140
tgttatttca tgaataatta ataaaatacc acaaatttat gacatggtaa atttattatg   1200
gcaaatcaat actttgtcat gtcaaaatca ttgcgtaata aataaactta ttcgtgatga   1260
tattgatcag cactatattc tctgaagttg ctggggatat tacaattgct gcaaatggag   1320
agtctttcct actgcataag gtactttcct gtcttcactt tctccagtct ttctttcaga   1380
aactttgtgc ctttggataa tttatgaagg tttgaacttc aaataaggtt agcaatatat   1440
ataaatcatc aggatataat atgtgttcaa gatcatgcat agtaggagag ggtgggctt    1500 tgtttaaaga cacttgtttg tttcctcttg gttgctaact agatagattg agattgtgat   1560
ggtggtaaaa tttgaaattc agaggattat cagagttggt tgacaatgtt cctgtagttt   1620
gatggattat taagattgga aaaccaaagt ttccattaat ggtgtatttg actatcaaaa   1680
aaagctacaa tacaattgtt gtagtgatgg tatacgtaat gtaagctaac tttaagatca   1740
caattttgga acaaattgaa gtttgaaaag aactccagct ggcatgtaat gcagctaaaa   1800
ataattctgt atctagaagc aagccccttg taacttgttg ttgtctttag accaacttta   1860
tcatgcctcg tcaagggcac tactagatga gatgacgcat cttatacatt gaaactttta   1920
attcaagcac ccagtggtaa tgacagtgaa gtctgtcata ttaaggacac tttagcaaat   1980
gattgaaatg gtcattcttt taggagtagc attgcgacaa atgctttcca gaaatcaatt   2040
ttatgattat aacatgtgaa tcttagcctt gtctgggcgt ttcatcatga actatttaat   2100
```

```
aattaactta tctcttcctt attcgacatt attagttaat tgcatacatc attcttgaag      2160
ttgataatta tgtgatgttt acaatagttt cccctggtat ctttgagtgg aaagatccag      2220
aagatggtgg cggatgccaa cgatccaaat ctcccagaat tggatttgac tcacgtacca      2280
ggaggacctg aaacatttga actggctgca aagttttgtt atggcatgaa ctttgagatc      2340
acaaccacaa acgtagcacg tttgcgctgt gtggcagaat acttggaaat gacagaagat      2400
tatcgtgaag agaatctcat tgcaagaaca gaaactttcc ttgatgaagt tgtctctcca      2460
agtcttgaaa aatccgtgca agtactttct tcctgtgaag ccctgcttcc tactgcagag      2520
gaggttggta ttccagatag atgcattgat gccattgcca ggaatgcttg tcaggagcaa      2580
cttgtatccg gtctatctcg tttagattgt gatactggat cttttggaact taaggacagg      2640 tgtcttgaat ggtgggtcga agatctatct gctctgagta ttgattttta tcgcagagtt      2700
atcatggcaa tgggacatgt tggggtacac atcgacagca ttattgcgtc cttgatgcat      2760
tacgcccagg tctctctaaa gggtattggg aaaccgcaaa tttggaatcc agccagatcg      2820
tatccttgta agggagaaaa ggggcagaga acaataatag aaactcttgt tagtctattg      2880
cctccagaaa agagttcatc tgttccgctg aattttcttt ttggggtgtt gaggataggt      2940
atcatggtgg atgccacgct agcctgcagg cttgaaattg agaggaggat tgccttcagg      3000
ctggaaatgg tcttacttga tgatttgctt ataccatctg tccagactac aggtgattct      3060
ttgtttgatg ttgacactgt caagcggata ttgatacatt tcctccaaag gattgaccag      3120
gaagaaaatg aagattgtgg atatgaatca caaggtattg attctccaag ccatggcgct      3180
ctattgaaag ttggacggct gatagacaca tatcttgctg aaatagctcc tgatccatat      3240
ttgagtcttg acaaattcac tgctatgata tcagtgttgc ctgagtatgc tcgtgtaatt      3300
gatgacggac tttacagagc tattgatgtt tatttgaagg tgaattttca agtttttagt      3360
tatagacctg tatattattc tagcaatccc tgctaatgat aacatgttct ttatattggt      3420
ggtctgaata ttcttctttg cgcatataaa gtgcacaaaa agaatatgtt gtgttttaac      3480
cctgcaagct gtttaatgct ttaagtaaaa tcacatctca accccttata aacatagttt      3540
tagttgattc tgccatttat ctctttgtga acttcactag gcccatccaa cgctaagtga      3600
gcatgaagcg aagaagctgt gcaagttcat agattgccag aagctctctc aagaagcatg      3660
caatcatgca gcacggaatg acagactccc agttcaaatg actgtccgag ttctctactt      3720
tgagcagctc cgccttaaga atgctctatc cggaagttgt ggagatactt ttgtatcaca      3780
aaagatcagt agtggtctta caagtgcagc tatgtcgcct agagatactt atgcttcttt      3840
aaggagagag aaccgagaac taaagctgga gatatcaaga atgagggtaa ggctcagtga      3900
cctggagaag gaacaagtgt tcatgaaaca aggtatgatg gataaaacag gacatggaaa      3960
aacattctta acttcccttt caagaggtat aggaagaatt ggtatattta gcagtccttc      4020
tggagaaaaa catcacaagt cgggtcgcaa atccaggaca tcagaaggta aaactggtag      4080
gagtaggaag tattctcttt cctagaaaag cttgtatgcc acaatgtaaa ttaatgcatg      4140
actcaagagt tttgcaaaag tggctaatta ttggtgagtg ctcgtttaat ttcttgctgt      4200
cctagccaat ctcttagata tcatgcttca cattgttgaa cttgtt                     4246
```

<210> SEQ ID NO 28
<211> LENGTH: 629
<212> TYPE: PRT
<213> ORGANISM: Artificial Sequence
<220> FEATURE:
<223> OTHER INFORMATION: Nitab4.5_0002006g0070.2 amino acid sequence

```
<400> SEQUENCE: 28

Met Gly Val Val Thr Val Ser Glu Leu Lys Pro Ser Ile Ser Gly Lys
1               5                   10                  15

Arg Ser Phe Arg Pro Ser Ser Ser Ala Arg His Ile Thr Glu Trp Pro
                20                  25                  30

Ile Ser Asp Val Ser Ser Asp Leu Thr Ile Glu Val Gly Ala Ala Ser
            35                  40                  45

Phe Ala Leu His Lys Phe Pro Leu Val Ser Arg Ser Gly Arg Ile Arg
        50                  55                  60

Lys Leu Leu Leu Glu Ala Lys Asp Thr Lys Ile Ser Arg Leu Asn Leu
65                  70                  75                  80

Thr Gly Leu Pro Gly Gly Ser Asp Ala Phe Glu Leu Ala Ala Lys Phe
                85                  90                  95

Cys Tyr Gly Val Asn Val Glu Ile Thr Ile Ser Asn Val Ala Met Leu
            100                 105                 110

Arg Cys Ala Ser Lys Phe Met Glu Met Asn Glu Asp Ile Ser Glu Lys
        115                 120                 125

Asn Leu Glu Ile Arg Thr Glu Val Phe Leu Lys Asp Thr Val Phe Thr
    130                 135                 140

Asn Ile Ser Asn Ser Ile Ser Val Leu His Arg Cys Glu Thr Leu Leu
145                 150                 155                 160

Pro Val Ser Glu Glu Val Asn Leu Val Ser Arg Leu Ile Asn Ala Ile
                165                 170                 175

Ala Asn Asn Ala Cys Lys Glu Gln Leu Thr Ser Gly Leu Ser Lys Leu
            180                 185                 190

Glu His Asn Phe Pro Pro Lys Pro Val Gln Ser Leu Asp Ser Glu Thr
        195                 200                 205

Pro Ile Asp Trp Trp Gly Lys Ser Leu Thr Val Leu Asn Leu Asp Phe
    210                 215                 220

Phe Gln Arg Val Val Ser Val Val Lys Ser Lys Gly Leu Lys Gln Asp
225                 230                 235                 240

Ile Ile Ser Arg Ile Leu Ile Asn Tyr Ala Lys Asn Ser Leu Gln Gly
                245                 250                 255

Leu Phe Ile Lys Asp Pro Gln Leu Val Lys Gly Ser Phe Leu Asp Leu
            260                 265                 270

Asp Leu Gln Lys Arg Gln Arg Val Ile Val Glu Thr Ile Ala Ser Leu
        275                 280                 285

Leu Pro Thr Gln Ser Arg Lys Ser Thr Val Pro Met Ala Phe Leu Ser
    290                 295                 300

Ser Leu Leu Lys Ser Ala Ile Ala Ala Ser Ala Ser Thr Ser Cys Arg
305                 310                 315                 320

Ser Asp Leu Glu Arg Arg Ile Gly Leu Gln Leu Asp Gln Ala Ile Leu
                325                 330                 335

Glu Asp Ile Leu Ile Pro Ala Asn Pro His Gly Asn Asn His Ser Pro
            340                 345                 350

Leu Tyr Asp Ile Asp Ser Ile Leu Arg Ile Phe Ser Phe Phe Leu Asn
        355                 360                 365

Leu Asp Glu Asp Asp Glu Glu Asp Asn Thr Leu Arg Asp Glu Ser Glu
    370                 375                 380

Met Val Tyr Asp Phe Asp Ser Pro Gly Ser Pro Lys His Ser Ser Ile
385                 390                 395                 400

Val Lys Val Ser Lys Leu Leu Asp Asn Tyr Leu Ala Glu Val Ala Leu
```

```
                  405              410              415
Asp Ser Asn Leu Thr Pro Ser Lys Tyr Ile Ala Leu Ala Glu Leu Leu
            420              425              430

Pro Asp His Ala Arg Leu Val Tyr Asp Gly Leu Tyr Arg Ala Val Asp
        435              440              445

Ile Phe Leu Lys Val His Pro Asn Ile Lys Asp Ser Glu Arg Tyr Arg
    450              455              460

Leu Cys Lys Thr Ile Asp Cys Gln Lys Leu Ser Gln Glu Ala Cys Ser
465              470              475              480

His Ala Ala Gln Asn Glu Arg Leu Pro Val Gln Met Ala Val Gln Val
            485              490              495

Leu Tyr Phe Glu Gln Ile Arg Leu Arg Asn Ala Met Asn Gly Gly His
            500              505              510

Asn Gln Phe Phe Gly Met Asn Asn Gln Phe Pro Gln Arg Ser Gly Ser
            515              520              525

Gly Ala Gly Ser Gly Cys Ile Ser Pro Arg Asp Asn Tyr Ala Ser Val
    530              535              540

Arg Arg Glu Asn Arg Glu Leu Lys Leu Glu Val Ala Arg Met Arg Met
545              550              555              560

Arg Leu Thr Asp Leu Glu Lys Asp His Val Ser Met Lys Gln Glu Leu
            565              570              575

Val Lys Ser His Pro Ala Asn Lys Leu Phe Lys Ser Phe Thr Lys Lys
            580              585              590

Leu Ser Lys Leu Asn Ala Leu Phe Arg Ile Lys Asp Leu Lys Pro Ile
            595              600              605

Gly Gly Lys Ala Asn Ser Glu Ser Arg Leu Leu Phe Gln Lys Arg Arg
    610              615              620

Arg His Ser Val Ser
625
```

```
<210> SEQ ID NO 29
<211> LENGTH: 1890
<212> TYPE: DNA
<213> ORGANISM: Artificial Sequence
<220> FEATURE:
<223> OTHER INFORMATION: Nitab4.5_0002006g0070.2 coding sequence

<400> SEQUENCE: 29
atgggagttg tcactgtttc tgaactgaag ccaagcatat ctgggaaaag gtcttttcgt      60
ccaagttcca gtgccagaca tattactgaa tggccaatat ctgatgtttc tagtgatctt     120
acaatagaag taggagctgc cagttttgct cttcacaagt ttcctctagt ttcccgaagc     180
ggaagaatta gaaagctgct gctagaggca aaggatacaa agatttcaag actcaatctt     240
accggtcttc ctggcggatc tgatgcattt gaacttgctg ctaagttctg ttatggcgtg     300
aacgttgaga ttaccatatc aaacgtggcg atgctaagat gtgcatccaa gttcatggaa     360
atgaacgaag acatctccga gaaaaacctg gaaattcgta ctgaagtatt ccttaaagat     420
acagtattca caaacatatc caactcgata tctgttcttc atcgctgtga aacactacta     480
ccggtatctg aagaagtcaa tctcgttagt cgattaatca atgcaattgc aaacaatgct     540
tgtaaagagc aactaacatc tggtttgtca agctggagc ataacttccc acccaaacct     600
gttcaaagcc ttgattctga cacccaata gactggtggg aaaatcatt gactgtgcta      660 aatctagatt ttttccagag agttgtatct gtagtgaagt caaaaggtct taaacaagac     720
attatcagca gaattttgat aaattatgcc aaaaaattcac ttcagggact tttcatcaag     780
```

```
gatcctcagt tggttaaagg aagtttcttg gatttggatt tgcagaaaag gcaaagggtt      840
atcgtcgaaa caatagctag cttactacca acacaatcca ggaaaagtac agtcccaatg      900
gcttttcttt caagtttgtt aaaatctgca atagcagcat cagcatccac ttcttgcaga      960
tctgatctag agaggcgcat tggtctgcag ctagatcagg caattctaga agatattctc     1020
atacctgcaa atccacatgg gaacaaccac agccctctct acgacataga ttctattttg     1080
aggatctttt cctttttctt gaatttggat gaggatgatg aagaggacaa cacactaaga     1140
gatgaaagcg aaatggttta cgactttgat agtcctggat ctcccaaaca tagctcaatt     1200
gttaaggtgt caaagttatt ggacaattat ctagcagaag ttgcactcga ttctaacctc     1260
acgccatcga agtatatagc actggctgag ttacttccag accacgcgcg tctagtttat     1320
gatggattat atcgagctgt agatattttc ctcaaggttc atcccaacat taaggactcg     1380
gaacgctatc gtctctgtaa aactattgat tgccagaaac tatcacaaga agcttgcagt     1440
catgcagcac aaaatgaacg gttgcctgtg caaatggcgg tccaagtgct atacttcgaa     1500
caaatcaggc tgagaaatgc gatgaacggg ggacataacc aattctttgg aatgaataat     1560
cagttccccc agcgttcagg cagcggagca ggaagcggat gcatctctcc gagagataac     1620
tacgcatcag tcaggagaga aaatagagaa ctgaagctcg aggttgcaag aatgagaatg     1680
aggcttacag atttagagaa agatcatgtt tccatgaaac aggagctagt aaagtcacat     1740
cctgccaata agttattcaa gtcatttaca aagaaattaa gcaagctgaa tgcactattc     1800
cgaataaaag atttaaaacc aataggaggg aaagctaact cagaaagccg gttacttttt     1860
cagaagagaa ggcgccattc ggtttcttga                                      1890
```

```
<210> SEQ ID NO 30
<211> LENGTH: 4787
<212> TYPE: DNA
<213> ORGANISM: Artificial Sequence
<220> FEATURE:
<223> OTHER INFORMATION: Nitab4.5_0002006g0070.2 genomic sequence
<220> FEATURE:
<221> NAME/KEY: misc_feature
<222> LOCATION: (1228)..(1241)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t

<400> SEQUENCE: 30
```

```
ggagtggtta atggttttgg ggaagttgag attctgctga gagaagatgg gagttgtcac       60
tgtttctgaa ctgaagccaa gcatatctgg gaaaaggtct tttcgtccaa gttccagtgc      120
cagacatatt actgaatggt atatttactc tctcttctat ctcaccaaac aactgctact      180
ttcacattac taatattta tgcccagctt ttcatttgtg tcatattttc ttaaaagaat      240
ttacatggat agtactgtaa ggatattcca cagaccattt tgatgatgta tcaatttcta      300
caattaatat ttcctacaac acttaagacg tggaaaagtc catattggta tagctagatg      360
atagcatgaa ttcttgttag ttgggtactt gtgattgtca attatgctga gttctaataa      420
aaggctcagt cctagacaaa ggatacatct tttcttttgg catagtaaaa ttagctaact      480
tggttccccc cccccccccc agatactaat actatgagat tataaaaagg gagtttctgc      540
```

```
aatttatcac taaaagttcc acttagagga agaagtttac tggtaacaac taaatggatc       600
atagaagaat taatgcaagg aaaaaactaa actcttcaac caccaaagta tctgaattta       660
tgagttaggt gattggacag aatttagttt ccaacattta tgacaaacca tgttcaggtg       720
ctgactaagt ggaaatggca atatacttat agctttagaa attgattgtg atggaactta       780
tcttaaaatc taagaatcta aagttattat cagatcctaa agtaaataaa agaaaacagc       840
agagtatgag tatacatgag cagtttctag ggctgcaatc attgaaaatg acaaatcaaa       900
tatttgactt tttaccacct acaacaaatg atagtggccc tgattccaat gtgttcaagt       960
ttcttgtttc aacatgtggt gtgaacggtg tagacagcta ctccctccgt ttcaatttat      1020
gtgaacccat ttgagtgggc acgaaattta agaaaagaga gaacttttaa actgtgttgt      1080
aaaatgaggg cacatatatt ttgtgtggct ataaatcatt gcataaaggt aaaataaacgg     1140 aggtagtata ttatttccct agttttcaac atatgtatct aatgagggcc ctctaccaag      1200
tacagatgag tcctgcaatt atctgttnnn nnnnnnnnnn naaangncac atatattttg      1260
tgtggctata aatcattgca taaaggtaaa ttgtttccaa ataaggaaag gtgtcattct      1320
ttttggcacg gaccaaaaag gaaataagtt cacataaatt gaaacggagg tagtatatta     1380
tttccctagt tttcaacata tgtatctaat gagggccctc taccaagtac agatgagtcc      1440
tgcaattatc tgttagatta ctacagacca caagataaat cacaaccagg aataaatttc      1500
aaagaaacca gaatatgact accacttgct atgttggatc taaacacatt gaataatctt      1560
tgtatccatt caagatattt gttttgagct tttccactca tagtgtccta tgatactttt      1620
ggtcgtaaat tgtggccgta tgtacaagcg ctagagcacg ataacatatg ctccccgaac      1680
cgttaaggtt tcatccgctt gaatttggat agctttaagg ttccaatatc cagcattaca      1740
gtgttgagat gtaagttgca ccatgtattg aaacttaggc taaaaatata aacagagaag      1800
tttattagta tatgtttttt tctcgacaca tttcctgttt ccggctttta atcattgacc      1860
atatattcta ttgcaggcca atatctgatg tttctagtga tcttacaata gaagtaggag      1920
ctgccagttt tgctcttcac aaggtacaaa tatgaagtat tagatcattc gtcttctcgt      1980
gtattttgat ctaccaatct tttcaaaatt ggaatgctca agtctatcaa aagcataaat      2040
tttgcaaaga aatggctgtc taatgtagct tgaaaatgat ttataagtta gctgttataa      2100
gtaggcaact gatattagga cagtcgtgtc cacatcggaa tttatttcat ggtgtcaaaa      2160
tagggaggga aaagaaaagt aaaaaggcag atgtaaaaac agaacttaag catcagtctg      2220
aaggtcagaa acaacagctg aagttgtttc aatgtagtgg atcttagact aagttatgtg      2280
cttcctgtta aaattaagaa aaatgaagga agaatacctt ggaaacattt ctaatgtgat      2340
tgctaatatc acactgtttg cagtttcctc tagtttcccg aagcggaaga attagaaagc      2400
tgctgctaga ggcaaaggat acaaagattt caagactcaa tcttaccggt cttcctggcg      2460
gatctgatgc atttgaactt gctgctaagt tctgttatgg cgtgaacgtt gagattacca      2520
tatcaaacgt ggcgatgcta agatgtgcat ccaagttcat ggaaatgaac gaagacatct      2580
ccgagaaaaa cctggaaatt cgtactgaag tattccttaa agatacagta ttcacaaaca      2640
tatccaactc gatatctgtt cttcatcgct gtgaaacact actaccggta tctgaagaag      2700
tcaatctcgt tagtcgatta atcaatgcaa ttgcaaacaa tgcttgtaaa gagcaactaa      2760
catctggttt gtcaaagctg gagcataact tcccacccaa acctgttcaa agccttgatt      2820
ctgagacacc aatagactgg tggggaaaat cattgactgt gctaaatcta gattttttcc      2880
agagagttgt atctgtagtg aagtcaaaag gtcttaaaca agacattatc agcagaattt      2940
```

```
tgataaatta tgccaaaaat tcacttcagg gacttttcat caaggatcct cagttggtta    3000
aaggaagttt cttggatttg gatttgcaga aaaggcaaag ggttatcgtc gaaacaatag    3060
ctagcttact accaacacaa tccaggaaaa gtacagtccc aatggctttt ctttcaagtt    3120
tgttaaaatc tgcaatagca gcatcagcat ccacttcttg cagatctgat ctagagaggc    3180
gcattggtct gcagctagat caggcaattc tagaagatat tctcatacct gcaaatccac    3240
atgggaacaa ccacagccct ctctacgaca tagattctat tttgaggatc ttttcctttt    3300
tcttgaattt ggatgaggat gatgaagagg acaacacact aagagatgaa agcgaaatgg    3360
tttacgactt tgatagtcct ggatctccca aacatagctc aattgttaag gtgtcaaagt    3420
tattggacaa ttatctagca gaagttgcac tcgattctaa cctcacgcca tcgaagtata    3480
tagcactggc tgagttactt ccagaccacg cgcgtctagt ttatgatgga ttatatcgag    3540
ctgtagatat tttcctcaag gtaagctgct taacctcatc cacattatct cactcacctg    3600
ttcaaaacaa ttagtatttc tcatgtgagt agtctaacaa tggaaactac acatatacta    3660
ttttttatac ttttcgtata aataatagcc gacaaaatat atattttta tatattaaca    3720 tgtaatatac atgttttata cataattagt atatactttt cgtatatttg gttagtcata    3780
aagttgctgc catgtgacca ggagatcacg ggttcgagcc gtggaagcaa cctcttgcag    3840
aaatgcaggg caaggctgtg tacaatagac ccttgtggtc cggccctttt ccagaccttg    3900
cgcgtagcgg gagcttaact gccctttta tatttagcta gcggatgtaa ttattttgg    3960 ctgatcggcc aaatgtgttt taatacaatg catgacattc tcacggcagg ttcatcccaa    4020
cattaaggac tcggaacgct atcgtctctg taaaactatt gattgccaga aactatcaca    4080
agaagcttgc agtcatgcag cacaaaatga acggttgcct gtgcaaatgg cggtccaagt    4140
gctatacttc gaacaaatca ggctgagaaa tgcgatgaac gggggacata accaattctt    4200
tggaatgaat aatcagttcc cccagcgttc aggcagcgga gcaggaagcg gatgcatctc    4260
tccgagagat aactacgcat cagtcaggag agaaaataga gaactgaagc tcgaggttgc    4320
aagaatgaga atgaggctta cagatttaga gaaagatcat gtttccatga aacaggagct    4380
agtaaagtca catcctgcca ataagttatt caagtcattt acaaagaaat taagcaagct    4440
gaatgcacta ttccgaataa aagatttaaa accaatagga gggaaagcta actcagaaag    4500
ccggttactt tttcagaaga gaaggcgcca ttcggtttct tgatgctcta ctctaatgtg    4560
aataagaaag agtatacagt gtttcacatt gctgaatttg gatgtgttga gagtgaagtt    4620
attgctttgc gttttgatcg tatccttgaa agaagagact cactcaaact tttactataa    4680
aggtatataa acaagtgtga gtttttttag cttcatgtag tttgcactac acgatcatcg    4740
agaaaatttt acaattgctc tttcccaata tttcttgtac tcatttg              4787
```

```
<210> SEQ ID NO 31
<211> LENGTH: 98
<212> TYPE: PRT
<213> ORGANISM: Artificial Sequence
<220> FEATURE:
<223> OTHER INFORMATION: BTB/POZ homodimerization domain

<400> SEQUENCE: 31

Ser Gln Glu Ile Pro Ser Asp Val Thr Val Asn Ala Gly Gly Ser Ala
1               5                   10                  15

Phe Ser Leu His Lys Phe Pro Leu Val Ser Lys Ser Gly Tyr Ile Arg
            20                  25                  30
```

```
Lys Ile Ile Ser Glu Ser Asn Asp Ala Asp Val Ser Ile Val Glu Ile
        35                  40                  45

Pro Asp Ile Pro Gly Gly Ser Asp Ala Phe Glu Leu Ala Ala Lys Phe
    50                  55                  60

Cys Tyr Gly Ile Asn Phe Glu Ile Ser Thr Glu Asn Ile Ala Leu Leu
65                  70                  75                  80

Arg Cys Thr Ala Glu Tyr Leu Glu Met Thr Glu Asp Tyr Ala Val Gly
                85                  90                  95

Asn Leu

<210> SEQ ID NO 32
<211> LENGTH: 275
<212> TYPE: PRT
<213> ORGANISM: Artificial Sequence
<220> FEATURE:
<223> OTHER INFORMATION: NPH3 domain sequence

<400> SEQUENCE: 32

Asp Trp Trp Ala Glu Asp Leu Ala Val Leu Arg Ile Asp Phe Phe Gln
1               5                   10                  15

Arg Val Leu Ile Ala Met Met Gly Arg Gly Phe Lys Gln Tyr Ala Leu
            20                  25                  30

Gly Pro Ile Leu Met Leu Tyr Ala Gln Lys Ser Leu Arg Gly Leu Glu
        35                  40                  45

Ile Phe Gly Lys Gly Arg Lys Lys Ile Glu Pro Lys Gln Glu His Glu
    50                  55                  60

Lys Arg Val Val Leu Glu Thr Ile Val Ser Leu Leu Pro Arg Glu Lys
65                  70                  75                  80

Asn Ala Leu Ser Val Ser Phe Leu Ser Met Leu Leu Arg Ala Ala Ile
                85                  90                  95

Tyr Leu Glu Thr Thr Val Ala Cys Arg Leu Asp Leu Glu Lys Arg Met
                100                 105                 110

Ala Leu Gln Leu Gly Gln Ala Val Leu Asp Asp Leu Leu Ile Pro Ser
            115                 120                 125

Tyr Ser Phe Thr Gly Asp Thr Leu Phe Asp Val Glu Thr Val Gln Arg
    130                 135                 140

Ile Ile Met Asn Phe Leu Asp Asn Glu Met Asp Gly Ser Arg Leu Gly
145                 150                 155                 160

Asp Glu Glu Tyr Val Ser Pro Ser Leu Ser Asp Met Glu Arg Val Gly
                165                 170                 175

Lys Leu Met Glu Asn Tyr Leu Ala Glu Ile Ala Ser Asp Arg Asn Leu
                180                 185                 190

Ser Val Ser Lys Phe Ile Ser Leu Ala Glu Val Ile Pro Glu Gln Ala
            195                 200                 205

Lys Ile Thr Glu Asp Gly Met Tyr Arg Ala Ile Asp Ile Tyr Leu Lys
    210                 215                 220

Ala His Pro Ala Leu Ser Asp Met Glu Arg Lys Lys Val Cys Gly Val
225                 230                 235                 240

Met Asp Cys Gln Lys Leu Ser Arg Glu Ala Cys Ala His Ala Ala Gln
                245                 250                 255

Asn Asp Arg Leu Pro Val Gln Thr Val Val Gln Val Leu Tyr Tyr Glu
                260                 265                 270

Gln Gln Arg
        275
```

-continued

```
<210> SEQ ID NO 33
<211> LENGTH: 374
<212> TYPE: PRT
<213> ORGANISM: Artificial Sequence
<220> FEATURE:
<223> OTHER INFORMATION: interactor, Nitab4.5_0000842g0110.2 protein
      sequence

<400> SEQUENCE: 33

Met Ala Ser Ser Ala Ile Phe His Phe Leu Pro Ser Ser Ser Ser Ser
1               5                   10                  15

Leu Thr Ser Leu Ser Phe Arg Asn Ser Arg Thr His Leu Ser Gln Thr
                20                  25                  30

Pro Asn Phe Tyr Lys Pro Leu Leu Val Lys Ala Ser Thr Ser Val Asn
            35                  40                  45

Phe Ser Ser Pro Ser Lys Ser Pro Thr Leu Thr Lys Asn Asn Asn Trp
    50                  55                  60

Leu Trp Lys Tyr Lys Asp Asn Ser Val Asn Ile Tyr Tyr Glu Glu His
65                  70                  75                  80

Asp Lys Gly Ser Asp Glu Pro Cys Lys Asn Val Leu Leu Ile Pro Thr
                85                  90                  95

Ile Ser Asp Val Ser Thr Val Glu Glu Trp Arg Ser Val Ala Lys Asp
            100                 105                 110

Ile Ala Gly Arg Ser Gly Lys Val Asn Tyr Arg Thr Thr Ile Val Asp
            115                 120                 125

Trp Pro Gly Leu Gly Tyr Ser Asp Arg Pro Lys Leu Asp Tyr Asn Ala
        130                 135                 140

Asp Val Met Glu Lys Phe Leu Ala Asp Phe Ile Asn Ala Pro Asn Ser
145                 150                 155                 160

Pro Val Asn Asn Ser Asp Lys Asp Leu Val Val Phe Gly Gly Gly His
                165                 170                 175

Ala Ala Thr Ile Ala Val Arg Ala Ala Lys Lys Gly Leu Val Lys Pro
                180                 185                 190

Thr Ala Ile Ala Ala Ile Ala Pro Thr Trp Ala Gly Pro Leu Pro Ile
            195                 200                 205

Val Phe Gly Arg Asp Ser Ser Met Glu Thr Arg Tyr Gly Leu Leu Arg
        210                 215                 220

Gly Thr Leu Arg Ala Pro Ala Val Gly Trp Met Met Tyr Asn Val Leu
225                 230                 235                 240

Val Ser Asn Glu Lys Ser Ile Gln Ser Gln Tyr Lys Ser His Val Tyr
                245                 250                 255

Ser Asp Pro Glu Lys Val Thr Pro Asp Ile Ile Glu Ser Arg Tyr Ala
                260                 265                 270

Leu Thr Lys Arg Gln Gly Ala Arg Tyr Val Pro Ala Ala Phe Leu Thr
            275                 280                 285

Gly Leu Leu Asp Pro Val Lys Ser Arg Glu Glu Phe Val Gln Leu Phe
        290                 295                 300

Ala Glu Leu Glu Gly Arg Ile Pro Val Leu Val Leu Ala Thr Ala Gly
305                 310                 315                 320

Ser Pro Lys Arg Ser Lys Ala Glu Met Glu Ala Leu Met Glu Ala Lys
                325                 330                 335

Gly Val Ser Lys Tyr Ile Glu Val Pro Gly Ala Leu Leu Pro Gln Glu
                340                 345                 350

Glu Tyr Pro Glu Ile Val Ala Glu Gln Leu Tyr Arg Phe Leu Gln Glu
            355                 360                 365
```

Lys Phe Glu Leu Gln Ala
    370

<210> SEQ ID NO 34
<211> LENGTH: 1125
<212> TYPE: DNA
<213> ORGANISM: Artificial Sequence
<220> FEATURE:
<223> OTHER INFORMATION: interactor, Nita4.5_0000842g0110.2 coding
      sequence

<400> SEQUENCE: 34
atggcatcct ctgctatttt ccactttctt ccatcatcat cttcttcctt gacttctctt      60
tccttcagaa acagcagaac ccatctttct caaaccccaa atttttacaa accccttta      120 gtaaaagctt ctacttctgt caatttttct tccccctcca aatcacctac attgacaaag      180
aataataact ggctatggaa atacaaggac aattctgtga atatttatta cgaggaacac      240
gataagggaa gcgatgagcc ttgtaagaac gttttgctga ttcctactat ttcagatgtt      300
agtactgtgg aggaatggag atcagtggct aaagacattg ctggacgaag tggtaaagtt      360
aattacagaa ctaccattgt agattggcct ggtttaggct actctgatag acccaagctt      420
gattacaatg ctgatgtcat ggaaaaattc ttggccgact tcattaatgc tcctaatagt      480
ccagtgaaca attcggataa ggacttggtg gtgttcggag gaggacatgc tgctacaata      540
gcagttcgtg ctgcaaagaa gggcttggtg aagccaacag cgattgctgc tattgctccc      600
acctgggctg gtccacttcc tattgttttt ggaagagatt ccagcatgga aacgaggtat      660
ggtctcctta gagggacctt aagggcccct gctgttggtt ggatgatgta taatgtactt      720
gtcagcaatg agaaatcaat acaatcacaa tataagtccc atgtttattc agatcccgaa      780
aaggtaactc cagatatcat cgagagccga tacgcactca caaagcggca aggtgctcgc      840
tatgtgcctg ctgctttctt gactggtttg cttgacccgg taaagtccag ggaagaattt      900
gtccaactat ttgctgagtt agagggtagg ataccagttc tagttctggc aacagcaggt      960
tctccgaaga ggtcaaaagc agagatggaa gcacttatgg aggccaaagg ggtgagcaag      1020
tatatcgaag tgccaggtgc tctccttccc caggaagagt atcctgaaat agttgcagaa      1080
cagctttaca ggtttctgca agagaagttt gagcttcagg cttaa      1125

<210> SEQ ID NO 35
<211> LENGTH: 6057
<212> TYPE: DNA
<213> ORGANISM: Artificial Sequence
<220> FEATURE:
<223> OTHER INFORMATION: interactor, Nitab4.5_0000842g0110.2 genomic
      sequence

<400> SEQUENCE: 35
gagatttcac aaaaatatcc ggaaaaaaaa aagtttctcc aaaaatcatt taattattta      60
tctaagaact ttcctaccta caatttaagc tagaacagga aaataaaaat aaaaaagaaa      120
aaatcaacac cagcggcttc tctctttcac acatacacaa agtcgcatac ccagaaaaaa      180
agaaacaatt tttgtgttgc agaagttaag gtaaagcttc cataattcac acaatacaca      240
gagcctccat taatcattca attcatggca tcctctgcta ttttccactt tcttccatca      300
tcatcttctt ccttgacttc tctttccttc agaaacagca gaacccatct ttctcaaacc      360
ccaaattttt acaaacccct tttagtaaaa gcttctactt ctgtcaattt ttcttccccc      420
tccaaatcac ctacattgac aaaggtaaga cttaaaatta gtgaaactgt ttatctcaaa      480

-continued

```
atcaattttt tgaatttttt catattttgt ttttgcagaa taataactgg ctatggaaat      540
acaaggacaa ttctgtgaat atttattacg aggaacacga taagggaagc gatgagcctt      600
gtaagaacgt tttgctgatt cctactattt cagatgttag tactgtggag gaatggagat      660
cagtggctaa agacattgct ggacgaagtg gtaaagttaa ttacagaact accattgtag      720
attggcctgg tttaggctac tctgatagac ccaagcttga ttacaatgct gatgtcatgg      780
aaaaattctt ggccgacttc attaatgctc ctaatagtcc agtgaacaat tcgggtaagc      840
taaaagagcc ttcttgatat attttctgga taaattagag tacaatttct aattttgcac      900
tctttgcata aactattgat atagtgaaat taatctgttt gtctgtggac ataggccaaa      960
tcatatatat tatggtatca ctattttgt tgttgttgtt gttgttgttg atgtcatatg     1020
ttgttgttct acataaatca agagtactac agaaatttct ttggagttaa atcgttaggt     1080
actctcttgg gaagaagatc caaggagcga ttctcaagga aatgtagcca aactctaggt     1140
gtaaatccag aaatagagat gttgaactta tgagtgctag gacatatttc caaaaaattt     1200
gtgaagttgg taaaaatgat gaactggaga agagaccaca actatgatca agatgttgaa     1260
gagaaggata acgccaatct tctttttgtg atggatgatt gtgcttgatt ggatgatgaa     1320
tgaatcatag atataggttg ttcgtactat atgtctcctt attgatactg gtttagccaa     1380
tatgaatctg ttagtagcgt caaaattttt ctgggaaaca acatcccaac caaaactatt     1440
acggattaat atggtgagaa tattgacgag agtttgacat attttcggac ccaacgaaag     1500
atttcatcta tctggatacc cttgattcta ataggtgcaa gttttcggcc aaaggttgtg     1560
tgatggtcat gaaggaggac ttattcatga tgaaggccag aaaagtcgaa agtttaatta     1620
ttttataacg tacccgtgtt atatgaattg ctgcaggctt ttcttctata cctgattatg     1680
aaattataac attgggatat atgaggttca gacatatgag cacgaagggg ctaattatgt     1740
tgaccaaatg tgaacttctt tgcgagcaaa ttacaagaaa ggtagagctt tgcgagctgt     1800
gcatctgaaa atcaagggag tcctaatttt agtattagta ttcataaaac aaaaggtatg     1860
ctagaccaca tcggagacct gcaagtgttt catgtaaagg tagaacgcaa tatttgctaa     1920
ccttttatat gattgctcaa caggaaaaga aaagtttacg tatatcttca gaaacactaa     1980
tatgaagctc tggacacttt taagaagtga aagaccttaa ttgagaagtc tgggaagcaa     2040
tcaaaaggct ttgatccatt aattttgtgt aagtgatttc aataaatgcc atgaggatca     2100
tgaaattggc agacacgtaa tgctataaaa gtttataaca gagtgacgtt gttgaacaca     2160
ttaatataac ctaattggag aaagaaaggt gtatgctgtc aaatgttcgt ctgcaaaggt     2220
ttctgagcta aaagctgtct ttatagcata ttacttggtg aactgcttac tgttcacggg     2280
tgttgagttc aaaacttaaa gaggtatggt ttggtctatc gggattattc aaatttgaaa     2340
accttggttg tcctgcttag atggatgtta gcggaggaaa gctagaacca agaaccaaaa     2400
attgtagttt ctttggttat gtattttggg gtgggagggc tgacgagcgc aaaacacaac     2460
acgaaattta tgcttgctag tcaaagatag tgtagttaag tgatcgtctc cacaggaaat     2520
ggatttaaac agtgttcgaa taatctttag ttaattacta tccaagaaaa ttaatacttg     2580
attcaatgat tatcaactac gattagctac taaaaattaa gcaattaata attgattacg     2640
gaagacacgg ttacaacaac aacaaaccca gtttgatctc ataaatgggg tctggggagg     2700
ggagggtagt gtgtacgcag accttacccc tagctcataa agatagagag gttgtttccg     2760
atagaccctc ggctcaagga acattgaaga taaagcaacg aagtagcaaa gaatattagc     2820
agcaatgtaa catggtaacg ggagtgaatg ccacaacatg cataataaag aacaataaat     2880
```

-continued

```
aggaaattac aaagatagtc ctagtactac tggtcggcct aggaggaaca cattacggaa      2940
gacacggttg agcaacaaaa aaatatcaat gagggaaata agggtaattg actagacagg      3000
tacacgacaa ttgactcggg atccaattct tgaatttgtt cactctataa tactgttgat      3060
tctcacgaat tcaacggata attagattac acttgaagtt aatgttcctc tttcgattaa      3120
acattaattt cagtaattaa tccaattgaa tcacagtgaa caattgcaac aaataaaatg      3180
acggttttag tcttaagggt aacttctcac gaatattttc ctattttcta gttcaattaa      3240
taattcaaga ggcttttttcg attacctagt tgaatcacta atttaaacta gagcataaga     3300
tgtaaagaaa ttcaatataa agcttctctt ccgattaagc aaaataataa ataacttcac      3360
aatacgattt aaaactccat caattaattc aaacaattgt caagaatcta atccctaatc      3420
aagttgtcaa tacaccatat ctgtcaacac tctaagggaa attactccat agcaatggaa      3480
aaagtcatct caataaggtt taaaaacata gaaaacatca atgctaataa ttcgatacaa      3540
actcccgtat tgcaccgatt gttggttgaa atcttgatga attcttgtgt cttcttgcct      3600
tagttgtttc tcaattcttt tgtaggtcaa aagtcccttc aaaaacgtat ttttggtgta      3660
tttataccat gtagaagtgg acccggacaa aactacccct ttcaagctga aacagaaaaa      3720
tacgctggga aaattgcaca ggcgcgccgc gccgcgcctc gcgtcgcacc atgcggcgcg      3780
cttgtgggaa ttatcagagg cttgtcaatt ttgttagcag gcgcattata cactgccgca      3840
ccacgtctcg cggcgcccca tgcggtgcgg tagtgcttat ttcttagagt aatatctttc      3900
ttctacttta tgacatcccg acttggtcct cgacccccga acgcgatccc ggcttaattt      3960
cttgggcttt actcagatgt caaagctcca atttgttcga ttcagctcca aattaacttc      4020
ttacctcaga atcacttcct gcaaggcata aaacacgtaa taagtgtaat tcattgcagt      4080
aattagagtg taaaacgcgc taaatcatga gtttctagcc taccatcaag ggcatagctt      4140
gcggtgtcct ggtcctatat ctccaatttt gttaagatta gaaatgttat gttagttttg      4200
ctaaatctct taaggtgacc cggagcgggg ttcatctatt gccttttgag acctatcagg      4260
tagatagttt atcaaagaaa gtggagattg aagtttacaa tccacagctt tcatgaacag      4320
caaaaggggt cgtcagttgg ggtgaccagt gccagggggt tgtccattgc accgagaaac      4380
ttgtaaagta acatggacac atccaaagcg ccgtgagcca taattggaaa tggaaagtag      4440
gccatcctat atctactgtt ttcccctccc tcgttctgct gctaactctc tgtttttttt      4500 ttttttttt ttgtgtgtgt gtgtgcttgt gagatgtttc agttttgttt gctctctgca      4560
tctggaaatg atgttccaag ttcctttatt ttggtaaaga tatctcatct tacattttct      4620
tggaagttct cttgttaata atttcaaatg aataaattag ataaggactt ggtggtgttc      4680
ggaggaggac atgctgctac aatagcagtt cgtgctgcaa agaagggctt ggtgaagcca      4740
acagcgattg ctgctattgc tcccacctgg gctggtccac ttcctattgt ttttggaaga      4800
gattccagca tggaaacgag gtacgcatag atctttcctt ccgttgcact tttcttgacc      4860 tttttatttta actaagagct ctgcagcttg ctaaataata cccattgcag ggctaggtcc      4920
aatatagaga acaaaaggac tacaagattc ggaagtttta agcagacatt aattcagttt      4980
ttgtaggaaa gaagcaaatg acatgagagt ctcctgcata gtaatgcatt ggataacaca      5040
atcagcaatc cacctttcaa aatatgaaat tttcatccga aaaaaataac aatagtattc      5100
aagattttca ccgtatttgc agaaatgata ttaccctact tcgtgattga tatttccttc      5160
tcattttcta caggtatggt ctccttagag ggaccttaag ggcccctgct gttggttgga      5220
```

```
tgatgtataa tgtacttgtc agcaatgaga aatcaataca atcacaatat aagtcccatg    5280
tttattcaga tcccgaaaag gtaactccag atatcatcga gagccgatac gcactcacaa    5340
agcggcaagg tgctcgctat gtgcctgctg ctttcttgac tggtttgctt gacccggtaa    5400
agtccaggga agaatttgtc caactatttg ctgagttaga gggtaggata ccagttctag    5460
ttctggcaac agcaggttct ccgaagaggt caaaagcaga gatggaagca cttatggagg    5520
ccaaaggggt gagcaagtat atcgaagtgc caggtgctct ccttccccag gaagagtatc    5580
ctgaaatagt tgcagaacag ctttacaggt ttctgcaaga gaagtttgag cttcaggctt    5640
aaaaatggtt atcagctcaa gacctaagta gtcaaaggta cagaattttc ccatgggcaa    5700
cagtgaggtt aagtggttaa atttgaaagt atgagatgac actggaagtg gctttatata    5760
tgataattca ggtgattaat gtatgaattt ttatctatat tgatagaggt tttccttctc    5820
ttaaaccaga cctagaatca cagaaagttg agtgctaaac cgatttatga caaacgatgt    5880
tcttattcaa tttgctgcta tggcagtttt atagtttttt ttaatttatt attacagata    5940
tattggttat ttagctgctc ttcatggctt tctatgagga gctgaatgtt acattgatct    6000
tttggttcat cataccatcg aggtcaattt tgatatttag caggtcagtt tgacttg       6057
```

```
<210> SEQ ID NO 36
<211> LENGTH: 1210
<212> TYPE: PRT
<213> ORGANISM: Artificial Sequence
<220> FEATURE:
<223> OTHER INFORMATION: interactor, Nitab4.5_0001620g0100.2 protein
      sequence

<400> SEQUENCE: 36

Met Gly Phe Ala Tyr Cys Leu Trp Gln Pro Asn Ala Ser His Cys Gly
1               5                   10                  15

Glu Ala Leu Asn Tyr Arg Ile Leu Asp Arg Lys Asn Ser Cys Asp Val
                20                  25                  30

Gly Leu Asn His Lys Leu Leu Gly Asn Ala Arg Val Leu Cys Lys Asn
            35                  40                  45

Arg Leu Gly Lys Arg Leu Lys Arg Ser Val Ala Cys Ser Asp Asn Ser
        50                  55                  60

Leu Ala Tyr Ser Arg Ile Arg Phe Asn Cys Ala Leu Trp Lys Ser Asp
65                  70                  75                  80

Ser Ser Gly Asn Leu Met Arg Arg Lys Ala Ser Arg Gly Val Lys Leu
                85                  90                  95

Pro Arg Cys Gln Gly Asn Asp Ser Val Ala Phe Ile Asp Gly Asn Gly
            100                 105                 110

Arg Asn Val Glu Ser Ser Glu Ser Ala Glu Asp Gly Ala Leu Ser Ala
        115                 120                 125

Asn Thr Asn Gly Ile Ala Glu Ile Ser Cys Ala Ile Glu Leu Glu Glu
        130                 135                 140

Asp Lys Glu Glu Glu Thr Glu Gly Asp Asn Leu Asp Glu Leu Arg Glu
145                 150                 155                 160

Leu Leu Gln Lys Ala Leu Lys Asp Leu Glu Val Ala Gln Leu Asn Ser
                165                 170                 175

Thr Met Phe Glu Glu Lys Ala Gln Lys Ile Ser Glu Ala Ala Ile Ala
                180                 185                 190

Leu Lys Asp Glu Ala Ala Asn Ala Trp Asp Asp Val Asn Lys Gln Leu
        195                 200                 205

Asp Ser Val Gln Glu Ile Val Ser Glu Glu Met Val Ala Lys Glu Ala
```

```
              210                  215                  220

Val Gln Lys Ala Thr Met Ala Leu Ser Phe Ala Glu Ala Arg Leu Gln
225                  230                  235                  240

Val Ala Leu Asp Ser Val Gln Ala Ala Lys Gln Arg Ile Met Ser Ser
                 245                  250                  255

Glu Thr Ser Glu Asp Ser Lys Gly Glu Asp Ser Thr Ser Leu Met Glu
                 260                  265                  270

Glu Glu Ala Ala Leu Leu Ala Ala Gln Glu Asp Ile Lys Glu Cys Leu
             275                  280                  285

Asp Arg Phe Gly Ser Cys Glu Ala Glu Leu Arg Arg Leu Gln Asn Lys
         290                  295                  300

Lys Glu Glu Leu Gln Lys Glu Val Asp Arg Leu Asn Glu Leu Ala Glu
305                  310                  315                  320

Gln Ala Gln Asn Asn Ala Leu Lys Ala Glu Glu Asp Val Ala Asn Ile
                 325                  330                  335

Met Leu Leu Ala Glu Gln Ala Val Ala Tyr Glu Leu Glu Ala Thr Gln
             340                  345                  350

Arg Val Ser Asp Ala Glu Ile Ala Leu Gln Lys Ala Glu Lys Asn Leu
         355                  360                  365

Ala Val Ser Ile Val Asp Ser Pro Glu Thr Ser Val Leu Gln Asn Gly
     370                  375                  380

Ser Ser Thr Gln Gly Gln Val Leu Val Asp Gly Thr Leu Ser Glu Asp
385                  390                  395                  400

Glu Val Leu Pro Arg Asn Ser Val Asp Ser Val Ile Glu Ile Asp Arg
                 405                  410                  415

Glu Val Gln Leu Glu Asp Ala Trp Ala Ala Ser Gly Pro Leu Ser Thr
             420                  425                  430

Glu Glu Ser Arg Ile Ser Asp Glu Ser Asp Glu Glu Asp Arg Lys Leu
             435                  440                  445

Val Leu Asp Ser Ser Lys Asp Ser Asp Ser Asp Thr Glu Lys Pro Lys
     450                  455                  460

Ser Val Gln Ser Leu Arg Gln Glu Val Asn Lys Glu Ser Ala Arg Asp
465                  470                  475                  480

Ser Ser Leu Asn Ala Pro Lys Ala Leu Leu Lys Lys Ser Ser Arg Phe
                 485                  490                  495

Leu Pro Ala Ser Phe Phe Ser Phe Pro Thr Asp Gly Glu Glu Phe Thr
             500                  505                  510

Pro Ala Ser Val Phe His Asn Leu Met Glu Ser Ala Arg Lys Gln Leu
             515                  520                  525

Pro Lys Leu Val Val Gly Ser Leu Leu Met Gly Ala Gly Ile Ala Phe
         530                  535                  540

Tyr Val Asn Arg Ser Glu Arg Ile Ser Gln Ser Phe Gln Gln Pro Asp
545                  550                  555                  560

Ile Ile Thr Thr Ser Ile Asp Glu Val Ser Thr Asn Ala Arg Pro Leu
                 565                  570                  575

Val Arg Gln Ile Arg Lys Leu Pro Lys Lys Leu Lys Thr Leu Met Glu
             580                  585                  590

Met Leu Pro His Gln Glu Ile Asn Glu Glu Glu Ala Ser Leu Phe Asp
             595                  600                  605

Met Leu Trp Leu Leu Leu Ala Ser Val Ile Phe Val Pro Ile Phe Gln
         610                  615                  620

Lys Ile Pro Gly Gly Ser Pro Val Leu Gly Tyr Leu Ala Ala Gly Ile
625                  630                  635                  640
```

-continued

```
Leu Ile Gly Pro Tyr Gly Leu Ser Ile Ile Arg His Val His Gly Thr
            645                 650                 655

Lys Ala Ile Ala Glu Phe Gly Val Val Phe Leu Leu Phe Asn Ile Gly
            660                 665                 670

Leu Glu Leu Ser Val Glu Arg Leu Ser Ser Met Lys Lys Tyr Val Phe
            675                 680                 685

Gly Leu Gly Thr Ala Gln Val Leu Val Thr Ala Val Val Val Gly Leu
            690                 695                 700

Val Ala His Phe Val Ala Gly Gln Ala Gly Pro Ala Ala Ile Val Ile
705                 710                 715                 720

Gly Asn Gly Leu Ala Leu Ser Ser Thr Ala Val Val Leu Gln Val Leu
            725                 730                 735

Gln Glu Arg Gly Glu Ser Thr Ser Arg His Gly Arg Ala Thr Phe Ser
            740                 745                 750

Val Leu Leu Phe Gln Asp Leu Ala Val Val Val Leu Leu Ile Leu Ile
            755                 760                 765

Pro Leu Ile Ser Pro Asn Ser Ser Lys Gly Gly Val Gly Phe Arg Ala
            770                 775                 780

Ile Ala Glu Ala Leu Gly Leu Ala Ala Val Lys Ala Ile Val Ala Ile
785                 790                 795                 800

Thr Ala Ile Ile Ala Gly Gly Arg Leu Leu Leu Arg Pro Ile Tyr Lys
            805                 810                 815

Gln Ile Ala Glu Asn Gln Asn Ala Glu Ile Phe Ser Ala Asn Thr Leu
            820                 825                 830

Leu Val Ile Leu Gly Thr Ser Leu Leu Thr Ala Arg Ala Gly Leu Ser
            835                 840                 845

Met Ala Leu Gly Ala Phe Leu Ala Gly Leu Leu Leu Ala Glu Thr Glu
            850                 855                 860

Phe Ser Leu Gln Val Glu Ser Asp Ile Ala Pro Tyr Arg Gly Leu Leu
865                 870                 875                 880

Leu Gly Leu Phe Phe Met Thr Val Gly Met Ser Ile Asp Pro Lys Leu
            885                 890                 895

Leu Leu Ser Asn Phe Pro Val Ile Met Gly Ser Leu Gly Leu Leu Ile
            900                 905                 910

Gly Gly Lys Thr Ile Leu Val Ala Leu Val Gly Lys Leu Phe Gly Ile
            915                 920                 925

Ser Ile Val Ser Ala Ile Arg Val Gly Leu Leu Leu Ala Pro Gly Gly
            930                 935                 940

Glu Phe Ala Phe Val Ala Phe Gly Glu Ala Val Asn Gln Gly Ile Met
945                 950                 955                 960

Ser Pro His Leu Ser Ser Leu Leu Phe Leu Val Val Gly Ile Ser Met
            965                 970                 975

Ala Leu Thr Pro Tyr Leu Ala Ala Gly Gly Gln Leu Ile Ala Ser Arg
            980                 985                 990

Phe Glu Leu His Asp Val Arg Ser  Leu Leu Pro Val Glu  Ser Glu Thr
            995                 1000                1005

Asp Asp  Leu Gln Asp His Ile  Ile Ile Cys Gly Phe  Gly Arg Val
    1010                1015                1020

Gly Gln  Ile Ile Ala Gln Leu  Leu Ser Glu Arg Leu  Ile Pro Phe
    1025                1030                1035

Val Ala  Leu Asp Val Arg Ser  Glu Arg Val Ala Val  Gly Arg Ala
    1040                1045                1050
```

```
Leu Asp Leu Pro Val Tyr Phe Gly Asp Ala Gly Ser Arg Glu Val
    1055                1060                1065

Leu His Lys Val Gly Ala Glu Arg Ala Cys Ala Ala Ala Ile Thr
    1070                1075                1080

Leu Asp Thr Pro Gly Ala Asn Tyr Arg Thr Val Trp Ala Leu Ser
    1085                1090                1095

Lys Tyr Phe Pro Asn Val Lys Thr Phe Val Arg Ala His Asp Val
    1100                1105                1110

Asp His Gly Leu Asn Leu Glu Lys Ala Gly Ala Thr Ala Val Val
    1115                1120                1125

Pro Glu Thr Leu Glu Pro Ser Leu Gln Leu Ala Ala Ala Val Leu
    1130                1135                1140

Ala Gln Ala Lys Leu Pro Met Ser Glu Ile Ala Ala Thr Ile Asn
    1145                1150                1155

Glu Phe Arg Ser Arg His Leu Ser Glu Leu Thr Glu Leu Cys Glu
    1160                1165                1170

Thr Ser Gly Ser Ser Leu Gly Tyr Gly Phe Ser Arg Val Val Asn
    1175                1180                1185

Lys Gly Lys Val Gln Pro Pro Asp Ser Ser Asp Glu Asn Gln Val
    1190                1195                1200

Ser Glu Gly Thr Leu Ala Ile
    1205                1210
```

```
<210> SEQ ID NO 37
<211> LENGTH: 3633
<212> TYPE: DNA
<213> ORGANISM: Artificial Sequence
<220> FEATURE:
<223> OTHER INFORMATION: interactor, Nitab4.5_0001620g0100.2 coding
      sequence

<400> SEQUENCE: 37
atgggctttg cttactgttt atggcagccg aatgcttcac attgtggtga agctttgaac      60
tacaggatat tagataggaa aaacagctgt gatgtagggt tgaatcataa attgcttgga     120
aatgctaggg ttttatgtaa gaataggctg gggaaaaggt tgaaacggag tgtggcctgt     180
agtgataata gtttagcata ttcaaggata cgatttaatt gtgctttgtg gaagtccgat     240
tcaagtggga atttgatgcg ccgtaaggct tctaggggag tgaaattgcc tcggtgtcag     300
ggaaatgatt cagttgcgtt tatcgatggt aatggtagaa atgtggagtc cagtgagagt     360
gctgaagatg gagctctgag tgctaatact aatggaatcg cggaaattag ttgcgcaatt     420
gagttggagg aagataaaga agaagaaaca gaaggagata atttggatga actaagggag     480
ttgttgcaga aggcactcaa ggatttggaa gttgcacagc tgaacagcac aatgtttgag     540
gaaaaagcac agaagatatc agaagctgct atagcgttaa aagatgaagc ggctaatgcc     600
tgggatgatg taaacaaaca acttgatagt gttcaagaga ttgtaagtga agagatggtc     660 gctaagaag cagttcaaaa agcaacaatg gcccttttctt ttgctgaggc aaggcttcag     720
gttgctcttg attcagtaca agctgcaaaa caaagaatta tgtcttcaga acgtctgaa     780 gatagcaaag gggaagattc aacttcattg atggaggaag aggcagcact cttagctgct     840
caggaagata taaaggagtg tctggaccgt tttggaagtt gtgaggctga gttgaggcgt     900
ctgcagaata aaaagaaga gctgcaaaag gaggttgaca gactgaatga gctagctgag     960
caagcacaaa acaatgcttt aaaagccgag gaagatgttg caaacataat gctttttagct    1020 gaacaagctg ttgcttatga gctggaggct actcaaaggg tcagtgacgc ggagatcgct    1080
```

-continued

```
ttgcagaaag ccgagaagaa cctagctgtg tcaattgttg actccccaga aacttcagtt    1140
ttacagaatg gatcatctac tcaagggcaa gtgttggtcg atgggaccct tagcgaggat    1200
gaggtactcc ctagaaattc agtcgatagt gttattgaaa tagataggga ggtacaactg    1260
gaggatgctt gggcggcaag tgggcctttg tcaactgagg agtcacgtat ctctgatgag    1320
agtgatgaag aagatagaaa gttagttcta gactcctcaa aagattctga ttctgataca    1380
gaaaaaccaa aaagtgttca aagtctgagg caggaggtca acaaggaatc agctagggac    1440
agttcactta atgctcccaa agcattattg aagaaatcat cccgtttctt gcctgcatct    1500
ttcttctcat ttcccacaga tggtgaagag ttcacacctg cttcagtttt ccacaatctc    1560
atggagtctg caaggaagca attgcccaag ctggtggttg gctcattact gatgggagca    1620
ggaattgcct tttacgtcaa tcgatcagag cgaatttctc agtcgtttca gcagccagac    1680
atcattacca ccagcattga tgaggtttca acaaatgcaa gacctctggt tcgacaaata    1740
agaaaactgc ccaagaaact taagacacta atggagatgc ttcctcatca agagataaat    1800
gaggaggaag cttctctttt tgacatgtta tggctattgc tcgcaagtgt tatctttgtg    1860
ccgatcttcc agaaaattcc aggaggaagt cctgttcttg ggtatttggc tgctggaatc    1920
ttgattggac cctatggtct ttctatcata cgtcatgtac atgggaccaa ggctatagct    1980
gaatttggag ttgtcttcct gctatttaac attggcctag agctttccgt tgagagacta    2040
agttcaatga agaaatacgt ttttgggttg ggtactgctc aggtcttagt gacagctgtt    2100
gtggtcgggt tagttgctca tttttgttgcc gggcaggctg gacctgctgc aatagtgatt    2160
gggaatggtc ttgccttatc ttccactgcg gttgtcctcc aggtattgca ggagcgaggt    2220
gagagcacat cacggcatgg acgagcgaca ttttctgtat tactctttca ggatctggcg    2280
gtggttgttc tactcatact gataccacta atttcaccaa attcatcaaa aggaggggtt    2340
ggtttcagag ccatagctga ggcccttggt ttggctgctg taaaggcaat tgtagccatc    2400
actgccatta ttgctggagg acgtctgctg ctgcggccta tttataagca gattgcagaa    2460
aaccaaaatg cagaaatatt ttcggcaaat acgcttcttg ttatccttgg gactagtctt    2520
ctgacagcca gggctggcct ctcaatggct ttaggtgcat ttttagctgg tttgcttctg    2580
gcagaaactg aattttcatt gcaagttgaa tcagatattg ctccatatcg tggactccta    2640
ttgggtctct ttttcatgac ggttggaatg tccattgatc ccaagcttct tctttcaaac    2700
tttccagtta ttatgggctc attgggactt ctaattggtg gcaagaccat cttggttgca    2760
ttagttggta aactgtttgg tatttcaatt gtatcggcaa taagagttgg tcttctactt    2820
gctcctggtg gagagtttgc ctttgtagct tttggtgaag ctgttaacca gggtataatg    2880
tctcctcact tgtcatctct gctatttctt gtggttggaa tttcaatggc cctcacgcca    2940
tatctagctg ctggaggcca attaatagca tctcgttttg agctgcacga tgtgcgaagt    3000
ttattgcctg tggaaagtga gacagatgat ttgcaggatc atatcattat ttgtggattt    3060
ggtcgtgttg gccagatcat tgcccaactt ctctccgagc gactgattcc gtttgttgca    3120
cttgatgtgc gaagtgaacg agttgcagtt ggtcgtgcac ttgaccttcc tgtatacttt    3180
ggtgatgctg gtagccgaga ggttctacat aaagttggag ctgaaagagc atgtgctgcc    3240
gcaataacat tagatactcc cggtgcaaat tacagaactg tttgggcctt gagcaagtac    3300
tttcccaatg tgaaaacatt tgtacgtgct catgatgtgg atcatggcct caatctagaa    3360
aaggctggag caacagcggt tgtgcctgag accttggaac caagcctgca gttggccgct    3420
```

```
gctgtccttg cacaagctaa gctgccaatg tcagagatag cggcaacaat caacgagttt   3480
aggtcccgcc acctctctga gcttacagag ctatgtgaaa ctagtggaag ttctctaggc   3540
tatggatttt ctcgtgtggt gaataaaggc aaagttcagc ctccagattc ttcggatgag   3600
aaccaagtca gtgaaggaac actagcaata tga                                3633
```

```
<210> SEQ ID NO 38
<211> LENGTH: 12416
<212> TYPE: DNA
<213> ORGANISM: Artificial Sequence
<220> FEATURE:
<223> OTHER INFORMATION: interactor, Nitab4.5_0001620g0100.2 genomic
      sequence
<220> FEATURE:
<221> NAME/KEY: misc_feature
<222> LOCATION: (8239)..(8263)
<223> OTHER INFORMATION: n is a, c, g, or t

<400> SEQUENCE: 38
```

```
gaagtttcca tcaaaacaat aagaagaagg gtaattgtgt aaatgcagaa aatggaatat     60
ccaccaataa accctctaat ccaattttgt catgttcccc aaatggaggg agaaaacaaa    120
acctgaaaaa gaaaaaaaag aaaagatttc ttctcattat ttcaactttt caagtaaccg    180
cagagtcgca aacgaaaggt tgttcttcgg acaaagctat aaaaaatcaa aactgatagg    240
aagagccaat aagcaaagtc aatccaatca ttttctgacc taattttccg ccatagatat    300
tcttctctca gaacttgaaa ctgtcacttc tatcggtata ttcaaacttc tctcttctgt    360
tttacttcat tttcactact gtcaacttta acttcagtat atgtatcgaa acggaatgtt    420
gattaatcgc gaaatcactt tcagtttttt cagcttgcaa atatttgttg tggtgatttt    480
aactgattgt ttgtggctcc tatgaattaa ttttcacttg tttgttgatt gaagttgaaa    540
acttgcttta tttgtttttt aggggtttga ttttgaggta atgagaattg gcggcattgt    600
tttggtgtat ttttgacgtt tagtgtgtta gaggagagga ggatgggctt tgcttactgt    660
ttatggcagc cgaatgcttc acattgtggt gaagctttga actacaggat attagatagg    720
aaaaacagct gtgatgtagg gttgaatcat aaattgcttg gaaatgctag ggtttttatgt   780 aagaataggc tggggaaaag gttgaaacgg agtgtggcct gtagtgataa tagtttagca    840
tattcaagga tacgatttaa ttgtgctttg tggaagtccg attcaagtgg gaatttgatg    900
cgccgtaagg cttctagggg agtgaaattg cctcggtgtc agggaaatga ttcagttgcg    960
tttatcgatg gtaatggtag aaatgtggag tccagtgaga gtgctgaaga tggagctctg   1020
agtgctaata ctaatggaat cgcggaaatt agttgcgcaa ttgagttgga ggaagataaa   1080
gaagaagaaa cagaaggaga taatttggat gaactaaggg agttgttgca gaaggcactc   1140
aaggatttgg aagttgcaca gctgaacagc acaatgtttg aggaaaaagc acagaagata   1200
tcagaagctg ctatagcgtt aaaagatgaa gcggctaatg cctgggatga tgtaaacaaa   1260
caacttgata gtgttcaaga gattgtaagt gaagagatgg tcgctaaaga agcagttcaa   1320
aaagcaacaa tggccctttc ttttgctgag gcaaggcttc aggttgctct tgattcagta   1380
caagctgcaa aacaaagaat tatgtcttca gaaacgtctg aagatagcaa aggggaagat   1440
tcaacttcat tgatggagga agaggcagca ctccttagctg ctcaggaaga tataaaggag  1500
tgtctggacc gttttggaag ttgtgaggct gagttgaggc gtctgcagaa taaaaaagaa   1560
gagctgcaaa aggaggttga cagactgaat gagctagctg agcaagcaca aaacaatgct   1620
ttaaaagccg aggaagatgt tgcaaacata atgctttag ctgaacaagc tgttgcttat     1680
```

-continued

```
gagctggagg ctactcaaag ggtcagtgac gcggagatcg ctttgcagaa agccgagaag   1740
aacctagctg tgtcaattgt tgactcccca gaaacttcag ttttacagaa tggatcatct   1800
actcaagggc aagtgttggt cgatgggacc cttagcgagg atgaggtact ccctagaaat   1860
tcagtcgata gtgttattga aatagatagg gaggtacaac tggaggatgc ttgggcggca   1920
agtgggcctt tgtcaactga ggagtcacgt atctctgatg agagtgatga agaagataga   1980
aagttagttc tagactcctc aaaagattct gattctgata cagaaaaacc aaaaagtgtt   2040
caaagtctga ggcaggaggt caacaaggaa tcagctaggg acagttcact taatgctccc   2100
aaagcattat tgaagaaatc atcccgtttc ttgcctgcat ctttcttctc atttcccaca   2160
gatggtgaag agttcacacc tgcttcagtt ttccacaatc tcatggagtc tgcaaggaag   2220
caattgccca agctggtggt tggctcatta ctgatgggag cagggtacaa ctactataaa   2280
actgttcatt ctttgttgct tttgaaagat gaagctattt ctttctagct gcatgtataa   2340
gtgcctcgtt aggatacaat ctttgtacca ttagattggt atagcttgtt tatggtactt   2400
gatatgcttt tgacgtctgt cacagaattg ccttttacgt caatcgatca gagcgaattt   2460
ctcagtcgtt tcagcagcca gacatcatta ccaccagcat tgatgaggtt tcaacaaatg   2520
caagacctct ggttcgacaa ataagaaaac tgcccaagaa acttaagaca ctaatggaga   2580
tgcttcctca tcaagaggca tgcttcttta actcccttta gtttaacgcc tgcaatcacc   2640
attttgttag gaaggggctt tacttctact tgctaatggt gttgttgctc atttcagata   2700
aatgaggagg aagcttctct ttttgacatg ttatggctat tgctcgcaag tgttatcttt   2760
gtgccgatct tccagaaaat tccaggaggt aattgaattt tgctaccttc ttttatcgca   2820
tgaggacagt gactaggggc ttcttatgtt aaattgttca ccaaacttgt tcttgatgta   2880
aaggtttcct cgtaggtctt tccttgaaca tgttctaaaa attgaaaaat gatatttgat   2940
tattagacac ttagttttcg gtgaccttga tgtatgtcac agatatgtgc cctttgctcc   3000
tctgtgacag acgtactctt gtttcttgtt aatggttcat cttctgtctg ctataatgtg   3060
taggaagtcc tgttcttggg tatttggctg ctggaatctt gattggaccc tatggtcttt   3120
ctatcatacg tcatgtacat gggaccaagg ctatagctga atttggagtt gtcttcctgc   3180
tatttaacat tggcctagag gtacagtcta ggaaaattga ctagtttatt tctttctgaa   3240
tgtgttacaa atactgcctt aataacctct gtttgtattc tctttgacag ctttccgttg   3300
agagactaag ttcaatgaag aaatacgttt ttgggttggg tactgctcag gtaattgaaa   3360
aaaattgagc acttgggagt tgttaagccc cctccataat gcttatagag tatggtctca   3420
acgttttagg tttccacact aattattaat atattcaaat gaacgcaggt cttagtgaca   3480
gctgttgtgg tcgggttagt tgctcatttt gttgccgggc aggctggacc tgctgcaata   3540
gtgattggga atggtcttgc cttatcttcc actgcggttg tcctccaggt aaatccttct   3600
atatatttag caggtcttcc ttgctggatg aatgatgggc gatttagctg gatgaatgat   3660
gggcgattta gcgtttgagt aatttgttgt actcattaag tacgttgatt tggtgaccgt   3720
ttcaacactc taattaaagt taatgcttaa gcaggcaata ttattatgct atgttcccca   3780
aaagtccaga agctataatg ctagataagg gttgatgccg agatatcaaa tcagcattgg   3840
agtttttctt atcatttcct tgttgattca ccatatttac tacaatcaag gaattgtagt   3900
ttatctataa ttggctttgt ctatgtgcct gtgaccctcc ctcttcgaaa aatgaaactt   3960
tagtaattaa tttattatgt tgcatatctg caggtattgc aggagcgagg tgagagcaca   4020
tcacggcatg gacgagcgac attttctgta ttactctttc aggtatctgc atagagacag   4080
```

```
tacaaaattg tcgcatcttt ctcctgagat gggtgaaact tggaatatta tgtgtatcta    4140
tgcatacacg cgaatcacat atatttactt gccatcacat ataggctgct ctcatgcact    4200
tgaaatgatg acagtcagtg ctgcggtact tttagatttt tctttctgat atgattaacc    4260
aaattcttcc ctttatcctc caggatctgg cggtggttgt tctactcata ctgataccac    4320
taatttcacc aaattcatca aaaggagggg tatagactct tgttaccgtc ttgtcttctg    4380
gaaaaattat ttaaaatttt tgtgtttatt ataattacga ttccagctat gtgaactgga    4440
cctgtaatat tcaccaaact gagagccaat agctaatccc ctaaagtcac acgtgaaaac    4500
aacattcttt gcttttgata gctgtgagtt acactatagc tgttttctca aactgccatt    4560
attataacag aacttatttc ttcttaggtt ggtttcagag ccatagctga ggcccttggt    4620
ttggctgctg taaaggcaat tgtagccatc actgccatta ttgctggagg acgtctggta    4680
aggtgtttgt tcatgtagaa tcacttccaa tattataaat gcttctgatt agtatataat    4740
ttttaagttc taactacatc tcttacgata ttttggactt tagtctttca tttgcttttg    4800
tctatacatt attaaagtag ggtttgatat ttatctattg caaaatataa ataggtttta    4860
attccgtttt tcactttgca agtcttgtaa gatacattgc tgtaatgtga ggacgttaat    4920
atttttgttc tctattccaa tttcagctgc tgcggcctat ttataagcag attgcagaaa    4980
accaaaatgc agaaatattt tcggcaaata cgcttcttgt tatccttggg actagtcttc    5040
tgacagccag ggtacttatg atcacattgt ttatgtgttc atgaatactg cccaattctg    5100
ttagaactgt tatcttgtta acgctatgat gtgttatctg atgtaaataa ttcaggctgg    5160
cctctcaatg gctttaggtg catttttagc tggtttgctt ctggcagaaa ctgaattttc    5220
attgcaagtt gaatcagata ttgctccata tcgtggactc ctattgggtc tcttttcat     5280 gacggtaggt gacaatcttg tttattgtac aatgtgaatg ctattttcta atcctacaat    5340
ttgtcatttg gagttaaggt aggataggtc ttggtaaggt gctatttaca tttaaagatt    5400
ctcactctgc aatctctagc accaacttgt agaccttagt tgtctctcct gagttgttct    5460
ctttgaatga atgtacttct cagtaacatt ttatctattt taatcaactt ttatccaggc    5520
tgaagggaga atcgtttatg aataaattat tataactagt gctactttgt gacttcaaaa    5580
ctgaacaatt atcatctggt tgcaggttgg aatgtccatt gatcccaagc ttcttctttc    5640
aaactttcca gttattatgg gctcattggg acttctaatt ggtggcaaga ccatcttggt    5700
tgcattagtt ggtaaactgt ttggtatttc aattgtatcg gcaataagag ttggtcttct    5760
acttgctcct ggtggagagt ttgcctttgt agcttttggt gaagctgtta accaggttta    5820
tctctgatag ctttaaccta ttacaagcaa ttctgagccg ttaataaaat tctttttattc   5880 catttctttt tctccgttct attgctatgc tgttcaaaca gcatcttcct ttatcaagga    5940
attgtggacc ttttctacaa ttgacctgtg tgctgaaatc aaatgttgag ctagtgagat    6000
cctgttattg gggaagtgga gacaaactac catcaaatcc ttccagtttc tatctatggc    6060
cgctgtctta cttctatttt acaaatcctc ttagagactt gttctttctc atagctaccc    6120
ttaaatagat tcagagctgc aacatatctg aacagtacaa tgctaagctc tctgaggatc    6180
tttgccccat gataaaaata tatcttatta gaataagttt attatcttat ttaattaaat    6240
tttctccatg attttgcttt tcttttttcca gggtataatg tctcctcact tgtcatctct    6300
gctatttctt gtggttggaa tttcaatggc cctcacgcca tatctagctg ctggaggcca    6360
attaatagca tctcgttttg agctgcacga tgtgcgaagt ttattgcctg tggaaagtga    6420
```

-continued

```
ggtatagtct cctacttggg ggcacaatct ctcttctttg gttttaagcg agaataaacc    6480
atttacatgt tcgtaaaatc ttattttttg acagtttggt ttcaggttgt caatagtaac    6540
agggtattgg aattaaagga ttaaggttaa ggggtcttaa tagttaatac tattgttaaa    6600
aaaaaaaaca gttgtggaga ctaggaaaac tggaattttg gtgatagaaa agcttccttt    6660
ttctcctctt ccctacctca aatttcttca tcttcattct tcatccctgt ctgctttctc    6720
ctttcagtgc ctttctttga tcctggttca tctcttaagt tttgtgctct actttgttgt    6780
tgctatttaa gtcccatgcc tcagtgttat ggtactaagc cttttggacc ctcgcagttt    6840
ctctatgcaa agattttttt ttccttgaaa atattgtcta ttgaattata gcttcatatc    6900
atcatctgat taggtttccg ctgaacctta tgcctcactt tgttttcctt ccgagcttat    6960
ttaacataat ttttttcttc ttctaatttt aagtgttcaa tacttaattt gttctttaac    7020
ttattgcttc tttgctttaa atttaattgc tattggtaat gtcagccttt attacgaaga    7080
tcatttgtct gagaagtaac agatattcag ttaccaaagc tcattacttg aaggactaca    7140
tcatttaatg atatctttct ggattattac cttcgtaaat gtaatgaaga tttcactgac    7200
ttaaatttat tgcataataa aaggtgtaga ctgatagtac ctttttttcct tcgcagacag    7260 atgatttgca ggatcatatc attatttgtg gatttggtcg tgttggccag gttttgcccc    7320
gtgcttcatg aattggttaa attgatcatt tgacagaatg attttcaaac tttggaacaa    7380
tgaagctatt tccatcttct gcctgttgaa ttagttttca tcttaacaga tcattgccca    7440
acttctctcc gagcgactga ttccgtttgt tgcacttgat gtgcgaaggt atgattctct    7500
ttttactcac attcaactga tttcagctcc tgtaggttca gtgaagattt catctgctgt    7560
ttgttaagct gacatagaat tttttcttcc atagtgtcat ttcctgatat ggtggttcta    7620
aaattttata ttttttcgtaa aagaaaagaa aaaaagcagg aggaagaact tatatctttt    7680
gaggtgtaag tgactttctg cctcagatct ctatattcct atgccgtgct taagttttct    7740
caccactatg gttcttttca caacttacga agcagcacct ccactatcaa ctactcttaa    7800
aagccaccag atctttatag ctgaccaaat gcaagaaaat ggtttttctt tataagatat    7860
tatatagttt gttaattgtg agtcatcagt cattatcaac ctttaggata ttaaagtaaa    7920 agttttttgtt tttctctatc taaataaaat gttcatattc atgcatgcat ccaagggatg    7980
acagtgaaag agaagcagat gatggttttc ctgtaagagt gccagtgcca agccagagaa    8040
ctgaggaaac tggtctagaa cagagaagtc cttaattgaa cttgttaaat agttatgtgt    8100
aaatagtcct agtcccatat gtaggagtag aatatgtatc atatatagag ttcattgcag    8160
tgttttaaaa agcgatcgat ctttaagcga gaagggacgc gaagcgatgg ctgctcgctt    8220
ttccatgcct gaggcgacnn nnnnnnnnnn nnnnnnnnnn nnntatatat gtgtgtgtgt    8280
gtgtgtgtgc gtgtgtgtgt tatattttag tttatttgat tttttttaata tgtatttcag    8340 tttataaaat taattattat atatattata gtagctttga ttttgctttt cctatggttt    8400
gtggaggatt tggtggtacc tactttttgag ttttttaaatt gaactttttg attatttata    8460
ttgtgtcttt gcaaggttta cattatattt tttaagaatt gcgcttcact tcaatgaagc    8520
gtgcgcttcg ctttttgaagc gagggggagcc tctgtcgctt ttttgcgctt ctcactctca    8580
aaaacactgg ctcattgcat cattgttaaa aaatagattt ttcttccgtg cattctcgca    8640
tggtatcaga gcttcagtga gaattatcgt tgtgcgtcat ccaacgacaa ttcgggaaga    8700
aagatctcat tgccgtgcaa ttttccggca atttcgtctt gttcccaggg ttcatcactg    8760
ctacaatggt actatgcata taccagtacc accatcagat ctgaaaccct tgtgcgacca    8820
```

-continued

```
aaccctaaaa attccagtcc catcggaaca gaaaagtcag taaccgtgcg tctttccggt   8880
tgacgattca agattgattt gcgttatctc ctcattggta agtgttgtgc gaaaaccaac   8940
actatcacct tgttcggaaa agtaagacga caaaacccca gtcaatcgct ccggcagaaa   9000
gtcacgtgcc gccagaacta gggtttcggc gagctacatt aacttttccg gcgcgtgtga   9060
gccatcccgg ccatttttg acaaaacttc tcaggacaac ttactcgtcc agtgattccg   9120
aacctaccca tataaattac atcaaattct gacaactttt attttttttgc gacatgaaca   9180 gtggttttcc ggcatgaaca gtaattccag aaaaagtttg tgtattctgg tggtgtttta   9240
gaatctattt tgtagtgtgg aattcggctt agtctcacta ttttcaaatt tttccggcaa   9300
ctgttcggcc aacttttgtt tatcagcaac cacctggttt tgttgctcag ggggagtcta   9360
gtggccttgt atgtcgaatg atcagcttgc agatattttc accaagtccc tcattggtcc   9420
tcatattagt tacatatgta acaacctcgg tacatatgat ttgtatgcac cggcttgagg   9480
gagagtgtta gatagttatg tgtaaatagt cttagtccta tatgtagtag gagtagaata   9540
tgtattatat atagagctca ttgcatcatt gttaaaaaat agatttttct tccgttcatt   9600
ctcacagaac ttttagatta tttcacaaat cagctatgtt gcgcggactc ctcatttcag   9660
cccgcacccg tgtctacatg acactagtaa gggtaagggt gtgagattca taccgaatgt   9720
ggtcaacccg acatcagata ctttgaccac aatccatgga caagtttgag gaaaaaaatg   9780
ggactttgat ttctcaagat aaaagttagt acatatttga agacatggga aatggcataa   9840
cttcaatagt cgaccgtat tcgtgaaatg tgtatccgta tctggatctt cacacctgat   9900
gatttaggat atttttataa atctatcttt agaatttga attattttc gccgaatccc   9960 ctcacccgta tctggatccc gtatccccaa atcttttaga ttatgaagga tccgaccttt   10020
ggatccgcac ccggatcgga tacccgcacc cgagtccgag caacatagca aatcagatat   10080
gaattagaat caaagttggt tcccatccaa agcttgtaat gttgctctct atagtactct   10140
ttaactaaga tggattgtgt ggctgaatgc agtatcttat gtagacacgg ttacatgaat   10200
ttctcaaaaa cataaagggg tactagagtt tccttatatg ctggagcttt gattgtaagt   10260
ggatcgtgac tatcatcata ttgctctaga gtactttgat attcagcagt tgattattag   10320
agcatcaaca agtattaact tgattactgc atctataaga aaggtttctt tgtggtggtg   10380
ggggcggagg gtgcaggaaa tgttgctttc acttaaattt tccaattgtt atcagttatc   10440
atgaatatcc tgaggctcat cttaatagat gtttctataa taaatgcagt gaacgagttg   10500
cagttggtcg tgcacttgac cttcctgtat actttggtgt tgctggtagc cgagaggtaa   10560
agcaaattcc tgaacttaag attatcattt cggatatttt attttgacat tctgtgttcc   10620
gattactagg ttctacataa agttggagct gaaagagcat gtgctgccgc aataacatta   10680
gatactcccg gtgcaaatta cagaactgtt tgggccttga gcaagtactt tcccaatgtg   10740
aaaacatttg tacgtgctca tgatgtggat catggcctca atctagaaaa ggctggagca   10800
acagcggtat ctttcttatt ctaatttctg ctattgatct tttcgttgga aactcgttca   10860
tattttttca cttagcattc tgtatatctc ttgataacat ttggattctg agtcttgaaa   10920
attttgtttt attgctggtg tattatgttg tgctatggta aaattttgta gttgtaacat   10980
atcatgcata aaagaggaaa tagttgcaca tttgatggtt ggataaatga tgaacaatgc   11040
attaactgag gtggataaaa actttttacag gttgtgcctg agaccttgga accaagcctg   11100
cagttggccg ctgctgtcct tgcacaagta agtggatttg ataagcacca cttcatcaaa   11160
```

-continued

```
aaagtagatt tgataagcac ctcagttagg aaaaagaaaa gaaaagaaaa gaaaattgat   11220
ggcccttgtt tgtctcattt tgactgattt agtttttaag ctggtaagta attgatcagt   11280
ataaccaaat tctaatttga gaagtttcgt cccaatactg tagagtgata tggatgatga   11340
ttcaatagct tatcatcatg tatcattcta cactagtcct tcagaatggt atagcatatg   11400
gctttctcaa ggtatagcat atggctttca gaatggtata ctttaacatt cttgacggaa   11460
aggaccaatt gttggatctt ctgatgcaat aatcttgctg cgcactgcat tttgcgtctc   11520
gacctccttg tagtctactt ttggcaatct ataaccatca tgaagcaaat aaaattctaa   11580
gaatatattg tgtcttctag gctaagctgc caatgtcaga gatagcggca acaatcaacg   11640
agtttaggtc ccgccacctc tctgagctta cagaggtaaa ttatacatgc actacttgtc   11700
ttagcttttg gaacgttgta cgaggtttca tagttcagat tttgtcagat attttatgct   11760
gcccacggga tttttgtttt cagctatgtg aaactagtgg aagttctcta ggctatggat   11820
tttctcgtgt ggtgaataaa ggcaaagttc agcctccaga ttcttcggat gagaaccaag   11880
tcagtgaagg aacactagca atatgattac cattagaaga aacagggatt tgcgttgatt   11940
ggacccaaaa aagaagaaga aggaattgag aagggaagat actcctgata agtgtatagt   12000
gttttactta accccccctgt tcttgaaaat tgtacagaag aaatatagta cgtagcaagc   12060
aacaagctat gcaggagagc aaatctattg gcataaccca agggcagctc aaggggaggc   12120
tggttaagcc tttgctttag gctcccaaaa ttttggggcc cagaaaactt ttaagggcaa   12180
aagcgttttt gatccctgaa ttattatttt attctgattt tagtcctcaa tttaaatgtg   12240
tgatattgct cctttaactt tgacatatgt taataattaa ctttagtact gttagttgaa   12300
gaagtaaaag ggggagaaag gatactagat ccattgcttc aacctgatca tcaccattac   12360
tgatttaaga tttactttta aatataccat ctaataaggg agaatgcgca tcctag        12416
```

<210> SEQ ID NO 39
<211> LENGTH: 329
<212> TYPE: PRT
<213> ORGANISM: Artificial Sequence
<220> FEATURE:
<223> OTHER INFORMATION: interactor, Nitab4.5_0001200g0070.2 protein
    sequence

<400> SEQUENCE: 39

```
Met Ala Thr Lys Phe Gly Phe Thr Ile Thr Ser Pro Arg Leu Phe His
1               5                   10                  15

Gly Pro Phe Arg Lys Lys Pro Ile Phe Ser Ser Ser Ser Ala Ser Leu
            20                  25                  30

Glu Asp Val Ser Phe Cys Ser Ser Asn Leu Lys Leu Ile Asn Phe Ala
            35                  40                  45

Gly Arg Lys Leu Ala Ile Lys His Arg Val Leu Val Leu Ser Pro Lys
        50                  55                  60

Ala Thr Thr Asp Gln Pro Gly Gln Leu Asn Glu Asp Glu Val Glu Asp
65                  70                  75                  80

Ser Lys Ile Met Gln Tyr Cys Ser Ile Asp Gly Lys Gly Lys Lys Ser
                85                  90                  95

Leu Gly Glu Met Glu Gln Glu Phe Leu Gln Ala Leu Gln Ser Phe Tyr
            100                 105                 110

Tyr Glu Gly Lys Ala Thr Met Ser Asn Glu Glu Phe Asp Asn Leu Lys
        115                 120                 125

Glu Glu Leu Met Trp Glu Gly Ser Ser Val Val Met Leu Ser Thr Asp
    130                 135                 140
```

```
Glu Gln Lys Phe Leu Glu Ala Ser Met Ala Tyr Val Ser Gly Asn Pro
145                 150                 155                 160

Ile Met Thr Asp Lys Glu Tyr Asp Lys Leu Lys Met Lys Leu Lys Arg
                165                 170                 175

Asp Gly Ser Asp Ile Val Val Glu Gly Pro Arg Cys Ser Leu Arg Ser
            180                 185                 190

Arg Lys Val Tyr Ser Asp Leu Ser Val Asp Tyr Leu Lys Met Phe Leu
        195                 200                 205

Leu Asn Val Pro Ala Ala Val Val Ala Leu Gly Leu Phe Phe Phe Leu
    210                 215                 220

Asp Asp Leu Thr Gly Phe Glu Ile Thr Tyr Leu Leu Glu Leu Pro Glu
225                 230                 235                 240

Pro Phe Ser Phe Ile Phe Thr Trp Phe Ala Ala Leu Pro Leu Ile Leu
                245                 250                 255

Tyr Leu Ser Phe Thr Ile Thr Asn Val Val Val Lys Asp Phe Leu Ile
                260                 265                 270

Leu Lys Gly Pro Cys Pro Asn Cys Gly Ala Glu Asn Thr Ser Phe Phe
            275                 280                 285

Gly Thr Ile Leu Ser Val Ser Ser Gly Gly Ser Thr Asn Lys Ile Lys
    290                 295                 300

Cys Ser Gly Cys Gly Thr Asp Leu Val Tyr Asp Ser Asp Thr Arg Leu
305                 310                 315                 320

Ile Thr Leu Pro Glu Gly Ile Ser Gly
                325
```

<210> SEQ ID NO 40
<211> LENGTH: 990
<212> TYPE: DNA
<213> ORGANISM: Artificial Sequence
<220> FEATURE:
<223> OTHER INFORMATION: interactor, Nitab4.5_0001200g0070.2 coding
      sequence

<400> SEQUENCE: 40

```
atggccacta aatttggatt tactataact agccctcgcc tttttcatgg ccctttcagg      60
aaaaaaccaa tattttcttc atcttcagct tctttagaag atgtttcatt ctgttcttca     120
aatctcaaat taattaattt tgctggaaga aagttagcta taaaacatag ggtattggtt     180
ctctctccta aggccacaac tgaccagcca ggtcagctca atgaggatga ggttgaagac     240
agtaaaatca tgcaatattg tagcattgac gggaaaggaa agaaatcttt aggagaaatg     300
gagcaagagt ttcttcaagc actgcaatca ttctattatg aaggaaaggc gaccatgtca     360
aatgaagaat ttgataacct taaggaagaa ttaatgtggg aagggagcag cgtcgtcatg     420
ctaagcactg atgaacagaa gtttctggaa gcttctatgg cttatgtatc tgggaatcca     480
attatgactg ataaagagta tgacaagctg aagatgaaac ttaagaggga tggcagtgat     540
attgtggttg agggtcctcg gtgcagtctt cgaagtagaa aggtttatag cgatctttct     600
gttgattatc tgaagatgtt cttgttaaat gtccctgctg ctgttgttgc tcttggattg     660 ttcttttttcc ttgacgattt aactggattt gagatcactt atcttttgga gcttccagag     720
cctttcagtt tcattttcac atggtttgct gctttgcctt tgatattgta tctatcgttt     780
acaatcacaa acgtcgttgt taaagatttt ctgatcttaa agggcccttg tccgaattgt     840
ggagcagaaa atacttcctt ctttggtacc atattatcag tatctagtgg tggttctacc     900
aacaaaataa aatgctcagg ttgtgggacg gatttggtct atgattcaga cacgcgtttg     960
```
atcacgttgc ctgaaggaat tagtggatga                                    990

<210> SEQ ID NO 41
<211> LENGTH: 5491
<212> TYPE: DNA
<213> ORGANISM: Artificial Sequence
<220> FEATURE:
<223> OTHER INFORMATION: interactor, Nitab4.5_0001200g0070.2 genomic
      sequence

<400> SEQUENCE: 41
tcaaaaaaca gttaaaaccg ggaaacgatt ttcttgaatt caaaaaaatc aagacaaaag     60
cttttcaaca ttcaacactc tccacacatt catacacata accttatctt catctcttat    120
caaaactcat caaattctcc atttttcagt tttttcacaa atgcaatatt cacttccact    180
tcactccctc caccaccacc actgctgccg ccgccgtcgc cgccgccgcc acaaatggcc    240
actaaatttg gatttactat aactagccct cgcctttttc atggcccttt caggaaaaaa    300
ccaatatttt cttcatcttc agcttcttta gaagatgttt cattctgttc ttcaaatctc    360
aaattaatta attttgctgg aagaaagtta gctataaaac atagggtatt ggttctctct    420
cctaaggcca caactgacca gccaggtaaa tcaatgagtt atcatctgca tgtccttctt    480
tatgaaatta cggattaatc ttatcgaaag attcacatgt aatttttttat tagtgacatg    540 attgtgtaaa tattttttata ctagtccatg tatataactt aaactatttt tttttcttct    600
ttgatcaaag tttgattaaa ttataaaggg tttaagttgt gtaagctgac gatgtcaaga    660
atttgtactc tatcgttgga atttgactag ttatagtaga ttattactct attttttcatg    720 ttaccatatt aggtttgata tgtagagttg catattgtgg gtcaacgtaa tctgatagtg    780
taaatattct ttaaactgtt agtgcacaga acacaagctc tattttgaat attttttaaca    840 tgtagtcggc ctactataac acttctcctt taccggttaa cgtataggaa actccaatat    900
gtttaaaaga taaatcattt atcactatgg taattaaatg tgcttgaaaa aggtggaatg    960
gatatagaga attcatatag cagaacccaa ctagtttgaa cggaacgaac ctgaaatgaa   1020
gggaatggat acatagaatt catacagcgg actccaagta gattgagatt gaggaatagt   1080
tgttgattga catttgataa agtatattct tgctataggt aggcctgtta gttgctgctt   1140
ctttttctat aactcaaaga aagcaattat tatgtatcat tgatttattg caaggccaac   1200
ttgatgttgc tgcaaataat agtgattttc ttggcataac taactaaccg ccctaagctt   1260
gacaaagaag atgcaatcaa tctttccata atctgtctcg tgcttttgct atcgatcaat   1320
ttacaatgcc ttattcccaa acataggttc tttgtattct tgatgcttca atgaaataac   1380
aaacttcatt gaccctcaaa tgttggttct atacatgaca cagtcctaag ctcaatgagg   1440
aatcaacaaa tgaatagaga tagaaagaag taataaagtg agaccaatat agagacaatc   1500
aacaactgat gttttcatat gaactgaaaa acactcttat accttctctc tctctgtgta   1560
tgtttgctct atgtttgtat gttttttcct cttctccaat ttcttctttt tatggtggcg   1620
tataccacat catttgaaga ctcacttttg ctttcaggtc agctcaatga ggatgaggtt   1680
gaagacagta aaatcatgca atattgtagc attgacggga aaggaaagaa atctttagga   1740
gaaatggagc aagagtttct tcaagcactg caagtaatga agcagaatca gttactaatt   1800
cgtcgattgt tttcattctc attctactaa agttaactaa ctctttcttg gttctgtacc   1860
acagtcattc tattatgaag gaaaggcgac catgtcaaat gaagaatttg ataaccttaa   1920
ggaagaatta atgtgggaag ggagcagcgt cgtcatgcta agtaagtaag aatttctgtc   1980

```
tgtttatgtc tcattggcac ttaaaatagg tatagtaaga gcaaattcct aacaatgcag      2040
gcactgatga acagaagttt ctggaagctt ctatggctta tgtatctggg aatccaatta      2100
tgactgataa agagtatgac aagctgaaga tgaaacttaa ggtacttggt tattagcatt      2160
ataaagtcag acctctctat aacataatcg ctatataaca gtcattcact ataaaagtca      2220
agttttttta tggaatcaat ttttatatta tactataata tatgttctct ataacaccac      2280
ttcgttatat caaccaataa aattcggaac aaataaggct gttatagaga ggtttgactg      2340
tattatttat tgttcttgat aagataagag aagatccaat aaatgaaaaa gatttgttat      2400
tttgacagtt ttttcaaaaa aagcaactga ttttactgta taatactgaa tgtgttgtac      2460
tttcttttcc tatcaccatt taattggtag tttaagctta tcaatttatg aagtagttga      2520
actatgttag tcattgctat tcttcaactt attgccctta caaatatgaa caaatcaagt      2580
tagttgttac cgttctttct gttgctttct ttgtttctta taatatcgcg gacttatgta      2640 gttttttcctg tattgacatc tcttaatttt tcagagggat ggcagtgata ttgtggttga      2700
gggtcctcgg tgcagtcttc gaagtagaaa ggtttgtact acttttctgc tcaatgagac      2760
atttactagc tggttaatag gtactcatct tttatattgc atctgtgaaa atacttattt      2820
tgtgccatca tacattcgaa gaggatcctt ggagtctccg tgtgactata ggtcatgggt      2880
tcgagctgtg gaagcaacca ctaatgcttg tattagagta ggttgtctaa tacattagct      2940
tcagtctgcg gcagatctgc ggtctgcaga tcaattctgc aaccgcagaa acgccctgca      3000
cttccaaaat tattttttcaa ctccccaacg cactgttcaa cccaaaaagt cggaaccgat      3060
tatcaacgca taagtctacc tcggcatcat gaaaccccgg gtttttaggtg aaatttttcg      3120 gggccttaca tcctccccgc ttaggatcat tcgtcctcga atgagggtca aaattcagta      3180
ttagcaccca atgtgactca gttgctatag ctcacaccgg cagttccaaa ttcgaagagg      3240
atgctttgtg cagcgggctg ccctttttag ccatcataca ttcgtgcaag atgtttatga      3300
ggttaagtgg ttaaatgaac tttacttgtt gcaggtttat agcgatcttt ctgttgatta      3360
tctgaagatg ttcttgttaa atgtccctgc tgctgttgtt gctcttggat tgtgagtact      3420
acttaaaact ctcagcatta taagtttca tttctttgta cattgtcatt agtttctcaa      3480
cccggttatg aagcaaccaa cattattatc ctctaataga tatgtttggc taatgtttgc      3540
taggttcttt ttccttgacg atttaactgg atttgagatc acttatcttt tggaggtaat      3600
catatcttgt tatctagcct ggttctttat tgtaatccct agattatcaa gtggttattt      3660
gcaaaagatc agagtattca ttaacctttg tcaaatgcta taattttgtc aattttgcag      3720
cttccagagc ctttcagttt cattttcaca tggtttgctg ctttgccttt gatattgtat      3780
ctatcgttta caatcacaaa cgtcgttgtt aaagattttc tgatcttaaa ggtaagattt      3840
cggaaacatt gtgcgcgtag tattatctta tatgctatgt gtttgatatt aacacacaat      3900
tttcagggcc cttgtccgaa ttgtggagca gaaaatactc ccttctttgg taccatatta      3960
tcagtatcta gtggtggttc taccaacaaa ataaaatgct cagggtaagt ccataagcct      4020 tagttttttag gtattttca tctttctctg cttgatctgt tcatagtgta atcatcgcca      4080
tgatctttcg cagttgtggg acggatttgg tctatgattc agacacgcgt ttgatcacgt      4140
tgcctgaagg aattagtgga tgattcgagg tacctatgct ctttaaccta tttgtaacag      4200
ctcagctcac taatgatatt gtccgctttg gtcttaggct cgtactgctt taaacacgcg      4260
ttactaatgt cttaagcttg ctttcctacc agtatctttt ccgtgttttg cagatataga      4320
```

-continued

```
atttgcctag ggtgtaacac tattattgct gcttggaaaa ttataggcgt tttagttgtc      4380
attgctcact tatctttcaa ggcgactgct aatagaagca tacctatgtc taaccttgag      4440
gggtcacccg acctcgtaaa cttcggtaga aatcttatat tttacacctt gaaaatgatt      4500
taatttaaat cgcttggctc cctgaatact aaaaccttta gggggcacta gttgaacaga      4560
ataccggtgc tccccgtcgt gctaaagtcc tgggtccgcc tctaactgct aatgcttagt      4620
gtacaaaaat aggacttaaa cctaagaatg gtttcccttg atccttccca acaatttaga      4680
taaactaatc tatgatatta cctttctcat ttcacataag acttcttttc ggttcatatt      4740
tgaaaataga tccagcactt actttcaaaa agaaaaatat agatttccaa aatgcaaatt      4800
ttctagataa aattttaata ttcttaactc gttttatttt tcttgaaatg aattcaaata      4860
ctattgttct ccaacccaaa cgccacataa tagttcactt aagcaccatc ttttatgttc      4920
tcagacctca atttacacta tattacttaa atatgacctg ctctacatcc tcgtacctct      4980
gttgtccttg agttacagac tatgttgcgc gaactttaaa aaatgttgtt gcatccatgt      5040
cggaacctcc aaaaatacag tacttatgac ggatccaaca cacacttaga gacattttca      5100
gaaagtccga gcaacataga ttacatgtca ttttcgatct aggaaaaaag agcttttttc      5160
gcaagtttat ctgtatttta tcgcttgtat ggagaagtat aaccggtgag aactttcctc      5220
gtacaggaaa accattgcca tttactaata acttggagtt ggagttggag atctgcacaa      5280
tagattgcac tagaacaagt tgcctattgg aagagccaaa taacatacat gagtcaagtt      5340
tgtaaaaatg gaaagcactt tcagtgttga aattgtgaat gttttgctac ttgtattttg      5400
tccaatatat tatgtaatgt gtgagtataa gtatatcaat acaaaaaatt aacaaccttt      5460
aatcacaggt gatgaaagaa tatcaaggtt c                                    5491
```

```
<210> SEQ ID NO 42
<211> LENGTH: 989
<212> TYPE: PRT
<213> ORGANISM: Artificial Sequence
<220> FEATURE:
<223> OTHER INFORMATION: interactor, Nitab4.5_0005803g0040.2 protein
      sequence

<400> SEQUENCE: 42

Met Ile Val Arg Val Gly Leu Val Val Ala Ala Ser Ile Ala Ala Tyr
1               5                   10                  15

Ala Val Lys Gln Ile Asn Val Lys Pro Ser Lys Pro Ser Glu Asn Gly
            20                  25                  30

Asp Ser Leu Pro Glu Lys Arg Ser Asp Glu Gly Asp Glu Lys Glu Glu
        35                  40                  45

Gln Leu Leu Tyr Ser Thr Asp Gly Pro Lys Glu Val Val Asp Glu Glu
    50                  55                  60

Glu Glu Lys Glu Glu Val Lys Leu Met Asn Gly Ile Ile Asn Pro Ala
65                  70                  75                  80

Gln Gly Asn Gln Leu Asp Leu Asp Asp Asp Leu Phe Pro Glu Phe Glu
                85                  90                  95

Asp Leu Leu Ser Gly Glu Ile Glu Phe Pro Leu Pro Ser Asp Lys Tyr
            100                 105                 110

Asp Thr Glu Arg Glu Glu Arg Glu Lys Val Tyr Gln Asn Glu Met Ala
        115                 120                 125

Asn Asn Glu Lys Glu Leu Glu Arg Leu Arg Asn Leu Val Lys Glu Leu
    130                 135                 140

Glu Glu Arg Glu Val Lys Leu Glu Gly Glu Leu Leu Glu Tyr Tyr Gly
```

-continued

```
145             150             155             160

Leu Lys Glu Gln Glu Ser Asp Ile Ile Glu Leu Gln Lys Gln Leu Arg
            165             170             175

Ile Lys Ser Val Glu Ile Asp Met Leu Asn Ile Thr Ile Asn Thr Leu
            180             185             190

Gln Ala Glu Lys Gln Lys Leu Gln Glu Glu Val Phe Asn Gly Thr Thr
            195             200             205

Ala Arg Lys Glu Leu Glu Ala Ala Arg Ser Lys Ile Lys Glu Leu Gln
        210             215             220

Arg Gln Met Gln Leu Glu Ala Asn Gln Thr Lys Ala Gln Leu Leu Leu
225             230             235             240

Leu Lys Gln His Val Ser Gly Leu Gln Glu Lys Glu Glu Asp Ala Phe
                245             250             255

Lys Arg Asp Val Glu Val Asp Lys Lys Leu Arg Leu Val Lys Glu Leu
            260             265             270

Glu Val Glu Val Met Glu Leu Lys Arg Lys Asn Lys Glu Leu Gln His
            275             280             285

Glu Lys Arg Glu Leu Val Ile Lys Leu Asp Ala Ala Glu Ser Lys Val
        290             295             300

Ala Asn Leu Ser Asn Met Thr Glu Asn Glu Met Val Ala Gln Val Arg
305             310             315             320

Glu Glu Val Thr Asn Leu Lys His Thr Asn Glu Asp Leu Leu Lys Gln
            325             330             335

Val Glu Gly Leu Gln Met Asn Arg Phe Ser Glu Val Glu Glu Leu Val
            340             345             350

Tyr Leu Arg Trp Val Asn Ala Cys Leu Arg Phe Glu Leu Arg Asn Tyr
            355             360             365

Gln Thr Pro Gln Gly Lys Val Ser Ala Arg Asp Leu Ser Lys Asn Leu
        370             375             380

Ser Pro Arg Ser Gln Gln Lys Ala Lys Gln Leu Met Leu Glu Tyr Ala
385             390             395             400

Gly Ser Glu Arg Gly Gln Gly Asp Thr Asp Leu Glu Ser Asn Phe Ser
            405             410             415

Gln Pro Ser Ser Pro Gly Ser Glu Asp Phe Asp Asn Ala Ser Ile Asp
            420             425             430

Ser Ser Thr Ser Arg Phe Ser Ala Phe Ser Lys Lys Pro Gly Leu Ile
        435             440             445

Gln Lys Leu Lys Arg Trp Gly Lys Ser Lys Asp Asp Ser Ser Val Met
    450             455             460

Ser Ser Pro Ala Arg Ser Leu Gly Gly Ala Ser Pro Gly Arg Thr Ser
465             470             475             480

Val Ser Phe Arg Ser Arg Gly Pro Leu Glu Ser Leu Met Leu Arg Asn
            485             490             495

Ala Gly Asp Gly Val Ala Ile Thr Ser Phe Gly Thr Ala Glu Gln Glu
            500             505             510

Tyr Asp Ser Pro Glu Thr Pro Arg Leu Pro Pro Ile Arg Thr Gln Asp
            515             520             525

Ser Ser Ala Glu Pro Leu Asn Ser Val Ala Ser Ser Phe Gln Leu Met
        530             535             540

Ser Lys Ser Val Glu Gly Val Leu Asp Glu Lys Tyr Pro Ala Phe Lys
545             550             555             560

Asp Arg His Lys Leu Ala Val Glu Arg Glu Lys Gln Ile Lys Val Lys
            565             570             575
```

```
Ala Glu Gln Ala Arg Ala Ala Arg Phe Glu Lys Ser Leu Pro Pro Lys
        580                 585                 590

Leu Ser Gln Leu Lys Glu Lys Arg Val Ser Val Ser Ala Ser Ala Ser
        595                 600                 605

Ala Pro Val Val Ser Ala Ser Gly Asp Ser Val Glu Gln Ser Gly Asp
        610                 615                 620

Ser Lys Thr Asp Ser Gln Ala Val Ser Lys Met Lys Pro Ile Asn Ile
625                 630                 635                 640

Glu Lys Arg Pro Pro Arg Thr Pro Arg Pro Pro Thr Arg Ser Ala
                645                 650                 655

Gly Gly Pro Ala Pro Ala Gly Asn Asn Val Thr Gly Gly Ala Pro Gly
                660                 665                 670

Gly Pro Pro Pro Pro Pro Pro Pro Gly Ala Pro Pro Pro Pro
                675                 680                 685

Pro Pro Gly Gly Gly Ala Pro Arg Pro Pro Pro Pro Gly Ser Leu
        690                 695                 700

Met Lys Gly Gly Ala Gly Gly Asp Lys Val His Arg Ala Pro Glu Leu
705                 710                 715                 720

Val Glu Phe Tyr Gln Ser Leu Met Lys Arg Glu Ala Lys Lys Asp Thr
                725                 730                 735

Ser Ser Pro Leu Ile Ser Ser Thr Ser Asn Thr Ser Asp Ala Arg Ser
                740                 745                 750

Asn Met Ile Gly Glu Ile Glu Asn Arg Ser Thr Phe Leu Leu Ala Val
        755                 760                 765

Lys Ala Asp Val Glu Ser Gln Gly Glu Phe Val Glu Ser Leu Ala Thr
        770                 775                 780

Glu Val Arg Ala Ala Ser Phe Thr Asn Ile Glu Asp Leu Val Ser Phe
785                 790                 795                 800

Val Asn Trp Leu Asp Glu Glu Leu Ser Phe Leu Val Asp Glu Arg Ala
                805                 810                 815

Val Leu Lys His Phe Asp Trp Pro Glu Gly Lys Ala Asp Ala Leu Arg
                820                 825                 830

Glu Ala Ala Phe Glu Tyr Gln Asp Leu Met Lys Leu Glu Lys His Val
        835                 840                 845

Thr Ser Phe Val Asp Asp Pro Asn Leu Pro Cys Asp Ala Ala Leu Lys
850                 855                 860

Lys Met Tyr Lys Leu Leu Glu Lys Val Glu Gln Ser Val Tyr Ala Leu
865                 870                 875                 880

Leu Arg Thr Arg Asp Met Ala Ala Ser Arg Tyr Arg Glu Phe Gly Ile
                885                 890                 895

Pro Thr Asn Trp Leu Gln Asp Ser Gly Val Val Gly Lys Ile Lys Leu
        900                 905                 910

Ser Ser Val Gln Leu Ala Arg Lys Tyr Met Lys Arg Val Ala Ser Glu
        915                 920                 925

Leu Asp Ala Met Gly Gly Pro Glu Lys Glu Pro Asn Arg Glu Phe Leu
        930                 935                 940

Ile Leu Gln Gly Val Arg Phe Ala Phe Arg Val His Gln Phe Ala Gly
945                 950                 955                 960

Gly Phe Asp Ala Glu Ser Met Lys Ala Phe Glu Glu Leu Arg Ser Arg
                965                 970                 975

Val Lys Ser Ser Gln Thr Glu Glu Thr Thr Gln Glu Gln
        980                 985
```

```
<210> SEQ ID NO 43
<211> LENGTH: 2970
<212> TYPE: DNA
<213> ORGANISM: Artificial Sequence
<220> FEATURE:
<223> OTHER INFORMATION: interactor, Nitab4.5_0005803g0040.2 coding
      sequence

<400> SEQUENCE: 43
atgatagtca gggtaggttt agtggttgct gcttctatag cagcctatgc agttaagcag     60
ataaatgtaa aaccctcaaa gccttcagaa aatggtgact cattgcctga aaaacgaagc    120
gatgaagggg atgaaaagga ggagcagctt ttgtattcta cagatggccc caaagaagtg    180
gttgatgagg aagaggagaa agaagaagtg aaattaatga atggaattat aaatccagca    240
cagggtaacc agcttgatct tgatgatgat ctttttccctg aattcgaaga tctttttatct    300 ggggaaattg aatttccatt accaagtgac aagtatgata cagaaagaga agagagagag    360
aaggtgtacc aaaatgagat ggccaacaat gaaaaagaac ttgaaagatt gcgaaatctt    420
gttaaggagc tcgaggaaag ggaggtgaaa cttgaagggg agttgttgga atattatggt    480
ttgaaggaac aagaatcaga tatcatcgag ttacaaaagc agctcaggat taagtctgta    540
gagatcgaca tgctcaacat cactataaat actttacagg ccgagaaaca aaagcttcaa    600
gaggaggttt tcaatggaac tactgctcgg aaagagctag aagcagcaag gagcaagatc    660
aaggagttgc agaggcagat gcagcttgaa gctaaccaaa cgaaagctca gttgttgttg    720
ctgaagcaac atgttagtgg acttcaagaa aaggaagagg atgctttcaa gagagatgtc    780
gaggttgaca agaagcttag acttgtgaag gaattagaag tggaggttat ggagcttaag    840
aggaagaaca aagaacttca gcatgaaaag agagagttgg ttataaaatt ggatgccgct    900
gaatctaaag tagcaaactt atccaatatg acagagaatg aaatggttgc ccaggtcagg    960
gaagaggtaa ctaatttgaa gcatacaaat gaggatcttc taaaacaagt agaaggactt   1020
caaatgaaca gattcagtga agttgaagag ctagtgtatc ttcgttgggt caatgcatgc   1080
ttaagatttg aacttcggaa ctaccaaaca cctcaaggaa aggtatcagc tcgtgatctc   1140
agtaaaaacc tgagcccaag atctcaacag aaggccaaac agttgatgtt agaatacgca   1200
ggatcagaac gtggccaagg agatacagat cttgaaagca atttttcgca gccatcttct   1260
cccggtagtg aagactttga taatgcttct attgacagtt ccacaagcag atttagtgct   1320
ttcagtaaaa agcctggcct aatccagaag ttgaagagat ggggcaaaag taaagacgat   1380
tccagtgtta tgtcttcacc agcaagatct cttgggggag catctccggg ccggacaagt   1440
gtaagtttta gatcaagggg tcctctggaa tcactaatgc tcagaaatgc aggtgatggt   1500
gtagccatca ctagttttgg aacagctgag caggaatatg attcccctga aacaccgcgg   1560
cttccaccga ttaggacaca agattcttct gctgagccac tgaactcagt tgcatcatcc   1620
ttccagctaa tgtctaaatc agttgaagga gttctagatg agaagtatcc tgcattcaaa   1680
gataggcata agctggcagt agagcgagag aagcaaatta aggtaaaggc cgagcaagca   1740
agagcagcaa ggtttgagaa gtccttgccc ccgaaacttt ctcaattgaa agagaagcga   1800
gtatcagtat cagcatcagc atcagcgcca gtggtctctg cctctggtga ctcagttgag   1860
cagtccggtg atagcaaaac tgactctcaa gcagttagca aaatgaaacc aattaatatt   1920
gagaaaagac ctcctaggac tcctcgtcca cctcctacac gatcagcagg tggtcccgct   1980
ccagctggta ataatgttac aggtgggggca cctggtggtc caccccacc acctcctccg   2040
```

-continued

```
cctggtgctc caccaccgcc gccgccacct ggtggaggag ctcctagacc acctcctcct    2100
cctggatctc taatgaaagg aggagctgga ggtgataagg tccatcgcgc tcctgaatta    2160
gttgaattct accaatcatt gatgaaacgc gaggcgaaga aggatacatc atcacctttg    2220
atatcctcta cttcaaacac atcagatgca agaagcaaca tgatcggaga gatagagaac    2280
agatccacat tcctgttagc tgtgaaagct gatgtggaaa gtcaaggtga atttgtcgag    2340
tcattggcaa ctgaagttcg tgctgcttca tttaccaata tcgaggatct agtgtcattt    2400
gtgaactggc tagatgaaga actctccttc ttggttgatg aacgagctgt cctcaagcac    2460
tttgactggc cagagggaaa agcagatgca ctgagagagg ctgccttcga ataccaagat    2520
ctaatgaaac tagaaaagca tgtaacctcc tttgttgatg acccaaatct tccatgtgat    2580
gctgctttga aaaagatgta caagttgctt gagaaggtgg aacaaagtgt ttatgcacta    2640
ttgcgtactc gcgacatggc tgcatcaaga tacagagaat ttggcattcc tactaattgg    2700
ttgcaagatt caggtgttgt tggcaagatc aagctttcgt cggtacaatt ggcgaggaag    2760
tacatgaaac gtgtagcatc agagcttgat gccatgggtg gacctgagaa ggaaccaaac    2820
agagaattct tgattctaca aggggttcgt tttgctttta gagttcatca gtttgctgga    2880
ggatttgatg ctgaaagcat gaaggctttt gaagaattaa ggagtcgtgt caaaagttca    2940
caaacagaag agactacaca agaacaatga                                     2970
```

<210> SEQ ID NO 44
<211> LENGTH: 5952
<212> TYPE: DNA
<213> ORGANISM: Artificial Sequence
<220> FEATURE:
<223> OTHER INFORMATION: interactor, Nitab4.5_0005803g0040.2 genomic
      sequence

<400> SEQUENCE: 44

```
agaatttcaa tcttgtttgg acaaagactg accactcaag aaattggtgg ttcttgtgcc      60
ctctatgtgt tcgacaattt gtctattaga cttttctagtt atcaacaaca ctttgcacat     120
aaccaaactt tttttttctt gataagatga tatagccatt aagttattca tagtgtccac     180
tttttaaaga attgtctaaa actgataatt ctctttcaag aattgcacct tttttgccat     240
ttttgatgag gccatgattt gagtttttgag ctatgggggtt tgagaaaaaa tgggtgggga    300
ttattttatg ttagtaaatg atttgaagct tcaatatttt ccattgaaaa tacctacatg     360
atagtcaggg taggtttagt ggttgctgct tctatagcag cctatgcagt taagcagata     420
aatgtaaaac cctcaaagcc ttcaggtaat tttctgtagt cagttgtatt tggactgttt     480
tattaaagtt gcaaataagt aaagaggctg ctaaattagt ataattggtt ttagacatat     540
tgataaaaca gtgtctataa agtttcaatt tttaatggag aaaatcatcc aagtgagtga     600
ctagagtgtt tttttgtggc taaattgtgt ttatcttatt gttttatgaa cgttggtgaa     660
cagaaaatgg tgactcattg cctgaaaaac gaagcgatga aggggatgaa aaggaggagc     720
agcttttgta ttctacagat ggccccaaag aagtggttgt aagtatttgt gtatagagaa     780
atttgtgtgc tttagaaaca aaaatttgtt agtcatttgg aaatttgttt aatatatgac     840
aacttgtagg atgaggaaga ggagaaagaa gaagtgaaat taatgaatgg aattataaat     900
ccagcacagg gtaaccagct tgatcttgat gatgatcttt tccctgaatt cgaagatctt     960
ttatctgggg aaattgaatt tccattacca agtgacaagt atgatacaga aagagaagag    1020
agagagaagg tgtaccaaaa tgagatggcc aacaatgaaa aagaacttga aagattgcga    1080
```

```
aatcttgtta aggagctcga ggaaagggag gtgaaacttg aaggggagtt gttggaatat   1140
tatggtttga aggaacaaga atcagatatc atcgagttac aaaagcagct caggattaag   1200
tctgtagaga tcgacatgct caacatcact ataaatactt tacaggccga gaaacaaaag   1260
cttcaagagg aggttttcaa tggaactact gctcggaaag agctagaagc agcaaggagc   1320
aagatcaagg agttgcagag gcagatgcag cttgaagcta accaaacgaa agctcagttg   1380
ttgttgctga agcaacatgt tagtggactt caagaaaagg aagaggatgc tttcaagaga   1440
gatgtcgagg ttgacaagaa gcttagactt gtgaaggaat tagaagtgga ggttatggag   1500
cttaagagga agaacaaaga acttcagcat gaaaagagag agttggttat aaaattggat   1560
gccgctgaat ctaaagtagc aaacttatcc aatatgacag aggtaaattt aactcctgat   1620
accagtattt ttcatgtaat tgatctttag gacaatcttt gtgtgtttcc tgcgtatagc   1680 ttttcttttct ttaagcatct tctttctact tttcaagtct gcaaaaatgt tttggaaatg   1740
tagagccgac tctgagcacc ttattgaccc cctttttctg attacttccc tttttacgcc   1800
acgctcataa ggtagttgag tccgttgaat actccagtga aacatgccca cattatggtt   1860
tcttgtaatt atcgtaattg tcattgctat gttttgctgt ttattatgct cattaatttc   1920
ttctatgtta attatcgtgt tgagctccca ccacttaacc attggagatt cttagcttct   1980
gaagagcttc atttggtgat gcgtttggtt ggtgtgtgaa ctgatgctat ttaattactg   2040
acttgtcttt ggcatgctgc ttcagaatga aatggttgcc caggtcaggg aagaggtaac   2100
taatttgaag catacaaatg aggatcttct aaaacaagta gaaggacttc aaatgaacag   2160
attcagtgaa gttgaagagc tagtgtatct tcgttgggtc aatgcatgct taagatttga   2220
acttcggaac taccaaacac ctcaaggaaa ggtatcagct cgtgatctca gtaaaaacct   2280
gagcccaaga tctcaacaga aggccaaaca gttgatgtta gaatacgcag gatcagaacg   2340
tggccaagga gatacagatc ttgaaagcaa tttttcgcag ccatcttctc ccggtagtga   2400
agactttgat aatgcttcta ttgacagttc cacaagcaga tttagtgctt tcagtaaaaa   2460
gcctggccta atccagaagt tgaagagatg gggcaaaagt aaagacgatt ccagtgttat   2520
gtcttcacca gcaagatctc ttgggggagc atctccgggc cggacaagtg taagtttag    2580 atcaaggggt cctctggaat cactaatgct cagaaatgca ggtgatggtg tagccatcac   2640
tagttttgga acagctgagc aggaatatga ttcccctgaa acaccgcggc ttccaccgat   2700
taggacacaa gattcttctg ctgagccact gaactcagtt gcatcatcct tccagctaat   2760
gtctaaatca gttgaaggag ttctagatga gaagtatcct gcattcaaag ataggcataa   2820
gctggcagta gagcgagaga agcaaattaa ggtaaaggcc gagcaagcaa gagcagcaag   2880
gtttgagaag tccttgcccc cgaaactttc tcaattgaaa gagaagcgag tatcagtatc   2940
agcatcagca tcagcgccag tggtctctgc ctctggtgac tcagttgagc agtccggtga   3000
tagcaaaact gactctcaag cagttagcaa aatgaaacca attaatattg agaaaagacc   3060
tcctaggact cctcgtccac ctcctacacg atcagcaggt ggtcccgctc cagctggtaa   3120
taatgttaca ggtggggcac ctggtggtcc accccccacca cctcctccgc ctggtgctcc   3180
accaccgccg ccgccacctg gtggaggagc tcctagacca cctcctcctc ctggatctct   3240
aatgaaagga ggagctggag gtgataaggt ccatcgcgct cctgaattag ttgaattcta   3300
ccaatcattg atgaaacgcg aggcgaagaa ggatacatca tcacctttga tatcctctac   3360
ttcaaacaca tcagatgcaa gaagcaacat gatcggagat atagagaaca gatccacatt   3420
cctgttagct gtatgtacaa cttctctttt actcctttga ataatgcatg tgcttattaa   3480
```

```
cctattctga ctcaatggag acttgtgcaa aaccaggtga aagctgatgt ggaaagtcaa    3540
ggtgaatttg tcgagtcatt ggcaactgaa gttcgtgctg cttcatttac caatatcgag    3600
gatctagtgt catttgtgaa ctggctagat gaagaactct ccttcttggt atttcctctt    3660
accattatac cttcaagttc ctcttcctta aataggacat gaatatacct atattcttaa    3720
tcatactttt atatgaaaat tgttgcttac attaatcttg ctcgagcgac aaggaccatg    3780
cagtttctgc attaaatacc tggagcattc attaacattg tatcccgttg attcttttca    3840
aggttgatga acgagctgtc ctcaagcact ttgactggcc agagggaaaa gcagatgcac    3900
tgagagaggc tgccttcgaa taccaagatc taatgaaact agaaaagcat gtaacctcct    3960
ttgttgatga cccaaatctt ccatgtgatg ctgctttgaa aaagatgtac aagttgcttg    4020
agaagtaagt ctctactgat atctttatct cttgtcttta aactagagaa tttcagtcag    4080
gtaggatgtg aaaatggttg aatcttaaat caaactattt tcagaccata tttaaacttc    4140
cacttatttg gaattggtac cctttcattt catgtgtagt tgttccttct tatcatttct    4200
gtcttgtcta tcgctagctc attttтttgtt actcctaagt cttaaaccct ttaatcttcg    4260
ggatgccagg gtggaacaaa gtgtttatgc actattgcgt actcgcgaca tggctgcatc    4320
aagatacaga gaatttggca ttcctactaa ttggttgcaa gattcaggtg ttgttggcaa    4380
ggtatgttct catatagaaa cttttgctatg ttgttctttg tgaaattgct tgaaccacaa    4440
taataaaaga aaaagaaaca aaataatcac actgcaagaa aaccttagaa tgtgatgttt    4500
tacttcatat tacttagaaa ttaggaaaac ttaccaacct cttttaactaa catgtactcc    4560 ctctatttca aaaagaacga acctatttga ttaggcaccg agtttaaaaa gaatgaaaga    4620
cttagatatt tgtgcggcat aaatcatctt attaggggta aaatgaaaag tttaaagtta    4680
cattatttcc aaatttagaa aggagtcaat ctatttgaat cgagttaaaa aggaaatagg    4740
ttcattcttt ttgaaacaga gggagtaaat ataatttctc ttcatcgtac ggacaataga    4800
aggaaaaaaa aaaggaagtg tgcagagaga tgatctatct atggcgtata agtatcgctg    4860
ttttcttctg cagatcaagc tttcgtcggt acaattggcg aggaagtaca tgaaacgtgt    4920
agcatcagag cttgatgcca tgggtggacc tgagaaggaa ccaaacagag aattcttgat    4980
tctacaaggg gttcgttttg cttttagagt tcatcaggta tacacacagc acctgcattt    5040
tgttcactta ccaaatctaa aaacaatacc aatctattta acaaattaaa catgttttag    5100
tagagttaca gattaatgaa tttacaactt tttctttttc ttttcagttt gctggaggat    5160
ttgatgctga aagcatgaag gctttttgaag aattaaggag tcgtgtcaaa agttcacaaa    5220
cagaagagac tacacaagaa caatgagaat atctgtattt tggttttggt cattgtaaat    5280
ttcatcattt tcttttctcc aagtatagca aacttactct atcttggact tctgtacaat    5340
tcaaaaggtg aataactcga ggagaatatc agatagcaca gattagttaa aagaaagttt    5400
aaaggataaa cattgtattg gaaaacacag agaaaactac attaaacaat gagtgaaatt    5460
tggaactgca taatcatgaa ttcacgagaa ggaaaaaatg cagcaagttg tcaaggtgtt    5520
ggatcatttg ttctgctttt ggggcaaaag tgaaaacctg tccctcttct ggggcctagt    5580
tgtactaggc aaaaaatcct catttctgtg aaatttaagt atattcatcc tagtacattt    5640
cagggtacaa gcattgtgca atagcaaaaa gaaaagaaga gaaactcata aaactgagtg    5700
ttcagcagct gctgtgaagt gactctctgt atgctcgtcg atgaacatgc aggtgaaggt    5760
tcttgatttc atctgttatc gcattgtaat aatgagattt ctgtctgcaa atttggcacc    5820
```

-continued

```
tccaaccttc ccttgaagtt gagatggtag acgaatgaca cgtctctgat caccagcctc    5880
taccaacaac tcagaccctc ctctaaactg caataaccag aattctgatt aatttcacct    5940
tttaatttga tt                                                         5952
```